(12) United States Patent
Seki et al.

(10) Patent No.: US 7,339,373 B2
(45) Date of Patent: Mar. 4, 2008

(54) MAGNETIC SHIELDING APPARATUS AND BIOMAGNETISM MEASURING DEVICE

(75) Inventors: Yusuke Seki, Tokyo (JP); Mitsuru Onuma, Tokyo (JP); Akihiko Kandori, Tokyo (JP); Daisuke Suzuki, Kokubunji (JP); Takuya Akashi, Musashino (JP); Masahiro Murakami, Hitachinaka (JP); Atsushi Watanabe, Hitachinaka (JP); Yoshio Matsuoka, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 355 days.

(21) Appl. No.: 11/196,750

(22) Filed: Aug. 4, 2005

(65) Prior Publication Data

US 2006/0055402 A1 Mar. 16, 2006

(30) Foreign Application Priority Data

Sep. 10, 2004 (JP) ............................. 2004-263192

(51) Int. Cl.
*G01R 33/035* (2006.01)
(52) U.S. Cl. ...................................... 324/248; 505/846
(58) Field of Classification Search ................ 505/162, 505/845–846; 326/5; 327/527; 335/216; 600/407, 409
See application file for complete search history.

(56) References Cited

U.S. PATENT DOCUMENTS 6,424,853 B1    7/2002 Tsukada et al.

(Continued)

FOREIGN PATENT DOCUMENTS

EP    0884601    12/1998

(Continued)

OTHER PUBLICATIONS

Suzuki et al., "A Mobile and space-saving high-temperature superconducting multichannel magnetocardiograph in a vertical magnetically shielded cylinder", Japanese Journal of Applied Physics, Part 1, Japan Soc. Appl. Phys Japan, vol. 43, No. 1 Jan. 2004 pp. 117-120.

*Primary Examiner*—Bot LeDynh
(74) *Attorney, Agent, or Firm*—Mattingly, Stanger, Malur & Brundidge, Plc.

(57) ABSTRACT

The object of the invention is to provide a biomagnetism measuring device using a high-performance cylindrical shielding apparatus provided with a flange-type plate having an opening formed on a circumferential face, an auxiliary cylinder in which one or plural cylindrical members are connected so that the central axis of the opening of the flange-type plate and each central axis of the cylindrical members are coincident, cylindrical shields having first, second and third angular ranges with the y-axis, a revolving door having a cutout in a portion parallel to the y-axis and acquired by integrating the cylindrical shields, shield bases for supporting the cylindrical shield to which the flange-type plate is connected in a circular-arc part at both ends, revolving parts for revolving the revolving door in a circumferential direction of the y-axis along a circumferential part of the cylindrical shield and opening or closing an opening in the circumferential direction, a cryostat arranged inside the opening of the auxiliary cylinder and the opening and a SQUID fluxmeter arranged on a measurement face parallel to an XY plane inside the cryostat held at low temperature and characterized in that the circumferential part of the cylindrical shield is inserted between the circumferential parts of the cylindrical shields when the revolving door is closed, cylindrical internal space is formed and an environmental magnetic field that invades the internal space is screened.

14 Claims, 62 Drawing Sheets

U.S. PATENT DOCUMENTS 6,528,994 B2 * 3/2003 Suzuki et al. ............... 324/248
2002/0050815 A1 5/2002 Suzuki et al.

FOREIGN PATENT DOCUMENTS

JP 63-272335 11/1988

* cited by examiner

FIG. 23

|  | OUTSIDE DIAMETER | INSIDE DIAMETER | THICKNESS OF SHIELD | ANGLE | LENGTH |
|---|---|---|---|---|---|
| OUTSIDE SHIELD | 122 | 116 | 0.2 | 255 | 200 |
| INTERMEDIATE SHIELD | 114 | 102 | 0.2 | 260 | 200 |
| INSIDE SHIELD | 100 | 94 | 0.2 | 200 | 200 |
| MAXIMUM ANGLE OF OPENING 9 |  |  |  | 100 |  |
| OVERLAPPED ANGLE OF UPPER OUTSIDE |  |  |  | 60 |  |
| OVERLAPPED ANGLE OF UPPER INSIDE |  |  |  | 60 |  |
| OVERLAPPED ANGLE OF LOWER OUTSIDE |  |  |  | 40 |  |
| OVERLAPPED ANGLE OF LOWER INSIDE |  |  |  | 95 |  |
| ONE-LAYER AUXILIARY SHIELD |  | 40 | 0.1 |  | 17 |

FIG. 24

|  | INSIDE DIAMETER | THICKNESS OF SHIELD | ANGLE | LENGTH | DIAMETER OF OPENING |
|---|---|---|---|---|---|
| FIG. 6 A | 100 | 0.2 | 360 | 200 | 0 |
| FIG. 6 B | 100 | 0.2 | 360 | 200 | 40 |
| FIG. 6 C | 100 | 0.2 | 360 | 200 | 40 |
| AUXILIARY SHIELD | 40 | 0.2 | 360 | 50 |  |

FIG. 25

|  | OUTSIDE DIAMETER | INSIDE DIAMETER | THICKNESS OF SHIELD | ANGLE | LENGTH |
|---|---|---|---|---|---|
| OUTSIDE SHIELD | 122 | 116 | 0.2 | 255 | 200 |
| INTERMEDIATE SHIELD | 114 | 102 | 0.2 | 260 | 200 |
| INSIDE SHIELD | 100 | 94 | 0.2 | 200 | 200 |
| MAXIMUM ANGLE OF OPENING 9 |  |  |  | 100 |  |
| OVERLAPPED ANGLE OF UPPER OUTSIDE |  |  |  | 60 |  |
| OVERLAPPED ANGLE OF UPPER INSIDE |  |  |  | 60 |  |
| OVERLAPPED ANGLE OF LOWER OUTSIDE |  |  |  | 40 |  |
| OVERLAPPED ANGLE OF LOWER INSIDE |  |  |  | 40 |  |

FIG. 26

|  | OUTSIDE DIAMETER | INSIDE DIAMETER | THICKNESS OF SHIELD | ANGLE | LENGTH | DIAMETER OF OPENING |
|---|---|---|---|---|---|---|
| OUTSIDE SHIELD | 122 | 116 | 0.2 | 255 | 200 | CUTOUT EXISTS |
| INTERMEDIATE SHIELD | 114 | 102 | 0.2 | 260 | 200 | 40 |
| INSIDE SHIELD | 100 | 94 | 0.2 | 200 | 200 | CUTOUT EXISTS |
| MAXIMUM ANGLE OF OPENING 9 |  |  |  | 100 |  |  |
| OVERLAPPED ANGLE OF UPPER OUTSIDE |  |  |  | 60 |  |  |
| OVERLAPPED ANGLE OF UPPER INSIDE |  |  |  | 60 |  |  |
| OVERLAPPED ANGLE OF LOWER OUTSIDE |  |  |  | 40 |  |  |
| OVERLAPPED ANGLE OF LOWER INSIDE |  |  |  | 40 |  |  |

FIG. 27

|  | OUTSIDE DIAMETER | INSIDE DIAMETER | THICKNESS OF SHIELD | ANGLE | LENGTH | DIAMETER OF OPENING |
|---|---|---|---|---|---|---|
| OUTSIDE SHIELD | 122 | 116 | 0.2 | 255 | 200 | CUTOUT EXISTS |
| INTERMEDIATE SHIELD | 114 | 102 | 0.2 | 260 | 200 | 40 |
| INSIDE SHIELD | 100 | 94 | 0.2 | 200 | 200 | CUTOUT EXISTS |
| MAXIMUM ANGLE OF OPENING 9 | | | | 100 | | |
| OVERLAPPED ANGLE OF UPPER OUTSIDE | | | | 60 | | |
| OVERLAPPED ANGLE OF UPPER INSIDE | | | | 60 | | |
| OVERLAPPED ANGLE OF LOWER OUTSIDE | | | | 40 | | |
| OVERLAPPED ANGLE OF LOWER INSIDE | | | | 40 | | |
| OUTSIDE AUXILIARY SHIELD | | 40 | 0.1 | | 17 | |
| INSIDE AUXILIARY SHIELD | | 52 | 0.1 | | 17 | |

FIG. 28

| | OUTSIDE DIAMETER | INSIDE DIAMETER | THICKNESS OF SHIELD | ANGLE | LENGTH | DIAMETER OF OPENING |
|---|---|---|---|---|---|---|
| OUTSIDE SHIELD | 122 | 116 | 0.2 | 255 | 200 | CUTOUT EXISTS |
| INTERMEDIATE SHIELD | 114 | 102 | 0.2 | 260 | 200 | 40 |
| INSIDE SHIELD | 100 | 94 | 0.2 | 200 | 200 | CUTOUT EXISTS |
| MAXIMUM ANGLE OF OPENING 9 | | | | | 100 | |
| OVERLAPPED ANGLE OF UPPER OUTSIDE | | | | 60 | | |
| OVERLAPPED ANGLE OF UPPER INSIDE | | | | 60 | | |
| OVERLAPPED ANGLE OF LOWER OUTSIDE | | | | 40 | | |
| OVERLAPPED ANGLE OF LOWER INSIDE | | | | 40 | | |
| OUTSIDE AUXILIARY SHIELD | | 40 | 0.1 | | 34 | |
| INSIDE AUXILIARY SHIELD | | 52 | 0.1 | | 34 | |

FIG. 34 A      FIG. 34 B
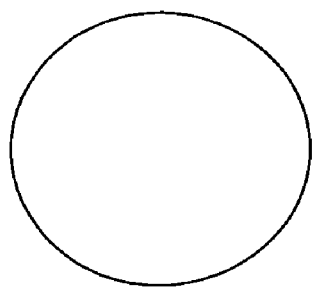
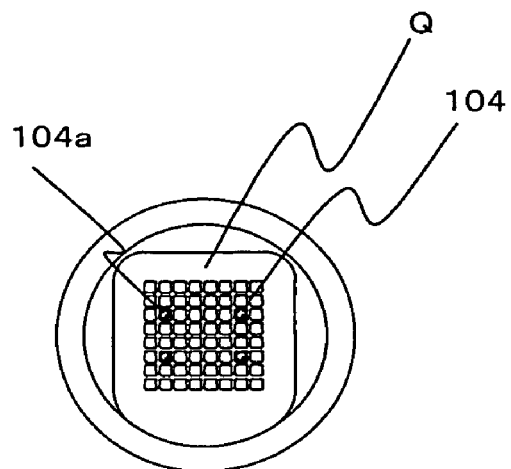
FIG. 34 C      FIG. 34 D      FIG. 34 E
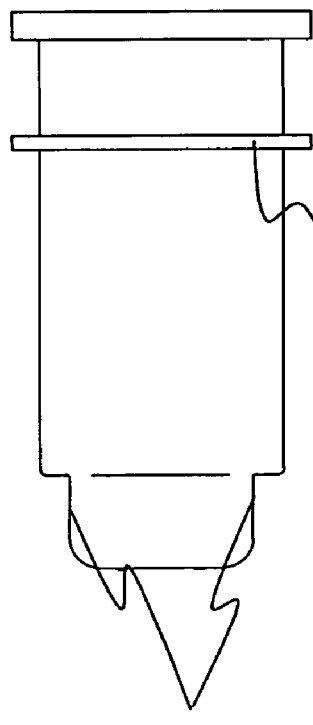
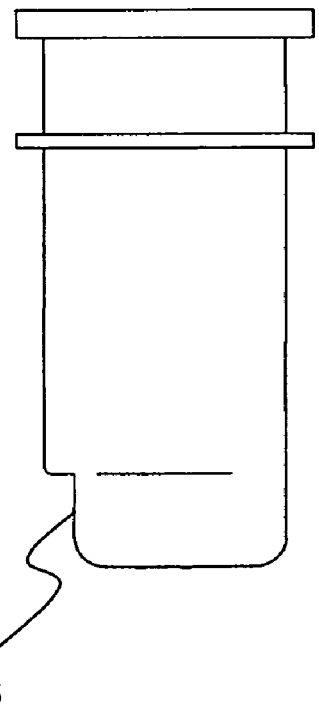
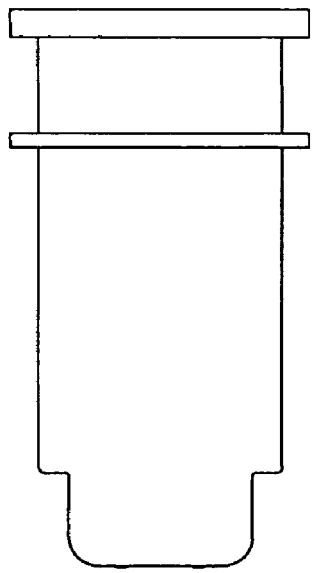

FIG. 44
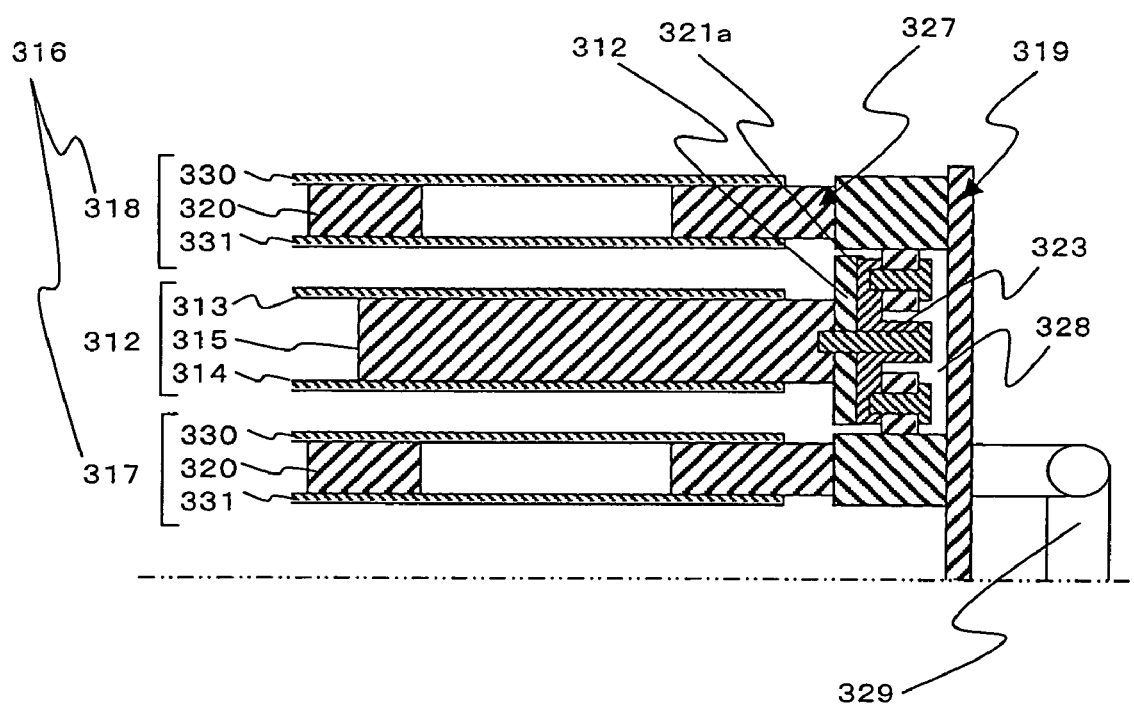
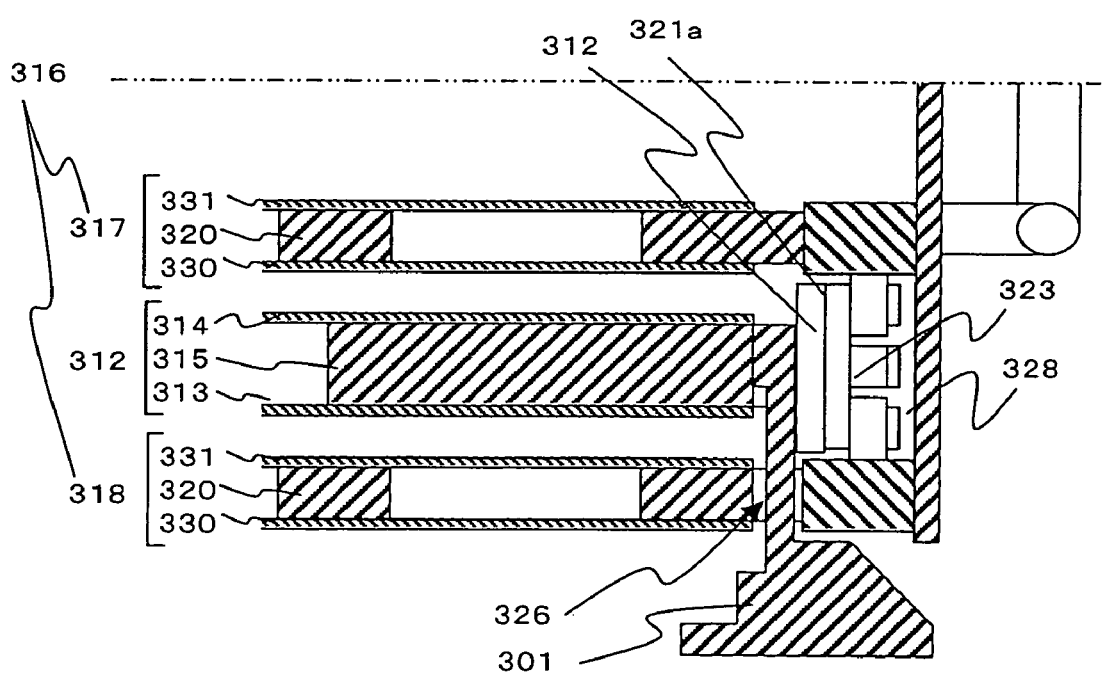

FIG. 60 A
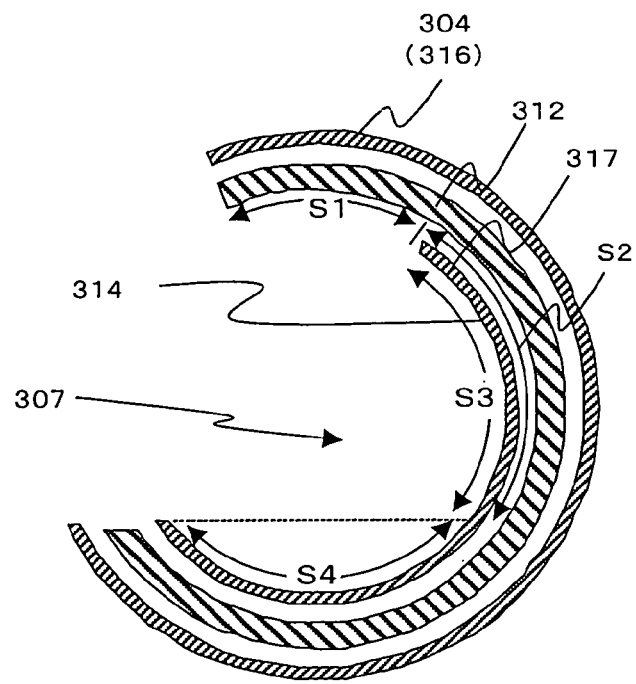
FIG. 60 B  FIG. 60 C  FIG. 60 D  FIG. 60 E
 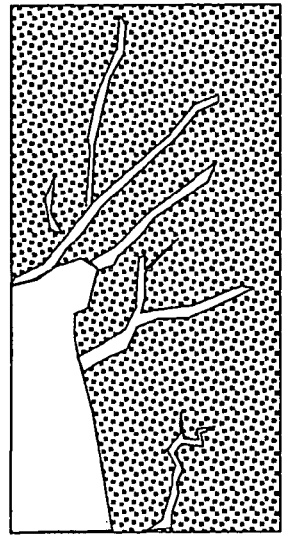 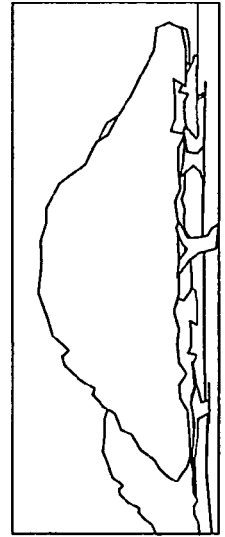 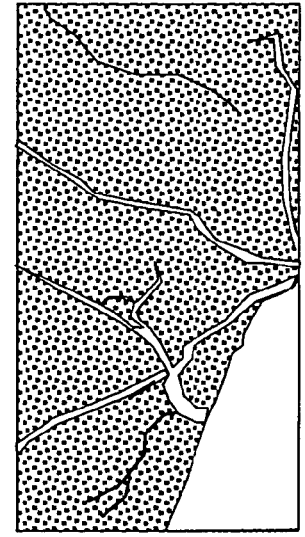
2.

FIG. 64 A
FIG. 64 B
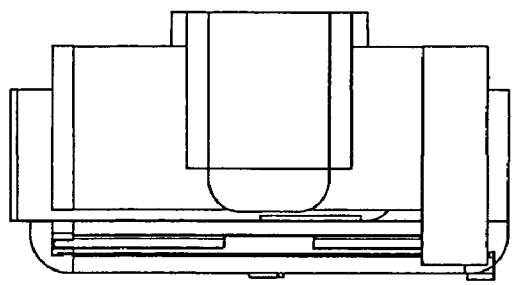
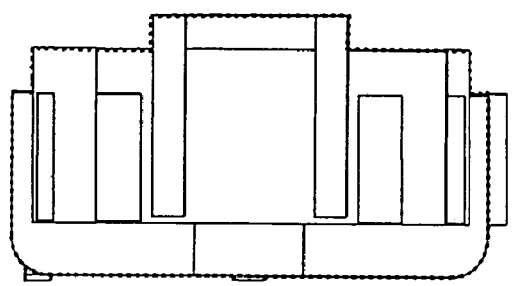
FIG. 64 C
FIG. 64 D
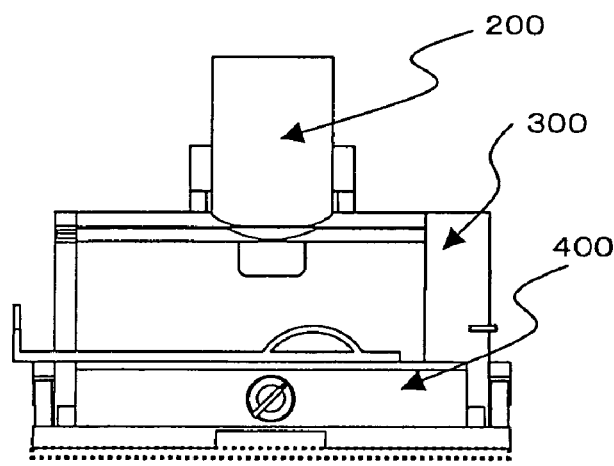
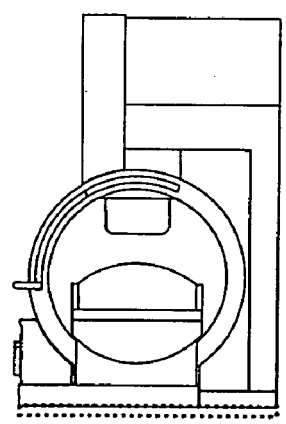
FIG. 64 E
FIG. 64 F
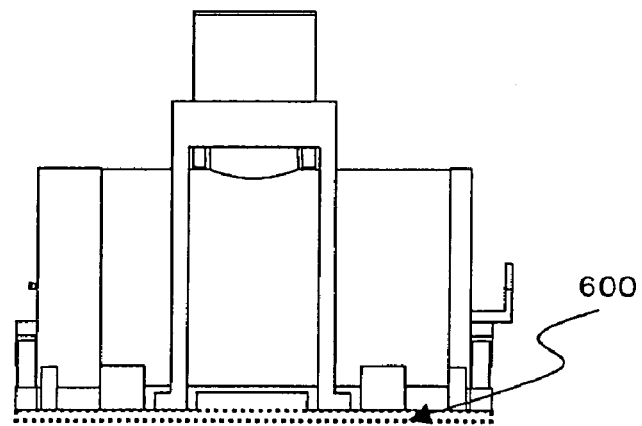
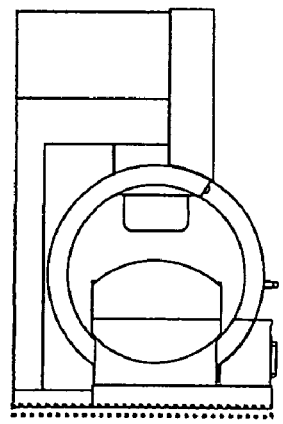

MAGNETIC SHIELDING APPARATUS AND BIOMAGNETISM MEASURING DEVICE

CLAIM OF PRIORITY

The present application claims priority from Japanese application JP No. 2004-263192 filed on Sep. 10, 2004, the contents of which are hereby incorporated by reference into this application.

FIELD OF THE INVENTION

The present invention relates to a magnetic shielding apparatus for shielding environmental magnetic noise, a biomagnetism measuring device using it, and a biomagnetism measuring method.

BACKGROUND OF THE INVENTION

Heretofore, a magnetic shielding apparatus which was used for measuring biomagnetism generated from an organism and which screened an environmental magnetic field (an external magnetic field) was manufactured by fastening and fixing a plate having high permeability (high-permeability material such as Permalloy) onto a frame made of aluminum and stainless steel without clearance by a bolt and others as a spatially closed box-type chamber. Besides, plates made of Permalloy were laminated, a magnetic shielding factor was enhanced, and a plate made of high-electric conductivity material such as aluminum was used for screening an electromagnetic wave. A small-sized light cylindrical magnetic shielding apparatus using sheet material having high permeability in place of Permalloy is reported (for example, see patent document 1).

It is known that the magnetic shielding factor of the cylindrical magnetic shielding apparatus is higher in a direction perpendicular to a cylindrical axis than in a direction of the cylindrical axis. Therefore, in case a magnetic field is measured inside the cylindrical magnetic shielding apparatus, a magnetic field component in the direction perpendicular to the cylindrical axis is often measured. In the measurement of biomagnetism in which a minute magnetic field is detected, a SQUID fluxmeter using a superconducting quantum interference device (SQUID) is generally used. For a method of inserting an object of examination inside the cylindrical magnetic shielding apparatus, two methods of (1) a method of inserting an object of examination from either open end at both ends of the cylindrical magnetic shielding apparatus and (2) a method of providing an openable door to the cylindrical magnetic shielding apparatus and inserting an object of examination via it are proposed (for example, see patent document 1.

[patent document 1] JP-A No. 136492/2002

SUMMARY OF THE INVENTION

As generally, the longitudinal, the lateral and the height dimensions of a floor of the conventional type magnetic shielding apparatus which is the box-type chamber are approximately 2 m and the conventional type magnetic shielding apparatus is heavy, the conventional type has a problem that a room where the apparatus can be installed is limited and in addition, the cost is also high.

In case the cylindrical magnetic shielding apparatus is used, a part or the whole of a cryostat for holding the SQUID fluxmeter at low temperature is required to be inserted inside the cylindrical magnetic shielding apparatus and in case the cryostat is longer than the inside diameter of the cylindrical magnetic shielding apparatus, an opening for inserting the cryostat is necessarily required to be provided on a circumferential face of the cylindrical magnetic shielding apparatus. However, as the opening is close to the SQUID fluxmeter and a direction in which an environmental (external) magnetic field invades is parallel to a direction of a magnetic field measured by the SQUID fluxmeter, there is a problem that the existence of the opening deteriorates the magnetic shielding factor of the cylindrical magnetic shielding apparatus.

In the above-mentioned method (1) of inserting an object of examination inside the cylindrical magnetic shielding apparatus, as no door is provided, the method has a merit that the structure is simple, however, the method has a problem that it is difficult for an examination engineer to observe an inside situation of the magnetic shielding apparatus and it is difficult for him/her to precisely adjust a position of examination. Besides, as a bed is required to be pulled out in a direction of the cylindrical axis to mount the object of examination on the bed, the method has a problem that a room is required to have the length of approximately 4 m so as to install the magnetic shielding apparatus if the length in the direction of the cylindrical axis of the magnetic shielding apparatus is approximately 2 m.

In the above-mentioned method (2) of inserting an object of examination inside the cylindrical magnetic shielding apparatus, as the door is provided, an examination engineer can easily observe the inside situation of the magnetic shielding apparatus and can precisely adjust a position of examination. Besides, as the bed is not required to be pulled out in the axial direction, effect that space required for examination can be reduced is acquired. However, for the conventional type cylindrical magnetic shielding apparatus, improvement for enabling an object of examination to take examination on a more comfortable condition, reducing a load onto the object of examination and for more enhancing the operability of an examination engineer is desired.

The object of the invention is to provide a small-sized light high-performance magnetic shielding apparatus having a large magnetic shielding factor, a biomagnetism measuring device using this and a biomagnetism measuring method wherein an object of examination can be easily carried inside and out of the magnetic shielding apparatus and an inside situation of the magnetic shielding apparatus can be easily observed.

The biomagnetism measuring device according to the invention is provided with the cylindrical magnetic shielding apparatus, singular or plural SQUID fluxmeters arranged on a plane parallel to an XY plane perpendicular to the z-axis, a cryostat for holding the SQUID fluxmeter at low temperature, a driving/detecting circuit for driving the SQUID fluxmeter and detecting a signal from the SQUID fluxmeter, a processor for collecting the output of the driving/detecting circuit and executing operation and a display for displaying the output of the processor.

The inside diameter of the cylindrical magnetic shielding apparatus is approximately 1 m and the length in an axial direction is approximately 2 m. Referring to FIG. 1, the representative configuration of the cylindrical magnetic shielding apparatus will be described below.

The cylindrical magnetic shielding apparatus is provided with a flange-type plate 24 having an opening formed on a circumferential face, an auxiliary cylinder 23 acquired by connecting singular or plural cylindrical members so that the opening of the flange-type plate and each central axis of the cylindrical members are coincident and cylindrical shields 1, 2, 3 (a first cylindrical shield, a second cylindrical shield and a third cylindrical shield) having first, second and third angular ranges for the z-axis.

A cutout 10 is provided to a portion parallel to the y-axis and a revolving door 4 is configured by integrating the cylindrical shields 2, 3. The cylindrical shield 1 to which the flange-type plate 24 is connected in a state that the flange-type plate encircles the opening 22 is supported by shield bases 6a, 6b in circular arc parts at both ends.

An opening 9 formed in a circumferential direction is opened or closed by revolving the revolving door 4 in a circumferential direction of the z-axis along a circumferential part of the cylindrical shield 1 by revolving parts 7a, 7b and. The cryostat is arranged inside an opening of the auxiliary cylinder and the opening 22.

In the cylindrical magnetic shielding apparatus, the circumferential part of the cylindrical shield 1 is inserted between circumferential parts of the cylindrical shields 2, 3 when the revolving door is closed, cylindrical inside space is formed, and an environmental magnetic field that invades the inside space is screened.

A component in a direction of the z-axis of a magnetic field generated from an object of examination carried in the inside space via the opening 9 in the circumferential direction formed when the revolving door is opened is measured when the revolving door 4 is closed.

Owing to the above-mentioned configuration, the cylindrical magnetic shielding apparatus has a large magnetic shielding factor and the biomagnetism measuring device according to the invention can precisely measure biomagnetism generated from the object of examination with high sensitivity. In the cylindrical magnetic shielding apparatus according to the invention, the large opening can be set by moving the revolving door in the circumferential direction, the cylindrical magnetic shielding apparatus is excellent in a feeling of liberation owing to the opening together with openings formed in positive and negative directions of the y-axis, is excellent in workability and operability such as the positioning of a patient performed by a doctor and an examination engineer, and an oppressive feeling and an uneasy feeling caused in the patient by being located in small space can be reduced.

According to the invention, it is easy to carry an object of examination into and out of the magnetic shielding apparatus, an inside situation of the magnetic shielding apparatus can be easily observed, the small-sized light and high-performance magnetic shielding apparatus having the large magnetic shielding factor, the biomagnetism measuring device using this and the biomagnetism measuring method can be provided.

BRIEF DESCRIPTION OF THE DRAWINGS

FIG. 2A shows the configuration of a cylindrical shield, FIG. 2B shows the configuration of another cylindrical shield, and FIG. 2C shows the configuration of further another cylindrical shield;

FIG. 5A is the sectional view viewed on the plane parallel to an XZ plane of the magnetic shielding apparatus shown in FIG. 3 and not passing the auxiliary cylinder 23, FIG. 5B is the sectional view viewed on the plane parallel to an XZ plane of the magnetic shielding apparatus shown in FIG. 4 and not passing the auxiliary cylinder 23, and FIG. 5C is the enlarged view showing a dotted part in FIG. 5B;

FIG. 6A is the perspective view showing a model of a cylindrical shield 61, FIG. 6B is the perspective view showing a model of a cylindrical shield 62, and FIG. 6C is the perspective view showing a model of a cylindrical shield to which an auxiliary cylinder 64 is connected;

FIG. 8A is the perspective view showing the second model configured by cylindrical shields 81, 82, 83, FIG. 8B is the perspective view showing the second model on which a circular opening is formed, FIG. 8C shows a transformed example of the cylindrical shield shown in FIG. 8B, and FIG. 8D shows a transformed example of the cylindrical shield shown in FIG. 8C;

FIGS. 15C and 15D are explanatory drawings for explaining the measurement of a magnetic field around the heart of the object of examination lying with his/her face down;

FIG. 16E shows a state in which the revolving door is open by a half, and FIG. 16F shows a state in which the revolving door is completely closed;

FIG. 19A shows an example of the configuration that a superconducting loop 191 is arranged over plural SQUID fluxmeters, FIG. 19B shows an example of the configuration that a reticular superconducting loop 192 is arranged over plural SQUID fluxmeters and FIG. 19C shows an example of the configuration that a superconducting loop 193 is arranged around plural SQUID fluxmeters;

FIG. 21A shows a state in which a revolving door is open by a half, and FIG. 21B shows a state in which the revolving door is completely closed;

FIG. 23 shows a table showing the size of the magnetic shielding apparatus shown in FIGS. 1 to 5;

FIG. 24 shows a table showing the size of the first model shown in FIG. 6;

FIG. 25 shows a table showing the size of the second model shown in FIG. 8A;

FIG. 26 shows a table showing the size of the second model shown in FIG. 8B;

FIG. 27 shows a table showing the size of the second model shown in FIG. 8C;

FIG. 28 shows a table showing the size of the second model shown in FIG. 8D;

FIG. 33A is a front view, FIG. 33B is a right side view, FIG. 33C is a back view, FIG. 33D is a plan, and FIG. 33E is a bottom view;

FIGS. 34A to 34E are outside drawings showing a measuring part in the first embodiment, FIG. 34A is a plan, FIG. 34B is a bottom view, FIG. 34C is a front view, FIG. 34D is a right side view, and FIG. 34E is a back view;

FIG. 35A shows only four projecting markers, FIG. 35B shows the projecting markers shown in FIG. 35A to which each cross mark is added, FIG. 35C shows markers acquired by combining the cross marks shown in FIG. 35B with another markers, FIG. 35D shows markers acquired by combining vertical columns and horizontal rows respectively passing the projecting markers, and FIG. 35E shows markers acquired by combining the projecting markers and a marker showing the periphery of a sensor;

FIG. 39A shows a lock state, and FIG. 39B shows a unlocking state;

FIG. 40A is the sectional view showing a locked state, and FIG. 40B is the sectional view showing an unlocking state;

FIG. 42A is a perspective view, FIG. 42B is a plan, and FIG. 42C is a front view;

FIG. 44 is a sectional view showing an opening/closing driving mechanism in the first embodiment;

FIG. 47A is a plan, FIG. 47B is a bottom view, FIG. 47C is a front view, and FIG. 47D is a right side view;

FIG. 57A is a perspective view, FIG. 57B is a back view, and FIG. 57C is a right side view;

FIGS. 60A to 60E are explanatory drawings for explaining the inside of a magnetic shielding room in a second embodiment, FIG. 60A is a schematic sectional view, and FIGS. 60B to 60E show patterns on an inside wall;

FIG. 61A is a schematic sectional view, and FIG. 61B shows a pattern on the inside wall viewed from the outside;

FIGS. 62A and 62B are schematic sectional views, and FIG. 62C shows a pattern on the inside wall viewed in shield space;

FIG. 63A is the perspective view showing a state in which an opening/closing body is opened, and FIG. 63B is the perspective view showing a state in which the opening/closing body is being closed;

FIGS. 64A to 64F are outside drawings showing the cardiac magnetism measuring device in the third embodiment, FIG. 64A is a plan, FIG. 64B is a bottom view, FIG. 64C is a front view, FIG. 64D is a right side view, FIG. 64E is a back view, and FIG. 64F is a left side view;

FIG. 66A is a perspective view showing a state in which an opening/closing body is opened, and FIG. 66B is a perspective view showing a state in which the opening/closing body is being closed;

FIG. 67A is a plan, FIG. 67B is a front view, FIG. 67C is a right side view, FIG. 67D is a back view, and FIG. 67E is a left side view.

DETAILED DESCRIPTION OF THE PREFERRED EMBODIMENTS

Figure 1:
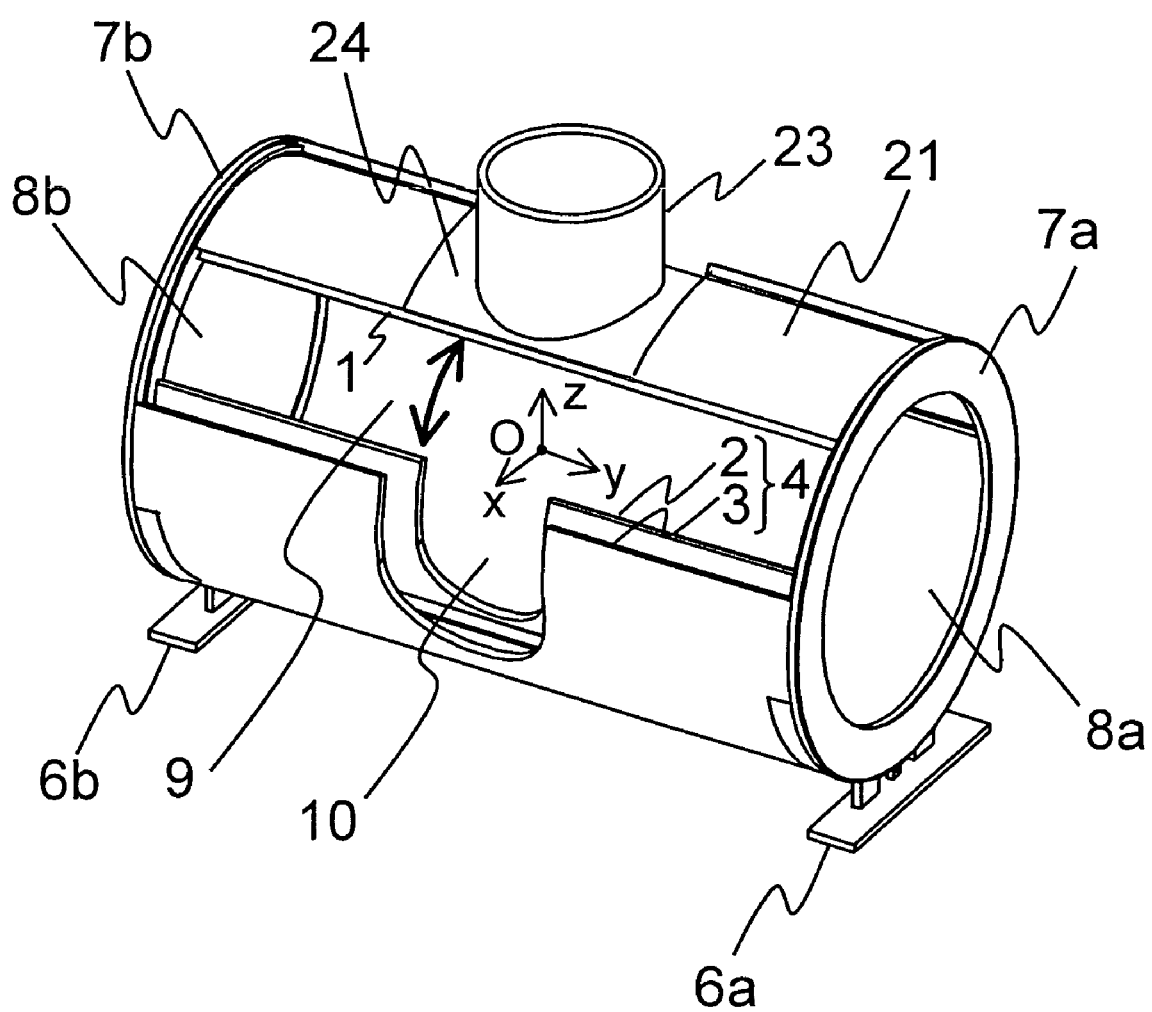
FIG. 1 shows a magnetic shielding apparatus equivalent to an embodiment of the invention and is a perspective view showing a state in which a revolving door is open by a half.
Figure 2:
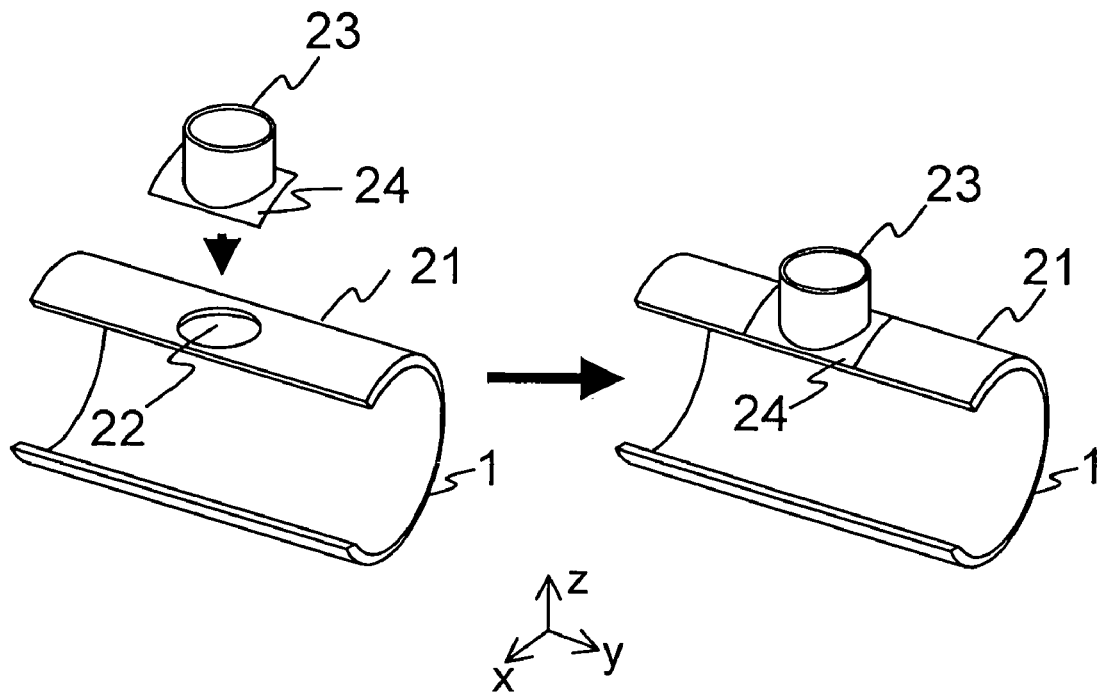
FIGS. 2A to 2C are perspective views showing the configuration of a main part of the magnetic shielding apparatus shown in FIG. 1.
Figure 2:
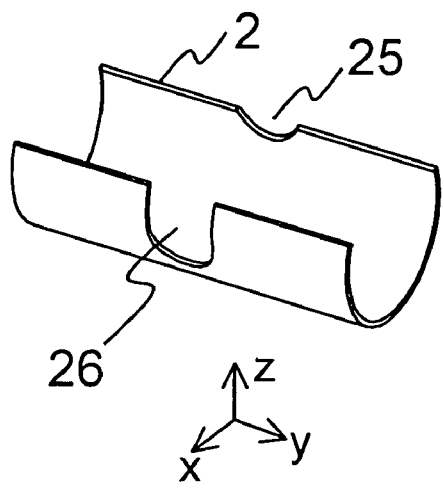
Figure 2:
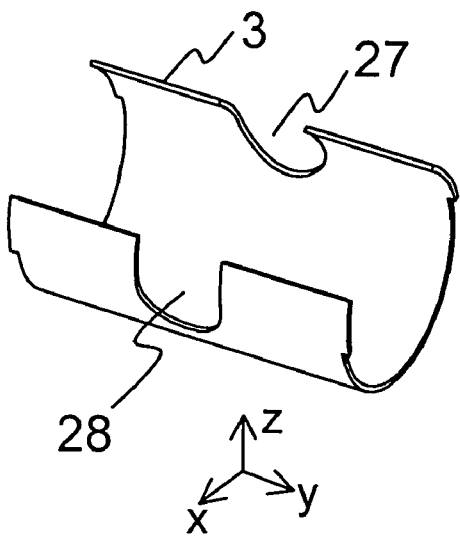

Referring to the drawings, embodiments of the invention will be described in detail below. In FIGS. 1 to 28, the same reference numeral is allocated to a component having the same function. In FIGS. 1 to 22, an origin (0, 0, 0) of a rectangular coordinate system (x, y, z) shall be the center O of a magnetic shielding apparatus, the y-axis shall be a central axis (a cylindrical axis) of the magnetic shielding apparatus, and the XY plane shall be a detection plane (a plane which each detection coil makes) of singular or plural SQUID fluxmeters, that is, a plane parallel to a measuring plane. The SQUID fluxmeter detects a component in a direction of the z-axis in a magnetic field generated from an object of detection.

On-the coordinate system (x, y, z) shown in FIGS. 1 to 22, in case the origin (0, 0, 0) is coincident with the center O of the magnetic shielding apparatus, the origin O is shown in the drawings. On the coordinate system (x, y, z) on which the origin O is not shown, the origin is shown in a state in which it is moved in parallel. The measuring plane by the singular or plural SQUID fluxmeters has only to be located in the vicinity of the central axis of the magnetic shielding apparatus, may be also coincident with the XY plane of the magnetic shielding apparatus, and may be also different from the XY plane of the magnetic shielding apparatus.

Figure 13:
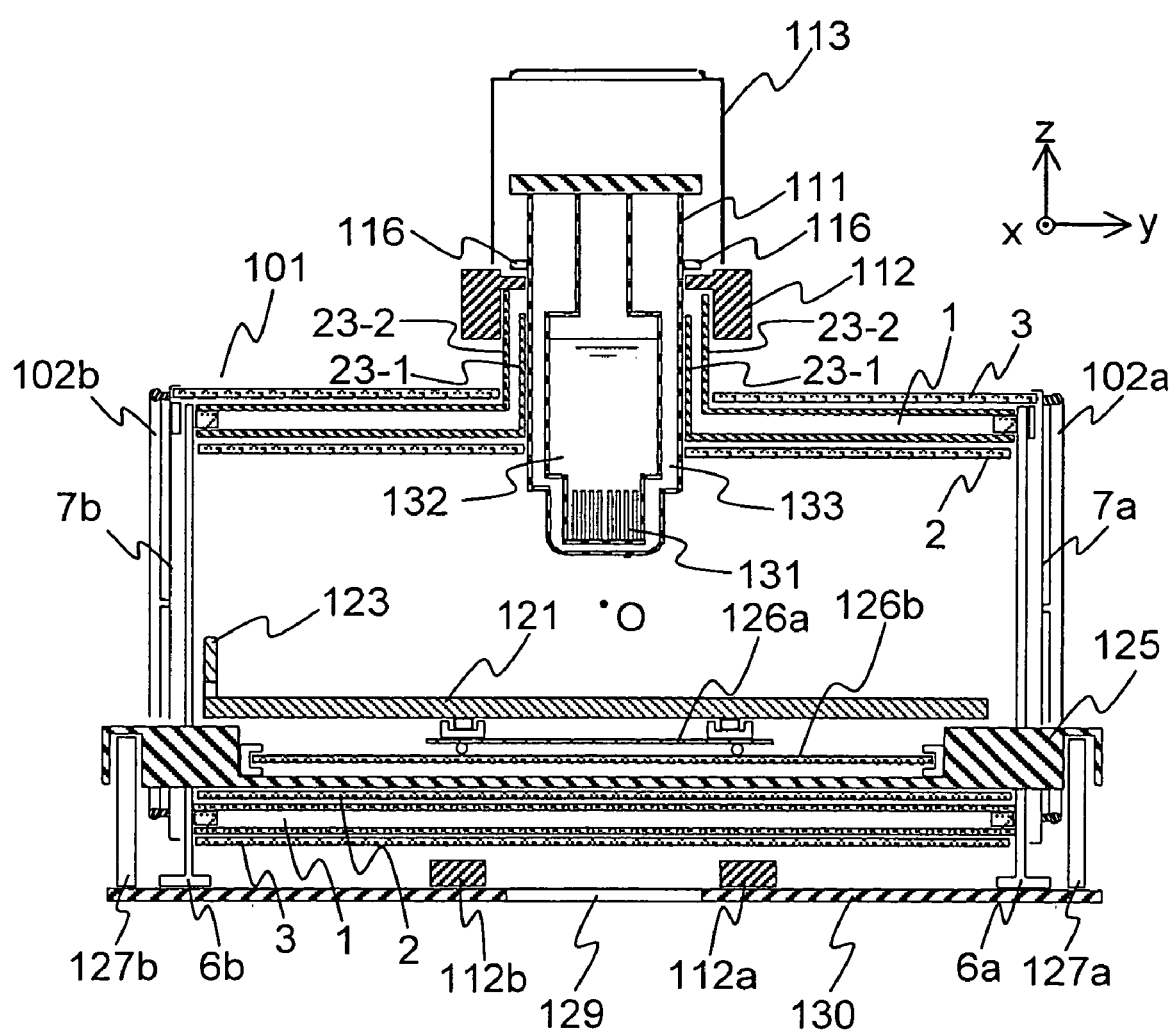
FIG. 13 is a sectional view showing a YZ plane of the biomagnetism measuring device shown in FIG. 10.

As shown in FIG. 13 described later, the SQUID fluxmeter 131 is cooled to be at low temperature by liquid helium 132 and is thermally insulated from external environment via a vacuum layer 133. The SQUID fluxmeter 131 is inserted into the inside of the magnetic shielding apparatus 1101. As environmental magnetic field noise is smaller and the distribution of a magnetic field is uniform in the center inside the magnetic shielding apparatus 1101, it is desirable that each detection coil not shown of the singular or plural SQUID fluxmeters 131 is arranged in the vicinity of the center O (the origin (0, 0, 0) of the rectangular coordinate system (x, y, z)) of the magnetic shielding apparatus 1101.

Generally, as high-permeability material has a property that the material permeates a magnetic flux a great deal, space shielded from an environmental (heterogeneous) magnetic field is formed inside the space encircled by the high-permeability material. The high-electric conductivity material has effect that shielding from an electromagnetic wave is enabled by eddy current.

In a magnetic shielding apparatus and a biomagnetism measuring device using it respectively equivalent to an embodiment of the invention, for high-permeability material, Permalloy, silicon steel and an amorphous substance can be used. For example, in the representative embodiment, for high-permeability material, a plate made of Permalloy and others which has large relative permeability from approximately ten thousand to approximately a hundred thousand or a sheet made of an amorphous alloy is used and for high-electric conductivity material, a plate made of aluminum and copper respectively having large electric conductivity can be used.

Components arranged in the inside of and in the vicinity of the magnetic shielding apparatus described in the following embodiment are made of non-magnetic material such as lumber, fiber reinforced plastic (FRP), aluminum and SUS.

For superconducting material forming the SQUID fluxmeter 131, superconducting loops 191, 193, 1201 and a net superconducting loop 192 respectively used in the apparatus equivalent to the following embodiment, low-temperature superconducting material acting at low temperature (for example, at liquid helium temperature) as a superconductor and having low superconductive transition temperature or high-temperature superconducting material acting at high temperature (for example, at liquid nitrogen temperature) as a superconductor and having high superconductive transition temperature can be used. Superconducting material having superconductive transition temperature between the liquid helium temperature and the liquid nitrogen temperature and superconducting material having superconductive transition temperature higher than the liquid nitrogen temperature can be also used.

In the following description, for simplification, cylindrical shields 3, 83, 83a are called outside shields, cylindrical shields 1, 81, 81a are called intermediate shields, cylindrical shields 2, 82, 82a are called inside shields, auxiliary cylinders 23-2, 86a, 86b are called outside auxiliary shields, auxiliary cylinders 23-1, 85a, 85b are called inside auxiliary shields, and the outside auxiliary shields and the inside auxiliary shields are called auxiliary shields together. The integrated cylindrical shields 2, 3 are called a revolving door 4.

FIG. 1 shows the magnetic shielding apparatus equivalent to the embodiment of the invention and is a perspective view showing a state that the revolving door 4 is open by a half.

The magnetic shielding apparatus shown in FIG. 1 is formed by main members of the cylindrical shields 1, 2, 3 arranged around the y-axis and the auxiliary cylinders 23 to which a flange-type plate 24 is magnetically connected. At both ends in a direction of the y-axis, openings 8a, 8b exist.

The cylindrical shield 2 is arranged inside the cylindrical shield 1 and the cylindrical shield 3 is arranged outside the cylindrical shield 1. The cylindrical shields 2, 3 where a cutout 10 is formed are integrated at both ends in the direction of the y-axis and can be turned along the cylindrical shield 1 around the y-axis as the revolving door 4.

The cylindrical shields 1, 2, 3 are made of the high-permeability material and the high-electric conductivity material. The auxiliary cylinder 23 is made of high-permeability material. The cylindrical shield 1 is connected and supported by shield bases 6a, 6b. The shield bases 6a, 6b are fixed on a floor or are fixed on each metallic plate (for example, an aluminum plate having the thickness of approximately 1 cm) and the metallic plates are put on the floor so as to disperse pressure.

The end in a positive area in the direction of the y-axis of the revolving door 4 is connected to a revolving part 7a and the end in a negative area in the direction of the y-axis of the revolving door 4 is connected to a revolving part 7b.

The revolving part 7a includes a revolving member, is connected to the outside side of the shield base 6a via the revolving member so that the revolving part can be turned, the revolving part 7b includes a revolving member, and is connected to the outside side of the shield base 6b via the revolving member so that the revolving part can be turned. For the revolving member, for example, a convex portion of a convex rail and a concave portion of a concave rail respectively made of non-magnetic material are mated, and a pulley and a ball bearing are used. The revolving door 4 can be turned around the y-axis in directions shown by both arrows shown in FIG. 1. A revolving handle 1102a is connected to the revolving part 7a, a revolving handle 1102b is connected to the revolving part 7b, and the revolving door 4 can be turned in the direction shown by both arrows shown in FIG. 1 by revolving the revolving handle 1102a or 1102b.

The revolving door may be also turned using pneumatics or a hydraulic pump and others by pressing a revolving button arranged on a top plate receiving mount 127c shown in FIGS. 10, 12, 14, 15, 16, 17 described later without revolving the revolving handle 1102a or 1102b. The revolving handles 1102a, 1102b are not shown in FIG. 1 and FIGS. 3 and 4 described later, however, they are shown in FIGS. 10, 13, 15, 16, 17, 20, 21A.

FIGS. 2A to 2C are perspective views showing the configuration of a main part of the magnetic shielding apparatus shown in FIG. 1. FIG. 2A shows the configuration of the cylindrical shield 1, FIG. 2B shows the configuration of the cylindrical shield 2, and FIG. 2C shows the configuration of the cylindrical shield 3.

The cylindrical shield 1 shown in FIG. 2A is provided with two circular arc parts at both ends having a first predetermined angular range and perpendicular to the central axis, two portions having a predetermined small width dimension and a predetermined length dimension, having predetermined small area and parallel to the central axis, a circular part 21 having the first predetermined angular range, and an opening 22 formed on the circular part 21. A cryostat for holding the singular or plural SQUID fluxmeters for detecting the magnetic field component in the direction of the z-axis at low temperature is arranged inside the opening 22 and the bottom of the cryostat is inserted inside the magnetic shielding apparatus.

To prevent the deterioration of a magnetic shielding factor of the magnetic shielding apparatus by the effect of an environmental magnetic field invading the inside of the magnetic shielding apparatus via the opening 22, in the embodiment of the invention, the auxiliary cylinder 23 is connected to the cylindrical shield 1 so that the auxiliary cylinder encircles the opening 22. To enhance the effect of the auxiliary cylinder 23, it is desirable that the auxiliary cylinder 23 has multilayered structure and besides, it is desirable that the auxiliary cylinder 23 is longer in its axial direction. It is desirable that the auxiliary cylinder 23 is magnetically connected to the cylindrical shield 1 and it is desirable that the auxiliary cylinder is integrated with the cylindrical shield 1.

However, as a working process of integration is difficult, the auxiliary cylinder 23 is attached by a method such as screwing so that the auxiliary cylinder is closely in contact with the cylindrical shield 1. In case the auxiliary cylinder 23 is attached by the method such as screwing in a state in which the auxiliary cylinder is closely in contact with the cylindrical shield 1, it is desirable that the flange-type plate 24 is formed on the auxiliary cylinder 23 by welding and others as shown in FIG. 2A so as to secure magnetic connection and that the flange-type plate 24 is attached to the cylindrical shield 1 in a closely contact state.

The flange-type plate 24 forms a circular face having the same radius of curvature as the outside face of the circular part 21. The contact area of the auxiliary cylinder 23 and the cylindrical shield 1 can be largely secured by forming the flange-type plate 24. As a result, the environmental magnetic field that invades the inside of the magnetic shielding apparatus through clearance between the auxiliary cylinder 23 and the cylindrical shield 1 is screened and the magnetic shielding factor is also enhanced.

As for the cylindrical shield 1 shown in FIG. 2A, the inside diameter of the circular part 21 of the cylindrical shield 1 is approximately 102 cm and the outside diameter is approximately 114 cm. The length of the central axis of the cylindrical shield 1 is approximately 200 cm and the first predetermined angular range is approximately 260 degrees. The flange-type plate 24 is formed on the auxiliary cylinder 23, is closely connected and fixed to the circular part 21, encircling the opening 22, and enhances magnetic connection between the auxiliary cylinder 23 and the cylindrical shield 1.

The cylindrical shield 2 shown in FIG. 2B is provided with two circular arc parts at both ends having a second predetermined angular range and perpendicular to the central axis, two portions where each cutout 25, 26 which has predetermined small area of a predetermined small width dimension and a predetermined length dimension and which is parallel to the central axis is formed and a circular part having the second predetermined angular range. Only the cutout 26 may be also formed. The cylindrical shield 2 is arranged inside the cylindrical shield 1. The cutouts 25, 26 have area including the section on the XY plane of the cryostat so that the cylindrical shield is prevented from colliding with the cryostat inserted inside the magnetic shielding apparatus when the cylindrical shield 2 is revolved around the central axis of the cylindrical shield 1. The inside diameter of the circular part of the cylindrical shield 2 is approximately 94 cm and the outside diameter is approximately 100 cm. The length of the central axis of the cylindrical shield 2 is approximately 200 cm and the second predetermined angular range is approximately 200 degrees.

The cylindrical shield 3 shown in FIG. 2C is provided with two circular arc parts at both ends having a third predetermined angular range and perpendicular to the central axis, two portions where each cutout 27, 28 which has predetermined small area of a predetermined small width dimension and a predetermined length dimension and which is parallel to the central axis is formed and a circular part having the third predetermined angular range. The cylindrical shield 3 is arranged outside the cylindrical shield 1.

The cutouts 27, 28 have area including the section on the XY plane of the cryostat so that the cylindrical shield is prevented from colliding with the cryostat inserted inside the magnetic shielding apparatus when the cylindrical shield 3 is revolved around the central axis of the cylindrical shield 1. The inside diameter of the circular part of the cylindrical shield 3 is approximately 116 cm and the outside diameter is approximately 122 cm. The length of the central axis of the cylindrical shield 3 is approximately 200 cm and the third predetermined angular range is approximately 255 degrees.

Figure 3:
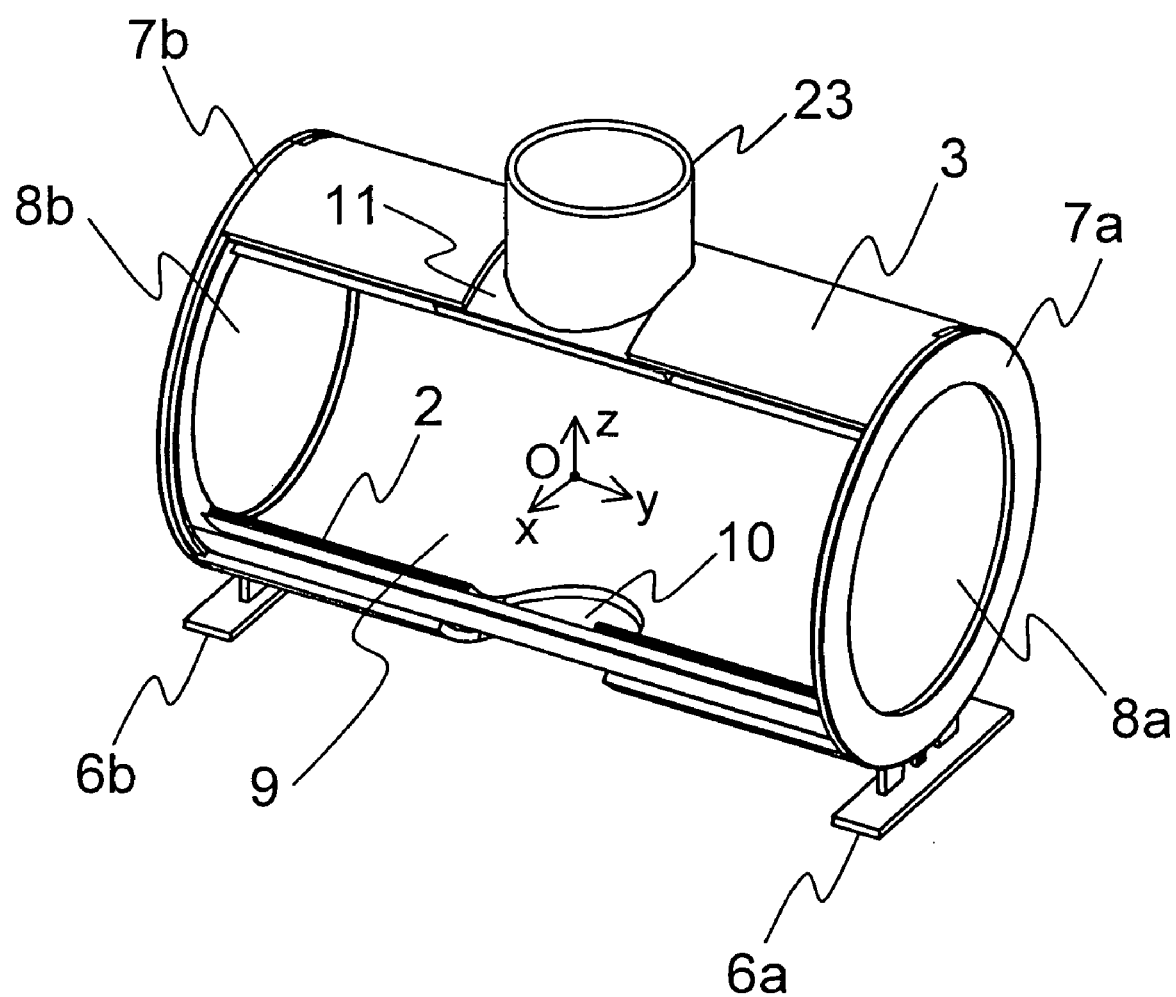
FIG. 3 is a perspective view showing a state in which the revolving door is completely open in the magnetic shielding apparatus shown in FIG. 1.

FIG. 3 is a perspective view showing a state in which an opening 9 is maximum, that is, a state in which the revolving door 4 is completely open in the magnetic shielding apparatus shown in FIG. 1.

A state in which the opening 9 in a circumferential direction of the magnetic shielding apparatus is maximum is formed by the turning in one direction around the y-axis of the revolving door 4. An object of examination can enter the inside of the magnetic shielding apparatus from a direction of the x-axis via the opening 9 in a state in which the revolving door 4 is completely open. A cutout 10 formed on the revolving door 4 is configured by the cutout 26 formed on the cylindrical shield 2 and shown In FIG. 2B and the cutout 28 formed on the cylindrical shield 3 and shown in FIG. 2C. A cutout 11 formed on the revolving door 4 is configured by the cutout 27 formed on the cylindrical shield 3 and shown in FIG. 2C (the cutout 25 formed on the cylindrical shield 2 is shown in FIG. 2B, however, the cutout 25 does not configure the cutout 11).

The cutout 11 has area including the section on the XY plane of the cryostat so that the revolving door 4 is prevented from colliding with the cryostat inserted inside the magnetic shielding apparatus when the revolving door 4 is turned around the central axis of the cylindrical shield 1. The opening 9 formed in the circumferential direction is closed by the turning of the revolving door 4 in another direction around the y-axis.

Figure 4:
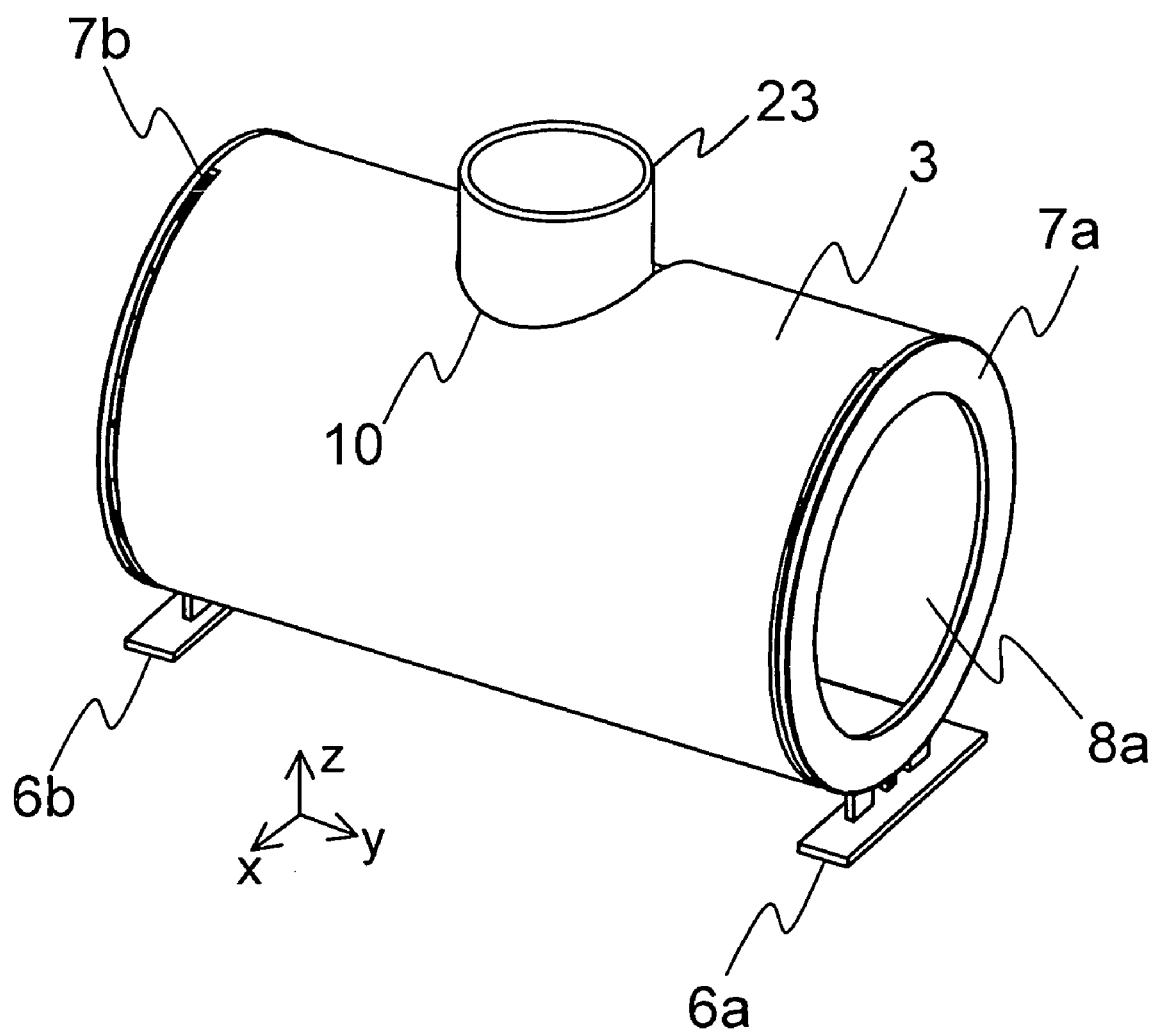
FIG. 4 is a perspective view showing a state in which the revolving door is completely closed in the magnetic shielding apparatus shown in FIG. 1.
Figure 5:
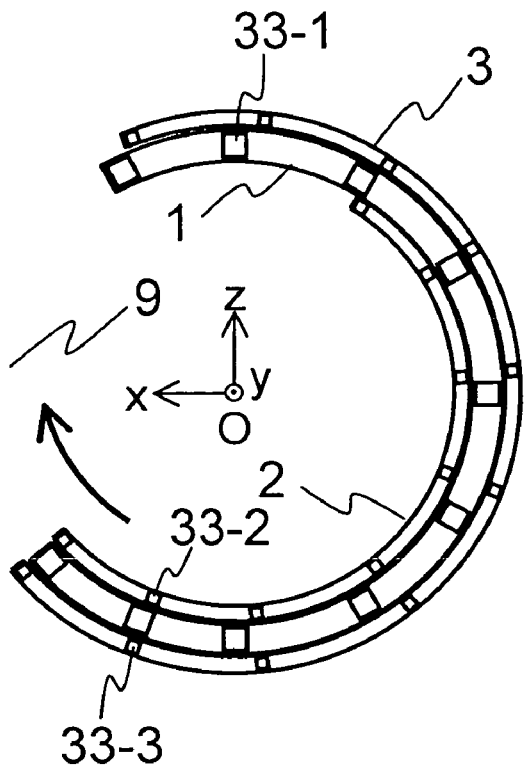
FIGS. 5A to 5C are sectional views viewed on a plane perpendicular to a central axis of the magnetic shielding apparatus shown in FIG. 1.
Figure 5:
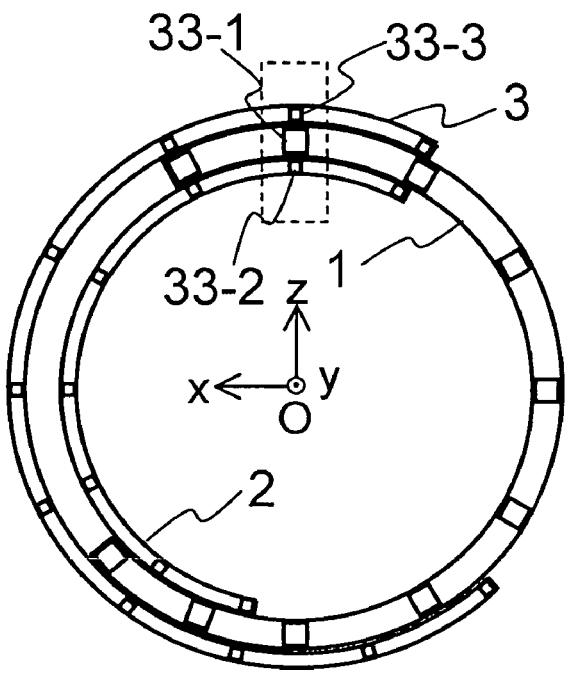
Figure 5:
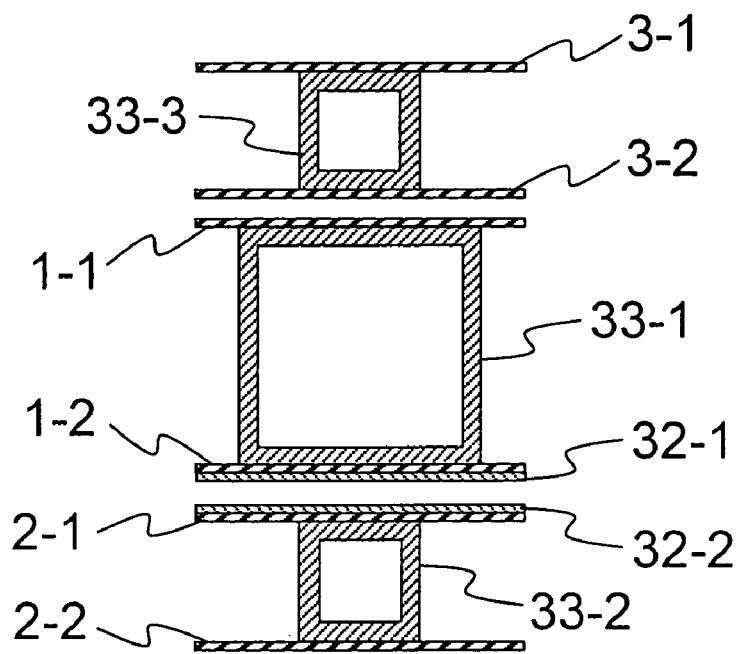
Figure 6:
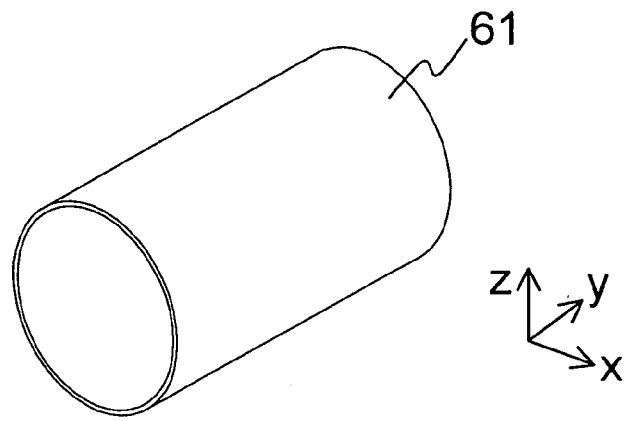
FIGS. 6A to 6C are perspective views showing a first model used for simulation analysis for evaluating a magnetic shielding factor of the magnetic shielding apparatus shown in FIG. 1.
Figure 6:
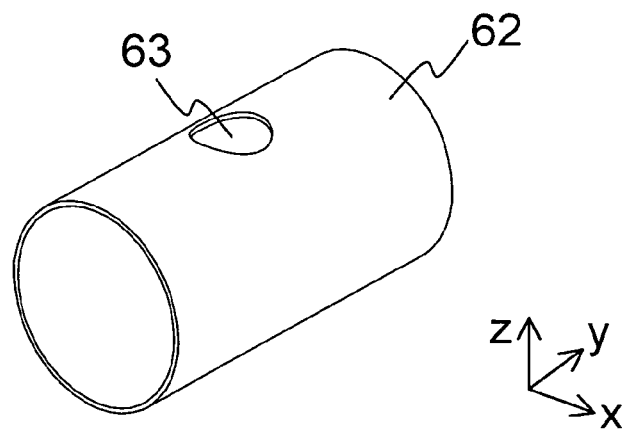
Figure 6:
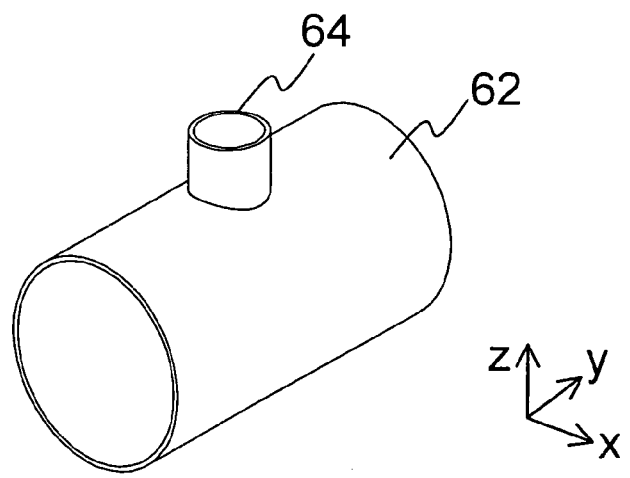

FIG. 4 is a perspective view showing a state in which the revolving door 4 is completely closed in the magnetic shielding apparatus shown in FIG. 1. As shown in FIG. 4, inside space encircled by the cylindrical shield 1 and the cylindrical shields 2, 3 is shielded from the environmental magnetic field and a magnetic field generated from the object of examination in the inside space is measured. The cutout 11 has the area including the section on the XY plane of the cryostat so that the revolving door 4 is prevented from colliding with the cryostat inserted inside the magnetic shielding apparatus when the revolving door 4 is turned around the central axis of the cylindrical shield 1.

The cylindrical shield 1 and the revolving door 4 can have an overlapped part owing to the cutout 10 formed on the revolving door 4 when the revolving door 4 is closed. As a result, the environmental magnetic field that invades the inside of the magnetic shielding apparatus via clearance made between the cylindrical shield 1 and the revolving door 4 is screened, the environmental magnetic field noise is reduced, and the magnetic shielding factor of the magnetic shielding apparatus can be enhanced.

FIGS. 5A to 5C are sectional views viewed on a plane (a plane not passing the auxiliary cylinder 23) perpendicular to the central axis of the magnetic shielding apparatus shown in FIG. 1. FIG. 5A is the sectional view viewed on the plane parallel to an XZ plane of the magnetic shielding apparatus shown in FIG. 3 and not passing the auxiliary cylinder 23 and FIG. 5B is the sectional view viewed on the plane parallel to an XZ plane of the magnetic shielding apparatus shown in FIG. 4 and not passing the auxiliary cylinder 23. FIG. 5A shows a state in which the revolving door 4 is open at the maximum and FIG. 5B shows a state in which the revolving door 4 is completely closed by the turning of the revolving door 4 in a direction shown by an arrow in FIG. 5A. The opening 22 into which the cryostat is inserted is formed on an extended line on the y-axis in the dotted line shown in FIG. 5B.

As shown in FIGS. 5A and 5B, the cylindrical shields 1, 2, 3 are configured by fixing high-permeability material (a plate made of Permalloy) and high-electric conductivity material (an aluminum plate) to reinforcing material which is non-magnetic material to be a framework. As shown in FIG. 5A, the opening 9 is formed in the circumferential direction by the turning in one direction around the y-axis of the revolving door 4 along a circumferential face of the cylindrical cylinder 1.

In a state in which the revolving door 4 is completely open, the opening 9 the central angle of which is approximately 100 degrees around the y-axis is formed in the circumferential direction. In this state, the magnetic shielding apparatus has the opening 9 approximately 70 cm long in its perpendicular direction and approximately 200 cm long in its horizontal direction, and the opening 9 has enough width to insert the object of examination inside the magnetic shielding apparatus in a state in which the object of examination lies on his/her back or with his/her face down and to carry the object of examination out of the inside.

As shown in FIG. 5B, the opening 9 formed in the circumferential direction is eliminated by the turning around the y-axis of the revolving door 4 along the circumferential face of the cylindrical shield 1. In a state in which the revolving door 4 is completely closed, circumferential parts of the cylindrical shield 1 and the cylindrical shield 2 are overlapped and close at both ends in the circumferential direction. On the upside, overlapped parts the central angle of which is approximately 60 degrees around the y-axis are formed in the circumferential direction and on the downside, overlapped parts the central axis of which is approximately 40 degrees are similarly formed. The circumferential parts of the cylindrical shield 1 and the cylindrical shield 3 are also overlapped and close at both ends in the circumferential direction, on the upside, overlapped parts the central angle of which is approximately 60 degrees around the y-axis are formed in the circumferential direction, and on the downside, overlapped parts the central angle of which is approximately 95 degrees are similarly formed in the circumferential direction.

The environmental magnetic field that invades the inside of the magnetic shielding apparatus via clearance made on a boundary between the cylindrical shield 1 and the cylindrical shield 2 and on a boundary between the cylindrical shield 1 and the cylindrical shield 3 is screened by the formation of these overlapped parts, is reduced, and the magnetic shielding factor of the magnetic shielding apparatus can be enhanced. It is desirable that the length of the overlapped parts in the circumferential direction is 10 times or more for the width of the clearance. The width of the clearance made between the cylindrical shield 1 and the cylindrical shield 2 is approximately 1 cm, while in the overlapped parts the central angle of which is approximately 40 degrees on the downside, the magnetic shielding factor is enhanced by setting the length of the overlapped parts in the circumferential direction to approximately 35 cm. Similarly in the other overlapped parts, the length of the overlapped parts in the circumferential direction is secured by 10 times or more of the width of the clearance and the magnetic shielding factor is enhanced.

In the example shown in FIGS. 1 to 5, the opening 22 into which the cryostat is inserted is formed on the upside of a positive area of the z-axis. In the example shown in FIGS. 1 to 5, the cutouts are formed in the portions at one end in the circumferential direction of the y-axis and parallel to the y-axis of the cylindrical shields 2, 3 and in the portions at the other end in the circumferential direction of the y-axis and parallel to the y-axis of the cylindrical shields 2, 3. In FIG. 2B, the cutout 25 is shown, however, the cutout 25 is not required to be formed in the portion at the other end in the circumferential direction of the y-axis and parallel to the y-axis of the cylindrical shield 2.

Considering a case that the cylindrical shields 1, 2, 3 are revolved leftward by approximately 60 degrees in the circumferential direction of the y-axis with the position of the opening 22 into which the cryostat is inserted kept as it is in FIGS. 5A and 5B, the left upside and the left downside in FIG. 5A are moved in positions lowered downward and a position in the circumferential direction of the y-axis is lowered downward. In such a case, the cutouts 25, 27 shown in FIGS. 2B and 2C are formed, the cutouts 26, 28 are not formed, and the revolving door 4 can be turned without colliding with the auxiliary cylinder 23. That is, the cutout 10 (that is, 26, 28) formed on the revolving door 4 is not required to be formed. Therefore, as the central position of the opening 22 is located on a YZ plane in a normal case, whether the formation of the cutouts 25, 26, 27, 28 shown in FIGS. 2B and 2C is required or not and the position of the opening 22 formed on the cylindrical shield 1 shown in FIG. 2A can be determined depending upon the position in the circumferential direction of the y-axis in which the cylindrical shield 1 is arranged. This is also similar in a magnetic shielding apparatus shown in FIG. 22 and described later.

FIG. 5C is an enlarged view showing a dotted part shown in FIG. 5B and is a sectional view showing the details of each structure of the cylindrical shields 1, 2, 3.

The cylindrical shield 3 arranged outside the cylindrical shield 1 is configured by high-permeability material (plates 1 mm thick made of Permalloy) 3-1, 3-2 and reinforcing material made of non-magnetic material (a square pipe 30 mm square manufactured by SUS) 33-3. The reinforcing material 33-3 reinforces and holds the high-permeability material 3-1, 3-2.

The cylindrical shield 2 arranged inside the cylindrical shield 1 is configured by high-permeability material (plates 1 mm thick made of Permalloy) 2-1, 2-2, high-electric conductivity material (a plate 0.5 mm thick made of aluminum) 32-2 and reinforcing material made of non-magnetic material (a square pipe 30 mm square manufactured by SUS) 33-2. The reinforcing material 33-2 reinforces and holds the high-permeability material 2-1, 2-2 and the high-electric conductivity material 32-2.

The cylindrical shield 1 arranged between the cylindrical shields 2, 3 and fixed to the shield bases 6a, 6b is configured by high-permeability material (plates 1 mm thick made of Permalloy) 1-1, 1-2, high-electric conductivity material (a plate 0.5 mm thick made of aluminum) 32-1 and reinforcing material made of non-magnetic material (a square pipe 60 mm square manufactured by SUS) 33-1. The reinforcing material 33-1 reinforces and holds the high-permeability material 1-1, 1-2 and the high-electric conductivity material 32-1.

FIG. 23 shows a table showing the size of the magnetic shielding apparatus shown in FIGS. 1 to 5.

In FIG. 23, approximate values are shown, the unit of an outside diameter, an inside diameter, the thickness of the shields showing the total thickness of the Permalloy plate and the length in a direction of the central axis is cm and the unit of an angle is a degree.

An upper outside overlapped angle showing the overlapped angle when the revolving door 4 is completely closed shows the overlapped angle on the upper outside of the outside shield and the intermediate shield, an upper inside overlapped angle shows the overlapped angle on the upper inside of the intermediate shield and the inside shield, a lower inside overlapped angle shows the overlapped angle on the lower inside of the inside shield and the intermediate shield, and a lower outside overlapped angle shows the overlapped angle on the lower outside of the intermediate shield and the outside shield.

FIGS. 6A to 6C are perspective views showing a first model used for simulation analysis for evaluating the magnetic shielding factor of the magnetic shielding apparatus shown in FIG. 1. The first model is acquired by simplifying the cylindrical shields shown in FIGS. 1 to 5.

FIG. 6A is the perspective view showing a model of a cylindrical shield 61 the diameter of which is 100 cm, the length of which is 200 cm and which is made of high-permeability material 2 mm thick having the relative permeability of 60,000.

FIG. 6B is the perspective view showing a model of a cylindrical shield 62 on which a circular opening 63 having the center in a position that crosses the z-axis on a cylindrical face of the cylindrical shield 61 shown in FIG. 6A and having a diameter of 40 cm is formed.

FIG. 6C is the perspective view showing a model of a cylindrical shield on which an auxiliary cylinder 64 made of high-permeability material having the relative permeability of 60,000, having the inside diameter of 40 cm, having the length in the direction of the z-axis of approximately 50 cm and having the thickness of 2 mm is connected along the periphery of the opening 63 of the cylindrical shield 62 shown in FIG. 6B.

In FIGS. 6A, 6B, 6C, an origin (0, 0, 0) of a rectangular coordinate system (x, y, z) shall be each center O of the magnetic shielding apparatuses 61, 62, a perpendicular direction shall be the z-axis, the central axis of the magnetic shielding apparatus shall be the y-axis, and an XY plane shall be a plane parallel to a plane measured by the singular or plural SQUID fluxmeters. The SQUID fluxmeter detects a component in the direction of the z-axis of a magnetic field.

FIG. 24 shows a table showing the size of a first model shown in FIGS. 6A to 6C.

In FIG. 24, the size shows approximate values and the unit is the same as the unit of the size related to the magnetic shielding apparatus shown in FIGS. 1 to 5 and shown in FIG. 23.

As for the first model shown in FIGS. 6A, 6B, 6C, magnetic distribution inside the magnetic shielding apparatus in case an even magnetic field is applied in the direction of the z-axis is acquired by simulation according to a three-dimensional finite element method.

Figure 7:
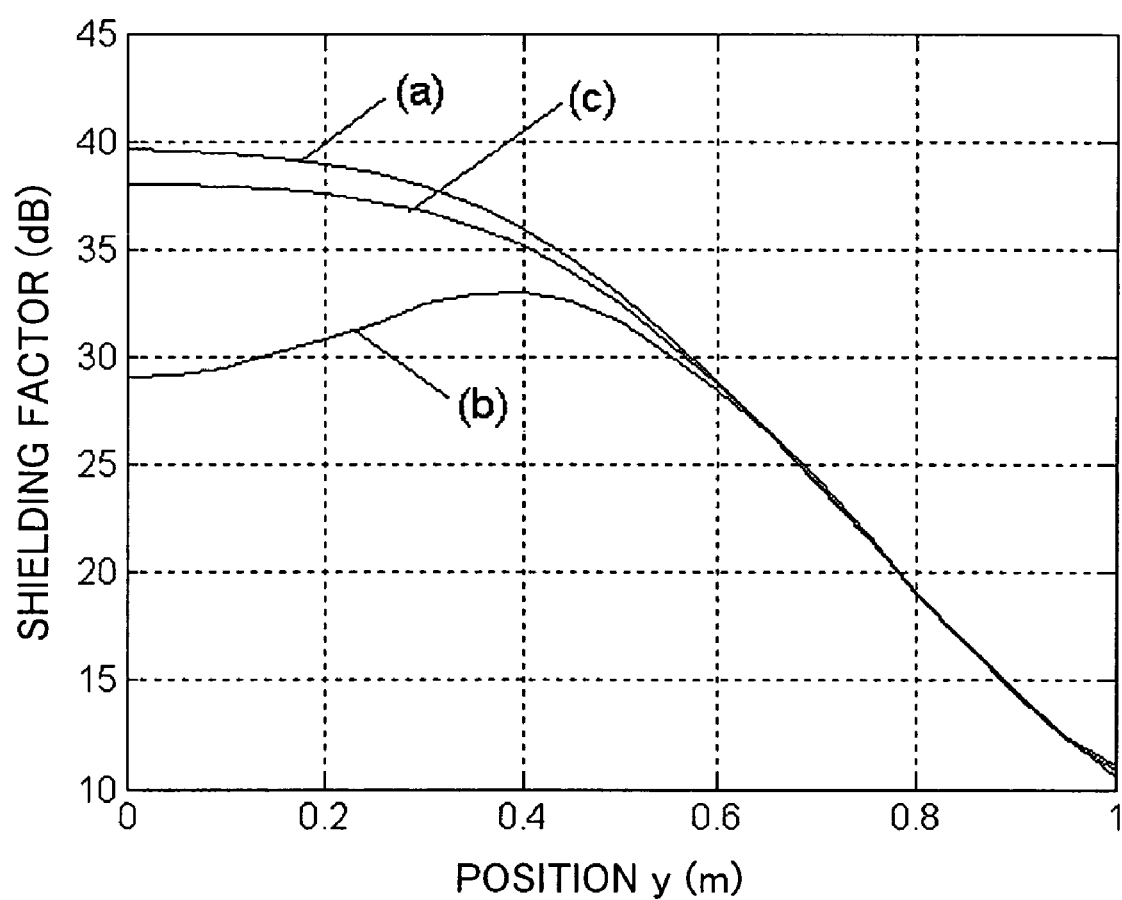
FIG. 7 is a graph showing the distribution of a magnetic shielding factor for the first model.
Figure 8:
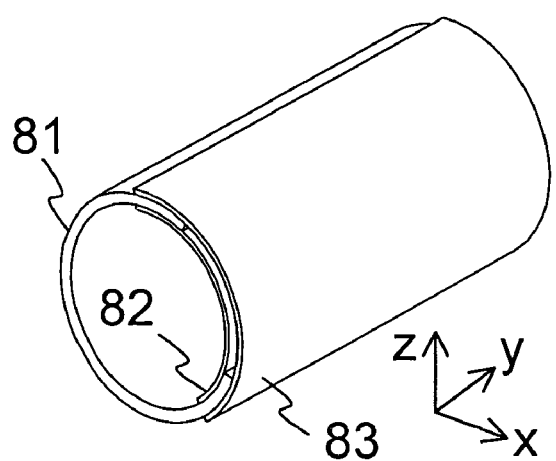
FIGS. 8A to 8D are perspective views showing a second model used for simulation analysis for evaluating a magnetic shielding factor of the magnetic shielding apparatus shown in FIG. 1.
Figure 8:
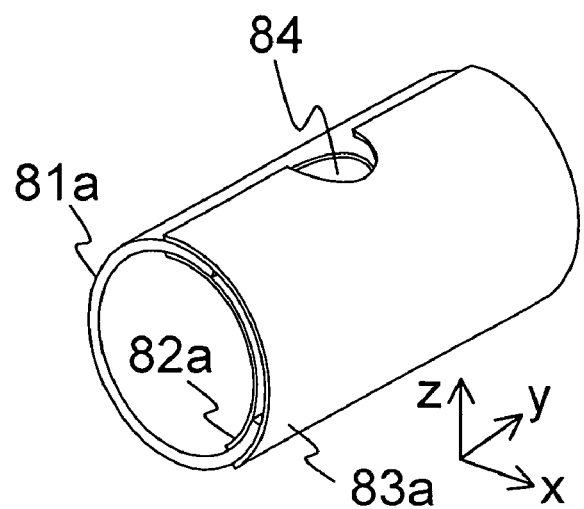
Figure 8:
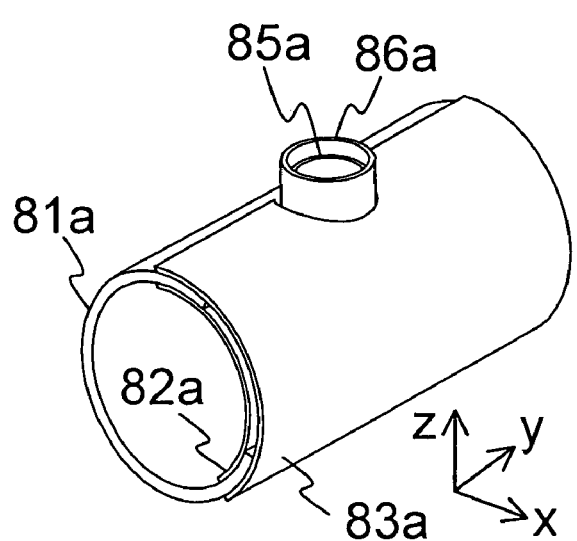
Figure 8:
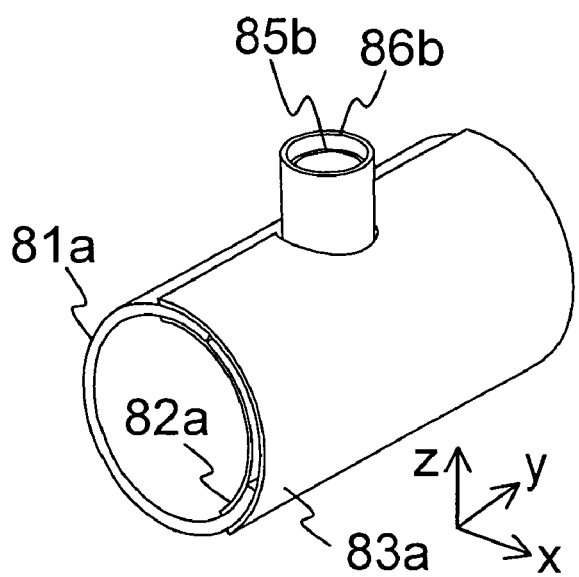

FIG. 7 is a graph showing the result (the distribution of a magnetic shielding factor) acquired by the simulation for the first model and the graph shows the magnetic distribution inside the magnetic shielding apparatus as the distribution of the magnetic shielding factor on the y-axis.

A magnetic shielding factor S (x, y, z)(dB) on the coordinates (x, y, z) when an even environmental magnetic field (having only a component in the direction of the z-axis) shall be (0, 0, B0), a magnetic field on the inside coordinates (x, y, z) of the magnetic shielding apparatus shall be {Bx (x, y, z), By (x, y, z), Bz (x, y, z)} and the magnitude of the magnetic field is a value acquired by an expression (1) is defined as a value acquired by an expression (2) (log means a common logarithm). FIG. 7 shows the variation of the magnetic shielding factor S (x, y, z) for a position y.

$$|B(x, y, z)| = \sqrt{\begin{array}{l}\{Bx(x, y, z) \times Bx(x, y, z) + \\ By(x, y, z) \times By(x, y, z) + \\ Bz(x, y, z) \times Bz(x, y, z)\}\end{array}} \quad (1)$$

$$S(x, y, z) = 20 \log\{|B0|/B(x, y, z)|\} \quad (2)$$

The axis y of an abscissa shown in FIG. 7 shows a y coordinate (unit: m) in the first model shown in FIGS. 6A, 6B, 6C. "y=0" shows a center position (an origin) of the magnetic shielding apparatus and "y=1 m" shows a position of the open end of the magnetic shielding apparatus. An axis of ordinates shown in FIG. 7 shows a magnetic shielding factor (dB) on the axis y of the abscissa (corresponding to the coordinates (0, y, 0) shown in FIGS. 6A to 6C).

A graph (a) shown in FIG. 7 shows the result for the first model shown in FIG. 6A. A magnetic shielding factor is maximum (approximately 40 dB) in the center position y=0 of the magnetic shielding apparatus, as a value on the axis of the abscissa approaches y=1 m from y=0, the magnetic shielding factor decreases, and is approximately 11 dB at y=1 m.

A graph (b) in FIG. 7 shows the result for the first model shown in FIG. 6B. A magnetic shielding factor is approximately 29 dB at y=0 and decreases by approximately 11 dB at y=0 by the effect of the opening 63, compared with the first model shown in FIG. 6A. As a value on the axis of the abscissa approaches y=1 m from y=0, a magnetic shielding factor first gradually increases, becomes maximum (approximately 33 dB) at y≈0.4 m, then starts to decrease, and at y≧0.6 m, has approximately the similar value to that of the first model shown in FIG. 6A.

A graph (c) in FIG. 7 shows the result for the first model shown in FIG. 6C. A magnetic shielding factor is maximum (approximately 38 dB) at y=0 and increases by approximately 9 dB at y=0 by the effect of the auxiliary cylinder 64, compared with that of the first model shown in FIG. 6B. The magnetic shielding factor decreases only by approximately 2 dB at y=0, compared with that of the first model shown in FIG. 6A. This shows that the auxiliary cylinder 64 very effectively acts on preventing the deterioration of the magnetic shielding factor by the opening 63. In the first model shown in FIG. 6C, a magnetic shielding factor is 35 dB or more in a range of −0.4 m≦y≦0.4 m.

FIGS. 8A to 8D are perspective views showing a second model used for simulation analysis for evaluating the magnetic shielding factor of the magnetic shielding apparatus shown in FIG. 1.

FIG. 8A is the perspective view showing the second model configured by cylindrical shields 81, 82, 83 which are made of high-permeability material having the relative permeability of 60,000, the length in a direction of the y-axis of which is 200 cm, the thickness of which is 1 mm and which are composed of two circumferential parts. The cylindrical shields 81, 82, 83 are respectively provided with two circular arc parts at both ends having a predetermined angular range and perpendicular to a central axis, two portions having a predetermined small width dimension and a predetermined length dimension, having predetermined small area and parallel to the central axis and a circumferential part having a predetermined angular range.

The cylindrical shields 82, 83 have the same angular range and the cylindrical shield 81 has the predetermined angular range different from those of the cylindrical shields 82, 83. The cylindrical shield 82 is arranged inside the cylindrical shield 81 and the cylindrical shield 83 is arranged outside the cylindrical shield 81.

The cylindrical shield 81 has a part overlapped with the cylindrical shields 82, 83. The inside diameter of the circumferential part of the cylindrical shield 81 is 102 cm, the outside diameter is 114 cm, and the predetermined angular range is 260 degrees.

The inside diameter of the circumferential part of the cylindrical shield 82 is 94 cm, the outside diameter is 100 cm, and the predetermined angular range is 200 degrees.

The inside diameter of the circumferential part of the cylindrical shield 83 is 116 cm, the outside diameter is 122 cm, and the predetermined angular range is approximately 200 degrees.

As shown in FIG. 8A, the cylindrical shields 82, 83 are overlapped by 60 degrees in a positive area of the z-axis with the cylindrical shield 81 and are overlapped by 40 degrees in a negative area of the z-axis. The second model shown in FIG. 8A is similar to configuration acquired by removing the opening 22, the cutouts 10, 11, the auxiliary cylinder 23 and the flange-type plate 24 from the configuration of the magnetic shielding apparatus shown in FIGS. 1 to 5.

FIG. 8B is the perspective view showing the second model on which a circular opening 84 having a center in a position that crosses the z-axis of a circumferential face of the cylindrical shield shown in FIG. 8A and having a diameter of 40 cm is formed.

The second model shown in FIG. 8B is configured by cylindrical shields 81a, 82a, 83a. The cylindrical shields 82a, 83a are the same in material and dimensions as the cylindrical shields 82, 83 except that the cylindrical shields 82a, 83a are respectively provided with a cutout in one of two portions parallel to the central axis of the cylindrical shields 82, 83 shown in FIG. 8A. The cylindrical shield 81a is the same in material and dimensions as the cylindrical shield 81 except that an opening having a diameter of approximately 40 cm with the y-axis as a central axis is formed on a circumferential part of the cylindrical shield 81 shown in FIG. 8A. The second model shown in FIG. 8B is similar to configuration acquired by removing the auxiliary cylinder 23 and the flange-type plate 24 from the configuration of the magnetic shielding apparatus described referring to FIGS. 1 to 5.

FIG. 8C shows a transformed example of the cylindrical shield shown in FIG. 8B and is the perspective view showing the second model having configuration in which auxiliary cylinders 85a, 86a are added to an opening.

The auxiliary cylinders 85a, 86a are approximately 17 cm long in a direction of the z-axis, are 1 mm thick, and are made of high-permeability material having the relative permeability of 60,000. A cylindrical shield 81a is the same in material and dimensions as the cylindrical shield 81 except that the opening having a diameter of approximately 40 cm with the z-axis as a central axis is formed on the circumferential part of the cylindrical shield 81 shown in FIG. 8A. The auxiliary cylinder 85a having a diameter of approximately 40 cm is magnetically connected to the opening of the cylindrical shield 81a and the auxiliary cylinder 86a having a diameter of approximately 52 cm is magnetically connected to the outside face of a circumferential part of the cylindrical shield 81a. The second model shown in FIG. 8C has the similar configuration to that of the magnetic shielding apparatus described referring to FIGS. 1 to 5, however, the second model is different in that the second model has the two auxiliary cylinders magnetically connected so that they encircles the opening.

FIG. 8D shows a transformed example of the cylindrical shield shown in FIG. 8C and is the perspective view showing the second model using auxiliary cylinders 85b, 86b acquired by changing the length in the direction of the z-axis (approximately 17 cm) of the auxiliary cylinders 85a, 86a shown in FIG. 8C to approximately 31 cm by extending the length by approximately 14 cm.

For the second model shown in FIGS. 8A, 8B, 8C, 8D, the distribution of a magnetic field inside the magnetic shielding apparatus in case an even magnetic field is applied in the direction of the z-axis is acquired by simulation according to a three-dimensional finite element method.

Figure 9:
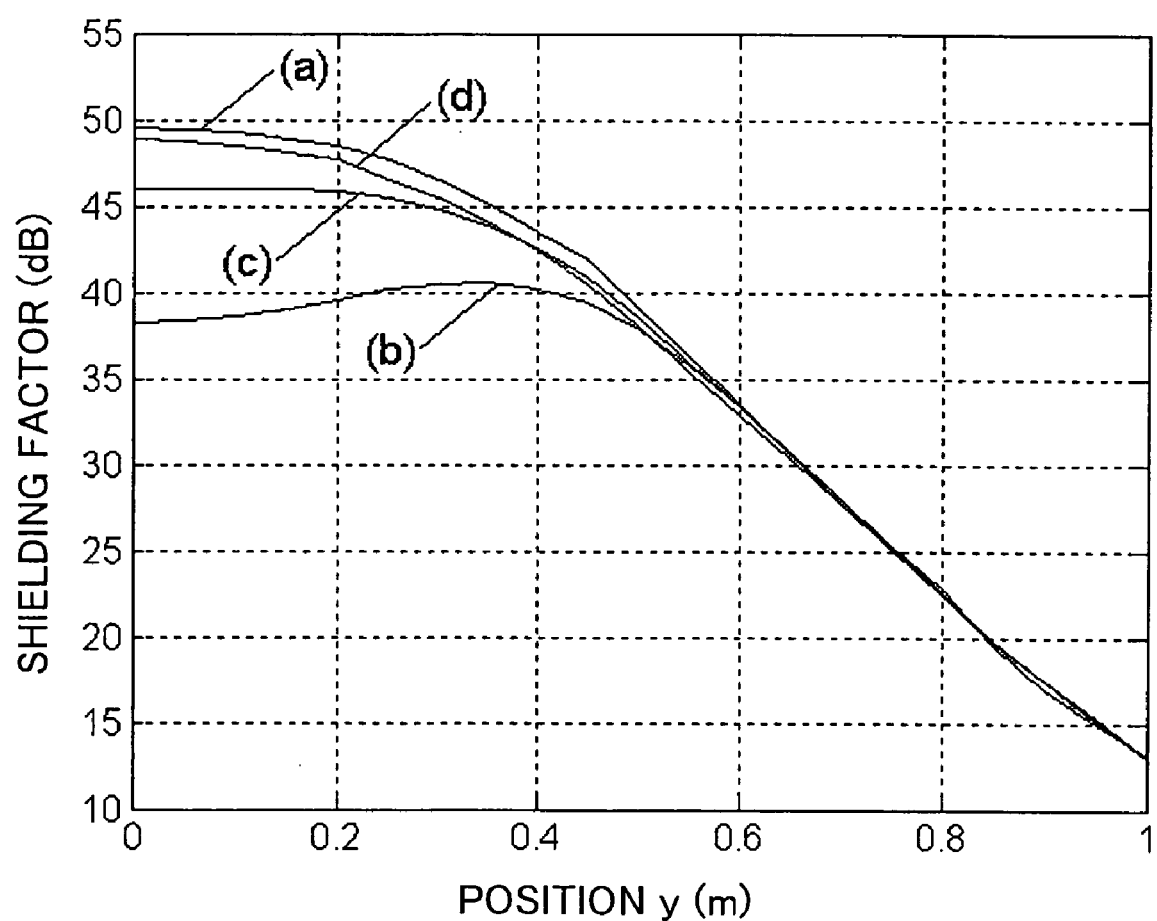
FIG. 9 is a graph showing the distribution of a magnetic shielding factor for the second model.

FIG. 9 is a graph showing the result (the distribution of a magnetic shielding factor) acquired by the simulation for the second model and is a graph showing the distribution of a magnetic field inside the magnetic shielding apparatus as the distribution of the magnetic shielding factor on the y-axis.

FIG. 25 shows a table showing the size of the second model shown in FIG. 8A.

FIG. 26 shows a table showing the size of the second model shown in FIG. 8B.

FIG. 27 shows a table showing the size of the second model shown in FIG. 8C.

FIG. 28 shows a table showing the size of the second model shown in FIG. 8D.

In FIGS. 25, 26, 27, 28, the size shows an approximate value and the unit is the same as the unit of the size shown in FIGS. 23 and 24 and related to the magnetic shielding apparatuses shown in FIGS. 1 to 5 and FIGS. 6A to 6C.

An axis of an abscissa shown in FIG. 9 shows a y coordinate in the second model and an axis of ordinates shows a magnetic shielding factor. The unit of the axis of the abscissa and the axis of ordinates shown in FIG. 9 is the same as that in FIG. 7.

A graph (a) shown in FIG. 9 shows the result for the second model shown in FIG. 8A. The magnetic shielding factor is maximum (approximately 50 dB) at y=0, decreases as a value on the axis of the abscissa approaches y=1 m from y=0, and is approximately 13 dB at y=1 m.

A graph (b) in FIG. 9 shows the result for the second model shown in FIG. 8B. The magnetic shielding factor is approximately 38 dB at y=0. The magnetic shielding factor decreases at y=0 by approximately 12 dB by the effect of the opening 84, compared with the second model on the graph (a). As a value on the axis of the abscissa approaches y=1 m from y=0, the magnetic shielding factor first gradually increases, becomes maximum (approximately 40 dB) at y≈0.35 m, then starts to decrease, and has approximately the similar value to the second model on the graph (a) at y≧0.6 m.

A graph (c) in FIG. 9 shows the result for the second model shown in FIG. 8C. A magnetic shielding factor is maximum (approximately 46 dB) at y=0. The magnetic shielding factor increases at y=0 by approximately 8 dB by the effect of the auxiliary cylinders 85a, 86a, compared with that on the graph (b). This shows that the auxiliary cylinders 85a, 86a very effectively contribute to preventing the deterioration of the magnetic shielding factor by the opening 84.

A graph (d) in FIG. 9 shows the result for the second model shown in FIG. 8D. A magnetic shielding factor is maximum (approximately 49 dB) at y=0. The magnetic shielding factor increases in a central position by approximately 11 dB by the effect of the auxiliary cylinders 85a, 86b, compared with that on the graph (b). In the second model shown in FIG. 8D, to prevent the deterioration of the magnetic shielding factor by the opening 84, the length in an axial direction of the auxiliary cylinders 85a, 86a shown in FIG. 8C is extended.

It is known from the comparison of the graphs (c) and (d) shown in FIG. 9 that the magnetic shielding factor increases at y=0 by 3 dB by the effect of extending the length of the auxiliary cylinders 85b, 86b. It is known from the comparison of the graphs (d) and (a) shown in FIG. 9 that in the graph (d), the magnetic shielding factor decreases at y=0 only by approximately 1 dB.

The above-mentioned result shows that the auxiliary cylinders 85b, 86b very effectively contribute to preventing the deterioration of the magnetic shielding factor by the opening 84. As clear from the result of the graphs (c) and (d) shown in FIG. 9, the longer the auxiliary cylinder is in the axial direction, the larger magnetic shielding effect is. In the second model shown in FIG. 8C, the magnetic shielding factor is 45 dB or more in a range of −0.29 m≦y≦0.29 m and in the second model shown in FIG. 8D, the magnetic shielding factor is 45 dB or more in a range of −0.32 m≦y≦0.32 m. It is desirable that the length in the axial direction of the auxiliary cylinder is equal to or longer than the inside diameter of the opening.

It is clear from the comparison of FIGS. 7 and 9 that the larger the total thickness T of the Permalloy plate in a direction perpendicular to the central axis of the magnetic shielding apparatus is, the more the magnetic shielding factor is enhanced. Therefore, in case the total thickness T is large in the first model shown in FIG. 6C, it is estimated based upon the comparison of FIGS. 7 and 9 that a characteristic of a magnetic shielding factor close to that in FIGS. 8C and 8D is acquired approximately in a range of −0.4 m≦y≦0.4 m, and it is estimated that the small-sized magnetic shielding apparatus having simple structure shown in FIG. 6C is also possible though an object of examination is required to be carried inside the apparatus from a direction of the central axis of the apparatus.

Figure 10:
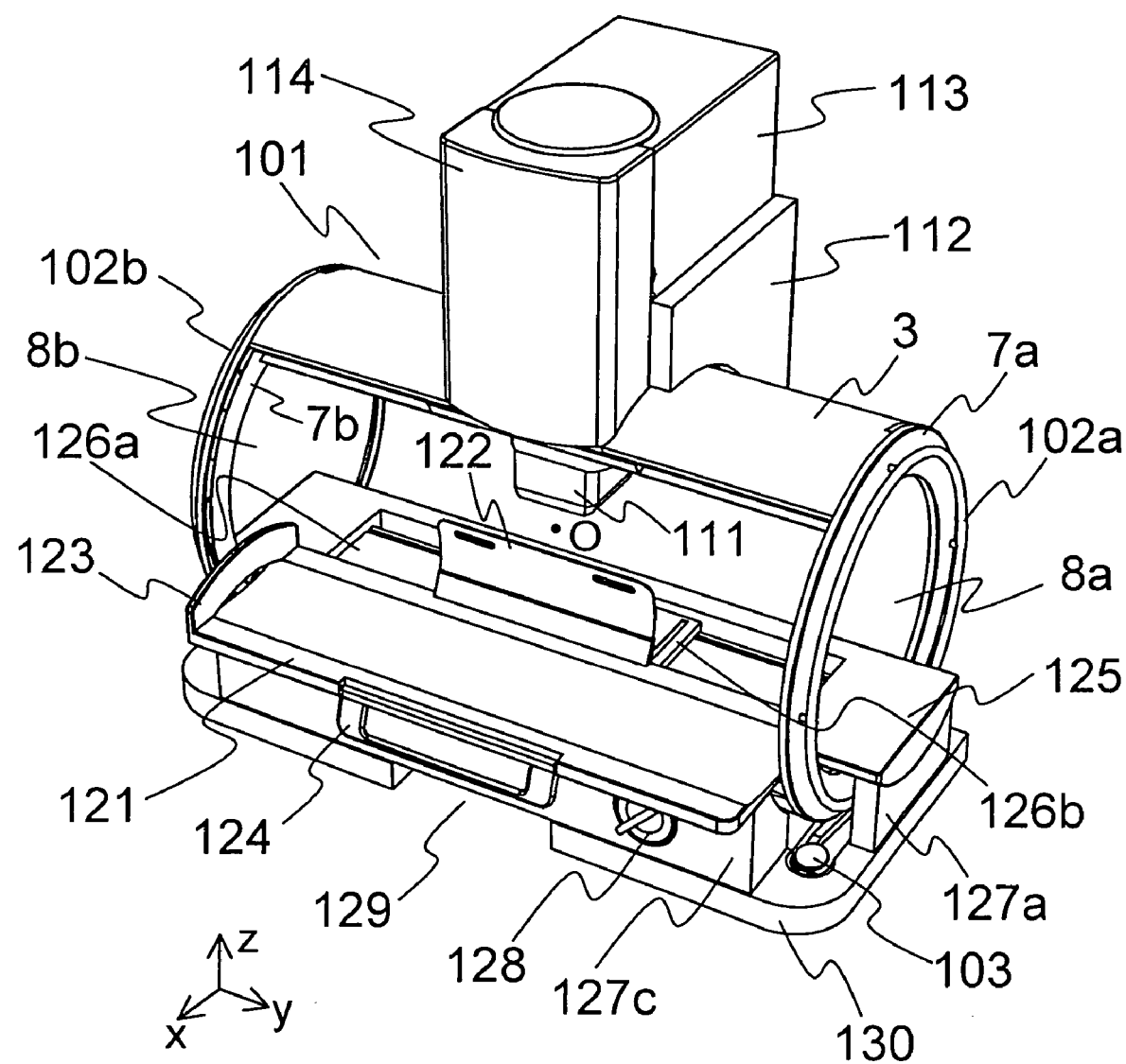
FIG. 10 is a perspective view showing the configuration of a main part of a biomagnetism measuring device equivalent to the embodiment of the invention.

FIG. 10 is a perspective view showing the configuration of a main part of the biomagnetism measuring device equivalent to the embodiment of the invention, shows a state in which the revolving door 4 of the magnetic shielding apparatus is completely opened (see FIG. 3), and shows a state in which a top plate 121 is pulled out of the magnetic shielding apparatus.

The size of the magnetic shielding apparatus described below and shown in FIGS. 10 to 17 is the same as the size of the second model shown in FIG. 8C.

Figure 11:
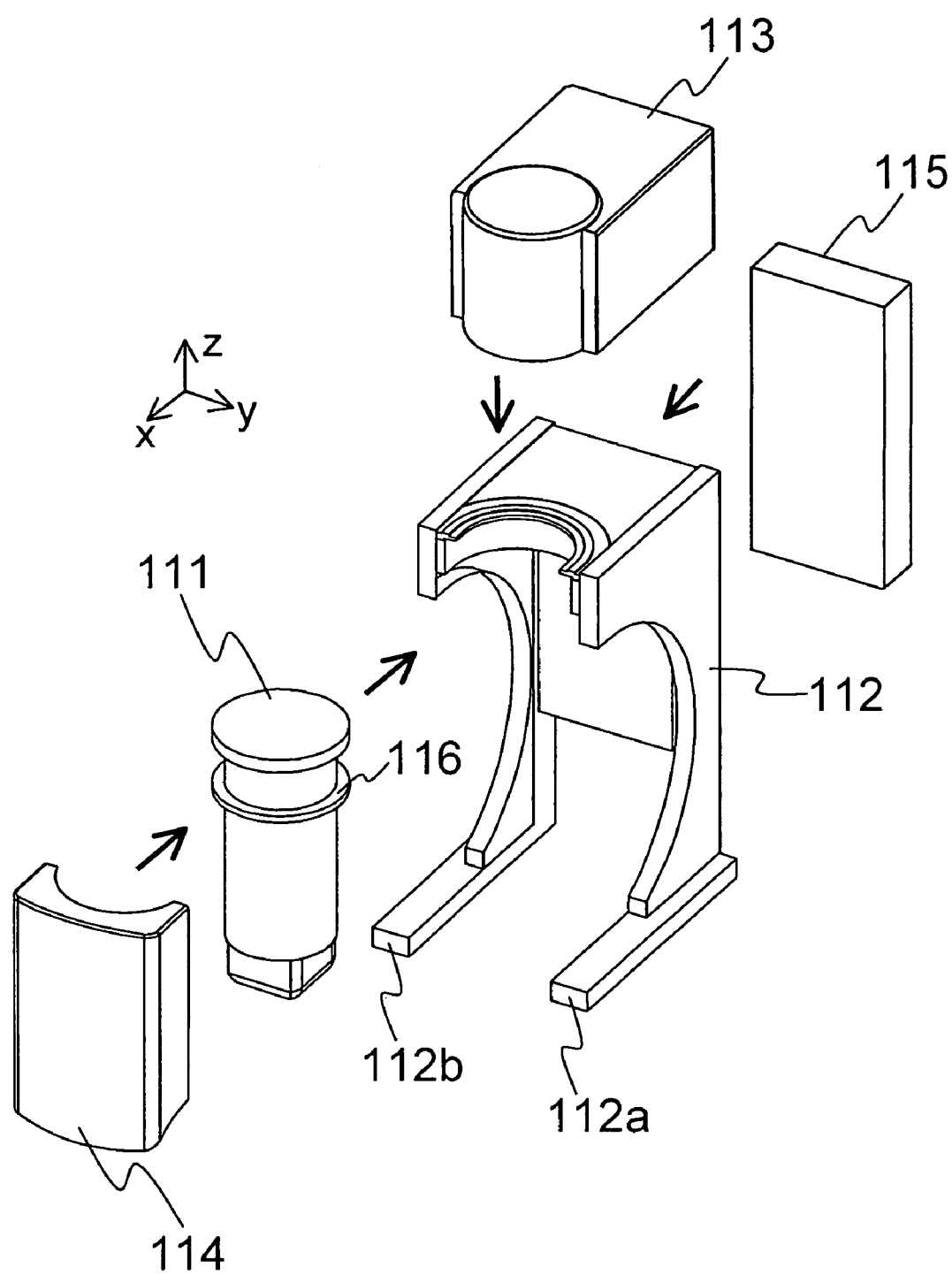
FIG. 11 is a perspective view showing the configuration of a cryostat and a gantry of the biomagnetism measuring device shown in FIG. 10.

FIG. 11 is a perspective view showing the configuration of a cryostat and a gantry in the biomagnetism measuring device shown in FIG. 10.

Figure 12:
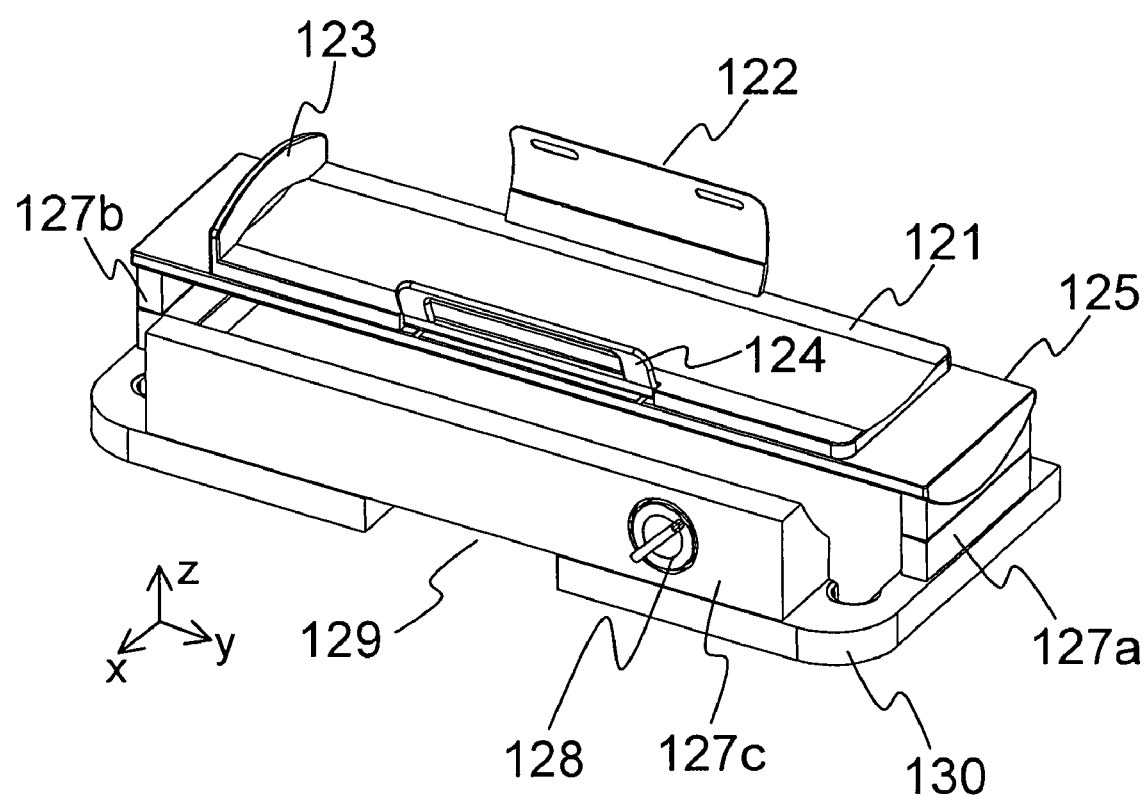
FIG. 12 is a perspective view showing the configuration of a bed of the biomagnetism measuring device shown in FIG. 10.

FIG. 12 is a perspective view showing the configuration of a bed in the biomagnetism measuring device shown in FIG. 10.

FIG. 13 is a sectional view viewed on a YZ plane showing the biomagnetism measuring device shown in FIG. 10.

Figure 14:
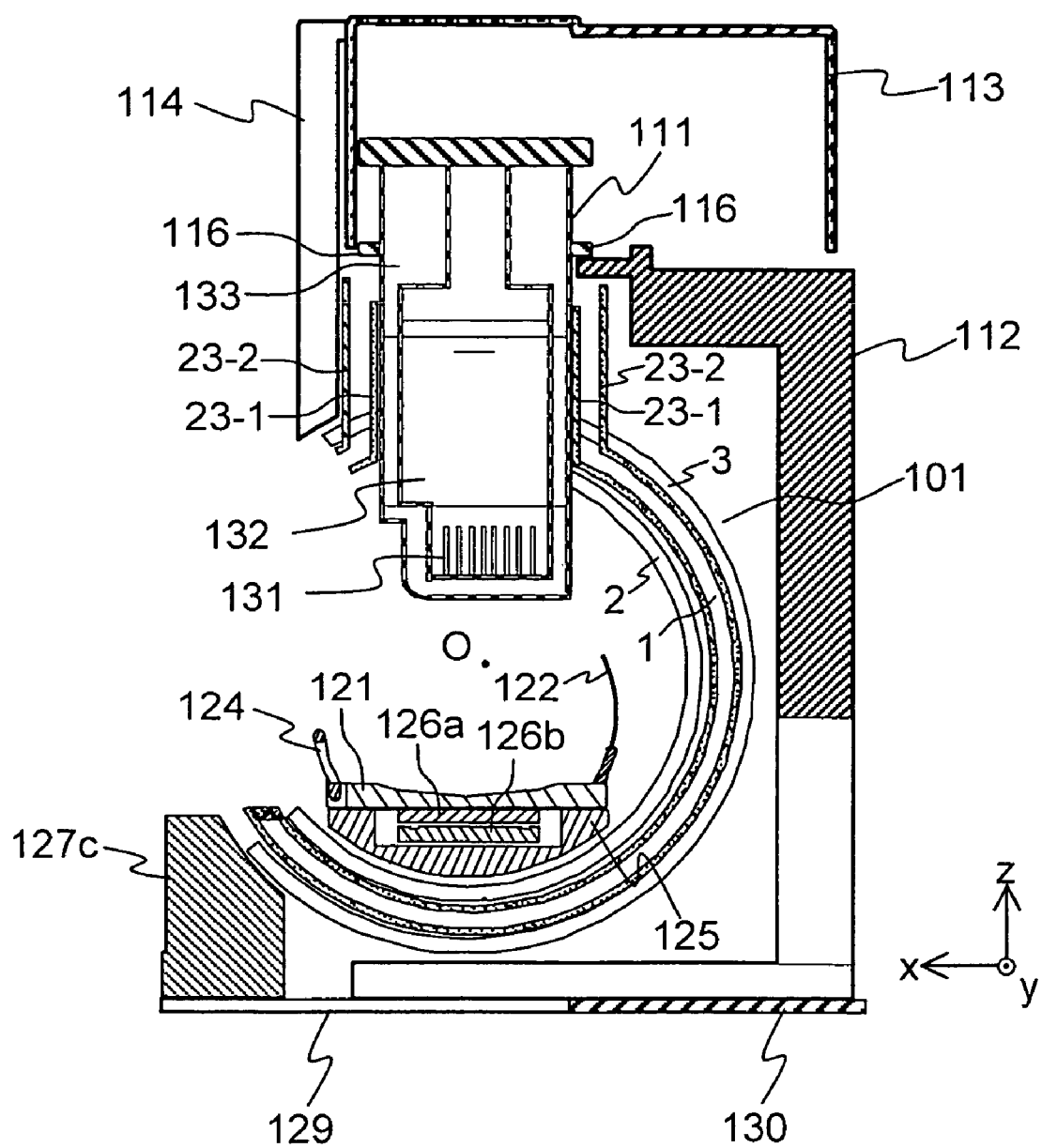
FIG. 14 is a sectional view showing a ZX plane of the biomagnetism measuring device shown in FIG. 10.
Figure 15:
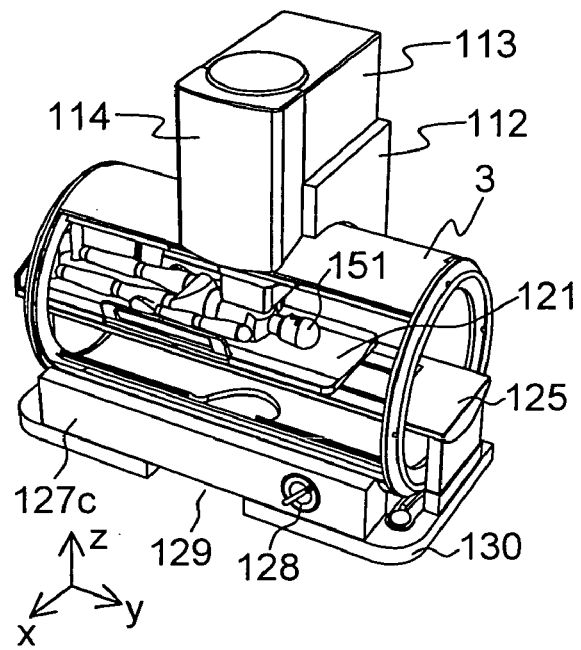
FIGS. 15A to 15D are explanatory drawings for explaining the measurement of a magnetic field around a heart by the biomagnetism measuring device shown in FIG. 10, FIGS. 15A and 15B are the explanatory drawing for explaining the measurement of a magnetic field around the heart of an object of examination lying on his/her back.
Figure 15:
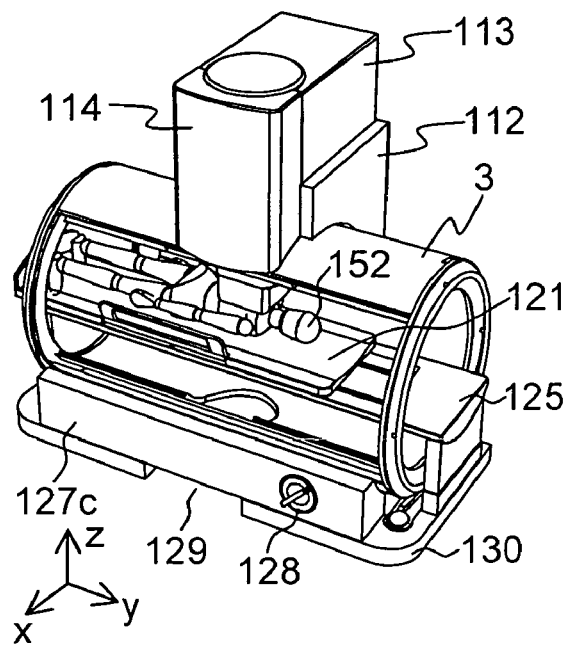
Figure 15:
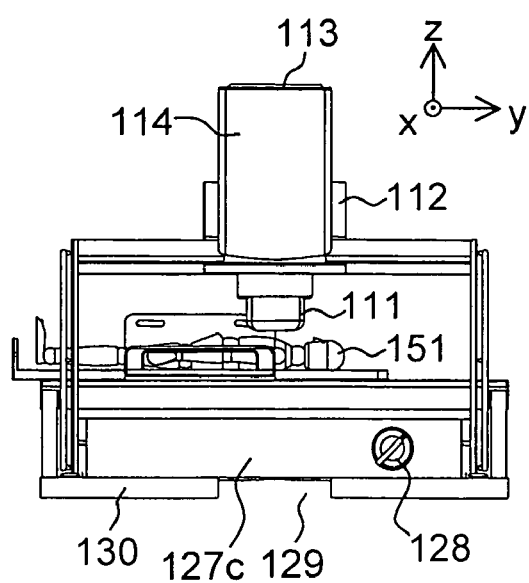
Figure 15:
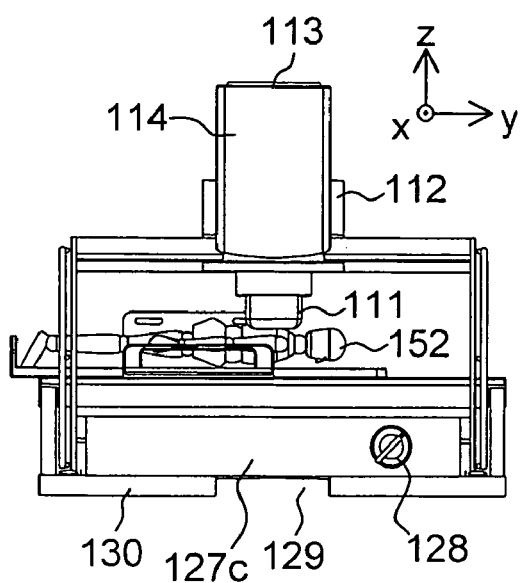
Figure 16:
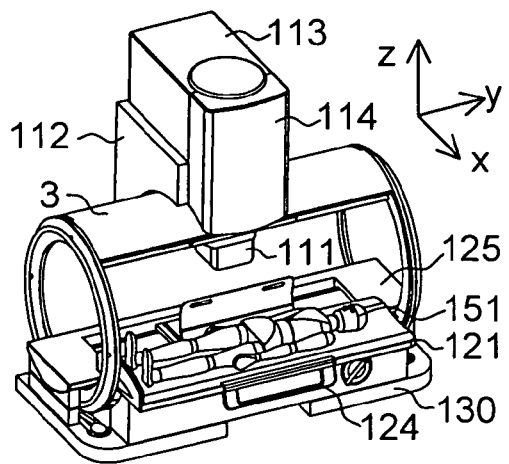
FIGS. 16A to 16F are perspective views for explaining a procedure for measuring a magnetic field around the heart using the biomagnetism measuring device shown in FIG. 10, FIGS. 16A to 16D show a state in which the revolving door of the magnetic shielding apparatus is completely opened.
Figure 16:
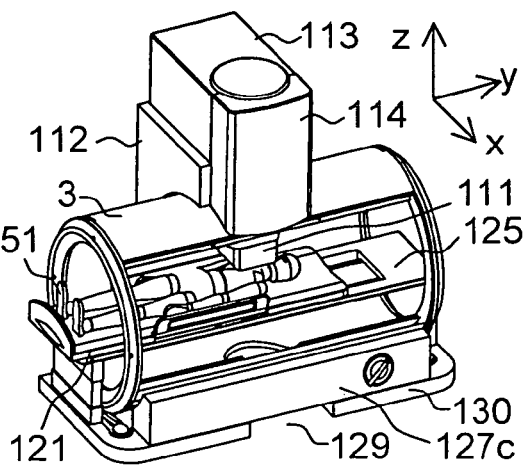
Figure 16:
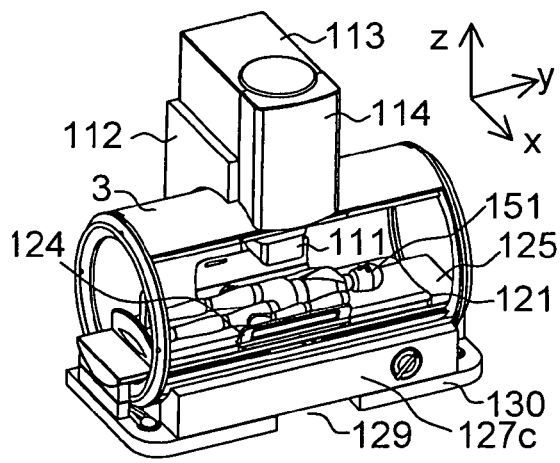
Figure 16:
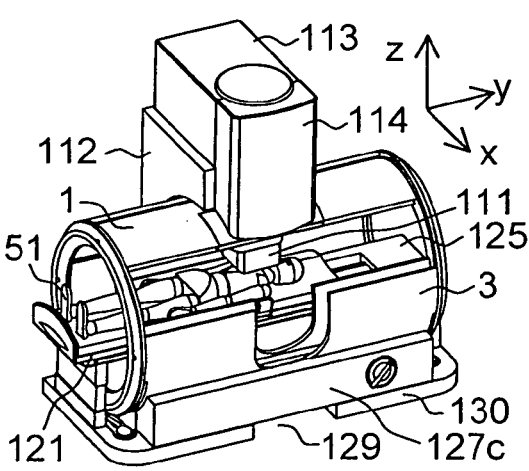
Figure 16:
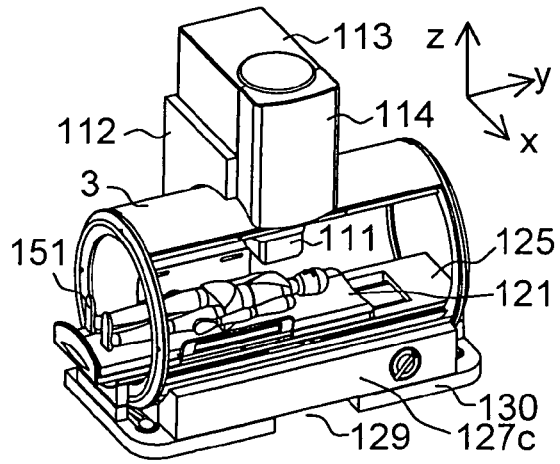
Figure 16:
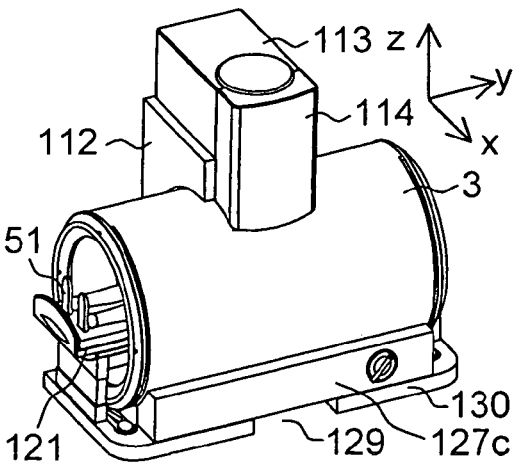

FIG. 14 is a sectional view viewed on a ZX plane showing the biomagnetism measuring device shown in FIG. 10.

FIGS. 13 and 14 show the mutual positional relation and the structure of two-layer auxiliary cylinders 23-1, 23-2, cylindrical shields 1, 2, 3, 11 of the magnetic shielding apparatus, the cryostat 111, plural SQUID fluxmeters 131, the gantry 112, the top-plate 121, elements 126a, 126b, 125, 127a, 127b, 127c for moving the top plate 121 in directions of the x-, y- and z-axes.

Figure 17:
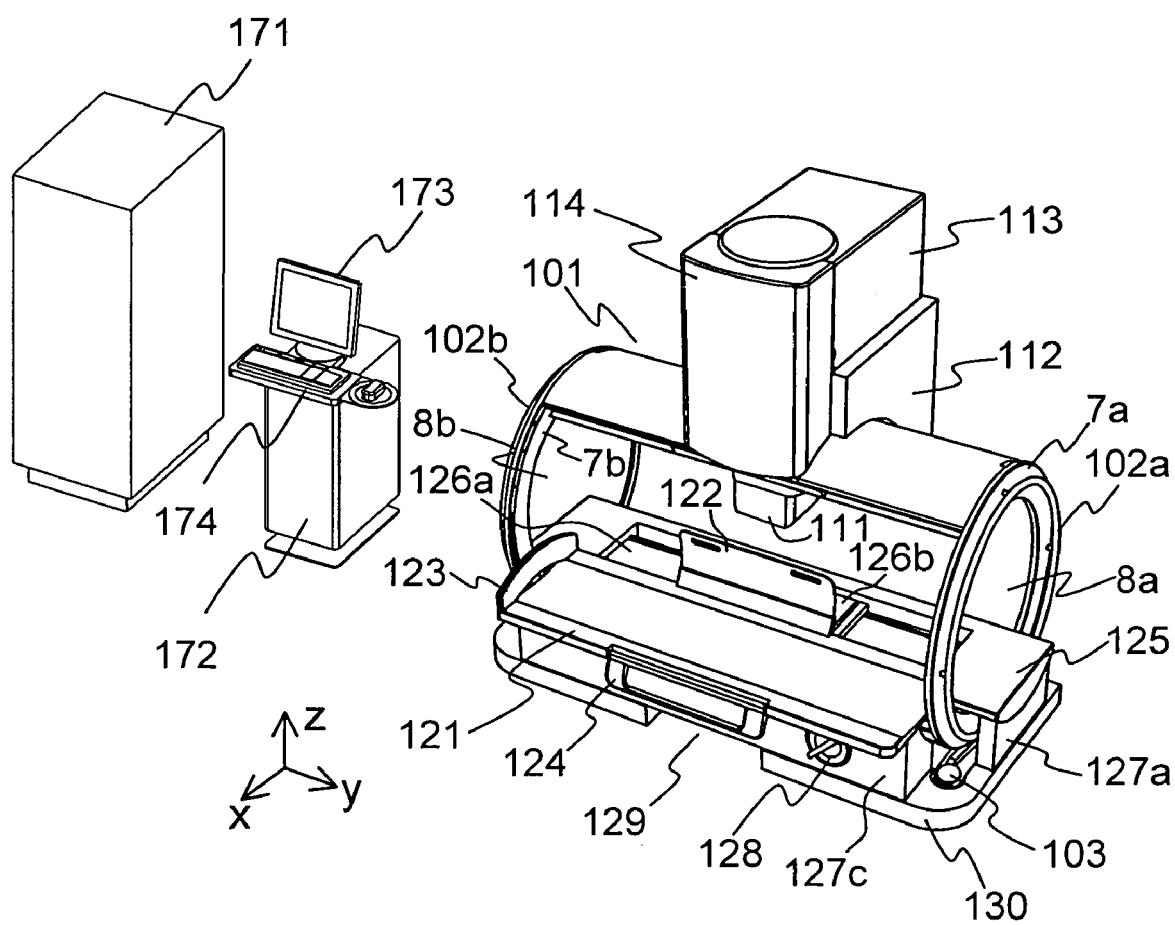
FIG. 17 is a perspective view showing the whole configuration of the biomagnetism measuring device equivalent to the embodiment of the invention.

The biomagnetism measuring device shown in FIG. 10 is roughly configured by a magnetic shielding part, a cryostat part, a gantry part, a bed part respectively shown in FIG. 10, a SQUID driving circuit, a processor (a computer), a display and an input device respectively not shown in FIG. 10. Components not shown in FIG. 10 are shown in FIG. 17 described later and will be described in detail below.

The magnetic shielding part is configured by a magnetic shielding apparatus 1101 having the similar configuration to that of the magnetic shielding apparatus shown in FIGS. 1 to 5. Revolving handles 1102a, 1102b used for opening and closing the revolving door 4 are connected to the revolving door 4 shown in FIG. 1, the revolving door 4 can be opened or closed by the manual revolution of the revolving handle 1102a or 1102b, and the area of the opening 9 varies. The revolving door 4 can be easily locked or unlocked by setting a foot on a locking mechanism 1103 of the revolving door 4. In FIG. 10, the locking mechanism 1103 is arranged in a positive area of the y-axis, however, it may be also arranged in a negative area of the y-axis.

A pneumatic or hydraulic pump is controlled by a control lever 128 arranged on a top plate bearer 127c and positional adjustment in a direction of the z-axis of a top plate support 125 for holding the top plate 121 can be easily made. Control over opening and closing the revolving door 4 can be easily made by revolving the revolving door using the pneumatic or hydraulic pump and others by a revolving button not shown arranged on the top plate bearer 127c. Further, the movement on a plane parallel to an XY plane of the top plate 121 can be controlled by a moving button not shown in a top plate moving part arranged on the top plate bearer 127c.

Therefore, as an examination engineer can adjust the position of the top plate 121 and can control opening and closing the revolving door 4 selecting and using the revolving button, the control lever and the moving button respectively arranged on the top plate bearer 127c if necessary, observing an object of examination in a position opposite to the magnetic shielding apparatus, the object of examination does not feel uneasy. Needless to say, the examination engineer can also adjust the position of the top plate 121 and can also open and close the revolving door 4 manually in the position opposite to the magnetic shielding apparatus, observing the object of examination.

The cryostat part holds the singular or plural SQUID fluxmeters at low temperature and holds the cryostat 111 housed in a lower part. It is desirable that the cryostat 111 is made of non-magnetic material such as FRP resin.

The gantry part includes the gantry 112 for holding the cryostat 111 in the cryostat part. It is desirable that the gantry part is made of non-magnetic material such as aluminum and SUS. The gantry 112 is fixed by gantry supports 112a, 112b and the gantry supports 112a, 112b are fixed to a bed supporting plate 130. A circular arc part for receiving a flange part 116 formed above the periphery of the cryostat 111 is formed in an upper part of the gantry 112.

The upside of the gantry 112 and the cryostat 111 is covered with an upper cover 113. The front of the gantry 112 and the cryostat 111 is covered with a front cover 114. It is desirable that the upper cover 113 and the front cover 114 are made of high-permeability material such as Permalloy and high-electric conductivity material such as aluminum. The upper cover 113 and the front cover 114 not only screen a leakage magnetic field but screen a high-frequency electromagnetic wave that deteriorates the performance of the SQUID fluxmeter.

The bed part includes the top plate 121 for mounting an object of examination, the top plate support 125 for holding the top plate 121, the top plate moving part for holding and moving the top plate 121 on the plane parallel to the XY plane, the top plate support moving parts 127a, 127b (not seen in the perspective view in FIG. 10 and shown in the perspective view in FIG. 12 showing the configuration of the bed part) for holding and moving the top plate support 125 in the direction of the z-axis and the top plate bearer 127c. It is desirable that the bed part is made of non-magnetic material such as lumber, aluminum and SUS.

A fence on this side 124 and a fence on the rear side 122 respectively on sides corresponding to both hands of an object of examination and a fence 123 on the side corresponding to both feet are arranged on the top plate 121. The fences 122, 124 are provided to prevent the object of examination from sticking out of the top plate 121 in a direction of the x-axis. The fence 123 is provided to prevent the feet of the object of examination from sticking out of the top plate 121 in a direction of the y-axis.

When a magnetic field generated from the object of examination is measured, the top plate 121 for mounting the object of examination is arranged inside the magnetic shielding apparatus 1101, however, in FIG. 10, the top plate 121 is moved on the top plate support 125 out of the magnetic shielding apparatus 1101 to mount the object of examination on the top plate 121 and a state in which the fence 124 on this side is pushed down is shown.

The top plate support 125 is arranged inside the magnetic shielding apparatus 1101 in a state piercing the openings 8a, 8b at both ends in the direction of the y-axis and is held by the top plate support moving parts 127a, 127b arranged outside the magnetic shielding apparatus 1101.

The top plate moving part includes the top plate moving plates 126a, 126b and components used for holding and moving the top plate 121 on the plane parallel to the XY plane. The components include combination of a convex portion of a convex rail and a concave portion of a concave rail, a pulley and a ball bearing respectively made of non-magnetic material. The movement on the plane parallel to the XY plane of the top plate 121 is performed by automatic control by the moving button in the top plate moving part arranged on the top plate bearer 127c or the manual movement of the top plate 121.

The top plate 121 is held on the top plate moving plate 126a arranged on the back of the top plate 121 and can be moved in the direction of the x-axis on the plane parallel to the XY plane on the top plate moving plate 126a. The convex portion of the convex rail arranged in the direction of the x-axis on the back of the top plate 121 is inserted into the concave portion of the concave rail arranged in the direction of the x-axis of the top plate moving plate 126a.

The top plate moving plate 126a can be moved in the direction of the y-axis on the plane parallel to the XY plane on the top plate moving plate 126b. The top plate moving plate 126a is held on the top plate moving plate 126b via the combination of the convex portion of the convex rail and the concave portion of the concave rail, the pulley and the ball bearing.

The top plate moving plate 126a can be moved in the direction of the x-axis on the plane parallel to the XY plane for the top plate support 125. Both ends in the direction of the y-axis of the top plate moving plate 126b are respectively inserted into a concave portion of a concave rail formed on an inside wall parallel to an XZ plane of both ends in a direction of the y-axis of a concave portion formed on an XY plane in a direction of the y-axis of the top plate support 125.

Figure 20:
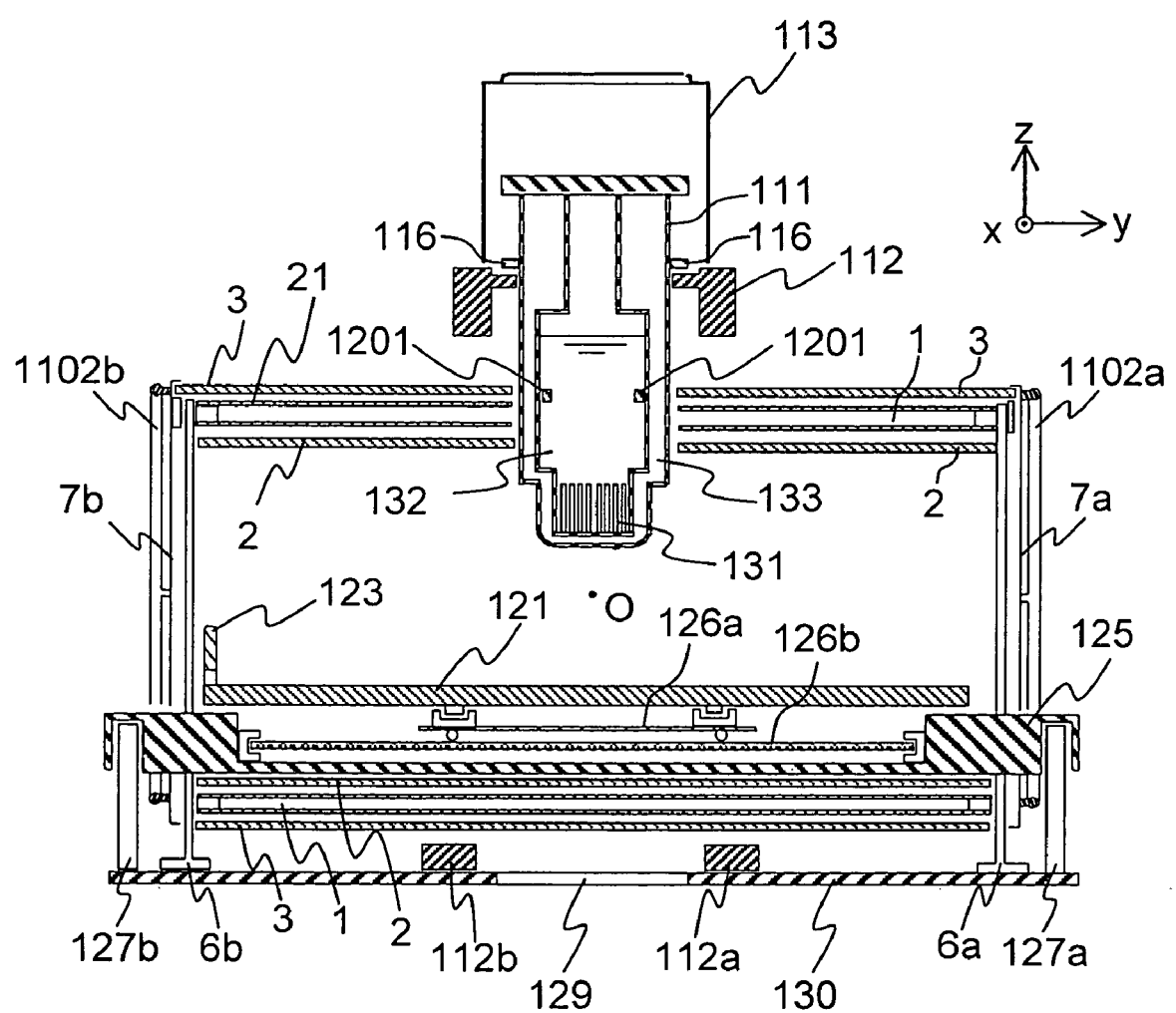
FIG. 20 is a sectional view showing the configuration of a magnetic shielding apparatus equivalent to another embodiment of the invention.
Figure 21:
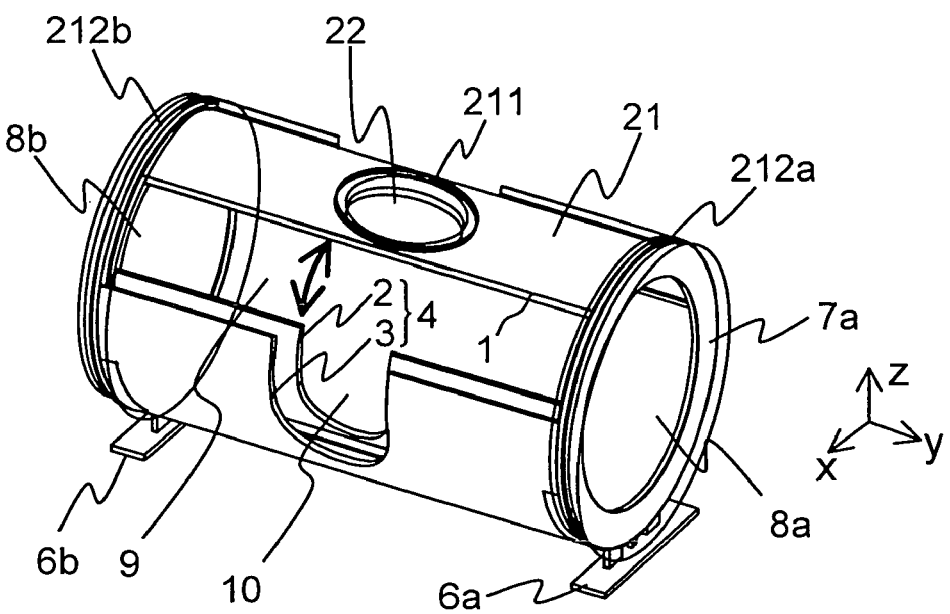
FIGS. 21A and 21B show the main configuration of a magnetic shielding apparatus equivalent to the other embodiment of the invention.
Figure 21:
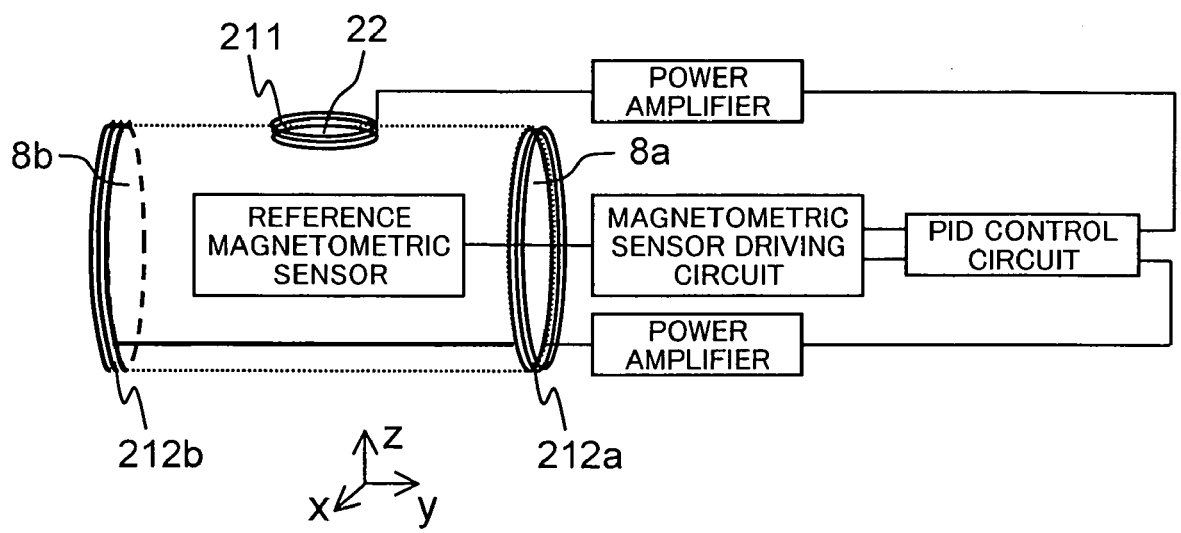

The movement in a direction of the z-axis of the top plate 121 is controlled by the control lever 128 arranged on the top plate bearer 127c arranged on this side. The top plate support moving parts 127a, 127b are housed and held in each concave portion arranged in the bed supporting plate 130. The concave portion formed on the bed supporting plate 130 is not shown in FIGS. 10, 12, 15 to 18 described later, however, it is shown in FIGS. 13, 14 and 20 described later. The top plate support moving parts 127a, 127b include the pneumatic or hydraulic pump made of non-magnetic material such as aluminum and SUS. The pneumatic or hydraulic pump is controlled by the control lever 128.

The magnetic shielding apparatus, the bed part and the gantry part are arranged mutually independently to prevent the mutual application of a load. A load of the magnetic shielding apparatus is supported by the shield bases 6a, 6b, a load of the bed part is supported by the top plate support moving parts 127a, 127b, and a load of the gantry part is supported by the gantry supports 112a, 112b.

The bed part is hold by the bed supporting plate 130. The gantry 112 connected to the top plate support moving parts 127a, 127b, the top plate bearer 127c and the gantry supports 112a, 112b is held by the bed supporting plate 130. The locking mechanism 1103 arranged in the positive or negative area of the y-axis is held on this side of the bed supporting plate 130. Further, a carriage insertion opening 129 through which a lower part (not shown) of a carriage (not shown) for carrying in a state in which the cryostat 111 is held at arbitrary height can be inserted into a lower part of the bed part is formed on this side of the bed supporting plate 130.

A mechanism for moving the top plate 121 in the directions of the x-, y- and z-axes and a mechanism for revolving the revolving door 4 will be described in detail later.

Next, a procedure for installing the cryostat 111 in the gantry 112 will be described in detail including the description of a part of a procedure for assembling the magnetic shielding apparatus and a part of the structure of the apparatus.

First, a case that the one-layer auxiliary cylinder 23 on which the flange-type plate 24 is formed is magnetically connected to the cylindrical shield 1 and is arranged so that the auxiliary cylinder encircles the opening 22 as in the magnetic shielding apparatus shown in FIGS. 1 to 5 or a case that multilayer auxiliary cylinders on which a flange-type plate is formed like the flange-type plate 24, for example the two-layer auxiliary cylinders 23-1, 23-2 are magnetically connected to the cylindrical shield 1 and are arranged so that the cylinders encircle the opening 22 as in the magnetic shielding apparatus shown in FIGS. 10 to 17 will be described (hereinafter called an installation procedure 1).

The carriage has a cryostat support that receives a front of the flange 116 and can fix and hold a circumferential part of the cryostat 111 over the flange 116. The height in the direction of the z-axis of the cryostat support of the carriage is adjusted, the cryostat 111 is received from a cryostat work bench (which has a form that receives the flange 116 and to which the cryostat is fixed and held), and is fixed to the carriage. The carriage that holds the cryostat 111 at predetermined height is moved along the x-axis and a lower part of the carriage is inserted into the carriage insertion opening 129.

The cryostat is inserted inside the one- or multilayer (for example, two-layer) auxiliary cylinders magnetically connected to the cylindrical shield 1 from the upside by moving the carriage along the direction of the x-, y- or z-axis if necessary and the flange 116 is inserted and fixed into/to a circular arc part on the upside of the gantry 112. The top faces of the one- or multilayer auxiliary cylinders are arranged on the downside of the circular arc part on the upside of the gantry 112 (see FIGS. 13 and 14).

In case it is difficult to detach the one- or multilayer auxiliary cylinders connected to the cylindrical shield 1 or in case the one- or multilayer auxiliary cylinders are manufactured in design in which it is not supposed to detach the auxiliary cylinders, the cryostat 111 is installed according to the above-mentioned procedure (the detachment will be described later). In this case, compared with an installation procedure 2 (the detachment will be described later) described below, excessive height is required in a location in which the cylindrical shield is installed.

The installation procedure 2 (the detachment will be described later) can be applied in case the one- or multilayer auxiliary cylinders are manufactured in design in which it is supposed to detach the auxiliary cylinders connected to the cylindrical shield 1. One example that an auxiliary cylinder is manufactured by dividing it in two and can be connected or detached to/from the cylindrical shield 1 will be described below. In this example, operation in a horizontal direction is main and this example has no strict condition on height in a location in which the cylindrical shield is installed. In addition to the following example, various methods are possible.

Next, a case that the opening 22 formed on the cylindrical shield 1 of the magnetic shielding apparatus shown in FIGS. 1 to 5, FIGS. 13 and 14 is formed by a different method will be described (hereinafter called the installation procedure 2). Differently from the installation procedure 1, in the installation procedure 2, a U-shaped cutout having the width of the diameter of the opening 22, having a straight part in contact with the opening 22 and perpendicular to the portion closer to the opening 22 and connected to the opening 22 is formed in the portion closer to the opening out of the two portions parallel to the central axis of the cylindrical shield 1 and described in relation to FIG. 2A in place of forming the opening 22 formed on the cylindrical shield 1.

First and second auxiliary plates for closing a part except the opening 22 of the U-shaped cutout of the cylindrical shield 1 are prepared beforehand. The first and second auxiliary plates respectively have a circumferential face having the same radius of curvature as the inner surface and the outer face of the circumferential part of the cylindrical shield 1.

In case the one-layer auxiliary cylinder 23 (see FIGS. 1 to 5) on which the flange-type plate 24 is formed is used (hereinafter called an installation procedure 2a), the auxiliary cylinder 23 on which the flange-type plate 24 is formed is configured by first and second divided bodies acquired by dividing the auxiliary cylinder 23 on which the flange-type plate 24 is formed together with the flange-type plate 24 on a plane passing the central axis of the auxiliary cylinder 23 and parallel to the central axis for example. A flange-type plate of the first divided body is magnetically connected to the outside face of the circumferential part of the cylindrical shield 1 beforehand as described in relation to FIG. 2A.

The flange 116 of the cryostat 111 is inserted and fixed into/to the circular arc part on the upside of the gantry 112 by inserting the cryostat inside the first divided body magnetically connected to the cylindrical shield 1 from the front side or the upside by moving the carriage holding the cryostat 111 at the predetermined height along the direction of the x-, y- or z-axis if necessary as in the installation procedure 1.

Next, as described in relation to FIG. 2A, a first auxiliary plate is magnetically connected to the straight part of the U-shaped cutout on the inner surface of the circumferential part of the cylindrical shield 1 and a second auxiliary plate is magnetically connected to the straight part of the U-shaped cutout on the outer surface of the circumferential part of the cylindrical shield 1. A flange-type plate of the second divided body is magnetically connected to the second auxiliary plate and/or the outer surface of the circumferential part of the cylindrical shield 1, the flange-type plate of the second divided body and the flange-type plate of the first divided body are magnetically connected, and an auxiliary cylinder of the second divided body and an auxiliary cylinder of the first divided body are magnetically connected.

In case multilayer auxiliary cylinders, for example, the two-layer auxiliary cylinders 23-1, 23-2 (see FIGS. 13 and 14) are used (hereinafter called an installation procedure 2b), the auxiliary cylinders 23-1, 23-2 on which a flange-type plate is respectively formed are configured by first and second divided bodies of the auxiliary cylinder 23-1 and first and second divided bodies of the auxiliary cylinder 23-2 acquired by dividing the auxiliary cylinders 23-1, 23-2 on which the flange-type plate is respectively formed together with the flange-type plate on a plane passing each central axis of the auxiliary cylinders 23-1, 23-2 and parallel to each central axis for example.

The flange-type plate of the first divided body of the auxiliary cylinder 23-1 is magnetically connected to the inner surface of the circumferential part of the cylindrical shield 1 beforehand as described in relation to FIG. 8C. The flange-type plate of the first divided body of the auxiliary cylinder 23-2 is magnetically connected to the outer surface of the circumferential part of the cylindrical shield 1 beforehand as described in relation to FIG. 8C.

As in the installation procedure 1 and the installation procedure 2a, the flange 116 of the cryostat 111 is inserted and fixed into/to the circular arc part on the upside of the gantry 112 by inserting the cryostat inside the first divided body of the auxiliary cylinder 23-1 magnetically connected to the cylindrical shield 1 from the front side or the upside by moving the carriage holding the cryostat 111 at the predetermined height along the direction of the x-, y- or z-axis if necessary.

Next, as in the installation procedure 2a, a first auxiliary plate is magnetically connected to a straight part of a U-shaped cutout on the inner surface of the circumferential part of the cylindrical shield 1 and a second auxiliary plate is magnetically connected to the straight part of the U-shaped cutout on the outer surface of the circumferential part of the cylindrical shield 1.

Next, as described in relation to FIG. 8C, the flange-type plate of the second divided body of the auxiliary cylinder 23-1 is magnetically connected to the first auxiliary plate and/or the inner surface of the circumferential part of the cylindrical shield 1 and is magnetically connected to the flange-type plate of the first divided body of the auxiliary cylinder 23-1. An auxiliary cylinder of the second divided body of the auxiliary cylinder 23-1 and an auxiliary cylinder of the first divided body of the auxiliary cylinder 23-1 are magnetically connected.

Similarly, the flange-type plate of the second divided body of the auxiliary cylinder 23-2 is magnetically connected to the second auxiliary plate and/or the outer surface of the circumferential part of the cylindrical shield 1 and is magnetically connected to the flange-type plate of the first divided body of the auxiliary cylinder 23-2. An auxiliary cylinder of the second divided body of the auxiliary cylinder 23-2 and an auxiliary cylinder of the first divided body of the auxiliary cylinder 23-2 are magnetically connected.

As described above, the cryostat 111 that holds and houses the SQUID fluxmeter at low temperature is supported and fixed by/to the gantry 112 via the inside of the one- or multilayer auxiliary cylinders, and the bottom of the cryostat 111 is arranged in a predetermined position inside the magnetic shielding apparatus 1101.

Next, an exhaust unit 115 provided with a function for monitoring and adjusting-pressure in the cryostat 111 is attached to the rear of the gantry 112 along the orientation of arrows shown in FIG. 11. The upper cover 113, the front cover 114 respectively for protecting the gantry 112 and the gantry 112 are attached along the orientation of the arrows shown in FIG. 11.

A flat cutout is formed in opposite two parts in a direction parallel to the central axis of the magnetic shielding apparatus 1101 on the side of the bottom of the cryostat 111 (parts in positive and negative areas of the y-axis) and in a part close to the opening into which an object of examination is inserted of the magnetic shielding apparatus 1101 (apart in a positive area of the x-axis)(see FIGS. 10, 11, 13, 14 and FIGS. 15 to 20 described later). The flat cutout formed in three portions on the side of the bottom of the cryostat 111 is arranged considering that the volume of a refrigerant housed in the cryostat 111 becomes as much as possible to prevent the object of examination from having oppressive feeling as much as possible.

Next, a procedure for detaching the cryostat 111 from the gantry 112 will be described in detail. The procedure for detachment is basically executed in order reverse to the procedure for installing the cryostat in the gantry.

First, preparatory work for detachment will be performed. As shown in FIG. 10, the revolving door 4 of the magnetic shielding apparatus is completely opened. The front cover 114 and the upper cover 113 are detached in orientation reverse to the orientation of the arrows shown in FIG. 11. The fixing of the flange 116 of the cryostat 111 and the circular arc part on the upside of the gantry 112 is released.

A detachment procedure 1 corresponding to the installation procedure 1 will be described below. The carriage in which the cryostat support is adjusted at desired height is moved along the x-axis, the lower part of the carriage is inserted into the carriage insertion opening 129, and when the front of the flange 116 is received by the cryostat support and a circumferential part of the cryostat 111 on the upside of the flange 116 is held, the cryostat 111 is held and fixed by the cryostat support.

After the cryostat support is moved upward and the cryostat 111 is pulled out of the inside of the one- or multilayer auxiliary cylinders, the lower part of the carriage is moved in a direction in which the lower part is pulled out of the carriage insertion opening 129, the cryostat support is moved downward, and the cryostat 111 is inserted and fixed into/to the cryostat work bench.

A detachment procedure 2 corresponding to the installation procedure 2 will be described below. After preparatory work for detachment is finished, the first and second auxiliary plates closing a part except the opening 22 of the U-shaped cutout, the flange-type plate of the second divided body and the auxiliary cylinder of the second divided body are detached. As a result, the front of the one-or multilayer auxiliary cylinders is detached and the front of the cryostat 111 is released. In this state, as in the detachment procedure 1, the cryostat 111 is held and fixed by the cryostat support of the carriage. After the cryostat support is slightly moved upward and the flange 116 is lifted from the circular arc part of the gantry 112, the lower part of the carriage is moved in the direction in which the lower part is pulled out of the carriage insertion opening 129 and as in the detachment procedure 1, the cryostat 111 is inserted and fixed into/to the cryostat work bench.

FIGS. 15A to 15D are explanatory drawings for explaining the measurement of a magnetic field generated from a heart of an object of examination (hereinafter called a cardiac magnetic field) by the biomagnetism measuring device shown in FIG. 10. FIGS. 15A to 15D show a state in which the revolving door 4 of the magnetic shielding apparatus shown in FIGS. 10 to 15 is completely opened (see FIG. 3).

FIGS. 15A and 15B are the explanatory drawings for explaining the measurement of a cardiac magnetic field from the object of examination 151 lying on his/her back on the top plate 121 and FIGS. 15C and 15D are the explanatory drawings for explaining the measurement of a cardiac magnetic field from the object of examination 151 lying with his/her face down on the top plate 121.

FIGS. 15A and 15C are perspective views and FIGS. 15B and 15D are front views viewed from a direction of the x-axis.

In FIGS. 15A and 15B, the object of examination 151 lies on high/her back on the top plate 121. After the position on a plane parallel to an XY plane of the top plate 121 and the position in a direction of the z-axis of the top plate bearer 125 are adjusted so that a chest of the object of examination 151 and the bottom of the SQUID fluxmeter 131 approach, the revolving door 4 is closed and a cardiac magnetic field is measured.

In FIGS. 15C and 15D, an object of examination 152 lies with his/her face down on the top plate 121. After a position on the plane parallel to the XY plane of the top plate 121 and a position in the direction of the z-axis of the top plate bearer 125 are adjusted as in FIGS. 15A and 15B so that the back of the back of the object of examination 152 and the bottom of the SQUID fluxmeter 131 approach, the revolving door 4 is closed and a cardiac magnetic field is measured. The distribution of current flowing in the heart can be more precisely measured by the measurement of the cardiac magnetic field from both of the chest and the back.

FIGS. 16A to 16F are perspective views for explaining a procedure for measuring a cardiac magnetic field using the biomagnetism measuring device shown in FIG. 10.

FIGS. 16A to 16D show a state in which the revolving door 4 of the magnetic shielding apparatus is completely opened (see FIG. 3), FIG. 16E shows a state in which the revolving door 4 is open by a half (see FIG. 1), and FIG. 16F shows a state in which the revolving door 4 is completely closed (see FIG. 4).

First, as shown in FIG. 16A, after the top plate 121 is pulled out of the magnetic shielding apparatus in a positive direction of the x-axis and the top plate 121 is locked to prevent the top plate from being moved, the fence 124 is pushed down and an object of examination 151 is told to lie. At this time, the object of examination 151 is told to lie on his/her back so that the axis of the body of the object of examination 151 is substantially parallel to the y-axis. The object of examination 151 is told to direct his/her feet toward the fence 123. This reason is that his/her feet are more apt to stick out of the top plate 121 than his/her head in case the object of examination 151 is very tall and the feet of the object of examination 151 are prevented from colliding with particularly the revolving part 7b (see FIGS. 10 and 13) of the magnetic shielding apparatus when the top plate 121 is inserted into the inside of the magnetic shielding apparatus.

As shown in FIG. 16A, when the object of examination lies on his/her back on the top plate 121, the fence 124 is pulled up, after the locking of the top plate 121 is released, the top plate 121 is moved in a negative direction of the x-axis, is inserted into the inside of the magnetic shielding apparatus, and alignment in a direction of the x-axis is performed.

After the alignment in the direction of the x-axis is finished, the top plate 121 is moved in a direction of the y-axis and alignment in the direction of the y-axis is performed. FIG. 16C shows a state in which the alignment in the directions of the x-axis and the y-axis is finished.

After the alignment in the directions of the x-axis and the y-axis is finished, the top plate 121 is lifted or lowered in a direction of the z-axis using the control lever 128 and the surface of the chest of the object of examination 151 is made to approach the vicinity of the bottom of the cryostat 111. FIG. 16D shows a state in which alignment in three directions of the x-, y- and z-axes is finished.

The alignment in the directions of the x-, y- and z-axes is performed by only visual observation, by identification by visual observation or by optical or/and electric automatic identification using one light source not shown that radiates a linear laser beam, two light sources not shown that radiate a sectorial laser beam and a laser marker accompanied with the surface of the body of the object of examination.

After the alignment in the three directions of the x-, y- and z-axes is finished, the revolving handle 1102a or 1102b is revolved, a state of the object of examination is observed in a state in which the revolving door 4 is turned open by a half from a completely opened state as shown in FIGS. 16D, 16E and 16F, and the revolving door 4 is locked manually or automatically in a state in which the revolving door 4 is completely closed. In this state, the measurement of a cardiac magnetic field is started.

After the measurement of the cardiac magnetic field is finished, the locking of the revolving door 4 is released by the locking mechanism 1103, the revolving door 4 is completely opened (a state shown in FIG. 16C), the top plate 121 is slowly lowered in the direction of the z-axis, next the top plate 121 is moved in the direction of the y-axis to restore to a state shown in FIG. 16B, next the top plate 121 is pulled out in the positive direction of the x-axis to restore to a state shown in FIG. 16A, the top plate 121 is locked to prevent it from moving, next the fence 124 is pushed down, the object of examination 151 is gotten to get out of the top plate 121, and a series of measurement is finished.

FIG. 17 is a perspective view showing the whole configuration of the biomagnetism measuring device equivalent to the embodiment of the invention. FIG. 17 shows a state in which the revolving door 4 of the magnetic shielding apparatus is completely opened as in FIG. 10 (see FIG. 3), and shows a state in which the top plate 121 is pulled out of magnetic shielding apparatus.

FIG. 17 shows the whole configuration of a biomagnetism measuring device in which a SQUID driving circuit 171, a processor (a computer) 172, a display 173 and an input device 174 are connected to the biomagnetism measuring device 1101 shown in FIG. 10. However, in FIG. 17, to simplify the drawing intelligibly, wiring connecting the biomagnetism measuring device, the SQUID driving circuit 171, the processor 172, the display 173 and the input device 174 is not shown.

The driving of the singular or plural SQUID fluxmeters 131 is controlled by the SQUID driving circuit 171. After a magnetic signal detected by the SQUID fluxmeter 131 is stored in a storage of the processor 172 as a digital signal, the magnetic signal is analyzed by the processor 172. The result of analysis is displayed on the display 173. A driving parameter of the SQUID driving circuit 171 can be changed and the contents of the screen of the display 173 can be changed respectively by a parameter input via the input device 174.

Figure 18:
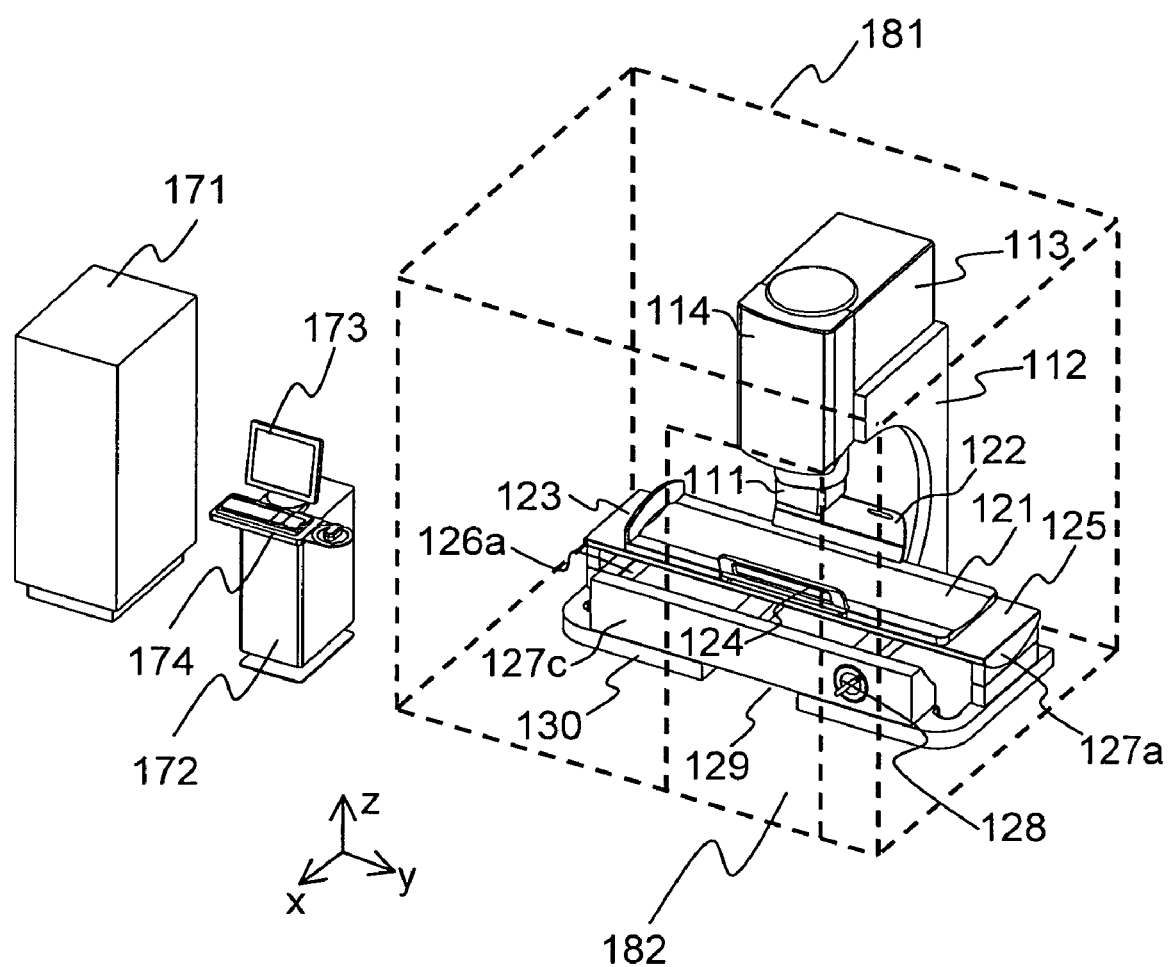
FIG. 18 is a perspective view showing the whole configuration of a biomagnetism measuring device equivalent to another embodiment of the invention.

FIG. 18 is a perspective view showing the whole configuration of a biomagnetism measuring device equivalent to another embodiment of the invention.

FIG. 18 shows the biomagnetism measuring device using a magnetic shielding chamber 181 shown by a dotted line in place of the magnetic shielding apparatus 1101 in the magnetic shielding apparatus 1101 in the biomagnetism measuring device shown in FIG. 17.

In FIG. 18, to make positional relation among components plain, the magnetic shielding chamber 181 is shown by the dotted line. The magnetic shielding chamber 181 is configured by two- or three-layer Permalloy plates approximately 2 mm thick and a one-layer aluminum plate approximately 1 mm thick. The longitudinal and lateral dimensions and the dimension of the height on a floor of the magnetic shielding chamber 181 are approximately 2 m and the weight is approximately 2000 kg.

The magnetic shielding chamber 181 is imposing and enormous, however, the magnetic shielding chamber has effect that its magnetic shielding factor is high, its internal space is large and the distortion caused by the influence of an environmental magnetic shield of a magnetic field generated from the object of examination is small. After a door 182 of the magnetic shielding chamber 181 is closed, the magnetic field generated from the object of examination is measured.

In the biomagnetism measuring device shown in FIG. 18, the configuration shown in FIGS. 10 to 17, configuration acquired by removing the cylindrical shields 1, 2, 3 forming the magnetic shielding apparatus and the mechanism for driving the revolving door 4 from configuration shown in FIGS. 19 and 20 described later, that is, the cryostat and the gantry respectively shown in FIG. 11 and the bed shown in FIG. 12 are arranged inside the magnetic shielding chamber 181. The configuration of a cryostat shown in FIGS. 19 and 20 described later can be adopted. A SQUID driving circuit 171, a computer 172, a display 173 and an input device 174 are the same as the configuration shown in FIG. 4 and are arranged outside the magnetic shielding chamber 181.

Therefore, effect that even if a leakage magnetic field that invades the inside of the magnetic shielding chamber 181 exists, it can be prevented from invading a measurement face is acquired. Besides, as an examination engineer can select and use a control lever and a moving button on a top plate bearer 127c in a front position of a bed if necessary, observing an object of examination and can control the adjustment of a position in three directions of the x-, y- and z-axes of a top plate 121, the object of examination does not feel uneasy. Needless to say, the examination engineer can also adjust the position in the three directions of the x-, y- and z-axes of the top plate 121 manually in the front position of the bed, observing the object of examination.

FIGS. 19A to 19C are perspective views showing examples of the configuration of the inside of a cryostat used in the biomagnetism measuring device equivalent to this embodiment of the invention. In FIGS. 19A to 19C, to make a state of the layout of a superconducting loop inside the cryostat plain, the outline of the cryostat 111 is shown by a dotted line. A plane formed by the superconducting loop and the measurement face by singular or plural SQUID fluxmeters are arranged in parallel.

FIG. 19A shows an example of configuration that the superconducting loop 191 is arranged over plural SQUID fluxmeters 131, FIG. 19B shows an example of configuration that a net superconducting loop 192 is arranged over plural SQUID fluxmeters 131, and FIG. 19C shows an example of configuration that a superconducting loop 193 is arranged encircling plural SQUID fluxmeters 131.

In FIGS. 19A to 19C, to screen an environmental magnetic field in the vicinity of the plural SQUID fluxmeters 131, the superconducting loops are arranged inside the cryostat 111 and the cryostat holds the superconducting loops together with the plural SQUID fluxmeters 131 at low temperature. It is desirable that the plane formed by each superconducting loop is parallel to a face of a detection coil not shown forming the SQUID fluxmeter 131. Inside the cryostat 111, temperature in the vicinity of the SQUID fluxmeter 131 is required to be held at temperature equal to or below the superconductive transition temperature of superconductive material forming the SQUID fluxmeter 131. As plural SQUID fluxmeters 131 and the superconducting loop are arranged inside the same cryostat 111, the cryostat for cooling only the superconducting loop is not required.

As the superconducting loop has a property that shielding current spontaneously flows in the superconducting loop so that a magnetic flux piercing the superconducting loop is constantly kept fixed, an environmental magnetic field in the vicinity of the SQUID fluxmeter 131 can be screened by the superconducting loop owing to the arrangement shown in FIGS. 19A to 19C. As the superconducting loop has spontaneous magnetic field shielding action only by cooling the superconducting loop at temperature equal to or below the superconductive transition temperature of a superconductor forming the superconducting loop, no control from an external device is required.

In FIG. 19A, a leakage magnetic field that invades the SQUID fluxmeter 131 from the upside can be screened by the superconducting loop 191. In FIG. 19B, a large magnetic field shielding factor can be secured by using the net superconducting loop 192 and a leakage magnetic field that invades the SQUID fluxmeter 131 from the upside can be more effectively screened than that in the example of the configuration shown in FIG. 19A. In the example of the configuration shown in FIG. 19C, as in the examples of the configuration shown in FIGS. 19A and 19B, a leakage magnetic field that invades the vicinity of the SQUID fluxmeter 131 can be also screened. In place of the superconducting loop 193, a loop made of a net superconductor like the net superconducting loop 192 shown in FIG. 19B may be also arranged in a state in which the loop encircles the SQUID fluxmeter 131.

Further, the examples of the configuration shown in FIGS. 19A to 19C can be also applied to the apparatuses shown in FIGS. 1 to 5, FIGS. 10 to 18 and FIGS. 21 and 22 described later. In case the examples of the configuration shown in FIGS. 19A and 19B are applied to the apparatuses shown in FIGS. 1 to 5, FIGS. 10 to 17 and FIGS. 21 and 22 described later, a leakage magnetic field that invades the inside of the magnetic shielding apparatus from the open end (an opening 22 in the case of an apparatus shown in FIGS. 21A and 21B and a right open end in the case of an apparatus shown in FIG. 22) on the upside of the auxiliary cylinder 23 or the auxiliary cylinders 23-1, 23-2 can be more effectively screened by arranging the superconducting loop 191 or the net superconducting loop 192 arranged inside the cryostat 111 in the vicinity of the cylindrical shield 3.

Besides, a leakage magnetic field that invades the inside of the magnetic shielding apparatus from the open end (the opening 22 in the case of the apparatus shown in FIGS. 21A and 21B and the right open end in the case of the apparatus shown in FIG. 22) on the upside of the auxiliary cylinder 23 or the auxiliary cylinders 23-1, 23-2 can be more effectively screened by arranging the superconducting loop 191 or the net superconducting loop 192 arranged inside the cryostat 111 between the outside high-permeability material 3-1 of the circumferential part of the cylindrical shield 3 and the inside high-permeability material 3-2 of the circumferential part.

It is desirable that the superconducting loop is manufactured by connecting both ends of a superconducting member such as superconducting wire in a superconductive state, however, the superconducting loop may be also manufactured by soldering.

To install the superconducting loops 191, 193 inside each cryostat, there are methods of (1) a method of manufacturing the cryostat so that the superconducting loop is finally put inside the cryostat, (2) a method of inserting the manufactured superconducting loop from the opening of the cryostat and installing it and (3) a method of inserting a superconducting member inside the cryostat and connecting both ends of the superconducting member inside the cryostat in a superconductive state or by soldering. However, in case the inside diameter of an opening at an entrance of inside one of a double container is smaller than the inside diameter of the bottom like a cryostat 111 shown in FIG. 20 described later, the above-mentioned method (1) or (2) is desirable. As a superconducting loop manufactured by the superconducting wire can be generally transformed, the superconducting loop can be also installed inside the cryostat 111 by the method (2). Besides, to install the net superconducting loop 192 inside the cryostat, the above-mentioned method (1) or (2) is desirable.

FIG. 20 is a sectional view viewed on a ZY plane showing the configuration of a magnetic shielding apparatus equivalent to another embodiment of the invention. In the magnetic shielding apparatus shown in FIG. 20, the auxiliary cylinder 23 or the auxiliary cylinders 23-1, 23-2 configuring the apparatuses shown in FIGS. 1 to 5, FIGS. 10 to 17 and FIG. 22 and described later are not used, a superconducting loop 1201 is arranged inside a cryostat 111, and an environmental magnetic field that invades the inside of the magnetic shielding apparatus from an opening 22 into which the cryostat 111 is inserted is screened.

The size described below of the magnetic shielding apparatus shown in FIG. 20 is substantially the same as the size of the above-mentioned second model shown in FIG. 8B.

Figure 22:
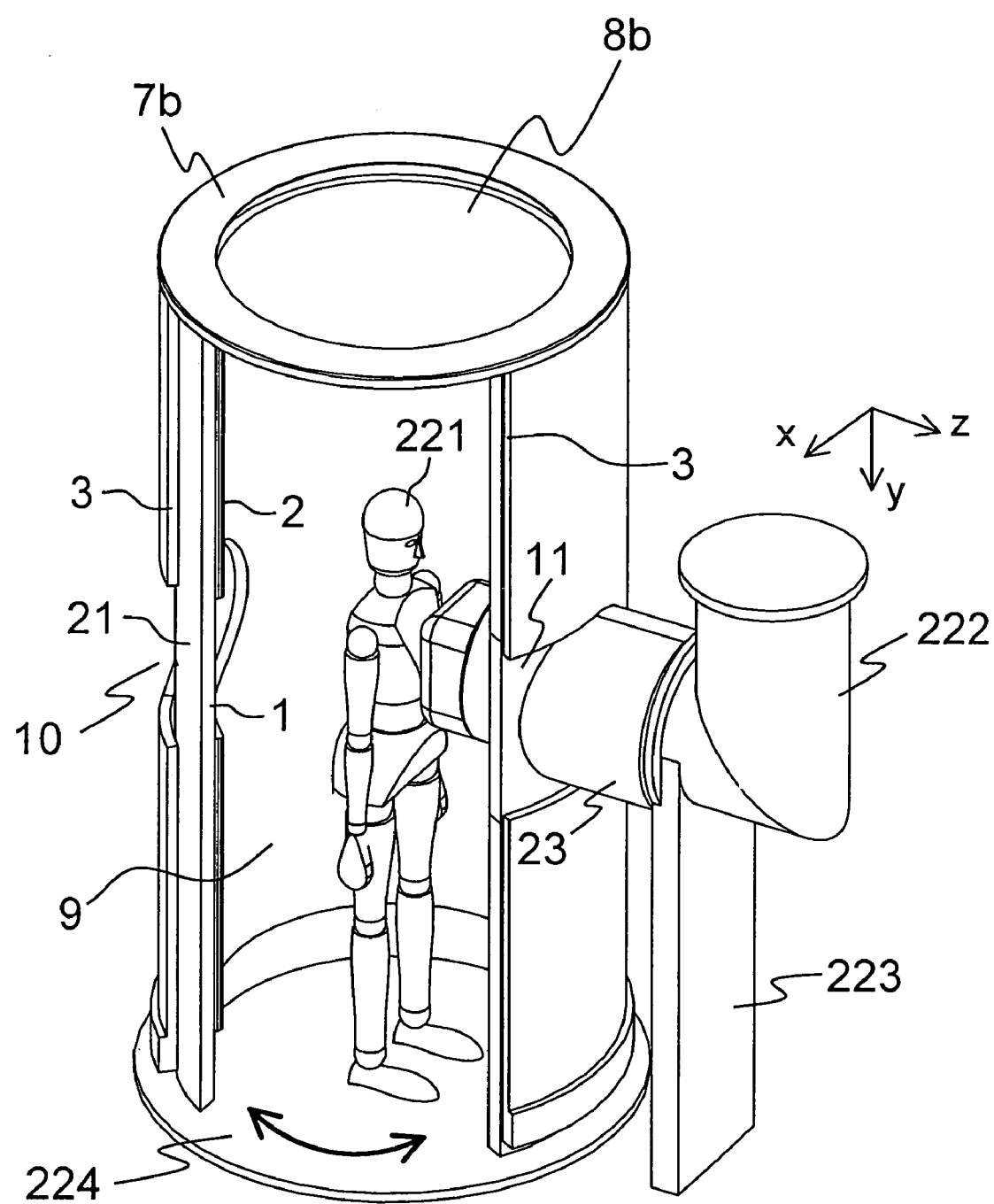
FIG. 22 is a perspective view showing the configuration of a main part of a biomagnetism measuring device equivalent to the other embodiment of the invention.

As in the example of the configuration shown in FIG. 19A, the superconducting loop 1201 is arranged above a SQUID fluxmeter 131 (on the right side in FIG. 22), is cooled at low temperature, and screens an environmental magnetic field that invades the SQUID fluxmeter 131 from the upside (from the right side in FIG. 22). As shown in FIG. 20, it is desirable that the superconducting loop 1201 is arranged in the vicinity of the opening 22. In place of the superconducting loop 1201, a net superconducting loop having the similar configuration to that of the net superconducting loop 192 in the example of the configuration shown in FIG. 19B can be used.

In the example of the above-mentioned configuration shown in FIG. 20, a leakage magnetic field that invades the inside of the magnetic shielding apparatus from the opening 22 can be more effectively screened by arranging the superconducting loop 1201 or the net superconducting loop between the outside high-permeability material 3-1 of the circumferential part of the cylindrical shield 3 and the inside high-permeability material 3-2 of the circumferential part.

Besides, the example of the configuration shown in FIG. 20 can be also applied to the apparatuses shown in FIGS. 1 to 5, FIGS. 10 to 18 and FIGS. 21 and 22 described later. In case the example of the configuration shown in FIG. 20 is applied to the apparatuses shown in FIGS. 1 to 5, FIGS. 10 to 17 and FIGS. 21 and 22 described later, a leakage magnetic field that invades the inside of the magnetic shielding apparatus from the open end (the opening 22 in the case of the apparatus shown in FIGS. 21A and 21B and the right open end in the case of the apparatus shown in FIG. 22) on the upside of the auxiliary cylinder 23 or the auxiliary cylinders 23-1, 23-2 can be effectively screened by arranging the superconducting loop 1201 or the net superconducting loop arranged inside the cryostat 111 in the vicinity of the cylindrical shield 3.

Besides, a leakage magnetic field that invades the inside of the magnetic shielding apparatus from the open end (the opening 22 in the case of the apparatus shown in FIGS. 21A and 21B and the right open end in the case of the apparatus shown in FIG. 22) on the upside of the auxiliary cylinder 23 or the auxiliary cylinders 23-1, 23-2 can be more effectively screened by arranging the superconducting loop 102 or the net superconducting loop between the outside high-permeability material 3-1 of the circumferential part of the cylindrical shield 3 and the inside high-permeability material 3-2 of the circumferential part.

Further, in the case of application to the apparatuses shown in FIGS. 1 to 5, FIGS. 10 to 17 and FIG. 22 described later, a leakage magnetic field that invades the inside of the magnetic shielding apparatus from the open end (the right open end in the case of the apparatus shown in FIG. 22) on the upside of the auxiliary cylinder 23 or the auxiliary cylinders 23-1, 23-2 can be also more effectively screened by arranging the superconducting loop 1201 or the net superconducting loop arranged inside the cryostat 111 in place of arranging it in the vicinity of the cylindrical shield 3 at the open end (the right open end in the case of the apparatus shown in FIG. 22) on the upside of the auxiliary cylinder 23 or the auxiliary cylinders 23-1, 23-2.

Further, in the case of application to the apparatuses shown in FIGS. 1 to 5, FIGS. 10 to 17 and FIG. 22 described later, a leakage magnetic field that invades the inside of the magnetic shielding apparatus from the open end (the right open end in the case of the apparatus shown in FIG. 22) on the upside of the auxiliary cylinder 23 or the auxiliary cylinders 23-1, 23-2 can be also more effectively screened by arranging the superconducting loop 1201 or the net superconducting loop at the open end (the right open end in the case of the apparatus shown in FIG. 22) on the upside of the auxiliary cylinder 23 or the auxiliary cylinders 23-1, 23-2 outside the cryostat 111 without using the superconducting loop 1201 or the net superconducting loop arranged inside the cryostat 111.

FIGS. 21A and 21B show the main configuration of a magnetic shielding apparatus equivalent to the other embodiment of the invention.

FIG. 21A is a perspective view showing the magnetic shielding apparatus and shows a state in which a revolving door 4 is open by a half (see FIG. 1). FIG. 21B is a perspective view (see FIG. 4) showing the magnetic shielding apparatus in a state in which the revolving door 4 is completely closed including a block diagram showing the main configuration of the magnetic shielding apparatus. In FIG. 21B, to clarify the arrangement of active compensating coils 1211, 212a, 212b, revolving parts 7a, 7b and shield bases 6a, 6b are omitted, and the outline of a cylinder formed in a state in which the revolving door 4 of the magnetic shielding apparatus is completely closed is shown by a dotted line.

The size described below in relation to FIGS. 21A and 21B of the magnetic shielding apparatus is substantially the same as the above-mentioned size of the second model shown in FIG. 8B.

In the magnetic shielding apparatus shown in FIGS. 21A and 21B, the active compensating coil 1211 is arranged in the vicinity of the opening 22 of the cylindrical shield 1 in place of the auxiliary cylinder 23 or the auxiliary cylinders 23-1, 23-2 of the apparatuses shown in FIGS. 1 to 5, FIGS. 10 to 17 and FIG. 22 described later and screens an environmental magnetic field that invades the inside of the magnetic shielding apparatus from the opening 22. For example, the active compensating coil 1211 can more effectively screen a leakage magnetic field that invades the inside of the magnetic shielding apparatus from the opening 22 by arranging the active compensating coil between the outside high-permeability material 1-1 of the circumferential part of the cylindrical shield 1 and the inside high-permeability material 1-2 of the circumferential part.

Besides, the active compensating coils 212a, 212b are arranged around the openings 8a, 8b (around an opening 8b in the apparatus shown in FIG. 22 and on a supporting plate 224 if necessary) at both ends of the central axis of the magnetic shielding apparatus and screen an environmental magnetic field that invades the inside of the magnetic shielding apparatus from the openings 8a, 8b. In case the length of the central axis of the magnetic shielding apparatus is long enough, the active compensating coils 212a, 212b are not required to be arranged when the magnitude of the environmental magnetic field that invades the vicinity of the center of the inside of the magnetic shielding apparatus from the openings 8a, 8b can be ignored.

A reference magnetic field sensor shown in FIG. 21B and arranged inside the magnetic shielding apparatus or in the vicinity of the openings 8a, 8b detects a component in a direction (a direction of the z-axis) perpendicular to a plane of the opening of an environmental magnetic field and a component in a direction (a direction of the y-axis) of the central axis of the magnetic shielding apparatus. For the reference magnetic field sensor, a SQUID fluxmeter or a flux-gate magnetometer is used.

The reference magnetic field sensor is driven by a magnetic field sensor driving circuit and magnetic signals of the component in the direction of the z-axis and the component in the direction of the y-axis respectively of an environmental magnetic field are transmitted to a PID control circuit. The PID control circuit adds each output of a comparator, an integrator and a differentiator. The gain of a signal output from the reference magnetic field sensor can be adjusted every frequency by suitably adjusting each gain of the comparator, the integrator and the differentiator.

Current output from the PID control circuit is amplified by a power amplifier and is transmitted to the active compensating coils 1211, 212a, 212b. A magnetic signal of the component in the direction of the z-axis of an environmental magnetic field is negatively fedback to the active compensating coil 1211 so that the component in the direction of the z-axis by the reference magnetic field sensor is 0 after suitable gain adjustment. Similarly, a magnetic signal of the component in the direction of the y-axis of an environmental magnetic field is negatively fedback to the active compensating coils 212a, 212b so that the component in the direction of the y-axis by the reference magnetic field sensor is 0.

In the above-mentioned configuration shown in FIGS. 21A and 21B, in place of the active compensating coils 1211, 212a, 212b, a superconducting loop can be also used. In this case, a leakage magnetic field from the opening 22 and the openings 8a, 8b can be screened by the superconducting loop, and the power amplifier, the reference magnetic field sensor, the magnetic field sensor driving circuit and the PID control circuit respectively shown in FIG. 21B are not required. However, as described in relation to FIGS. 19A to 19C, a cryostat for cooling the superconducting loop is not required. When the magnitude of an environmental magnetic field that invades the vicinity of the center of the inside of the magnetic shielding apparatus form the openings 8a, 8b can be ignored, no superconducting loop is required to be arranged in the vicinity of the openings 8a, 8b.

Further, in the apparatuses shown in FIGS. 1 to 5, FIGS. 10 to 17 and FIG. 22 described later, an active coil or a superconducting coil may be also arranged at least in one location in the vicinity of the open end (the right open end in FIG. 22) on the upside of the auxiliary cylinder 23 or the auxiliary cylinders 23-1, 23-2 and the openings 8a, 8b (the upper opening 8b and the upside of the supporting plate 224 respectively in FIG. 22).

As a result, a leakage magnetic field that invades the inside of the magnetic shielding apparatus at least from one location in the vicinity of the opening (the right opening in FIG. 22) on the upside of the auxiliary cylinder 23 or the auxiliary cylinders 23-1, 23-2 and the openings 8a, 8b (the opening 8b on the upside and the upside of the supporting plate 224 respectively shown in FIG. 22) can be more effectively screened.

Further, as described in relation to FIGS. 19A to 19C, the configuration shown in FIGS. 21A and 21B can be also applied to an apparatus to which the configuration shown in FIGS. 19A to 19C is applied. In this case, the superconducting loop inside the cryostat 111 shown in FIGS. 19A to 19C is not required to be necessarily arranged.

Further, as described in relation to FIG. 20, the configuration shown in FIGS. 21A and 21B can be also applied to an apparatus to which the configuration shown in FIG. 20 is applied. In this case, the superconducting loop inside the cryostat 111 shown in FIG. 20 is not required to be necessarily arranged.

FIG. 22 is a perspective view showing the configuration of a main part of a biomagnetism measuring device equivalent to the other embodiment of the invention.

In the magnetic shielding apparatuses shown in FIGS. 1 to 21, the central axis is arranged horizontally, however, in the magnetic shielding apparatus shown in FIG. 22, the central axis is arranged vertically. That is, in the biomagnetism measuring device using each magnetic shielding apparatus shown in FIGS. 1 to 21, measurement for an object of examination lying on his/her back or lying with his/her face down is made, however, in the biomagnetism measuring device shown in FIG. 22, measurement for an object of examination standing or seated is made. In the configuration shown in FIG. 22, a revolving door 4 acquired by integrating cylindrical shields 2, 3 can be revolved around the y-axis in directions shown by both arrows. FIG. 22 shows a state in which the revolving door 4 is open by a half in the directions shown by both arrows (see FIG. 1).

The size of the magnetic shielding apparatus shown in FIG. 22 and described below is substantially the same as the size of the apparatus shown in FIGS. 1 to 5 and described above.

The biomagnetism measuring device shown in FIG. 22 is largely different from the biomagnetism measuring device shown in FIG. 10 mainly in that the central axis of the magnetic shielding apparatus is perpendicular (horizontal in FIG. 10), no bed is used (used in FIG. 10), an L-type cryostat 222 is used (the linear cryostat 111 in FIG. 10), a measurement face is perpendicular (horizontal in FIG. 10) and the revolving door 4 is vertically revolved (revolved laterally in FIG. 10).

Though the biomagnetism measuring devices shown in FIGS. 22 and 10 have such difference, the magnetic shielding apparatus in the biomagnetism measuring device shown in FIG. 22 has substantially the similar configuration to that of the magnetic shielding apparatus shown in FIGS. 1 to 5. However, in FIG. 22, in place of the shield bases 6a, 6b shown in FIG. 1, the supporting plate 224 supports the weight of the magnetic shielding apparatus. The L-type cryostat 222 that holds plural SQUID fluxmeters arranged on a plane parallel to an XY plane at low temperature is supported by a gantry for the L type 223.

The gantry 223 is fixed on a floor. An auxiliary cylinder 23 is inserted into an opening 22 which is an opening for inserting the L-type cryostat 222 and screens an environmental magnetic field that invades the inside of the magnetic shielding apparatus from the opening 22. Multilayer auxiliary cylinders may be also used in place of the one-layer auxiliary cylinder 23. In place of the auxiliary cylinder 23, two-layer auxiliary cylinders 23-1, 23-2 may be also used.

A cutout having a flat portion is formed at least in four directions on an end face of the cryostat 222 on the side which an object of examination faces. That is, the cutouts in opposite two parts (parts in positive and negative areas of the y-axis) in directions parallel to the central axis of the magnetic shielding apparatus and the cutouts in opposite two parts (parts in positive and negative areas of the x-axis) in directions of the central axis of the auxiliary cylinder 23 and perpendicular to the central axis of the magnetic shielding apparatus are at least formed.

The cutouts (having a flat part) in four directions are formed so that the volume of a refrigerant housed in the cryostat 222 is increased as much as possible, considering so that the object of examination does not feel uneasy possibly.

After the object of examination 221 stands inside, brings his/her chest close to the end face of the L-type cryostat 222 and is at a standstill, the measurement of a cardiac magnetic field is executed. When a cardiac magnetic field is measured, the revolving door 4 composed of integrated cylindrical shields 2, 3 is closed as in the magnetic shielding apparatus shown in FIGS. 4 and 16F. In the device shown in FIG. 22, measurement is enabled in a state in which the object of examination 221 stands and the apparatus shown in FIG. 22 has effect that area occupied by the apparatus can be reduced, compared with the apparatuses shown in FIGS. 4 and 16F and in which measurement is performed in a state in which the object of examination lies on the bed on his/her back or with his/her face down.

In FIG. 22, as not top plate 121 for mounting the object of examination is used, a mechanism for moving the top plate 121 in the directions of the x-, y- and z-axes is not required. Though in FIG. 22, the details of a mechanism for revolving the revolving door 4 are not shown, the similar revolving mechanism to the revolving mechanism used in the magnetic shielding apparatus of the biomagnetism measuring device shown in FIG. 10 is applied.

Besides, in FIG. 22, a chair for the object of examination to sit can be used and a moving mechanism for moving the chair in the directions of the x-, y- and z-axes and a revolving mechanism for revolving the chair around an axis parallel to the y-axis can be used.

The area of the supporting plate 224 is increased and the gantry 223 may be also fixed onto the supporting plate 224. Besides, the supporting plate 224 and the gantry 223 are fixed onto a metallic plate (for example, an aluminum plate approximately 1 cm thick) and the metallic plate may be also put on the floor to disperse pressure.

In the above-mentioned embodiments, the measurement of a cardiac magnetic field has been described as an example, however, the biomagnetism measuring devices equivalent to the embodiments of the invention can be applied to the measurement of a magnetic field generated from the brain of the object of examination because of the activity of cranial nerves (hereinafter called a cerebral magnetic field) and the measurement of a cardiac magnetic field and a cerebral magnetic field of an unborn baby in the mother's body. Besides, in the above-mentioned embodiments, the auxiliary cylinders 23, 23-1, 23-2 and the cylindrical shields 1, 2, 3 have been described as a cylinder type the cross section of which on a plane perpendicular to their central axes is circular, however, they may be also a box type the cross section of which is elliptic and oval and which is a polygon having the number of sides of 4, 6, 8.

Further, the components described in relation to each drawing described above may be also combined. For example, the superconducting loops 191, 193 and the net superconducting loop 192 respectively shown in FIGS. 19A to 19C and the superconducting loop 1201 shown in FIG. 20 can be arranged inside each cryostat 111 shown in FIGS. 10, 11 and FIGS. 13 to 18, inside the cryostat shown in FIG. 22 and further, inside the cryostat used in the apparatus shown in FIGS. 21A and 21B.

Besides, the bed supporting plate 130 shown in FIG. 10, FIGS. 12 to 18 and FIG. 20 is fixed to a metallic plate (for example, an aluminum plate approximately 1 cm thick) or the bed supporting plate 130 itself is made of a thick metallic plate (for example, an aluminum plate approximately 1 cm thick) and the metallic plate may be also put on the floor to disperse pressure.

According to the embodiments of the invention, the magnetic shielding factor of a leakage magnetic field is enhanced, the small-sized light cylindrical magnetic shielding apparatuses having a high magnetic shielding factor can be realized, the biomagnetism measuring device in which the higher-sensitivity and more precise measurement is enabled can be realized, and limits and conditions required for installing the biomagnetism measuring device can be alleviated.

According to the embodiments of the invention, effect that an examination engineer can adjust the position of the top plate 121 for example in the three directions of the x-, y- and z-axes in front of the bed by automatic control or manually, observing an object of examination and the object of examination does not feel uneasy is acquired.

Figure 19:
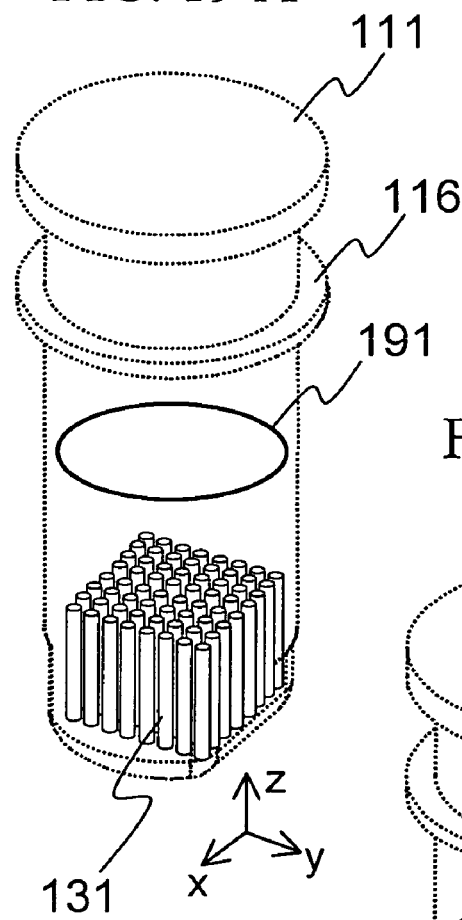
FIGS. 19A to 19C are perspective views showing an example of the configuration of the inside of the cryostat used in the biomagnetism measuring device equivalent to the embodiment of the invention.
Figure 19:
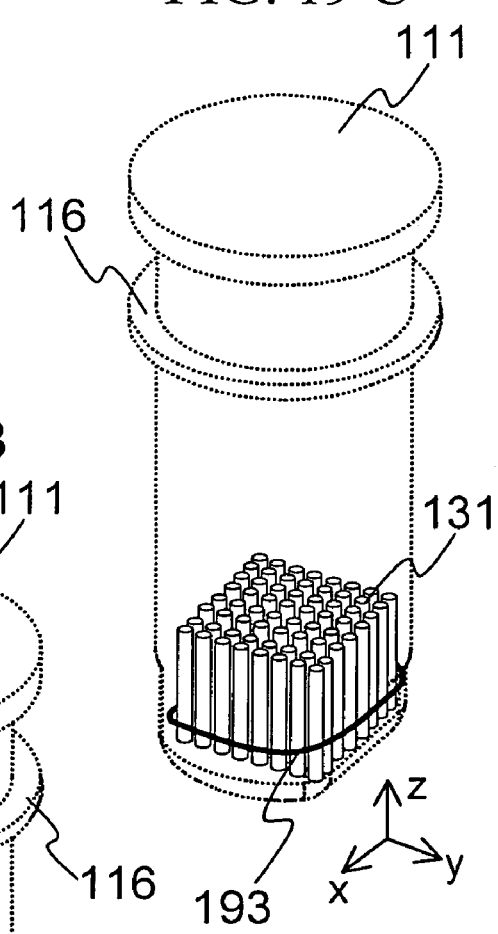
Figure 19:
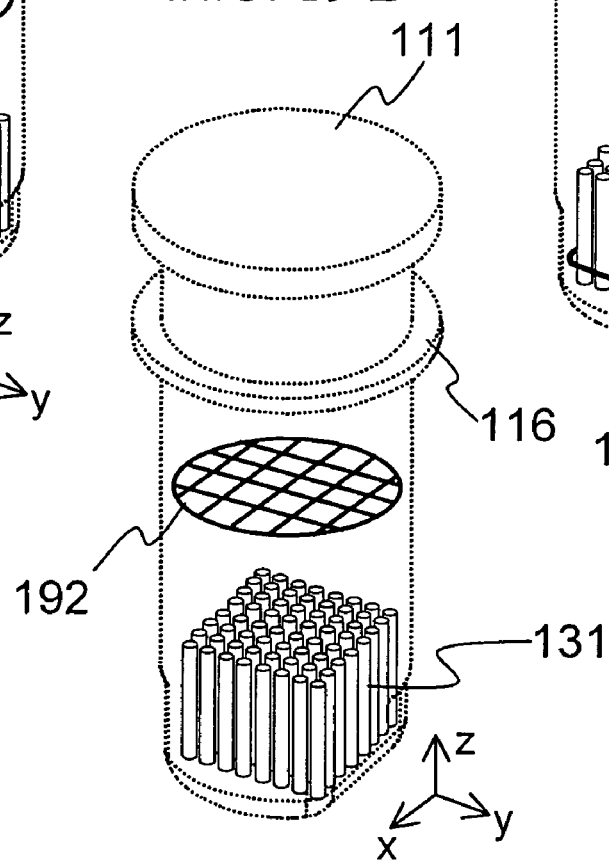

Further, according to the biomagnetism measuring device equivalent to the embodiment of the invention and adopting the configuration of the cryostats shown in FIGS. 19 and 20, in case the cylindrical magnetic shielding apparatus or the magnetic shielding chamber 181 shown in FIG. 18 is used, effect that the invasion of a leakage magnetic field to the measurement face can be prevented and higher-sensitivity and more precise measurement is enabled is acquired even if the leakage magnetic field that invades the inside of the cylindrical magnetic shield apparatus or the magnetic shielding chamber 181 exists. As a result, the design of the size of the suitable cylindrical magnetic shielding apparatus according to the area of a room for installing the apparatus is also enabled.

The configuration of the invention will be put in order below. First, the magnetic shielding apparatuses according to the invention will be described.

(1) The magnetic shielding apparatus according to the invention is provided with (a) the first cylindrical shield made of high-permeability material and containing a circumferential part having first thickness and having the first angular range in the circumferential direction of the y-axis perpendicular to the z-axis, the first opening formed on the circumferential part, the portions parallel to the y-axis at both ends of the first angular range, the two circular arc parts parallel to a plane perpendicular to the y-axis and the first auxiliary cylinder the central axis of which is coincident with the central axis of the first opening and which is connected to the circumferential part, (b) the second cylindrical shield containing the circumferential part having second thickness and having the second angular range in the circumferential direction of the y-axis and the two portions parallel to the y-axis at both ends of the second angular range, made of high-permeability material and arranged inside the circumferential part of the first cylindrical shield, (c) the third cylindrical shield containing the circumferential part having third thickness and having the third angular range in the circumferential direction of the y-axis and the two portions parallel to the y-axis at both ends of the third angular range, made of high-permeability material and arranged outside the circumferential part of the first cylindrical shield, (d) the bases for fixing and supporting the first cylindrical shield in two locations in the direction of the y-axis and (e) the revolving part for revolving the second and third cylindrical shields in the circumferential direction of the y-axis along the circumferential part of the first cylindrical shield, and is characterized in that the opening in the circumferential direction of the y-axis is formed by the revolution in one direction and a leakage magnetic field that invades the closed internal space formed in the circumferential direction of the y-axis is screened by the revolution in the other direction.

(2) The magnetic shielding apparatus according to the invention is provided with (a) the first cylindrical shield made of high-permeability material and containing the circumferential part having first thickness and having the first angular range in the circumferential direction of the y-axis perpendicular to the z-axis, the first opening formed on the circumferential part, the portions parallel to the y-axis at both ends of the first angular range, the two circular arc parts parallel to a plane perpendicular to the y-axis and the first auxiliary cylinder the central axis of which is coincident with the central axis of the first opening, which is connected to the circumferential part, which is arranged on a plane parallel to the XY plane perpendicular to the z-axis and in which the cryostat for holding the SQUID fluxmeter for detecting a component in the direction of the z-axis of a magnetic field generated from an object of examination at low temperature pierces the inside of the cylinder member and the first opening, (b) the second cylindrical shield containing the circumferential part having the second thickness and having the second angular range in the circumferential direction of the y-axis, the two portions parallel to the y-axis at both ends of the second angular range and the cutout formed in least one of the two portions, made of high-permeability material and arranged inside the circumferential part of the first cylindrical shield, (c) the third cylindrical shield containing the circumferential part having the third thickness and having the third angular range in the circumferential direction of the y-axis, the two portions parallel to the y-axis at both ends of the third angular range and the cutout formed at least in one of the two portions, made of high-permeability material and arranged outside the circumferential part of the first cylindrical shield, (d) the bases for fixing and supporting the first cylindrical shield in two locations in the direction of the y-axis and (e) the revolving part for revolving the second and third cylindrical shields in the circumferential direction of the y-axis along the circumferential part of the first cylindrical shield, and is characterized in that the opening for inserting an object of examination is formed in the circumferential direction of the y-axis by the revolution in one direction, the first auxiliary cylinder is arranged inside the cutouts of the second and third cylindrical shields and a leakage magnetic field that invades the closed internal space formed in the circumferential direction of the y-axis is screened by the revolution in the other direction.

(3) The magnetic shielding apparatus according to the invention is based upon the magnetic shielding apparatus described in (1) or (2) and is characterized in that the cryostat arranged on a plane parallel to the XY plane perpendicular to the z-axis for holding the SQUID fluxmeter for detecting a component in the direction of the z-axis of a magnetic field generated from an object of examination located in the internal space at low temperature is arranged piercing the inside of the cylinder member and the first opening.

(4) The magnetic shielding apparatus according to the invention is based upon the magnetic shielding apparatus described in (1) or (2) and is characterized in that the cryostat arranged on a plane parallel to the XY plane perpendicular to the z-axis for holding the SQUID fluxmeter for detecting a component in the direction of the z-axis of a magnetic field generated from an object of examination located in the internal space at low temperature is arranged piercing the inside of the cylinder member and the first opening and the flat cutout is provided in the portion opposite in a direction parallel to the y-axis to the portion on the bottom side of the cryostat and in the portion on the side which faces the opening in the circumferential direction of the y-axis formed by the revolution in one direction.

(5) The magnetic shielding apparatus according to the invention is based upon the magnetic shielding apparatus described in (1) or (2) and is characterized in that the opening is provided at least in one of the positive and negative directions of the y-axis.

(6) The magnetic shielding apparatus according to the invention is based upon the magnetic shielding apparatus described in (1) or (2) and is characterized in that the cutout is formed in one of the parallel two portions of the second and third cylindrical shields.

(7) The magnetic shielding apparatus according to the invention is based upon the magnetic shielding apparatus described in (1) or (2) and is characterized in that the cutout is formed in one of the parallel two portions of the second and third cylindrical shields and when the internal space closed in the circumferential direction of the y-axis is formed by the revolution in the other direction, the first auxiliary cylinder is arranged inside the cutout.

(8) The magnetic shielding apparatus according to the invention is based upon the magnetic shielding apparatus described in (1) or (2) and is characterized in that the cutout is formed in one of the parallel two portions of the second and third cylindrical shields, the cutout is formed in the other of the parallel two portions of the third cylindrical shield and when the internal space closed in the circumferential direction of the y-axis is formed by the revolution in the other direction, the first auxiliary cylinder is arranged inside the cutout formed in one of the parallel two portions of the second and third cylindrical shields and when the opening in the circumferential direction of the y-axis is formed by the revolution in one direction, the first auxiliary cylinder is arranged inside the cutout formed in the other of the parallel two portions of the third cylindrical shield.

(9) The magnetic shielding apparatus according to the invention is based upon the magnetic shielding apparatus described in (1) or (2) and is characterized in that the cutout is formed in the parallel two portions of the second and third cylindrical shields.

(10) The magnetic shielding apparatus according to the invention is based upon the magnetic shielding apparatus described in (1) or (2) and is characterized in that the cutout is formed in the parallel two portions of the second and third cylindrical shields, when the internal space closed in the circumferential direction of the y-axis is formed by the revolution in the other direction, the first auxiliary cylinder is arranged inside the cutout formed in one of the parallel two portions of the second and third cylindrical shields and when the opening in the circumferential direction of the y-axis is formed by the revolution in one direction, the first auxiliary cylinder is arranged inside the cutout formed in the other of the parallel two portions of the second and third cylindrical shields.

(11) The magnetic shielding apparatus according to the invention is based upon the magnetic shielding apparatus described in (1) or (2) and is characterized in that an object of examination is carried in the internal space from the opening in the circumferential direction of the y-axis formed by the revolution in one direction.

(12) The magnetic shielding apparatus according to the invention is based upon the magnetic shielding apparatus described in (1) or (2) and is characterized in that the flange-type plate having the circumferential face on which the opening having an inside diameter equal to the inside diameter of the first opening is formed is provided, the cylinder member provided with the flange is formed by connecting the cylinder member and the flange-type plate in a state in which the central axis of the cylinder member and the central axis of the opening of the flange-type plate are coincident and the circumferential face of the flange-type plate connected to the cylinder member provided with the flange is connected to the circumferential part of the first cylindrical shield.

(13) The magnetic shielding apparatus according to the invention is based upon the magnetic shielding apparatus described in (1) or (2) and is characterized in that the flange-type plate having the circumferential face on which the opening is formed is provided, the cylinder member provided with the flange is formed by connecting the cylinder member and the flange-type plate in a state in which the central axis of the cylinder member and the central axis of the opening of the flange-type plate are coincident, when the inside diameter of the first opening is D and $D1>D>D2$, the first cylinder member provided with the flange the outside diameter of the cylinder part of which is D1 and the second cylinder member provided with the flange the outside diameter of the cylinder part of which is D2 are formed and the circumferential face of the flange-type plate connected to the first and second cylinder members provided with the flange is connected onto the circumferential part of the first cylindrical shield.

(14) The magnetic shielding apparatus according to the invention is based upon the magnetic shielding apparatus described in (1) or (2) and is characterized in that the flange-type plate having the circumferential face on which the opening is formed is provided, the cylinder member provided with the flange is formed by connecting the cylinder member and the flange-type plate in a state in which the central axis of the cylinder member and the central axis of the opening of the flange-type plate are coincident, when the inside diameter of the first opening of is D and $D1>D>D2$, the first cylinder member provided with the flange the outside diameter of the cylinder part of which is D1 and the second cylinder member provided with the flange the outside diameter of the cylinder part of which is D2 are formed, the circumferential face of the flange-type plate connected to the first cylinder member provided with the flange is connected to the outside face of the circumferential part of the first cylindrical shield and the circumferential part of the flange-type plate connected to the second cylinder member provided with the flange is connected to the inside face of the circumferential part of the first cylindrical shield.

(15) The magnetic shielding apparatus according to the invention is based upon the magnetic shielding apparatus described in (1) or (2) and is characterized in that the first and third cylindrical shields are provided with a magnetic shielding member in parts overlapped by the revolution in the other direction.

(16) The magnetic shielding apparatus according to the invention is based upon the magnetic shielding apparatus described in (1) or (2) and is characterized in that the base fixes and supports the circular arc part of the first cylindrical shield.

(17) The magnetic shielding apparatus according to the invention is based upon the magnetic shielding apparatus described in (1) or (2) and is characterized in that the base is provided with a circular arc part in the first angular range that fixes and supports the circular arc part of the first cylindrical shield.

(18) The magnetic shielding apparatus according to the invention is based upon the magnetic shielding apparatus described in (1) or (2) and is characterized in that the base is provided with an indented continuous circular arc part that fixes and supports the circular arc part of the first cylindrical shield.

(19) The magnetic shielding apparatus according to the invention is based upon the magnetic shielding apparatus described in (1) or (2) and is characterized in that the revolving part is provided with a member for connecting the second and third cylindrical shields to the base so that they can be revolved.

(20) The magnetic shielding apparatus according to the invention is based upon the magnetic shielding apparatus described in (1) or (2) and is characterized in that the revolving part is provided with a member for connecting the second and third cylindrical shields to the circumferential part of the first cylindrical shield so that they can be revolved.

(21) The magnetic shielding apparatus according to the invention is based upon the magnetic shielding apparatus described in (1) or (2) and is characterized in that the first angular range is from 250 to 270 degrees, the second angular range is from 190 to 210 degrees and is from 245 to 265 degrees.

(22) The magnetic shielding apparatus according to the invention is based upon the magnetic shielding apparatus described in (1) or (2) and is characterized in that the first angular range is from 250 to 270 degrees, and the second and third angular ranges are from 190 to 210 degrees.

(23) The magnetic shielding apparatus according to the invention is based upon the magnetic shielding apparatus described in (1) or (2) and is characterized in that when the internal space closed in the circumferential direction of the y-axis is formed by the revolution in the other direction, the first and second cylindrical shields are overlapped in an angular range of 50 to 70 degrees in one portion and in an angular range of 30 to 50 degrees in the other portion and the first and third cylindrical shields are overlapped in an angular range of 50 to 70 degrees in one portion and in an angular range of 80 to 100 degrees in the other portion.

(24) The magnetic shielding apparatus according to the invention is based upon the magnetic shielding apparatus described in (1) or (2) and is characterized in that when the internal space closed in the circumferential direction of the y-axis is formed by the revolution in the other direction, the first and second cylindrical shields are overlapped in an angular range of 50 to 70 degrees in one portion and in an angular range of 30 to 50 degrees in the other portion and the first and third cylindrical shields are overlapped in an angular range of 50 to 70 degrees in one portion and in an angular range of 30 to 50 degrees in the other portion.

(25) The magnetic shielding apparatus according to the invention is based upon the magnetic shielding apparatus described in (1) or (2) and is characterized in that when the internal space closed in the circumferential direction of the y-axis is formed by the revolution in the other direction, the overlapped length of the first and second cylindrical shields in the circumferential direction of the y-axis of the first and second cylindrical shields and the overlapped length of the first and third cylindrical shields are equivalent to 10 times or more of a larger interval of an interval between the inside circumferential face of the circumferential part of the first cylindrical shield and the outside circumferential face of the circumferential part of the second cylindrical shield and an interval between the outside circumferential face of the circumferential part of the first cylindrical shield and the inside circumferential face of the circumferential part of the third cylindrical shield.

(26) The magnetic shielding apparatus according to the invention is based upon the magnetic shielding apparatus described in (1) or (2) and is characterized in that the angular range in the circumferential direction of the y-axis of the opening in the circumferential direction of the y-axis formed by the revolution in one direction is from 90 to 110 degrees.

(27) The magnetic shielding apparatus according to the invention is based upon the magnetic shielding apparatus described in (1) or (2) and is characterized in that the diameter of the inside circumferential face of the circumferential part of the second cylindrical shield is in a range of 0.8 to 1.2 m, the length in a direction parallel to the y-axis of the first cylindrical shield is in a range of 1.6 to 2.4 m and the inside diameter of the first auxiliary cylinder is in a range of 0.35 to 0.45 m.

(28) The magnetic shielding apparatus according to the invention is based upon the magnetic shield apparatus described in (1) or (2) and is characterized in that the plate is arranged on a floor and the base is fixed to the plate.

(29) The magnetic shielding apparatus according to the invention is based upon the magnetic shielding apparatus described in (1) or (2) and is characterized in that the plate is arranged on a floor, the base is fixed to the plate and a part of a portion in contact with the floor of the plate is cut out so that a portion close to the floor of the carriage for carrying the cryostat used when the cryostat pierces the inside of the cylinder member and the first opening or when the cryostat is extracted from the inside of the cylinder member and the first opening can be inserted.

Next, the biomagnetism measuring device according to the invention will be described.

(30) The biomagnetism measuring device according to the invention is characterized in that (A) the magnetic shielding apparatus described in (1), (B) the cryostat for holding the SQUID fluxmeter for detecting a component in the direction of the z-axis of a magnetic field generated from an object of examination at low temperature, (C) the gantry for holding the cryostat, (D) the top plate bearer for holding the top plate for mounting the object of examination located in the closed internal space formed in the circumferential direction of the y-axis perpendicular to the z-axis by the magnetic shielding apparatus, (E) the top plate moving part for moving the top plate on a plane parallel to the XY plane perpendicular to the z-axis, (F) the top plate bearer moving part for moving the top plate bearer in a direction perpendicular to the axis and (G) the plate arranged on the floor for holding the top plate bearer moving part are provided.

(31) The biomagnetism measuring device according to the invention is based upon the biomagnetism measuring device described in (30) and is characterized in that when the opening in the circumferential direction of the y-axis is formed by the revolution in one direction, the top plate is moved in a direction parallel to the XY plane by the top plate moving part, the top plate is moved outside the magnetic shielding apparatus, an object of examination is mounted on the top plate from the opening in the circumferential direction of the y-axis, the top plate is moved in the direction parallel to the XY plane and is moved inside the magnetic shielding apparatus, the top plate bearer is moved in a direction parallel to the z-axis by the top plate bearer moving part and after positional relation between the bottom of the cryostat and an examined portion of the object of examination is adjusted, the internal space closed in the circumferential direction of the y-axis is formed by the revolution in the other direction.

The characteristics of the configurations described in (3) to (29) are also applied to the biomagnetism measuring devices described in (30) and (1).

(32) The biomagnetism measuring device according to the invention is characterized in that (A) the magnetic shielding apparatus described in (2), (B) the gantry for holding the cryostat, (C) the top plate bearer for holding the top plate for mounting an object of examination located in the closed internal space formed in the circumferential direction of the y-axis by the magnetic shielding apparatus, (D) the top plate moving part for moving the top plate on a plane parallel to the XY plane perpendicular to the z-axis, (E) the top plate bearer moving part for moving the top plate bearer in a direction perpendicular to the axis and (F) the plate arranged on a floor for holding the top plate bearer moving part are provided.

(33) The biomagnetism measuring device according to the invention is based upon the biomagnetism measuring device described in (32) and is characterized in that when the opening in the circumferential direction of the y-axis is formed by the revolution in one direction, the top plate is moved in a direction parallel to the XY plane by the top plate moving part and is moved outside the magnetic shielding apparatus, an object of examination is mounted on the top plate from the opening in the circumferential direction of the y-axis, the top plate is moved in the direction parallel to the XY plane and is moved inside the magnetic shielding apparatus, the top plate bearer is moved in a direction parallel to the z-axis by the top plate bearer moving part and after positional relation between the bottom of the cryostat and an examined portion of the object of examination is adjusted, the internal space closed in the circumferential direction of the y-axis is formed by the revolution in the other direction.

The characteristics of the configurations described in (3) to (29) are also applied to the biomagnetism measuring devices described in (32) and (33).

(34) The biomagnetism measuring device according to the invention is provided with (A) the cylindrical shield containing the opposite openings in a direction parallel to the y-axis perpendicular to the z-axis, the circumferential part having the y-axis as a central axis and the first opening formed on the circumferential part and having the z-axis as a central axis and made of high-permeability material, (B) the auxiliary cylinder containing the opposite openings in a direction parallel to the z:axis and the circumferential part having the z-axis as the central axis and made of high-permeability material and (C) the cryostat arranged on a plane parallel to the XY plane perpendicular to the z-axis for holding the SQUID fluxmeter for detecting a component in the direction of the z-axis of a magnetic field generated from an object of examination at low temperature, and is characterized in that the auxiliary cylinder is connected to the circumferential part of the cylindrical shield in a state in which the central axis of the auxiliary cylinder is coincident with the central axis of the first opening, the cryostat is arranged in the internal space of the cylindrical shield piercing the opening of the auxiliary cylinder and the first opening and a leakage magnetic field that invades the inside space of the cylindrical shield is screened.

(35) The biomagnetism measuring device according to the invention is based upon the biomagnetism measuring device described in (34) and is characterized in that the cylinder provided with the flange containing the flange-type plate which has a radius of curvature equal to the radius of the outside face of the circumferential part of the cylindrical shield on one face, on which the opening having a diameter equal to the inside diameter of the opening of the auxiliary cylinder is formed and which is made of high-permeability material and formed by connecting one end of the auxiliary cylinder to the flange-type plate is configured and at least the face having the radius of curvature and the cylindrical shield are connected.

(36) The biomagnetism measuring device according to the invention is based upon the magnetism measuring device described in (34) and is characterized in that the first superconducting closed loop arranged inside the cryostat and arranged on the upside of the inside of the auxiliary cylinder is provided and the first superconducting closed loop is arranged in-parallel with a face of the detection coil of the SQUID fluxmeter.

(37) The biomagnetism measuring device according to the invention is based upon the biomagnetism measuring device described in (34) and is characterized in that the third superconducting closed loop arranged inside or outside at least one opening of the opposite openings in a direction parallel to the y-axis and parallel to the opposite openings in the direction parallel to the y-axis is provided.

(38) The biomagnetism measuring device according to the invention is based upon the biomagnetism measuring device described in (34) and is characterized in that the third superconducting closed loop arranged inside or outside at least one opening of the opposite openings in a direction parallel to the y-axis and parallel to the opposite openings in the direction parallel to the y-axis is provided.

(39) The biomagnetism measuring device according to the invention is based upon the biomagnetism measuring device described in (34) and is characterized in that the first active compensating coil arranged in the inside or in the outside on the upside of the auxiliary cylinder is provided and a face of the first active compensating coil is arranged in parallel with a face of the detection coil of the SQUID fluxmeter.

(40) The biomagnetism measuring device according to the invention is based upon the biomagnetism measuring device described in (34) and is characterized in that the second active compensating coil arranged inside or outside at least one opening of the opposite openings in a direction parallel to the y-axis and parallel to the opposite openings in the direction parallel to the y-axis is provided.

(41) The biomagnetism measuring device according to the invention is provided with (A) the cryostat for holding the SQUID fluxmeter that detects a component in a direction of the z-axis of a magnetic field generated from an object of examination and is arranged on a plane parallel to the XY plane perpendicular to the z-axis at low temperature, (B) the gantry for holding the cryostat, (C) the auxiliary cylinder acquired by connecting the flange-type plate and the cylinder member in a state in which each central axis of the opening of the flange-type plate having the opening formed on the circumferential face and the cylinder member is coincident, (D) the first cylindrical shield which has the circular arc part in the first angular range for the y-axis perpendicular to the z-axis, on which the first opening is formed and to which the auxiliary cylinder is connected in a state in which each central axis of the first opening and the cylinder member of the auxiliary cylinder is coincident, (E) the second cylindrical shield having the circular arc part in the second angular range for the y-axis, (F) the third cylindrical shield having the circular arc part in the third angular range for the y-axis, (G) the revolving door acquired by integrating the second and third cylindrical shields and having a cutout in a portion parallel to the y-axis, (H) the shield base for supporting the cylindrical shield by the circular arc part at both ends and (I) the revolving part for opening and closing the opening in the circumferential direction of the y-axis by revolving the revolving door along the circumferential part of the first cylindrical shield in the circumferential direction of the y-axis, and is characterized in that the cryostat is arranged inside the opening of the auxiliary cylinder and the first opening, when the revolving door is closed, the circumferential part of the cylindrical shield is inserted between the circumferential part of the second cylindrical shield and the circumferential part of the third cylindrical shield, the cylindrical internal space is formed, an environmental magnetic field that invades the internal space is screened and a component in a direction of the z-axis of a magnetic field generated from an object of examination carried in the internal space when the revolving door is open via the opening in the circumferential direction of the y-axis is measured when the revolving door is closed.

The characteristics of the configurations described in (3) to (29) are also applied to the biomagnetism measuring device described in (41).

(42) The biomagnetism measuring device according to the invention is provided with (A) the cylindrical shield containing the opposite openings in a direction parallel to the y-axis perpendicular to the z-axis, the circumferential part having the y-axis as a central axis and the first opening formed on the circumferential part and having the z-axis as a central axis and made of high-permeability material, (B) the cryostat for holding the SQUID fluxmeter arranged on a plane parallel to the XY plane perpendicular to the z-axis for detecting a component in a direction of the z-axis of a magnetic field generated from an object of examination at low temperature and (C) the first superconducting closed loop arranged on the upside of the inside of the cryostat and arranged in parallel with a face of the detection coil of the SQUID fluxmeter, and is characterized in that the cryostat is arranged in the internal space of the cylindrical shield piercing the first opening and a leakage magnetic field that invades the internal space of the cylindrical shield is screened.

(43) The biomagnetism measuring device according to the invention is based upon the biomagnetism measuring device described in (42) and is characterized in that the second superconducting closed loop arranged inside or outside at least one opening of the opposite openings in a direction parallel to the y-axis and parallel to the opposite openings in the direction parallel to the y-axis is provided.

(44) The biomagnetism measuring device according to the invention is based upon the biomagnetism measuring device described in (42) and is characterized in that the first active compensating coil arranged inside or outside at least one opening of the opposite openings in a direction parallel to the y-axis and parallel to the opposite openings in the direction parallel to the y-axis is provided.

(45) The biomagnetism measuring device according to the invention is provided with (A) the cylindrical shield containing the opposite openings in a direction parallel to the y-axis perpendicular to the z-axis, the circumferential part having the y-axis as a central axis and the first opening formed on the circumferential part and having the z-axis as a central axis and made of high-permeability material, (B) the cryostat arranged on a plane parallel to the XY plane perpendicular to the z-axis for holding the SQUID fluxmeter for detecting a component in a direction of the z-axis of a magnetic field generated from an object of examination at low temperature and (C) the active compensating coil arranged inside or outside the first opening and arranged in parallel with a face of the detection coil of the SQUID fluxmeter, and is characterized in that the cryostat is arranged in the internal space of the cylindrical shield piercing the first opening and a leakage magnetic field that invades the internal space of the cylindrical shield is screened.

(46) The biomagnetism measuring device according to the invention is based upon the biomagnetism measuring device described in (45) and is characterized in that the first superconducting closed loop arranged inside or outside at least one opening of the opposite openings in a direction parallel to the y-axis and parallel to the opposite openings in the direction parallel to the y-axis is provided.

(47) The biomagnetism measuring device according to the invention is based upon the biomagnetism measuring device described in (45) and is characterized in that the first active compensating coil arranged inside or outside at least one opening of the opposite openings in a direction parallel to the y-axis and parallel to the opposite openings in the direction parallel to the y-axis is provided.

(48) The biomagnetism measuring device according to the invention is characterized in that (A) the cryostat arranged on a plane parallel to the XY plane perpendicular to the z-axis for holding the SQUID fluxmeter for detecting a component in a direction of the z-axis of a magnetic field generated from an object of examination at low temperature and (B) the first superconducting closed loop arranged in parallel with a face of the detection coil of the SQUID fluxmeter and arranged inside the cryostat are provided.

The configuration of the magnetic shielding apparatuses and the biomagnetism measuring devices equivalent to the embodiments of the invention will be described with the more concrete handling and operation of these apparatuses and devices in the center in detail below.

The biomagnetism measuring device according to the invention is provided with the bed having a bed part for mounting an object of examination on its top face and a cylindrical magnetic shield the central axis of which is held horizontal. The magnetic shield is provided with a first body having a doorway for putting the bed part in or out through a part of the cylindrical circumferential face and a second body for opening and closing a bed input port. The first body is provided with a measuring part in which plural sensors are built in the center of the upside. The second body is held in the first body so that the second body can be moved along a cylindrical circumferential direction. The bed is provided with the top plate for holding the bed part, legs for holding the top plate in the cylindrical magnetic shield, a pulling-out mechanism for putting the bed part outside the magnetic shield via the doorway, a Y direction moving mechanism for moving the bed part in a direction of the central axis of the magnetic shield, an X direction moving mechanism for moving the bed part in a direction perpendicular to a direction of the central axis in the magnetic shield and a Z direction moving mechanism for moving the bed part in a vertical direction in the magnetic shield.

According to the invention, the small-sized biomagnetism measuring device which an examination engineer can-easily handle without imposing a load and easiness on an object of examination is provided.

Referring to FIGS. 29 to 68, the biomagnetism measuring device according to the invention will be described in detail below. In the following description, an object of example shall be a living body and a cardiac magnetic field measuring device for measuring a magnetic field generated from the heart will be described as an example. However, the invention is not limited to this example. For example, the invention can be also applied to an instrument for detecting magnetism such as whether a magnetic substance is included in a general object of examination or not, the amount and the distribution of the magnetic substance. The following disclosure is only one embodiment of the invention and does not limit a technical scope of the invention. Further, in FIGS. 29 to 68, the same reference numeral is allocated to the same part and the same function and the duplicate description is omitted.

First Embodiment

Figure 29:
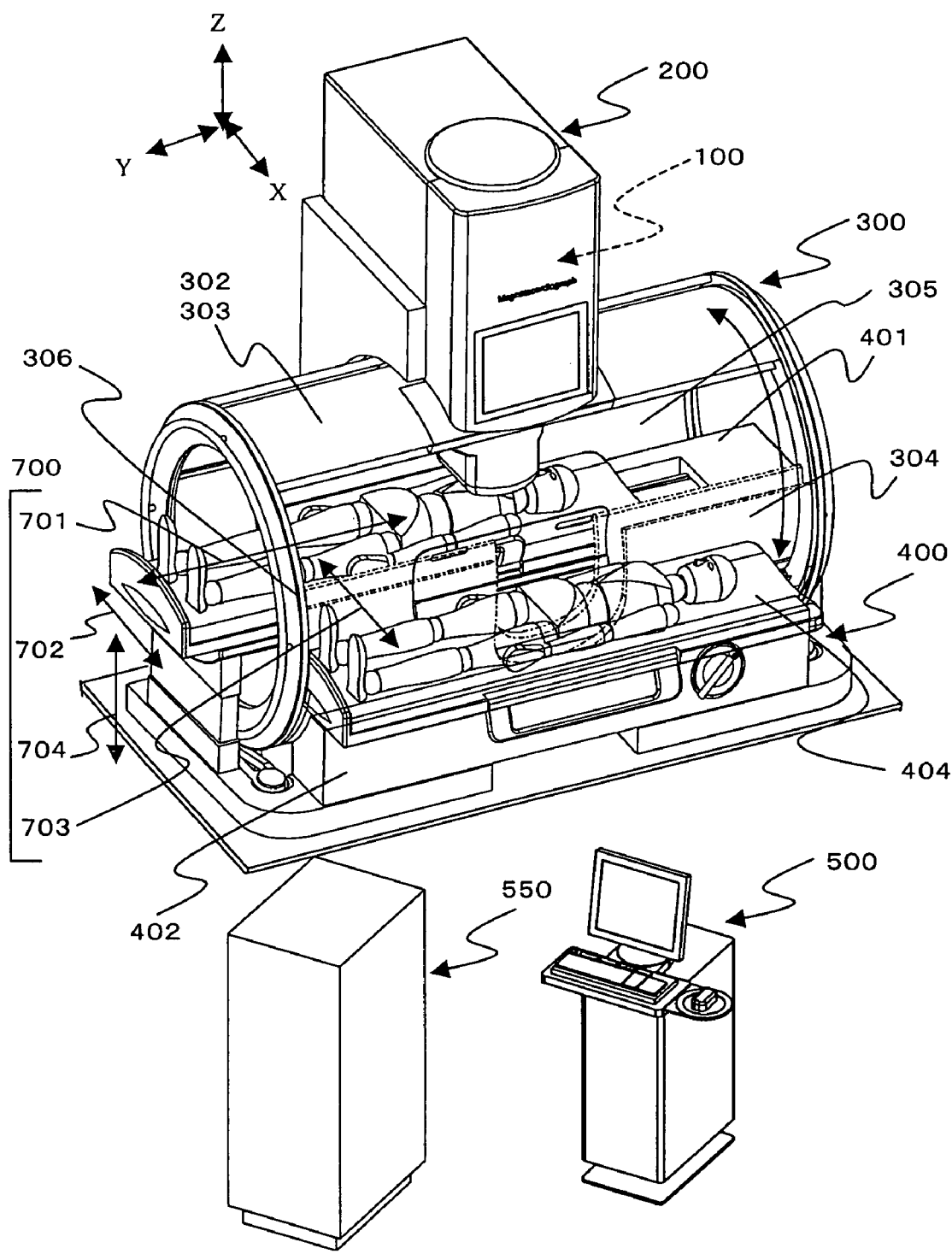
FIG. 29 is an outside drawing showing a cardiac magnetism measuring device equivalent to a first embodiment.

FIGS. 29 to 59 show a cardiac magnetic field measuring device equivalent to a first embodiment. FIG. 29 is an outside drawing showing the device, FIG. 30 is a block diagram showing the device, FIG. 31 shows a principle of measurement, FIGS. 32 to 48 are structural drawings showing the details of each device, FIGS. 49 to 54 show used states, FIGS. 55 to 58 are explanatory drawings for explaining a positioning device for positioning a subject, and FIGS. 62A to 62C show another combination.

First, referring to FIGS. 29 and 30, the schematic structure of the cardiac magnetic field measuring device equivalent to this embodiment will be described. FIG. 29 is an outside drawing showing the cardiac magnetic field measuring device. FIG. 30 is a block diagram showing the cardiac magnetic field measuring device.

Figure 30:
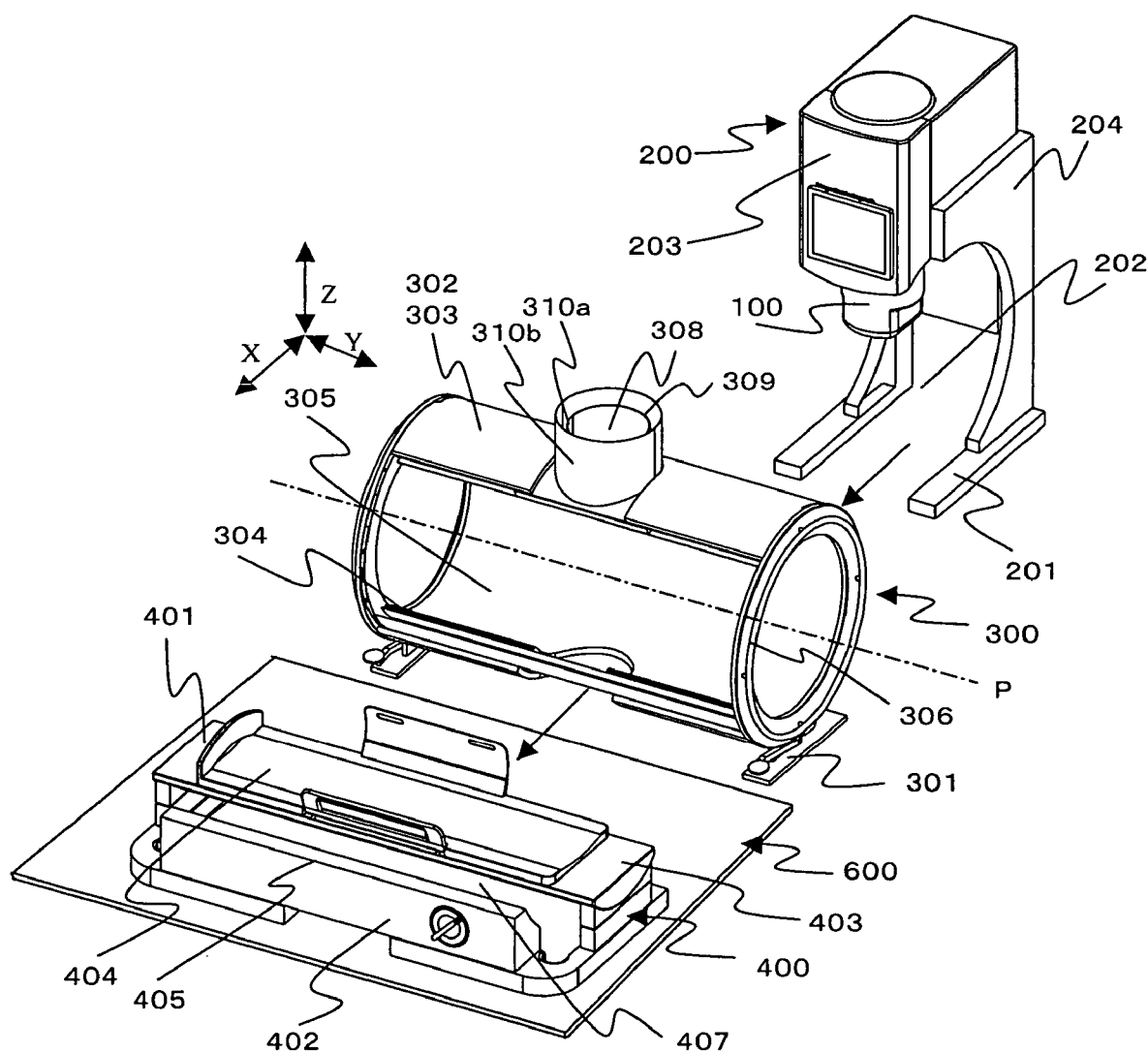
FIG. 30 is a block diagram showing the cardiac magnetism measuring device equivalent to the first embodiment.
Figure 31:
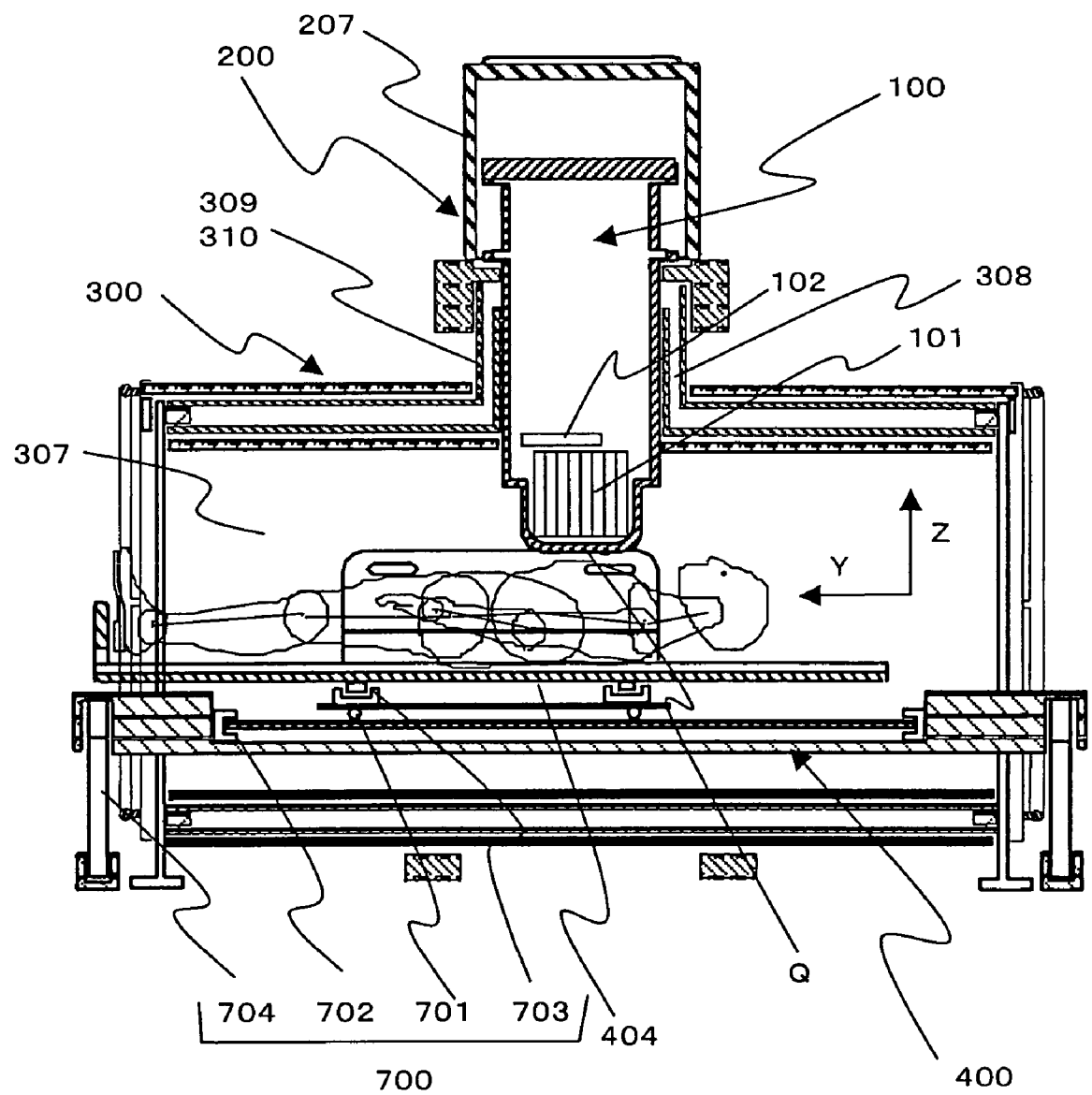
FIG. 31 is a longitudinal section for explaining a measurement principle in the first embodiment.

As shown in FIGS. 29 and 30, the cardiac magnetic field measuring device includes a gantry 200 for holding a measuring part 100 provided with a fluxmeter (hereinafter called a sensor) for measurement using a superconducting quantum interference device (SQUID), a magnetic shield 300 including the measuring part 100 in measurement for screening an external magnetic field, a bed 400 provided with a bed part 404 for mounting a subject, a data collection/analysis device 500 for making various analysis such as adjusting magnetic data input from the measuring part 100 and setting a measuring condition and a magnetic measurement drive unit 550 for analyzing magnetic data collected from the sensor.

The gantry 200, the magnetic shield 300 and the bed 400 are provided with legs 201, 301, 402, are configured so that they can be mutually detached, and in installation, they are mounted directly on a floor via each leg or on a base 600 installed on the floor.

The gantry 200 is provided with housing space 202 for housing the magnetic shield 300 in a lower part of the front and an examination support 203 for holding the measuring part 100 is provided on its upside. In the gantry 200 equivalent to this embodiment, the legs 201 are protruded forward from vertical posts 204 and the examination support 203 for stably supporting the gantry 200 and further, holding the measuring part 100 is arranged so that the examination support is protruded forward from the upside of the posts 204. Hereby, as the measuring part 100 is held on the upside of the legs 201, the balance of the center of gravity of the gantry 200 in a state in which the measuring part 100 is attached is made satisfactory and the measuring part 100 can be stably supported. As in the gantry 200, the legs 201 and the examination support 203 are protruded forward, the large housing space 202 can be formed between the legs 201 and the examination support 203. In addition, according to the structure of the gantry 200, the measuring part 100 can be located on the upside of the magnetic shield 300.

The magnetic shield 300 is installed in the housing space 202 on the upside of the legs 201 of the gantry 200. Hereby, as space in which the gantry 200 is installed and space in which the magnetic shield 300 is installed can be shared, the efficiency of installation can be enhanced.

The magnetic shield 300 is configured by the body of the shield 302 and the legs 301 for supporting the body. The body of the shield 302 is formed by ferromagnetic material such as Permalloy, an amorphous alloy respectively having the high relative permeability of approximately 10,000 to 100,000 and aluminum having high electric conductivity, has a cylindrical outside shape, and is supported by the legs 301 so that the central axis P is horizontal. In this embodiment, the body of the shield 302 is configured by a main body 303 supported by the legs 301 and an opening/closing body 304 attached to the main body 303 so that the opening/closing body can be slid.

On the main body 303, the upside of the front, that is, the upside (approximately ¼ of the cylindrical periphery) of the side opposite to the posts 204 of the gantry 200 is opened and a doorway 305 for a subject is provided. The opening/closing body 304 has appearance in the shape of an arc forming a part of a cylinder and is attached to the main body 303 so that the opening/closing body can be circumferentially slid so as to open or close the doorway 305 via an opening/closing drive mechanism 306. Owing to this structure, as the opening/closing body 304 forms cylindrical magnetically shielded space 307 together with the main body 303 in a state in which the opening/closing body is closed, is housed along the periphery of the main body 303 in an open state and releases the doorway 305, the subject can easily get in and out of the magnetically shielded space 307 from the side.

The main body 303 is provided with an opening 308 for inserting the measuring part 100 into the magnetically shielded space 307 on the upside. A mounting part 309 the front of which is cut out and which is protruded is formed around the opening 308 and a pair of covers 310a, 310b for closing clearance between the mounting part 309 and the measuring part 100 and screening an external magnetic field are provided. Owing to this structure, the sensor in the measuring part 100 held by the gantry 200 is located in the magnetically shielded space 307 screening an external magnetic field and the measuring part 100 can be stably supported.

The bed 400 is configured by the leg 402 fixed on the floor and a top plate 401 arranged on the upside of the leg 402. The top plate 401 is supported by the leg 402 so that its longitudinal direction is located in the magnetically shielded space 307 on the central axis P of the magnetic shield 300. In this embodiment, both ends of the top plate 401 are protruded from the magnetic shield 300 by forming the top plate 401 longer than the length in the longitudinal direction of the magnetic shield 300 and the leg 402 supports both ends. Hereby, as space in which the bed 400 is installed, the space in which the gantry 200 is installed and the space in which the magnetic shield 300 is installed can be shared, the efficiency of installation can be enhanced.

Besides, the top plate 401 is provided with a top plate base 403 supported by the leg 402 and a bed part 404 attached to the top plate base 403 so that the bed part can be moved via a bed moving mechanism 700. The bed moving mechanism 700 is provided with a Y direction bed moving mechanism 701 for moving in a direction of the y-axis which is the central axis P of the cylindrical magnetic shield 300, an X direction bed moving mechanism 702 for moving the bed part 404 in a direction of the x-axis perpendicular to the direction of the y-axis and a pulling-out mechanism 703 for moving the bed part 404 in the direction of the x-axis and pulling the bed part 404 out of the magnetically shielded space 307.

The pulling-out mechanism 703 helps the bed part 404 to be pulled out of the magnetic shield 300 in a state in which the opening/closing body 304 is opened. Hereby, the subject can mount on the bed part 404 in released space. As the bed part 404 can be moved in the magnetically shielded space 307 in a state in which the subject lies on the bed part 404, the subject feels easy and a doctor (an examination engineer and a nurse) can also have the subject get in or out of the magnetically shielded space 307 by simple operation.

Besides, the leg 402 is provided with a front coupling part 405 for supporting the pulled-out bed part 404 on the downside. Hereby, the strength when the bed part 404 is pulled out is enhanced the pulling-out mechanism 703 can be small-sized.

Further, the bed moving mechanism 700 is provided with a Z direction bed moving mechanism 704 for vertically moving the top plate 401 in the leg 402.

As described above, according to this embodiment, as the bed part 404 in the magnetically shielded space 307 can be moved in the directions of the x-, y- and z-axes by driving the Y direction bed moving mechanism 701, the X direction bed moving mechanism 702 and the Z direction bed moving mechanism 704, a measured portion of the subject in a state in which he/she lies on the bed part 404 can be moved in a satisfactory position of the measuring part 100.

Besides, in this embodiment, as the data collection/analysis device 500 is provided next to the magnetic shield 300, the operability of the examination engineer is enhanced.

One of characteristics of the cardiac magnetic field measuring device equivalent to this embodiment is in that the easiness of installation is enhanced by configuring the gantry 200, the magnetic shield 300 and the bed 400 so that they can be mutually detached. Generally, to install a large-sized system such as the cardiac magnetic field measuring device, unless it is carried in the form of parts from a factory to a location of installation, a wall and others of a building to be installed are required to be broken. In the meantime, in case the large-sized system is carried in a state in which it is disassembled into parts, it is troublesome to assemble them unless a disassembled unit is devised. Particularly, in the case of the cardiac magnetic field measuring device, the sensor for which accuracy is required, shielding performance for screening an external magnetic field, the balance of a heavy member such as Permalloy and the precision of the moving mechanism are required to be considered. Besides, other used states are required to be considered.

In this embodiment, to solve the problem, the device related to measurement is disassembled into three units (the gantry 200, the magnetic shield 300 and the bed 400). That is, in this embodiment, as the cylindrical magnetic shield 300 is provided, measurement is enabled without installing a large-sized magnetic shielding room in a building. However, there is also a demand for using the cardiac magnetic field measuring device in a large-sized magnetic shielding room. In this case, in case the measuring part 100 is attached to the cylindrical magnetic shield 300, a large change in a design is required to enable using the measuring part 100 in the large-sized magnetic shielding room.

In this embodiment, to solve the problem, the measuring part 100 is separated from the magnetic shield 300 and is supported by the gantry 200. According to this structure, the measuring part 100 supported by the gantry 200 is separated from the cylindrical magnetic shield 300 and can be used in large-sized magnetic shielding room. In the meantime, in case the measuring part is used in a state in which the measuring part is combined with the cylindrical magnetic shield 300, the sensor of the measuring part 100 can be attached to a predetermined position in the cylindrical magnetically shielded space 307 by attaching the measuring part 100 to the gantry 200 after the cylindrical magnetic shield 300 is installed in the housing space 202 of the gantry 200. In addition, an external magnetic field can be screened by the mounting part 309 and a pair of covers 309a, 309b for connecting the cylindrical magnetic shield 300 and the measuring part 100.

For the cylindrical magnetic shield 300, shielding performance for screening an external magnetic field is important. Then, in this embodiment, the cylindrical magnetic shield 300 is made independent and the bed 400 required to be installed in the magnetically shielded space 307 is installed independently. Hereby, the gantry 200 provided with the measuring part 100, the cylindrical magnetic shield 300 and the bed 400 may be also used in a state in which they are combined, and the gantry 200 provided with the measuring part 100 and the bed 400 may be also used in a large-sized magnetic shielding room in a state in which they are combined.

Besides, one of other characteristics of this embodiment is in that the doorway 305 for the subject to get in or out of the cylindrical magnetic shield 300 is provided on a cylindrical circumferential face. In this type of cardiac magnetic field measuring device, it is effective to reduce distance between a position for the subject to mount on the bed 400 or to leave the bed and a position in which actual examination is made. In this embodiment, in examination, a longitudinal direction of the bed 400 is made incident with the central axis P of the cylindrical magnetic shield 300. Therefore, the bed part 404 can be pulled out or returned in shortest distance from the position of examination by providing the doorway 305 on the cylindrical circumferential face. In this embodiment, as the position for mounting or leaving the bed is set in parallel with the position of examination and outside the cylindrical magnetic shield 300, the subject can lie on the released bed part 404 without a sense of incompatibility and in addition, in the position for mounting or leaving the bed, the examination engineer can easily take care of the subject. The bed part 404 is moved from the position for mounting or leaving the bed to the position of examination via the bed moving mechanism 700 and the measuring part 100 can be aligned with the heart of the subject lying on the bed part 404.

Referring to FIGS. 31 to 60, the cardiac magnetic field measuring device equivalent to this embodiment will be described further in detail below.

First, referring to FIG. 31, a principle of measurement using the cylindrical magnetic shield 300 will be described. FIG. 31 is a longitudinal sectional view for explaining the principle of measurement.

As shown in FIG. 31, in this embodiment, the measuring part 100 is fixed and arranged in the predetermined position in the magnetically shielded space 307. Therefore, the heart of the subject is aligned with the measuring part 100 by the bed moving mechanism 700. FIG. 31 shows a state in which the subject lies with his/her head held on a pillow inside the magnetic shield 300 for examination.

The measuring part 100 is a cooling container, plural measuring sensors 101 and a first sensor for reference 102 are arranged at the bottom of the inside, and these are cooled by a liquid refrigerant filled in the measuring part 100. In this embodiment, the sensors (fluxmeters) 101, 102 which are made of a high-temperature superconductor and which can be operated at the temperature of liquid nitrogen are used and the inside of the measuring part 100 is filled with liquid nitrogen so as to cool the measuring sensor 101 and the first sensor for reference 102. The measuring part 100 is held in the gantry 200.

The units arranged inside the magnetic shield 300 such as the top plate 101 and the measuring part 100 are made of non-magnetic material such as FRP and aluminum. Detection coils of the plural measuring sensors (fluxmeters for measurement) 101 are arranged on the same measurement face Q parallel to an XY plane perpendicular to the direction of the z-axis and the face of the detection coil is perpendicular to the direction of the z-axis. In this case, the direction of the y-axis means a direction of the central axis P of the cylindrical magnetic shield 300, the direction of the x-axis means a direction from the front to the rear (a direction of the depth in FIG. 31) perpendicular to the central axis P, and the direction of the z-axis means a vertical direction perpendicular to the central axis P. The measuring sensor 101 detects a magnetic field component in the direction of the z-axis. The first sensor for reference 102 is provided to detect a component in the direction of the y-axis of an external magnetic field and is arranged in the vicinity of the measuring sensor 101 so that a direction in which the magnetic field is detected is the direction of the y-axis.

Operation for driving the plural measuring sensors 101 and the first sensor for reference 102 is controlled by the magnetic measurement drive unit 550 connected via a signal line not shown in FIG. 31 and in the magnetic measurement drive unit 550, an analog signal according to the magnitude of a magnetic-field detected by each sensor 101, 102 is processed in an analog signal processing circuit including an amplifier, a band-pass filer and a notch filter.

The signal line is configured by plural cables and is composed of a bundle of cables for transmitting a signal detected by the magnetic measurement drive unit 550 from the measuring sensor 101 and the first sensor for reference 102 and a bundle of cables for applying bias current, feedback current and current for a heater from the magnetic measurement drive unit 550 to the measuring sensor 101 and the sensor for reference 102.

The output of the magnetic measurement drive unit 550 is converted to a digital signal and is sent to the data collection/analysis device 500. In the data collection/analysis device 500, various signal processing is applied to the sent signal.

An external magnetic field includes three components in the directions of the x-, y- and z-axes. As the shielding performance of the cylindrical magnetic shield 300 is excellent in the directions of the z- and x-axes perpendicular to the direction of the y-axis shown in FIG. 31, the components in the directions of the z- and x-axes of the external magnetic field are largely attenuated inside the cylindrical magnetic shield 300.

In the meantime, the components in the directions of the x- and y-axes of the external magnetic field are perpendicular to a magnetic detection direction of the measuring sensor (the SQUID fluxmeter) 101 and most are not detected by the measuring sensor 101. Therefore, most are screened in the magnetic shield 300 and the external magnetic field in the direction of the x-axis in which the sensitivity of the measuring sensor (the SQUID fluxmeter) 101 is low can be practically ignored.

Most of the component in the direction of the z-axis of the external magnetic field can be cancelled by calculating difference between the output signals of the adjacent measuring sensors 101. The difference can be calculated after data is input to the data collection/analysis device 500.

The data collection/analysis device 500 corrects the component in the direction of the y-axis of the external magnetic field by subtracting a value acquired by multiplying a signal measured by the first sensor for reference 102 by a first predetermined factor from the difference between the output signals of the adjacent measuring sensors 101 and operates to acquire a first measurement signal in which an effect of the external magnetic field is reduced.

As described above, in this embodiment, as measurement heretofore performed in a magnetically shielded room is enabled in a location without large-sized magnetically shielding facilities by providing the structure, the cost of facilities can be largely reduced and space for installing the device can be reduced. In addition, in this embodiment, as a subject is measured in the pierced cylindrical magnetic shield 300, a confined feeling and uneasiness are reduced. Further, as an examination engineer exists next to the small-sized cylindrical magnetic shield 300, the uneasiness of the subject is reduced.

Figure 32:
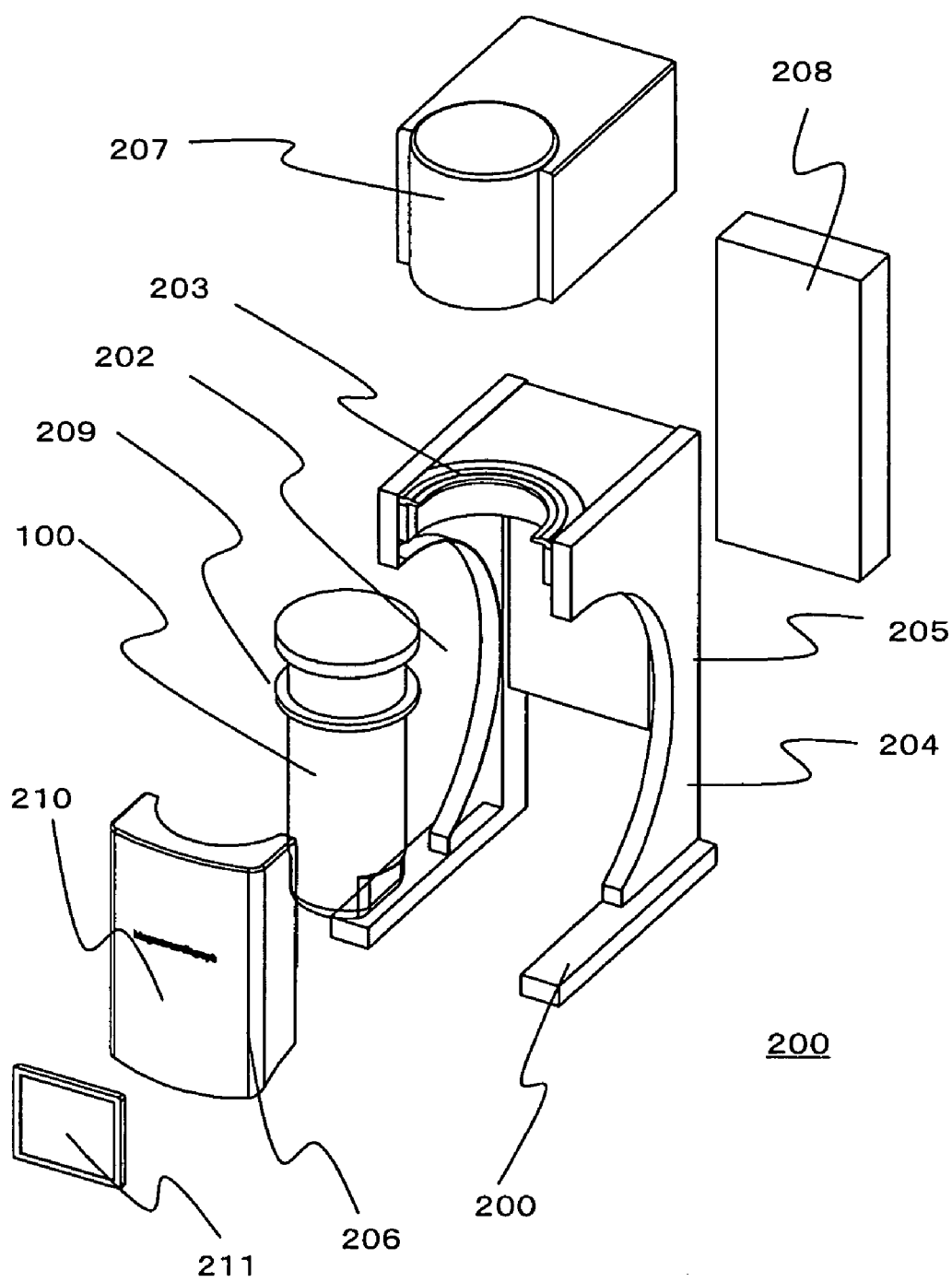
FIG. 32 is an exploded view showing parts of a gantry in the first embodiment.
Figure 33:
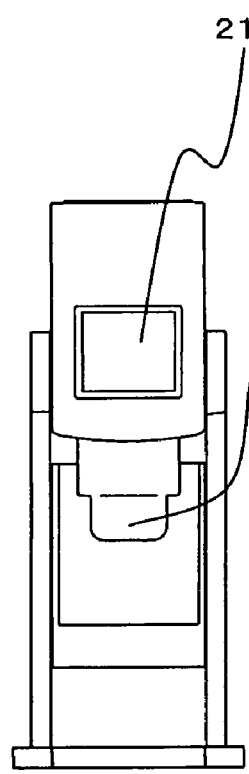
FIGS. 33A to 33E are outside drawings showing the gantry in the first embodiment.
Figure 33:
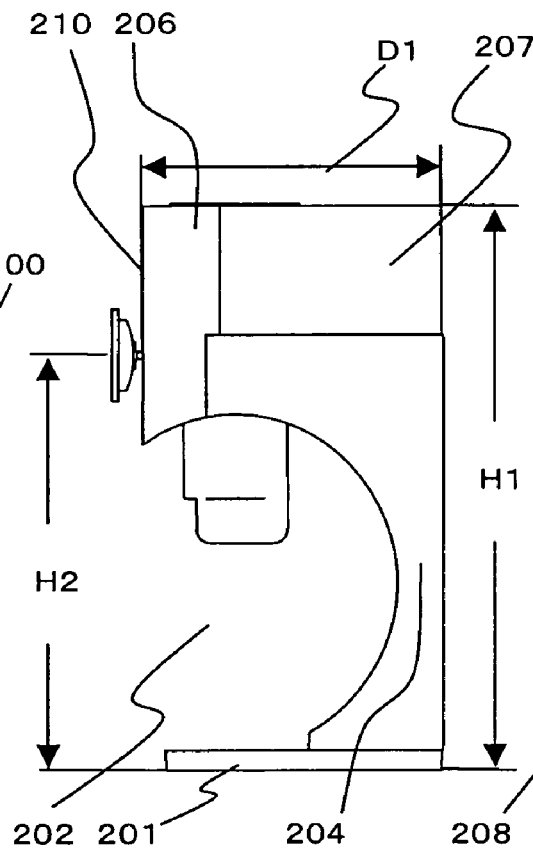
Figure 33:
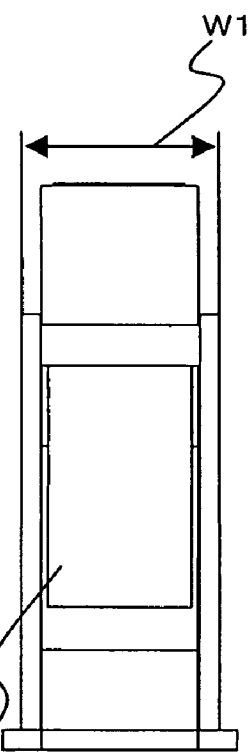
Figure 33:
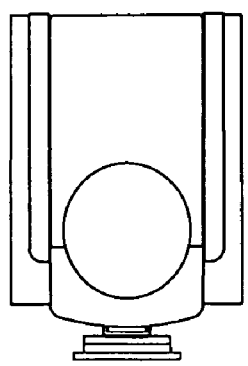
Figure 33:
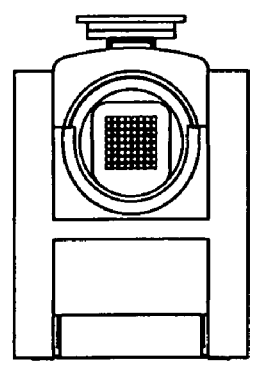

Next, referring to FIGS. 32 and 33, the structure of the gantry 200 will be described in detail. FIG. 32 is an exploded view showing parts of the gantry. FIGS. 33A to 33E are outside drawings showing the gantry, FIG. 33A is a front view, FIG. 33B is a right side view, FIG. 33C is a back view, FIG. 33D is a plan, and FIG. 33E is a bottom view. A left side view is symmetrical with the right side view.

First, As shown in FIGS. 32 and 33, the gantry 200 in this embodiment includes a gantry base 205 forming a skeleton of the gantry 200, the cylindrical measuring part 100, a gantry front cover 206 covering the front of the examination support 203, a gantry upper cover 207 covering the upside of the gantry 200 and a refrigerant discard controller 208 for controlling a refrigerant in the measuring part 100.

The gantry base 205 is mainly configured by a pair of side plates arranged on both sides and is provided with the posts 204 vertically standing, the legs 201 protruded forward below the posts 204 and configured by a pair of side plates and the examination support 203 protruded on the upside of the posts 204. The posts 204 contain the refrigerant discard controller 208 between the side plates. In the meantime, the end of the examination support 203 is formed in the shape of a semicircle and the examination support can support the cylindrical measuring part 100.

The measuring part 100 is a cylindrical container the upper end of which is covered with an openable lid and vertically long and is attached to the examination support 203 with the central axis vertical. The measuring part 100 is provided with a flange 103 protruded outside on the upside of the cylinder and the measuring part is held by the examination support 203 via the flange 103.

The gantry upper cover 207 is formed by a member for screening an external magnetic field such as aluminum. That is, in this embodiment, as shown in FIG. 31, an effect of an external magnetic field upon the measuring part 100 is reduced by housing the downside which is a lower part of the measuring part 100 of the flange 103 in the magnetic shield 300 and covering the upside of the flange 103 with the gantry upper cover 207. An effect of an external magnetic field is reduced by covering the circumference of the opening 308 with the mounting part 309 and the cover 310 (310a, 310b) respectively protruded upward.

As shown in FIG. 32 again, the gantry front cover 206 covers the front of the gantry upper cover 207 and the opening 308. Hereby, as the flange 103 of the measuring part 100 and a connection of the gantry upper cover 207 vertically covering the flange 103 and the cover 310 can be shielded, design can be enhanced. Besides, in this embodiment, as the gantry front cover 206 having a large plane can cover the circumference of the connection, the large plane can be used for an operation display arrangement face 210. In this embodiment, a thin-type display provided with a touch panel 211 is arranged on the operation display arrangement face 210.

The front of the gantry front cover 206 on which the thin-type display 211 is arranged is located in the center of the magnetic shield 300 and in addition, is located at the front end of the cylinder. In addition, the height H is 1,600 mm and is a position suitable for an examination engineer to operate and to verify the contents of display. In this embodiment, keys for various operations of the cardiac magnetic field measuring device and a monitor image can be displayed on the thin-type display 211. In this embodiment, the similar operation and the similar monitoring of an image of examination are also enabled in the data collection/analysis device 500. In this embodiment, a tilting mechanism is provided to a part to which the thin-type display 211 is attached and a screen can be adjusted at an arbitrary angle.

As shown in FIGS. 33A to 33E, for the gantry 200 in this embodiment, the whole height H1 is set to 2,200 mm, the width W1 is set to 760 mm, and the depth D1 is set to 1,150 mm.

Figure 35:
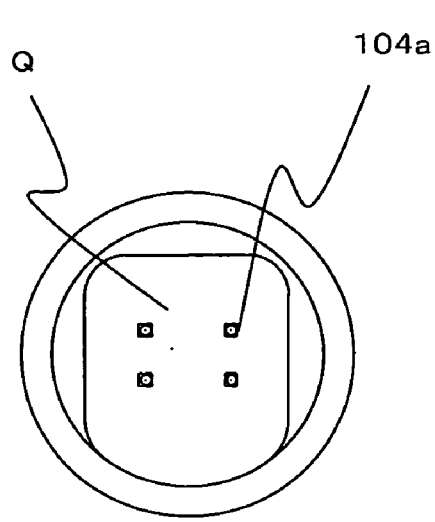
FIGS. 35A to 35E are exploded views showing applied examples of a mark shown in the bottom view showing the measuring part in the first embodiment.
Figure 35:
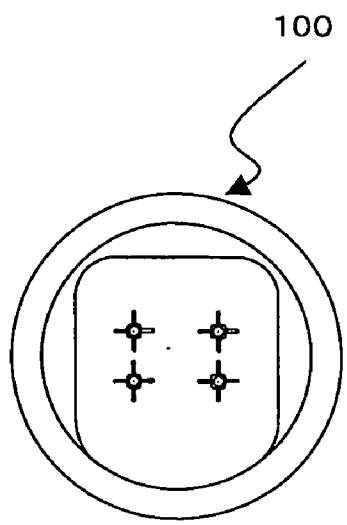
Figure 35:
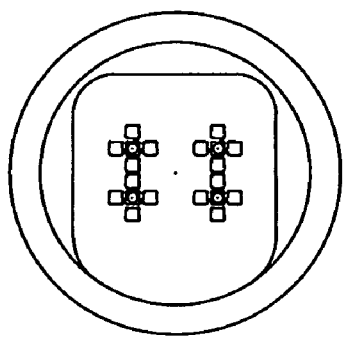
Figure 35:
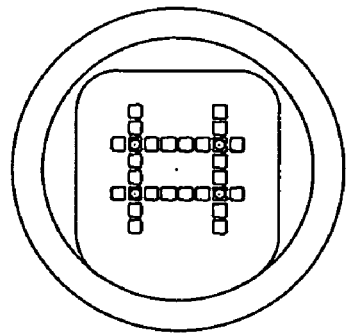
Figure 35:
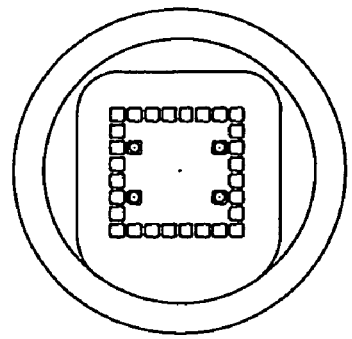

Next, referring to FIGS. 34 and 35, the measuring part 100 will be described in detail. FIGS. 34A to 34E are outside drawings showing the measuring part, FIG. 34A is a plan, FIG. 34B is a bottom view, FIG. 34C is a front view, FIG.

34D is a right side view, and FIG. 34E is a back view. As a left side view is symmetrical with the right side view, it is omitted. FIGS. 35A to 35E show applied examples of a mark provided in the bottom view of the measuring part.

As shown in FIGS. 34A to 34E, the measuring part 100 has appearance based upon a cylinder. A lower part of the measuring part 100 is cut linearly in three of four directions to have three planes. That is, in the measuring part 100, a part of circumferences of the front and both sides is cut linearly. It can be reduced by a cutout 105 on the front side for a subject in getting in or out of the magnetically shielded space 307 or for an examination engineer to hit the end of the measuring part 100. Besides, it can be reduced by a cutout 106 on both sides even if the head of the subject is located on the left or right side for the head (the chin) of the subject to hit the end of the measuring part 100 when the bed moving mechanism 700 is operated.

Inside the end of the measuring part 100, 64 (8×8) pieces of sensors are arranged in a grid on a measurement face Q. Therefore, considering an array of the sensors, the end of the measuring part 100 may be also cut to have four planes. However, in this embodiment, the circulation in the container of a liquid refrigerant such as liquid nitrogen is made satisfactory because the back side which has no effect upon the operation of the subject and the examination engineer is formed in the shape of a circular arc.

As described above, the measuring part 100 has a characteristic that the cooling efficiency of the sensors is made satisfactory, reducing it for the subject and the examination engineer to hit the end of the measuring part 100.

On the measurement face Q, a marker 104 showing positions of the sensors arrayed in a grid is formed. In an example shown in FIG. 34B, all the sensors are shown. Hereby, the examination engineer can align the heart of the subject in a predetermined position, seeing the marker 104.

Further, as for the marker 104 shown in FIGS. 34A to 34E, projecting markers 104a are provided in four locations located on a second column from both sides and on a third row from the upside and the downside. These projecting markers 104a are equivalent to a part in which a xiphisternum of a subject is located in case the heart of the average subject is set to a central position of the measurement face Q. In the cardiac magnetic field measuring device equivalent to this embodiment, as measurement in a state in which the subject lies on his/her back and in a state in which he/she lies with his/her face down is enabled and the measurement of the right side and the left side of the head of the subject is enabled, the projecting markers 104a are set in four locations symmetrical laterally and longitudinally. Hereby, the examination engineer can easily align a diseased part.

Further, as the projecting markers 104a are formed in a convex shape (protruded by 3 to 8 mm) visible from the front, the examination engineer can align the diseased part without looking at the measurement face Q.

FIGS. 35A to 35E show various applied examples of the marker 104. In these examples, if positions of the projecting markers 104a are shown, the projecting markers do not hinder work for alignment at least. For example, FIG. 35A shows only four projecting markers 104a, FIG. 35B shows a mark acquired by adding each cross mark to the projecting markers 104a shown in FIG. 35A to enhance the accuracy of alignment, FIG. 35C shows a mark acquired by combining the cross marks shown in FIG. 35B with another markers 104, FIG. 35D shows a mark acquired by combining vertical columns and horizontal rows respectively passing the projecting markers 104a, and FIG. 35E shows a mark acquired by combining the projecting markers 104a and a marker showing the periphery of the sensors.

Figure 36:
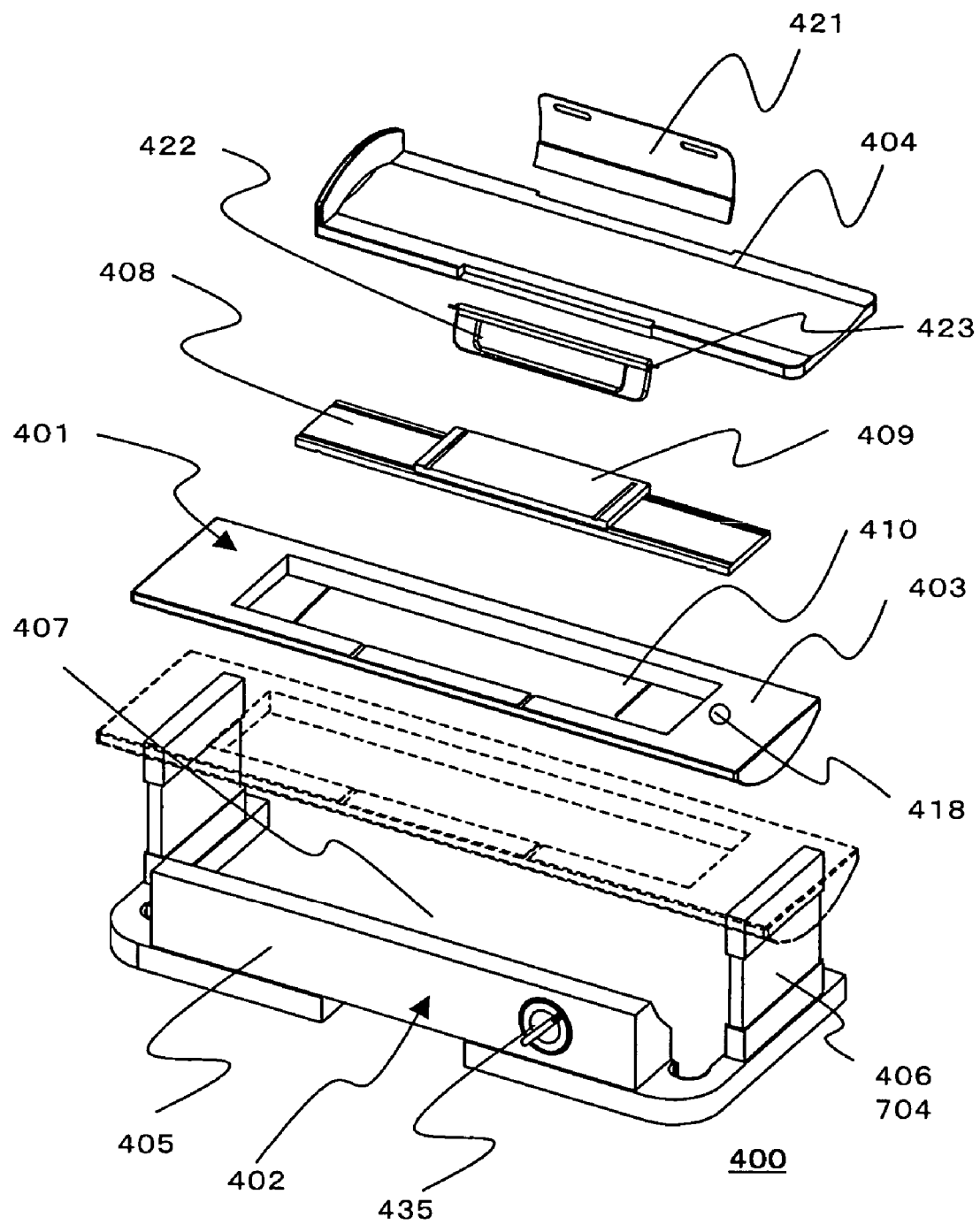
FIG. 36 is an exploded view showing parts of a bed in the first embodiment.
Figure 37:
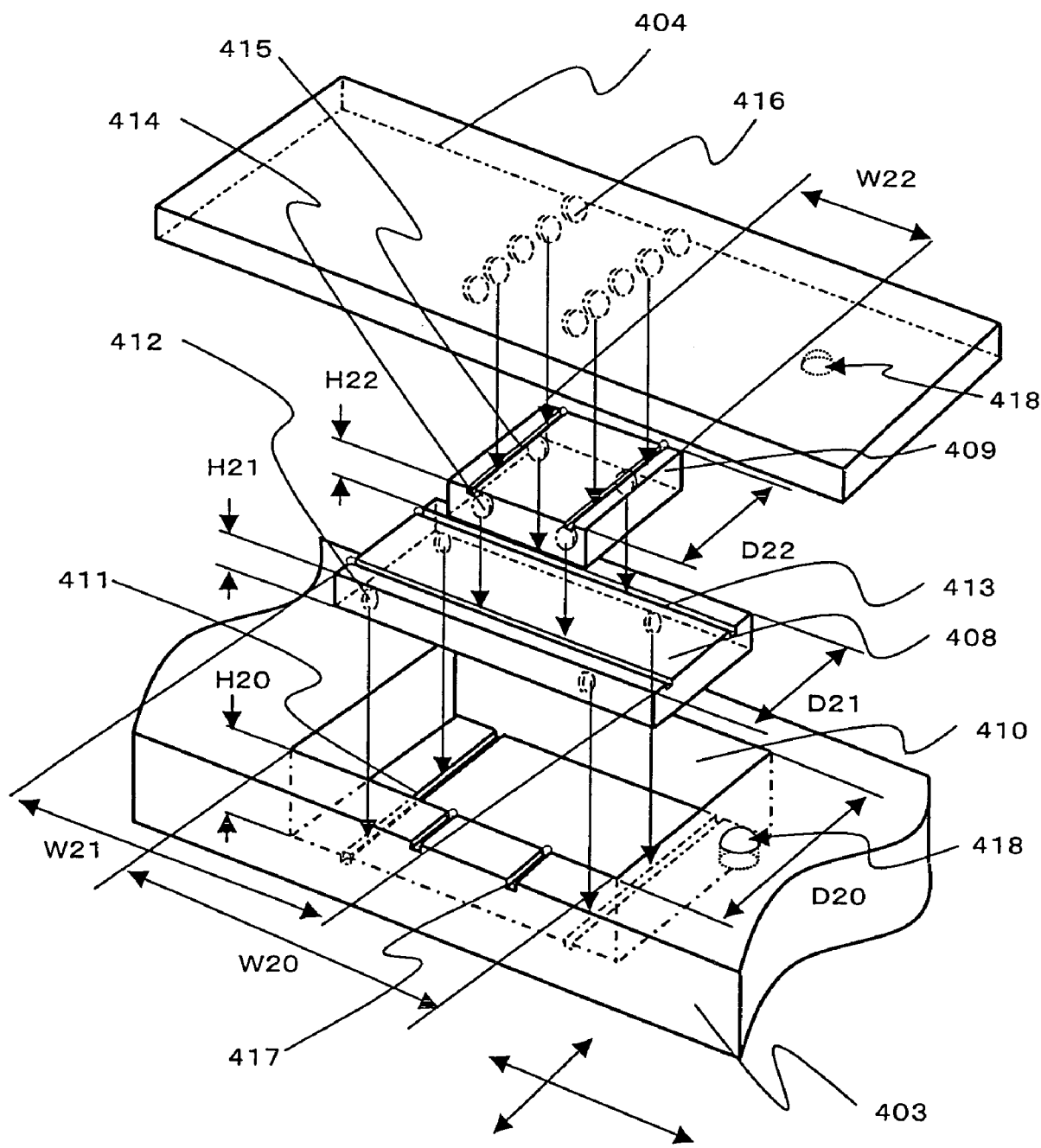
FIG. 37 shows an operational principle of a bed moving mechanism in the first embodiment.
Figure 38:
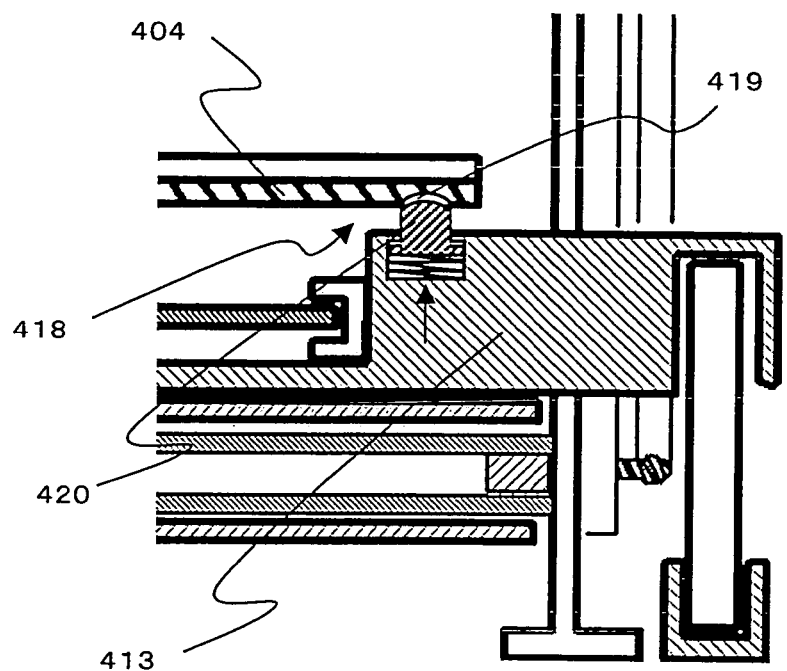
FIG. 38 is a sectional view showing a bed locking mechanism in the first embodiment.
Figure 39:
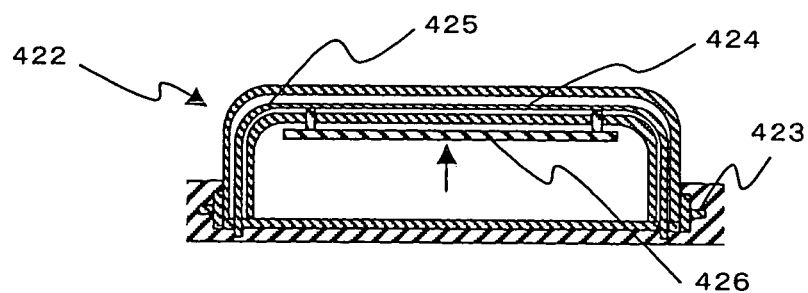
FIGS. 39A and 39B are sectional views showing a handle in the first embodiment.
Figure 39:
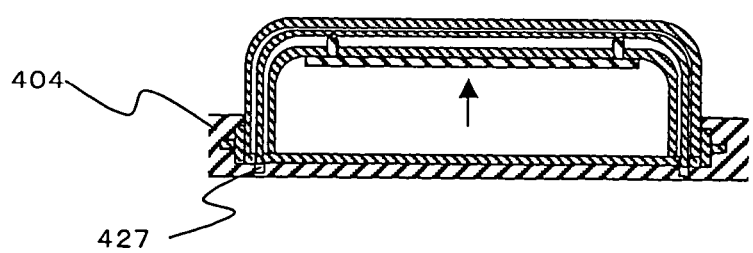
Figure 40:
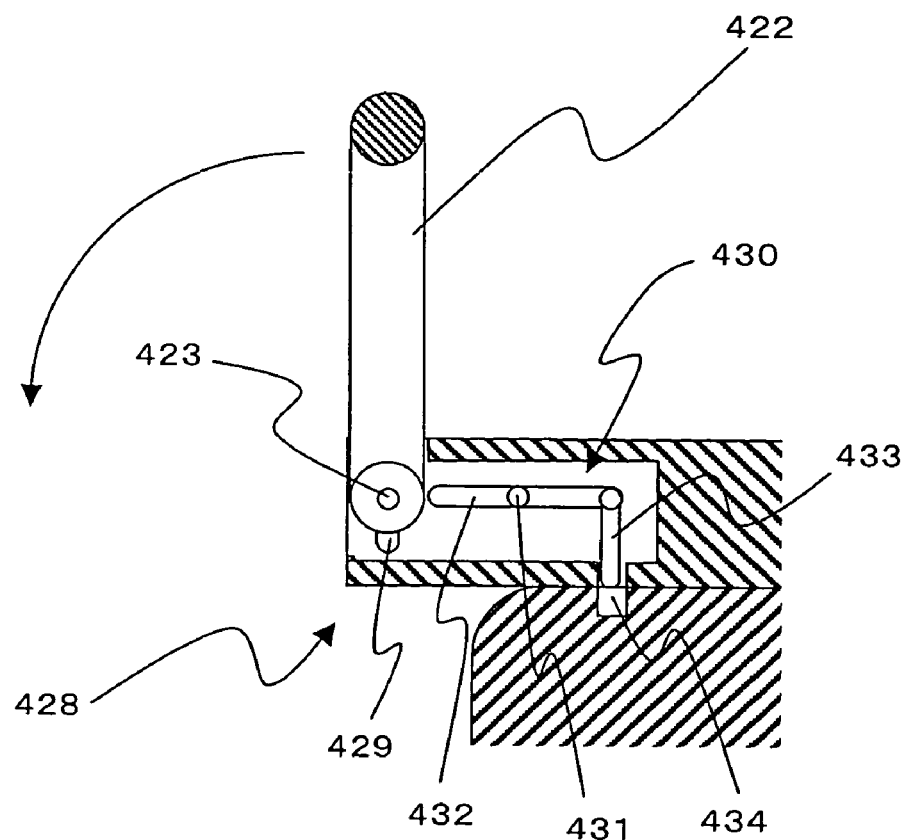
FIGS. 40A and 40B are sectional views showing a pulled-out bed locking mechanism in the first embodiment.
Figure 40:
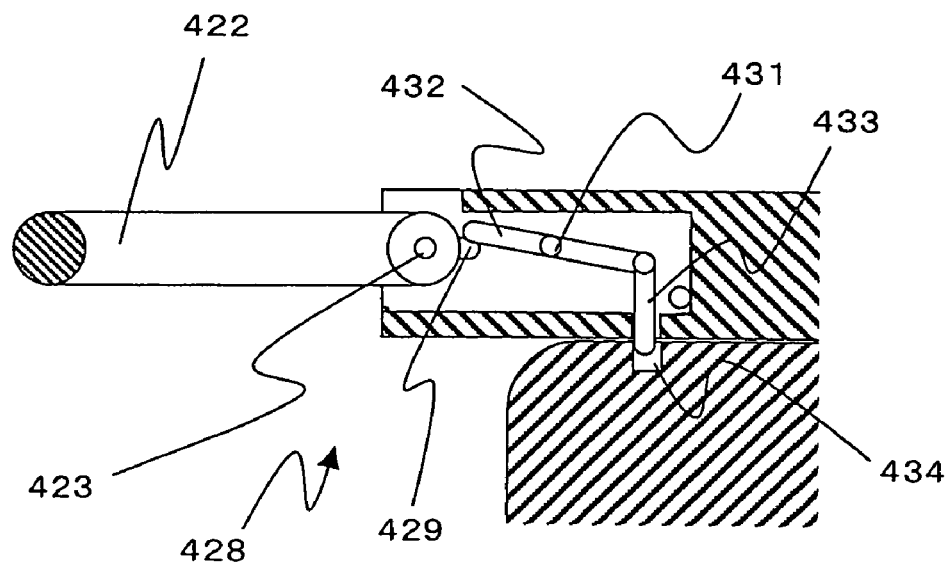
Figure 41:
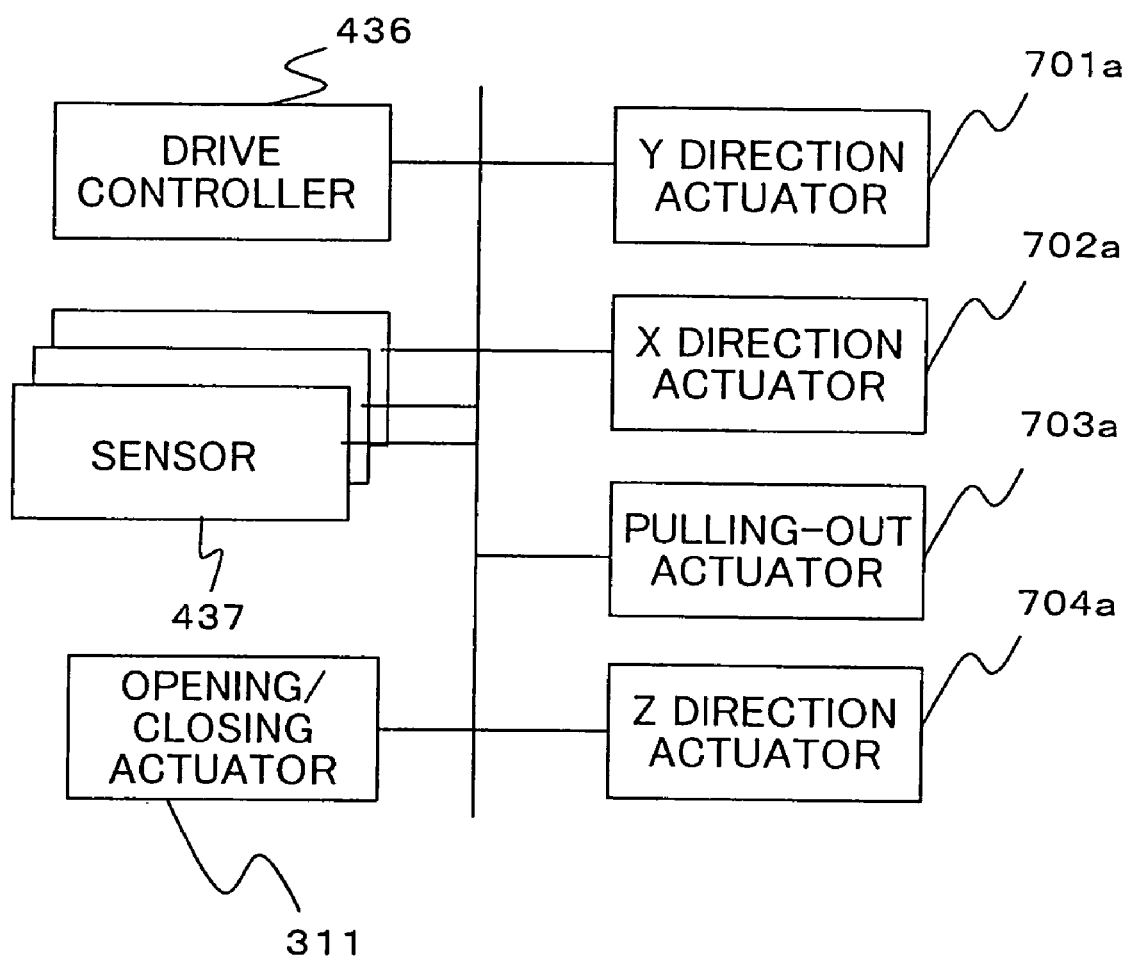
FIG. 41 is a block diagram showing an operating device in case the bed moving mechanism in the first embodiment is automated.
Figure 42:
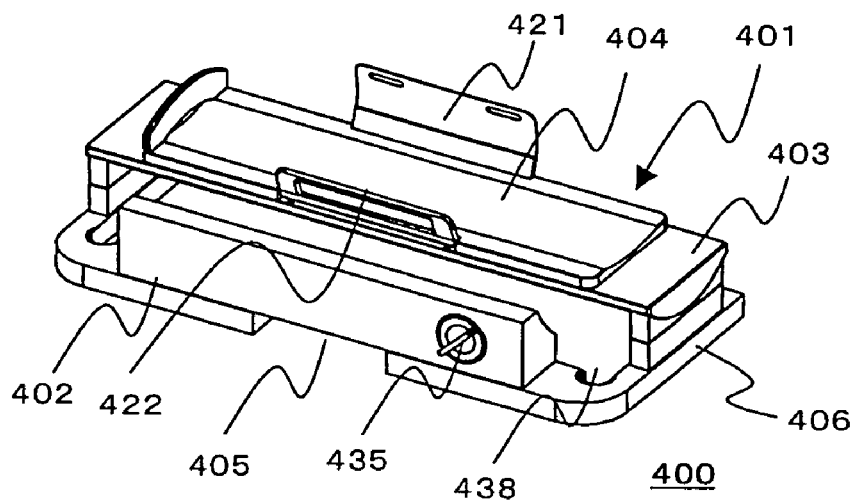
FIGS. 42A to 42D are outside drawings showing the bed in the first embodiment.
Figure 42:
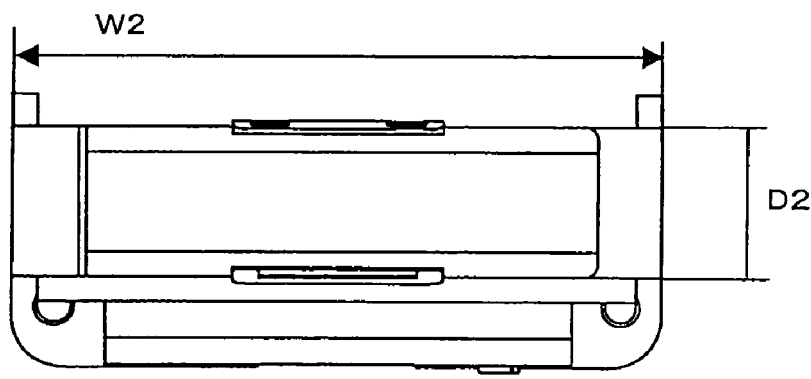
Figure 42:
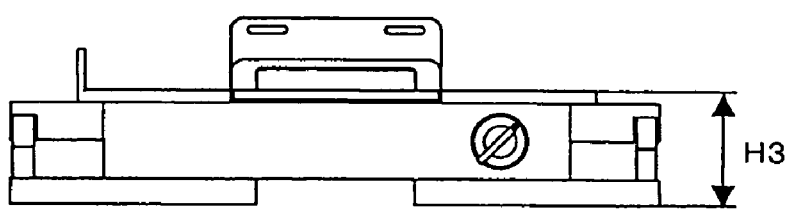
Figure 42:
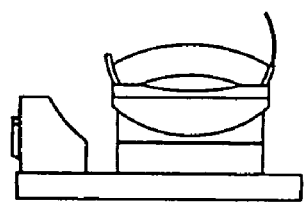

Next, referring to FIGS. 36 to 42, the detailed structure of the bed will be described. FIG. 36 is an exploded view showing parts of the bed. FIG. 37 shows a principle of the operation of the bed moving mechanism. FIG. 38 is a sectional view showing a bed locking mechanism. FIGS. 39A and 39B are sectional views showing a handle, FIG. 39A is the sectional view showing a locked state, and FIG. 39B is the sectional view showing a state in which locking is released. FIGS. 40A and 40B are sectional views showing a pulled-out bed locking mechanism, FIG. 40A is the sectional view showing a locked state, and FIG. 40B is the sectional view showing a state in which locking is released. FIG. 41 is a block diagram showing an operating system in case the bed moving mechanism is automated. FIGS. 42A to 42D are outside drawings showing the bed, FIG. 42A is a perspective view, FIG. 42B is a plane, FIG. 42C is a front view, and FIG. 42D is a right side view.

As described in relation to FIG. 36, the bed 400 is configured by the leg 402 and the top plate 401. The leg 402 is composed of a pair of supports 406 for supporting both ends in a longitudinal direction of the top plate 401 and the front coupling part 405 for coupling each front of the supports 406. The support 406 is provided with the Z direction bed moving mechanism 704 having a hydraulic cylinder not shown in FIG. 36 inside.

The top plate 401 is attached to the supports 406 so that clearance 407 in the shape of a slit is formed between the front coupling part 405 and the side end on the front side of the top plate 401 in a state in which the leg 402 is attached. According to this embodiment, a lower part of the magnetic shield 300 is housed in housing space encircled by the top plate 401, the supports 406 and the front coupling part 405 and the opening/closing body 304 can be opened or closed through the clearance 407.

As shown in FIG. 30, as the measuring part 100 is attached to the cylindrical magnetic shield 300 in this embodiment in a state in which the measuring part is protruded from the upside, the opening/closing body 304 cannot be housed in a circumferential direction of an upper part of the cylindrical magnetic shield 300. However, as nothing protruded is arranged on a circumferential face from the downside to the back side of the cylindrical magnetic shield 300, the opening/closing body 304 can be housed. Therefore, according to this embodiment, the doorway for a subject 305 can be largely released by housing the opening/closing body 304 on the downside of the magnetic shield 300, the doorway for a subject 305 largely released is closed by closing the opening/closing body through the clearance 407, and the magnetically shielded space 307 can be formed.

As shown in FIG. 36 again, the top plate 401 is provided with a top plate base 403 attached to the leg 402, the bed part,on which a subject lies, a first driving plate 408 attached onto the top plate base 403 and a second driving plate 409 installed on the first driving plate 408 so that the second driving plate can be moved for moving the bed part 404 in the direction of the x-axis. The top plate base 403 is provided with a concave portion 410 for housing the first driving plate 408 and the second driving plate 409 on its top face.

In this embodiment, diverse movement of the bed part 404 is enabled by providing the moving mechanism between plural members. This mechanism will further be described referring to FIG. 37.

As shown in FIG. 37, the depth D20 of the concave portion 410 is set so that it is longer than the depth D21 of the first driving plate 408 and the width W20 of the concave portion 410 is set so that it is longer than the width W22 of the second driving plate 409. Difference between the two lengths is equivalent to a range in which the bed part 404 is moved. The height H20 of the concave portion 410 is equivalent to length acquired by adding the height H21 of the first driving plate 408 and the height H22 of the second driving plate 409, and the top face of the second driving plate 409 and the top face of the top plate base 403 are substantially at the same level.

A pair of first rails 411 for moving the first driving plate 408 are provided to the upside of the concave portion 410 in the direction of the x-axis perpendicular to a longitudinal direction of the top plate 401. In the meantime, a group of first rollers 412 corresponding to the pair of first rails 411 are attached at the bottom of the first driving plate 408. The group of first rollers 412 and the first rails 411 configure the X direction bed moving mechanism 702, the bed part 404 is moved in the direction of the x-axis via the X direction bed moving mechanism 702, and the heart to be measured of a subject can be aligned under the measuring part 100.

A pair of second rails 413 parallel to the longitudinal direction of the top plate 401 are provided to the upside of the first driving plate 408. In the meantime, a group of second rollers 414 corresponding to the pair of second rails 413 are attached at the bottom of the second driving plate 409. The group of second rollers 414 and the second rails 413 configure the Y direction bed moving mechanism 701, the bed part 404 is moved in the direction of the y-axis via the Y direction bed moving mechanism 701, and the heart to be measured of a subject can be aligned under the measuring part 100 or the bed part 404 can be moved to a predetermined position (a home position) to pull out the bed part from the magnetically shielded space 307.

As described above, in this embodiment, the bed part 404 on which a subject lies is moved in the directions of the x-, y- and z-axes by the two moving mechanisms (the Y direction bed moving mechanism 701 and the X direction bed moving mechanism 702) and the Z direction bed moving mechanism 704 and a diseased part of the subject can be aligned under the measuring part 100.

Further, in this embodiment, the pulling-out mechanism 703 for pulling out the bed part 404 from the magnetically shielded space 307 is provided. That is, a pair of third rails 415 perpendicular to the longitudinal direction of the top plate 401 are provided on a top face of the second driving plate 409. In the meantime, a group of third rollers 416 corresponding to the pair of third rails 415 are attached at the bottom of the bed part 404. The group of third rollers 416 and the third rails 415 configure the X direction bed moving mechanism and the bed can be moved in the direction of the x-axis via the X direction bed moving mechanism.

Fourth rails 417 continuous from the third rails 415 in predetermined positions (home positions) are provided to the top face of the top plate base 403. In this embodiment, as the top face of the top plate base 403 and the top face of the second driving plate 409 are at the same level, the third rail 415 and the fourth rail 417 can be continued when the second driving plate 409 moved on the second rails 413 is located in the predetermined position (the home position) in the direction of the y-axis. The predetermined position (the home position) is a position in which the bed part 404 is put in or out of the magnetically shielded space 307. Conversely, except the predetermined position (the home position), the bed part 404 cannot be put in or out.

Besides, in this embodiment, a bed locking mechanism 418 for temporarily holding the bed part 404 in a predetermined position (a home position) is provided. For example as shown in FIG. 38, a bed locking mechanism in which a fitting concave portion 419 and a fitting projection 420 for fitting it into the fitting concave portion 419 are divided between the bed part 404 and the top plate 401 can be also adopted.

According to this structure, the fitting concave portion 419 and the fitting projection 420 which constantly tries to maintain a fitted state by a spring and others can be fitted in a predetermined position (a home position). The fitted state has only to have strength enough to at least temporarily maintain a coupled state of the third rail 415 and the fourth rail 417. Hereby, as an examination engineer can recognize that the current position is the predetermined position (the home position), the bed part 404 can be operated so that it is put in or out in the predetermined position (the home position).

In this case, positions for attaching the fitting concave portion 419 and the fitting projection 420 are not limited between the bed part 404 and the top plate 401. For example, the positions may be also provided between faces on which the second driving plate 409 and the first driving plate 408 are touched or between the bed part 404 and the first driving plate 408.

As shown in FIG. 36 again, in this embodiment, it is reduced by providing a hand rail 421 and a handle 422 in the centers of both sides in the longitudinal direction of the bed part 404 that a subject falls off the bed part 404 and they help the subject to mount and leave the bed part 404 in a state in which the bed part 404 is pulled out. Besides, in this embodiment, an examination engineer and a nurse hold the handle 422 arranged on this side of the bed part 404 and can manually put the bed part 404 in or out of the magnetically shielded space 307. Further, in a state in which the bed part 404 is pulled out, the handle 422 is turned with a turning shaft 423 on the downside in the center and can be pushed down. Hereby, it is facilitated for a subject to mount and leave the bed part 404 or for an examination engineer to take care of the subject. FIGS. 39A and 39B show one example of the structure.

As shown in FIGS. 39A and 39B, FIG. 39A is a sectional view showing a locked state and FIG. 39B is a sectional view showing a unlocking state. In this embodiment, the handle 422 is formed in a reverse U shape, and the handle 422 and the bed part 404 are coupled via the turning shafts 423 provided at both ends so that the handle can be turned. A through hole 424 is formed inside the handle 422 and a locking bar 425 in a reverse U shape is housed in the through hole 424. A lever 426 coupled to the locking bar 425 is attached on the downside of a grip in the center of the handle 424. Both ends of the locking bar 425 can be protruded or pulled back from both ends of the through hole 424, when both ends of the locking bar are protruded, they are fitted into fitting holes 427 formed in the bed part 404, and when they are pulled up, the fitting is released. According to this structure, as the lever 426 is kept a state in which it is pulled down by a spring and others in a normal state, a fitted state is maintained. That is, as the handle 422 is kept vertical, it can be reduced by the handle 422 in vertical posture for a subject to fall off the bed part 404 and an examination engineer can move the bed part 404 utilizing the handle 422.

In the meantime, as the locking bar 425 is pulled up by pulling up the lever 426, the fitting of both ends of the locking bar 425 and the fitting holes 427 is released. Hereby, the handle 422 can be pushed down.

Besides, in this embodiment, a pulled-out bed locking mechanism 428 for maintaining the pulled-out bed part 404 in a fixed state is provided. The pulled-out bed locking mechanism 428 has only to fix the bed part 404 and the top plate 401 or the leg 402 to maintain a state in which the bed part 404 is pulled out. In this embodiment, the pulled-out bed locking mechanism 428 is operated utilizing the operation of pushing down the handle 422. This will be described referring to FIGS. 40A and 40B below.

As for FIGS. 40A and 40B, FIG. 40A is a sectional view showing a locked state and FIG. 40B is a sectional view showing a unlocking state. As shown in FIG. 40A, in this embodiment, the handle 422 is maintained in a vertical state by the fitting of the locking bar 425 and the fitting holes 427. In this state, as the handle 422 is fixed to the bed part 404, an examination engineer can pull the bed part 404 out of the magnetic shield 300 utilizing the handle 422. In a state in which the bed part 404 is pulled out, a locked state is released by operating the lever 426 and the handle 422 can be pushed down by turning the handle with the turning shaft 423 in the center. A protruded part 429 formed in the vicinity of the turning shaft 423 acts upon a crank mechanism 430 provided to the bed part 404 by the operation of pushing down. The crank mechanism 430 means structure for rocking a coupling bar 432 based upon a center shaft 431 like a seesaw. The protruded part 429 acts upon one side of the coupling bar 432 and converts the operation of pushing down the handle 422 to operation of pulling up one side of the coupling bar 432. In the meantime, a locking pole 433 is coupled to the other side of the coupling bar 432, the other side of the coupling bar 432 is pulled down when one side of the coupling bar 432 is pulled up, and the locking pole 433 is protruded downward. In this embodiment, a fitting hole 434 fitted to the locking pole 433 is provided on the top face of the front coupling part 405. Therefore, as the locking pole 433 and the fitting hole 434 are fitted when the handle 422 is pushed down in a state in which the bed part 404 is pulled out of the magnetic shield 300, the bed part 404 can be fixed in a position in which the bed part is pulled out. Hereby, as the bed part 404 is fixed in a pulled-out state, a subject can safely mount and leave this bed part 404.

As shown in FIG. 36 again, a turning handle 435 for manually driving the Z direction bed moving mechanism 704 is provided on the front of the leg 402. In this embodiment, the movement of the bed part 404 is automated by providing the bed moving mechanism 700. However, it is also supposed that an actuator is not driven because of any cause. Then, in this embodiment, the turning handle 435 for increasing or decreasing the pressure of the hydraulic cylinder adopted in the Z direction bed moving mechanism 704 is provided.

As shown in FIG. 41, in this embodiment, a drive controller 436 is provided inside the bed 400 to automate the bed moving mechanism 700. Further, plural sensors 437 are provided to each location of the bed moving mechanism 700 and the opening/closing drive mechanism 306. A Y direction actuator 701a is provided to the Y direction bed moving mechanism 701, an X direction actuator 702a is provided to the X direction bed moving mechanism 702, a pulling-out actuator 703a is provided to the pulling-out mechanism 703, and a Z direction actuator 704a is provided to the Z direction bed moving mechanism 704. The drive controller 436 acquires the positional information of each mechanism from the sensors 437 and makes the bed moving mechanism 700 execute operation according to a signal from the thin-type display 211. Besides, the drive controller 436 also controls an opening/closing actuator 311 of the opening/closing drive mechanism 306. Hereby, the linkage operation of the bed moving mechanism 700 and the opening/closing drive mechanism 306 is enabled. The arrangement of the drive controller 436 is not limited to the bed part 404.

It is described above that in this embodiment, the hydraulic cylinder is adopted in the Z direction actuator 704a, however, the similar hydraulic cylinder may be also adopted in another actuator or a magnetically shielded drive motor may be also adopted.

As shown in FIGS. 42A to 42D, the leg 402 is formed by the front coupling part 405 and the supports 406 extended backward on both sides in a U shape when the leg is viewed from the top. The top plate base 403 is provided so that it crosses the pair of supports 406. The width W2 of the top plate base 403 is 2,700 mm, the depth D2 is 600 mm, and the height H3 (a home position) is 450 mm.

Besides, space 438 from which the legs 301 of the magnetic shield 300 are exposed is provided at the back of both sides of the front coupling part 405. The space 438 exposes a release lever 332 provided to the end of the leg 301. The release lever 332 releases the opening/closing drive mechanism 306 to enable manually opening the opening/closing body 304 in the case of emergency. As the space 438 has a large radius of a circle when it is viewed from the top, a problem that an examination engineer stumbles on a corner on both sides is reduced and an impression of the compact device can be also acquired. In addition, as the height is substantially at the same level as the leg 301 of the magnetic shield 300, an examination engineer can operate the release lever 332 provided to the leg 301 with his/her foot.

Further, as clearance 439 is formed on the downside of the center of the front coupling part 405 and space for the legs of an examination engineer for taking care of a subject is secured.

Figure 43:
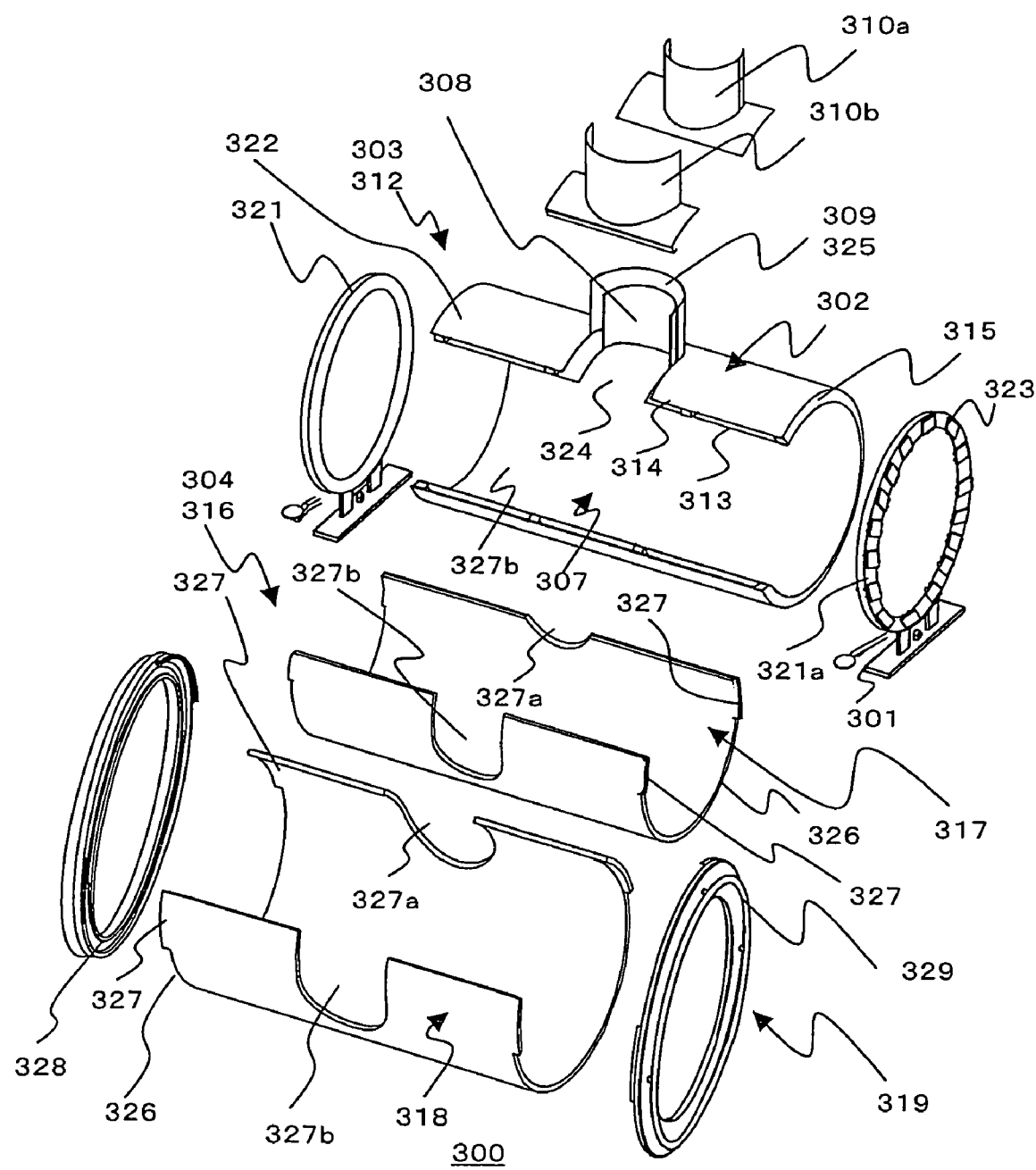
FIG. 43 is an exploded view showing parts of a magnetic shielding room in the first embodiment.
Figure 45:
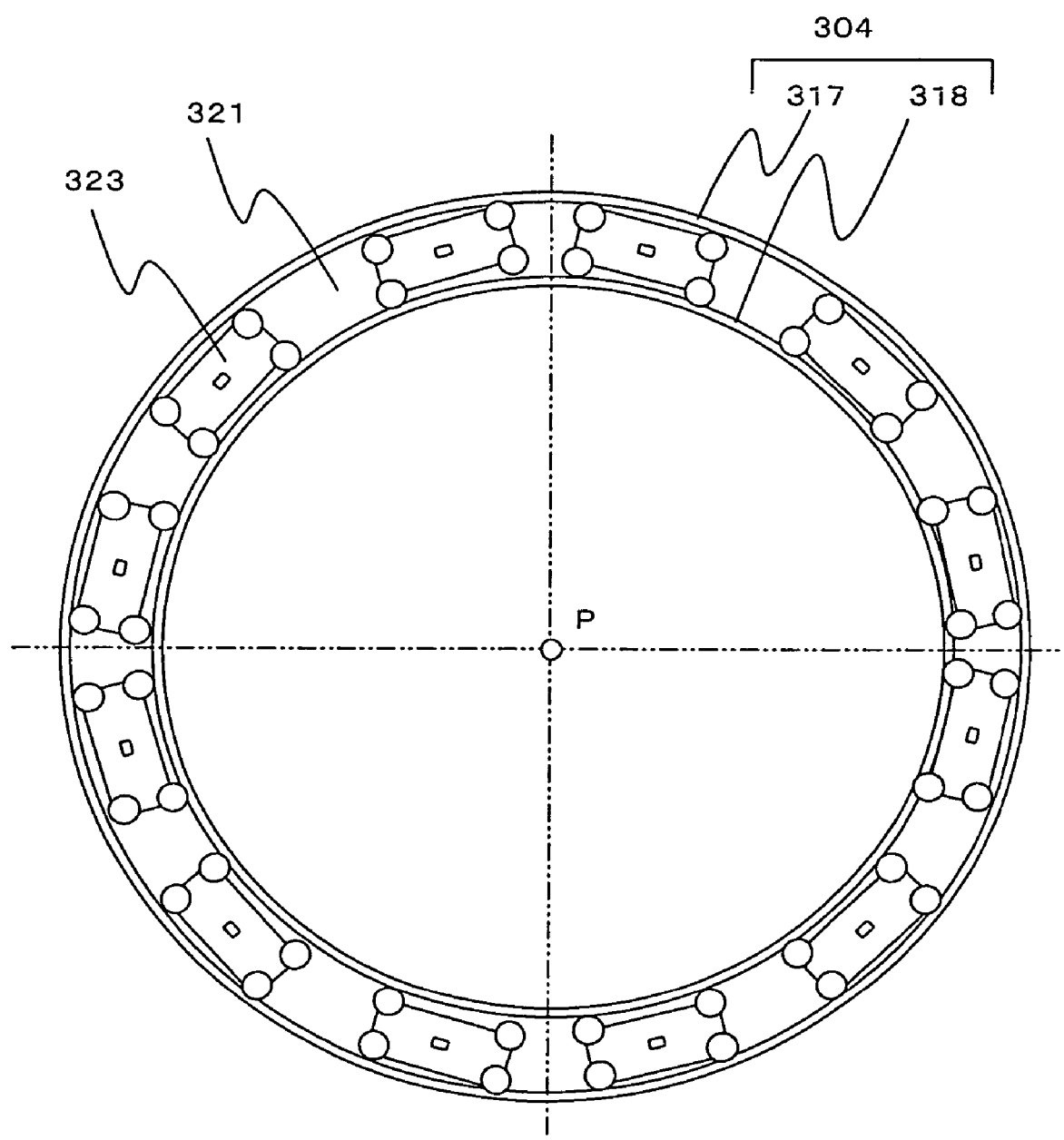
FIG. 45 shows a layout of a roller assembly in the first embodiment.

Next, referring to FIGS. 43 to 45, parts and the outside structure of the magnetic shield will be described. FIG. 43-*is* an exploded view showing the parts of the magnetic shield. FIG. 44 is a sectional view showing the opening/closing drive mechanism. FIG. 45 is a layout drawing showing a roller assembly.

In this embodiment, lightening is designed by forming the main body 303 configuring the body of the shield 302 and the opening/closing body 304 in double structure formed by thin ferromagnetic plates and the shielding factor of an external magnetic field is enhanced thereby. That is, the shielding performance of ferromagnetic material such as Permalloy is not acquired by only thickening ferromagnetic material. Hollow structure of suitable size enhances shielding performance.

In this embodiment, a main armor 312 of the main body 303 is configured by an outside armor 313 formed by Permalloy, an inside armor 314 and a framework 315 (see FIG. 44) provided between both armors 313, 314. The framework 315 is suitably arranged between the two armors 313, 314 and enhances the strength and the magnetically shielding performance of the main armor, forming a hollow part inside the main armor 312.

In the meantime, for a cover armor 316 of the opening/closing body 304, an inside cover armor 317 arranged inside the main armor 312 and an outside cover armor 318 arranged outside the main armor 312 are coupled by an outer ring 319 attached to both ends of the cover armor 316. The inside cover armor 317 and the outside cover armor 318 are configured by a pair of inside and outside armors made of Permalloy and a framework 320 for coupling the pair of armors like the main armor 312 as shown in FIG. 41. The structure will be described in FIG. 44 in detail later.

The main body 303 is configured by the main armor 312, a ring rail 321 attached to both sides in the direction of the y-axis of the main armor 312 and the covers 310. The upside of the front equivalent to approximately ¼ of a circumference of the main armor 312 is the released doorway for a subject 305. In case the doorway for a subject 305 is largely opened, the doorway can be largely formed, however, conversely, as the opening/closing body 304 is largely formed, the opening/closing drive mechanism 306 is large-sized. Then, in this embodiment, the problem is solved by selecting the best position of the doorway for a subject 305. The contents will be described referring to FIG. 48 below.

Figure 48:
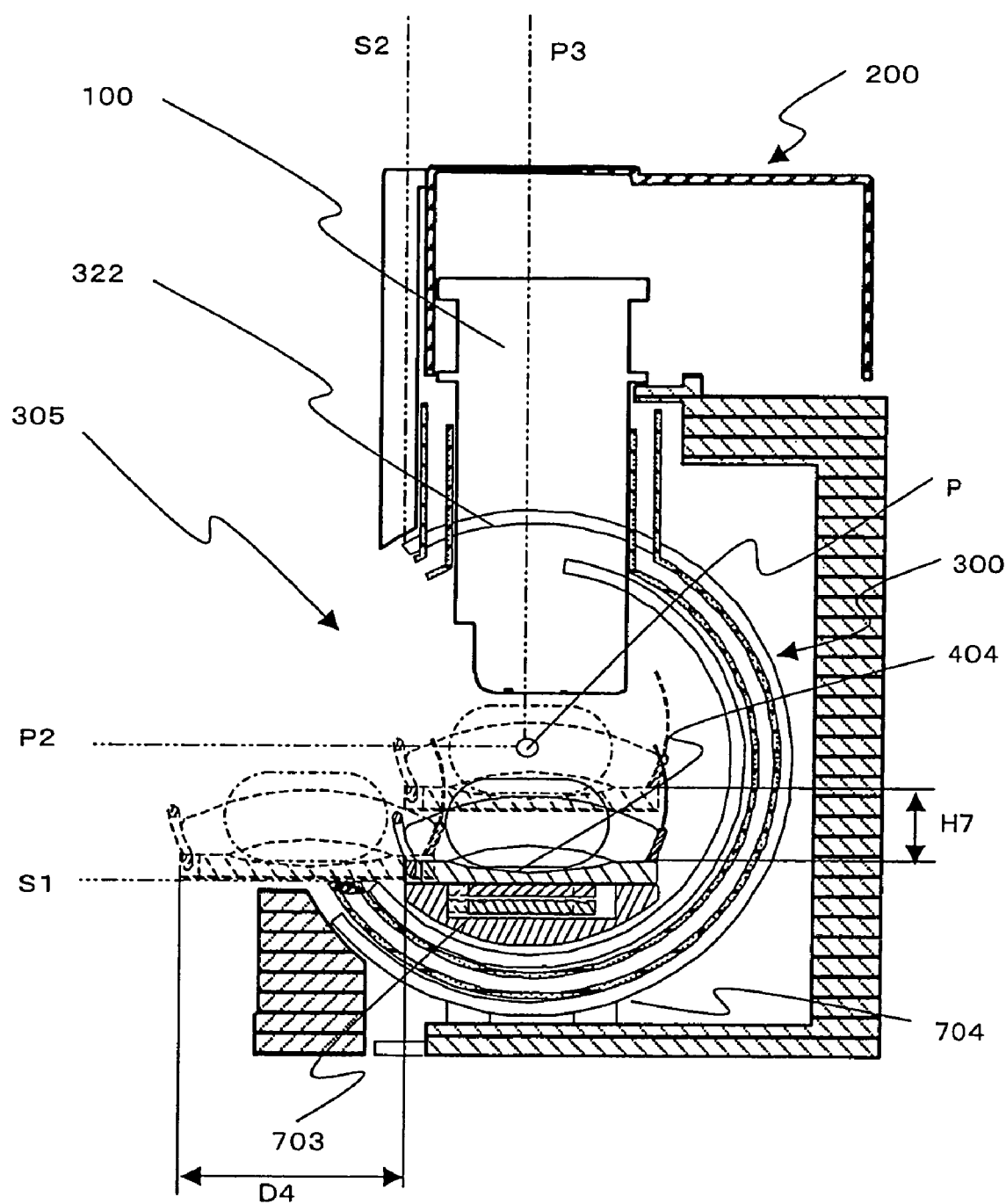
FIG. 48 is a central longitudinal section showing the cardiac magnetism measuring device in the first embodiment.

As shown in FIG. 48, a lower part of the doorway for a subject 305 is opened as far as a position S1 under a horizontal line P2 passing a central axis P of the cylindrical magnetic shield 300 when the cylindrical magnetic shield is viewed from the side and conversely, an upper part of the doorway 305 is opened only as far as S2 in front of a perpendicular P3 passing the central axis P. According to this structure, as an orbit of the pulling-out mechanism 703 can be drawn in a low position, the subject can easily mount and leave the bed part in a state in which the bed part 404 is pulled out of the cylindrical magnetic shield 300. Further, as the upper part of the cylindrical magnetic shield 300 is formed so that its ceiling 322 is left, the subject feels no sense of incompatibility. Further, as the measuring part 100 is arranged on the upside of the cylindrical magnetic shield 300, the measuring part 100 can be firmly held by the ceiling 322 and the gantry 200 for holding the measuring part 100 can be screened from the inside of the cylinder (eyes of the subject).

As shown in FIG. 43 again, the ring rail 321 is attached to the framework 315 provided to both ends of the main armor 312. The ring rail 321 forms the opening/closing drive mechanism 306 together with the armor ring 319 and is provided with plural roller assemblies 323 on a ring face 321a directed outside. This will be described referring to FIG. 45 below.

As shown in FIG. 45, the roller assembly 323 has structure provided with a wheel at four corners of a substantially rectangle and is arranged at an equal interval on the ring face 321. In this embodiment, 12 pieces of roller assemblies 323 are provided. According to this structure, the outside cover armor 318 is supported outside the roller assemblies 323 and the inside cover armor 317 can be supported by the inside wheels. In this embodiment, a case of four rollers is described, however, the invention is not limited to four pieces. The whole device can be small-sized by supporting the opening/closing body 304 between the inside cover armor 317 and the outside cover armor 318.

As shown in FIG. 43 again, the leg 301 is attached to a lower part of the ring rail 321. Therefore, the magnetic shield 300 is supported by a pair of legs 301 provided to the lower part of each ring rail 321 attached to both sides of the body of the shield 302.

The opening 308 for attaching the measuring part 100 is formed in the center of an upper part of the main body 303. The opening 308 has only to be a sectional form of the measuring part 100, for example, a circular opening in this embodiment if only the opening has structure for inserting and attaching the measuring part 100 from the upside. However, in case the measuring part 100 attached to the gantry 200 is attached to the circular opening 308, it is required to be inserted into the opening 308 after the vertically long measuring part 100 is once lifted upward. Therefore, there is a problem that the device according to the invention can be installed only in a room having a high ceiling.

Then, in this embodiment, the front of the opening 308 is cut out. Therefore, as the measuring part 100 can be inserted via a cutout 324 from the front when the measuring part 100 is attached, the device can be installed even in a room having a low ceiling. Besides, in this embodiment, in installation, the measuring part 100 is once detached from the gantry 200, the magnetic shield 300 is installed in the housing space 202, and the measuring part 100 is required to be attached to the gantry again. In this embodiment, a fixture not shown for mounting the measuring part 100 is separately prepared, however, it helps to prevent the device from being large-sized.

Besides, in this embodiment, as the opening 308 is provided on the upside of the cylindrical magnetic shield 300, the expulsion of an external magnetic field around the opening 308 is a serious problem. Particularly, though the shielding performance of the lower part of the measuring part 100 inserted inside the magnetic shield 300 is kept, the shielding performance of an exposed part on the upside is required to be kept. In this embodiment, the problem is solved by covering an upper part of the gantry 200 with the gantry upper cover 207. In this case, as the top face of the magnetic shield 300 in this embodiment is in the shape of a circular arc, a lower part of the gantry upper cover 207 is required to be in a shape fitted to the circular arc or the top face of the magnetic shield 300 is required to be horizontal according to the lower shape of the gantry upper cover 207. Hereby, the invasion of an external magnetic field from contact surfaces of the magnetic shield 300 and the gantry upper cover 207 can be reduced. However, the above-mentioned structure has a problem that it is difficult to form the contact surfaces of the magnetic shield 300 and the gantry upper cover 207.

Then, in this embodiment, a cylindrical extended part 325 protruded upward is provided around the opening 308 and the measuring part 100 is attached to the extended part 325. The gantry upper cover 207 covers the whole part in which the measuring part 100 and the extended part 325 are attached. That is, in this embodiment, the shielding performance is more enhanced by wrapping a connection between Permalloy.

In this embodiment, as the opening 308 is cut out forward, the cutout 324 is covered with the covers 310 and as a whole, the cylindrical extended part 325 protruded upward is formed around the opening 308. Hereby, in structure that the measuring part 100 is inserted from the front, the shielding performance can be also enhanced. Needless to say, the covers 310 also have double structure.

The opening/closing body 304 is configured by the cover armor 316 composed of the inside cover armors 317 and the outside cover armor 318 which respectively make a pair and the outside ring 319 attached to both sides of the cover armor 316. The cover armor 316 is attached to the main armor 312 so that the main armor 312 is held from the inside and the outside as described above. According to this structure, the magnetically shielded space 307 is secured and the whole can be small-sized.

For example, for another embodiment, an opening/closing body 304 having similar double structure only inside a main armor 312 may be also provided. However, in this case, as the thick opening/closing body 304 seems to be moved from a subject located in magnetically shielded space 307, the subject may feel uneasy. Then, when the opening/closing body 304 is thinned, the shielding performance of an external magnetic field has a problem. Then, in this embodiment, structure that a main armor 312 is held by a cover armor 316 from the inside and the outside is provided. According to this structure, a part (an inside cover armor 317) moved in the magnetically shielded space 307 of the opening/closing body 304 can be thinned and the shielding performance can be also maintained by providing ferromagnetic quadruple structure having a hollow part to the opening/closing body 304.

However, in case the structure is adopted, an outside cover armor 318 located outside a main body 303 fixed by legs 301 and the inside cover armor 317 located inside the main body are required to be simultaneously supported and the opening/closing body 304 composed of the two armors is required to be attached to the main body 303 avoiding the legs 301 so that the opening/closing body can be turned.

Then, in this embodiment, structure that the cover armor 316 (the inside cover armor 317 and the outside cover armor 318) and an outside ring 319 are attached via a connection 327 formed on both sides of each except both central parts 326 of the cover armor 316 is provided. According to this structure, as a groove 326a can be formed in the central part 326 along the circumference, the opening/closing body 304 can be turned in a circumferential direction avoiding the leg 301 by passing a strut of the leg 301 in the groove 326a. That is, in this embodiment, the length of the groove 326a is equivalent to a range in which the opening/closing body 304 can be turned. As the groove 326a is located in the vicinity of a circular opening on both sides of the cylindrical magnetic shield 300, an external magnetic field that invades from the groove 326a can be ignored.

Besides, in this embodiment, as a circumferential direction of the cylindrical magnetic shield 300 is equivalent to a doorway for a subject 305, an external magnetic field passing clearance between the main armor 312 and the cover armor 316 is required to be screened. Then, in this embodiment, performance in screening an external magnetic field is enhanced by increasing the area of an opening of the doorway for a subject 305 out of the area of a circumferential face of the cover armor 316 and increasing area in the circumferential direction when the opening/closing body 304 is closed in which the main armor 312 and the cover armor 316 are overlapped. In addition, in this embodiment, as structure that the main armor 312 is held between a pair of cover armor 316 is provided, the shielding performance can be more enhanced.

However, in case such structure is adopted, a measuring part 100 provided in the center of the upside of the magnetic shield 300 hinders the movement of the opening/closing body 304. Then, in this embodiment, the problem is solved by forming cutouts 327a, 327b for avoiding the measuring part 100 at both ends on the side of the doorway for a subject 305 of the opening/closing body 304. Hereby, the large doorway for a subject 305 can be acquired, expelling an external magnetic field.

The outside ring 319 configures the opening/closing drive mechanism together with the ring rail 321, a concave groove 328 for holding the roller assembly 323 from the inside and the outside is formed on its inner face, and a ring handle 329 for manually opening and closing the opening/closing body 304 is provided to the outer face.

Next, referring to FIG. 44, the opening/closing drive mechanism 306 will be described further in detail. FIG. 44 is a sectional view showing the cylindrical magnetic shield 300, the right is enlarged, and the center is omitted.

The inside cover armor 317 and the outside cover armor 318 are respectively configured by an outer plate 330, an inner plate 331 and a framework 320. The main armor 312 having the similar structure is located between the inside cover armor 317 and the outside cover armor 318. The frameworks 315, 320 are provided at each end of both sides of each armor, and the ring rail 321 and the outside ring 319 are attached to the frameworks 315, 320.

The inside cover armor 317 and the outside cover armor 318 are connected to the outside ring 319 at a connection 327 (shown on the right upside of FIG. 44), however, in the center 326 (shown on the right downside of FIG. 44), the inside cover armor 317 and the outside cover armor 318 are not coupled. Therefore, the strut of the leg 301 can pierce an uncoupled part.

In the meantime, the ring rail 321 to the ring face 321a of which plural roller assemblies 323 are attached is attached to the framework 315. The rollers of the roller assembly 323 are touched to the periphery and the inner face of the concave groove 328 by inserting it into the concave groove 328 and the opening/closing body 304 is supported in the circumferential direction so that the opening/closing body can be turned.

The revolution in the circumferential direction of the opening/closing body 304 is not hindered because the leg 301 pierces the central part 326.

Figure 46:
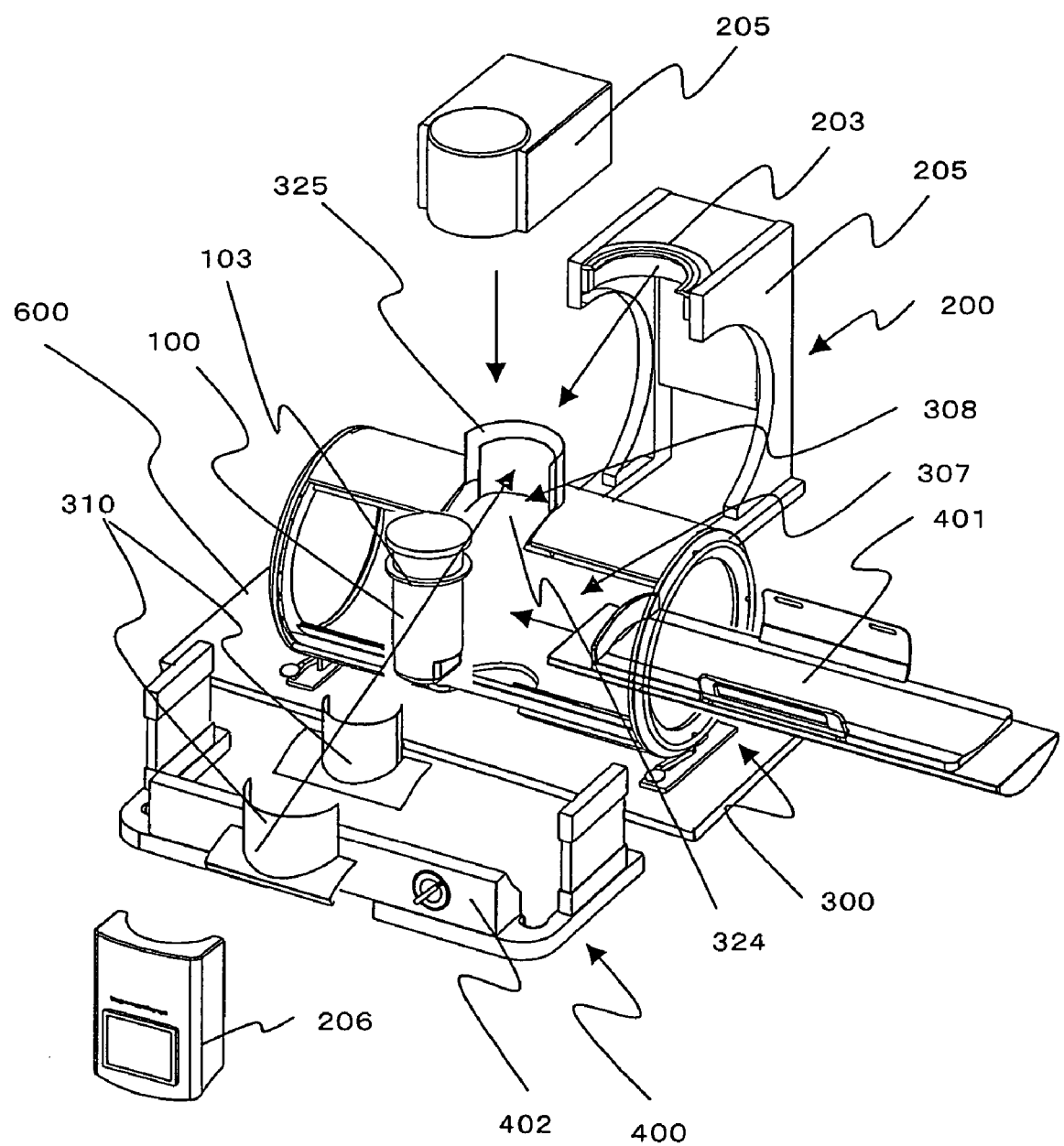
FIG. 46 is an assembly drawing showing the cardiac magnetism measuring device in the first embodiment.

Next, referring to FIG. 46, a method of installing the cardiac magnetic field measuring device will be described further in detail. FIG. 46 is an assembly drawing showing the device. As described above, in this embodiment, the cardiac magnetic field measuring device is configured by assembling each unit independent every function in an installed location. Particularly, the measuring part 100, the gantry 200, the magnetic shield 300 and the bed 400 are manufactured in a manufacturing site as an independent unit and each unit is assembled in the installed location.

In installation, a basic device, for example the magnetic shield 300 is mounted over the base 600. The gantry 200 is inserted into the opening 308 of the magnetic shield 300 from the back so that the examination support 203 is aligned and is attached to the base 600. At this time, only the gantry base 205 is attached from the back and the measuring part 100 is attached to the examination support 203 from the front utilizing the fixture not shown in FIG. 46. The center of the measuring part 100 is located in the magnetically shielded space 307, the center is touched to the extended part 325, and the flange 103 is attached to the examination support 203.

Afterward, a pair of covers 310 (310a, 310b) are attached so that they cover the cutout 324 and the extended part 325 and further, the gantry upper cover 207 and the gantry front cover 206 are sequentially attached to the gantry base 205.

As for the bed 400, the leg 402 from which the top plate 401 is removed is inserted from the front of the magnetic shield 300 and is attached to the base 600, afterward the top plate 401 is attached to the leg 402, each unit is wired, and installation is completed.

Figure 47:
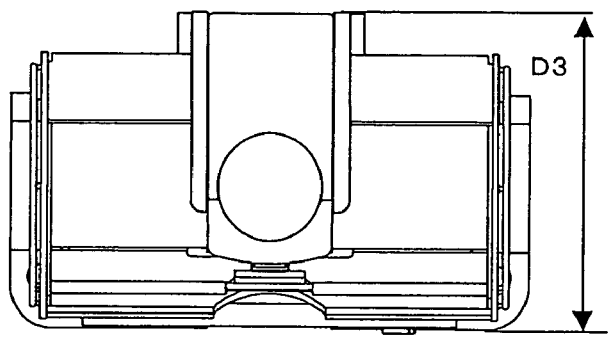
FIGS. 47A to 47D are outside drawings showing the cardiac magnetism measuring device in the first embodiment.
Figure 47:
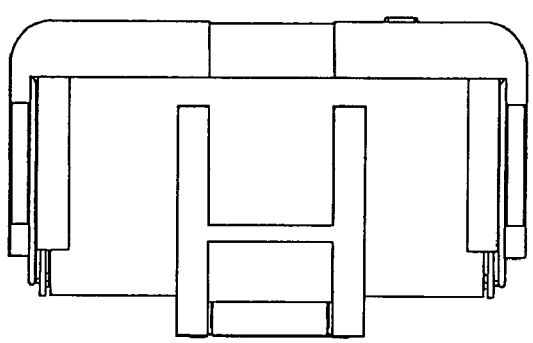
Figure 47:
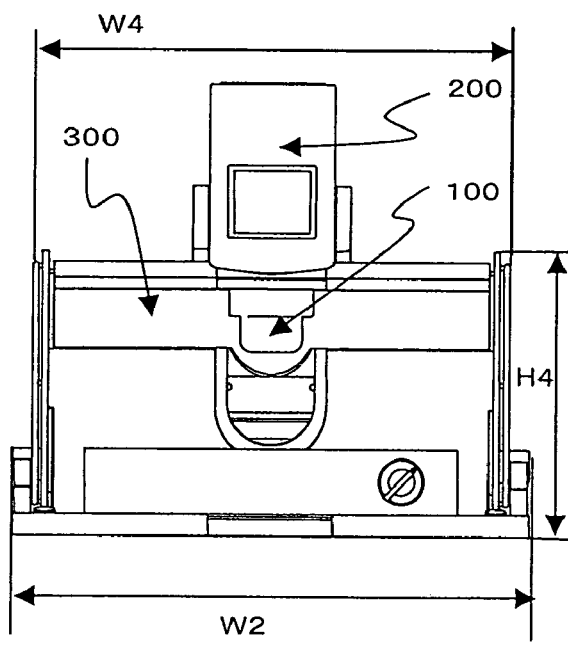
Figure 47:
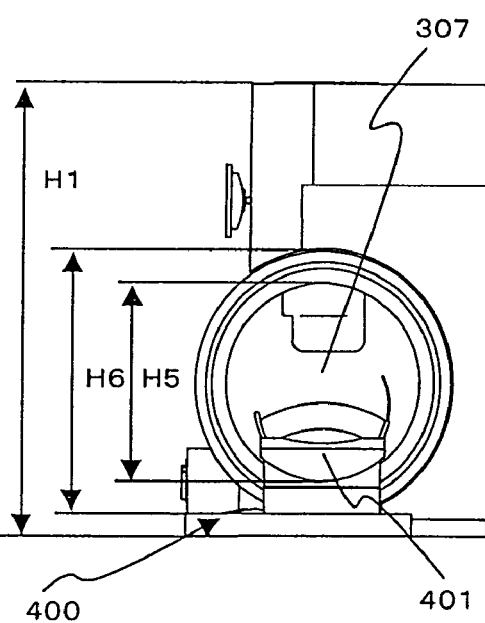

Next, referring to FIGS. 47 and 48, the structure of the cardiac magnetic field measuring device in a state in which each unit is assembled will be described further in detail. FIGS. 47A to 47D are outside drawings showing the cardiac magnetic field measuring device, FIG. 47A is a plan, FIG. 47B is a bottom view, FIG. 47C is a front view, and FIG. 47D is a right side view. FIG. 48 is a longitudinal section showing the center of the cardiac magnetic field measuring device. As for each drawing of FIGS. 47A to 47D, to simplify description, the opening/closing body 304 is shown in a state in which it is closed as far as an intermediate position.

A shown in FIGS. 47A to 47D, the cardiac magnetic field measuring device equivalent to this embodiment has basic structure bilaterally symmetrical that the center of an upper part of the magnetic shield 300 is protruded upward when the measuring device is viewed from the front by combining the cylindrical magnetic shield 300 in horizontal posture and the gantry 200 vertically long in a central position of the magnetic shield 300. Besides, the magnetic shield 300 and the gantry 200 are in such a shape that the tall gantry 200 bites at the cylindrical magnetic shield 300 when they are viewed from the side. The bed 400 is built in the magnetic shield 300 and is integrated with the magnetic shield 300.

The inside diameter H5 of the magnetic shield 300 is set to 900 mm and the width W4 is set to 2,300 mm. That is, in this embodiment, the width W4 of the magnetic shield 300 is set to the length of twice or more of the inside diameter H5 and the measuring part 100 is set to substantially the center of the width W4. Hereby, magnetically shielding performance is enhanced. The top plate 401 is held outside the magnetically shielded space 307 and can be lifted or lowered in the direction of the z-axis in the magnetically shielded space 307 respectively by making the length W3 (2,700 mm) of the top plate 401 longer than the width W4 of the magnetic shield 300.

Besides, in this embodiment, as only the upper part of the central gantry 200 has height H1 and the height H4 of the magnetic shield 300 on both sides is set to 1,350 mm, the device has such a shape that a subject does not feel the whole device large. Particularly, as the magnetic shield 300 is cylindrical and the top face is formed in the shape of a circular arc, the subject does not feel the height of H4.

As space in which the three units (the gantry 200, the magnetic shield 300 and the bed 400) are installed is shared, the cardiac magnetic field measuring device has compact structure having installation space that the width is W3 and the depth is D3 (1,450 mm).

Next, as shown in FIG. 48, in this embodiment, a range H7 moved by the Z diction bed moving mechanism 704 is set to 200 mm on the upside of a home position. A position sensor 437 is provided at a lower end of the measuring part 100, issues a signal when an obstacle (a subject) exists in predetermined distance, and can stop the movement of the Z direction bed moving mechanism 704. Hereby, an examination engineer can adjust distance between a diseased part and the measurement face Q to suitable distance in accordance with the physique of the subject and the safety is enhanced.

In the meantime, a range D4 moved by the pulling-out mechanism 703 is set to 500 mm in front from a home position. Hereby, as the bed part 404 is largely pulled out in front, it is facilitated for a subject to mount or leave the bed part 404.

Figure 49:
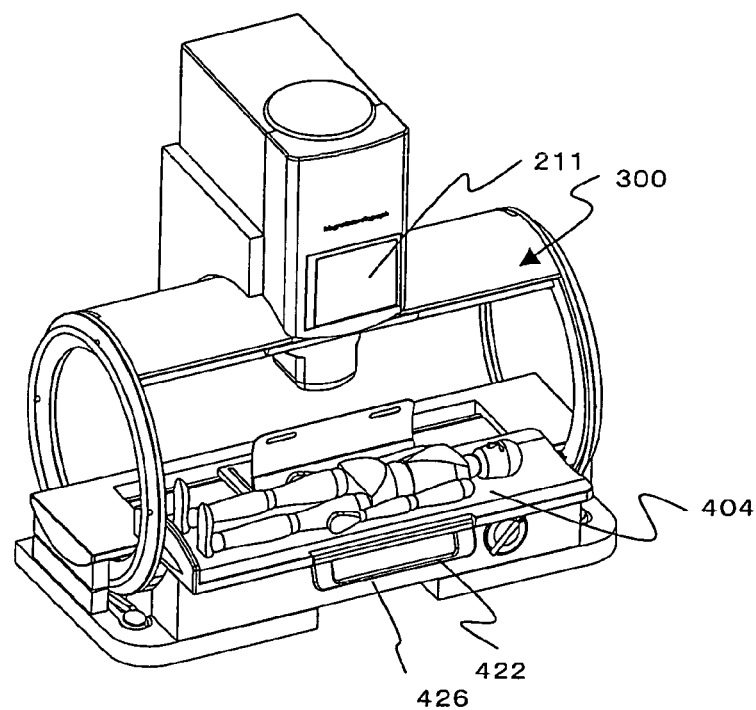
FIG. 49 is a perspective view showing a state in which the bed is pulled out.
Figure 51:
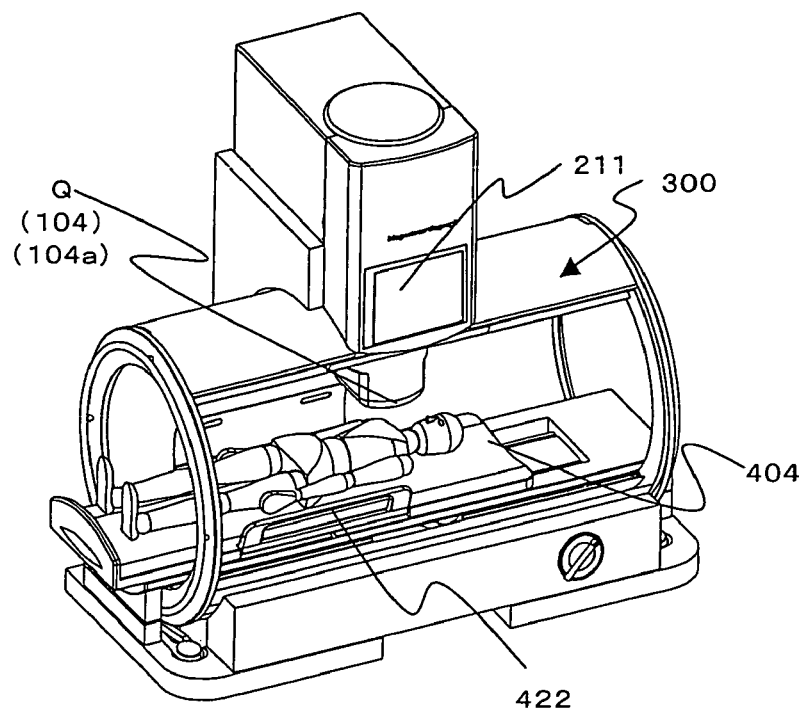
FIG. 51 is a perspective view showing a state in which an XY direction in the first embodiment is aligned.
Figure 52:
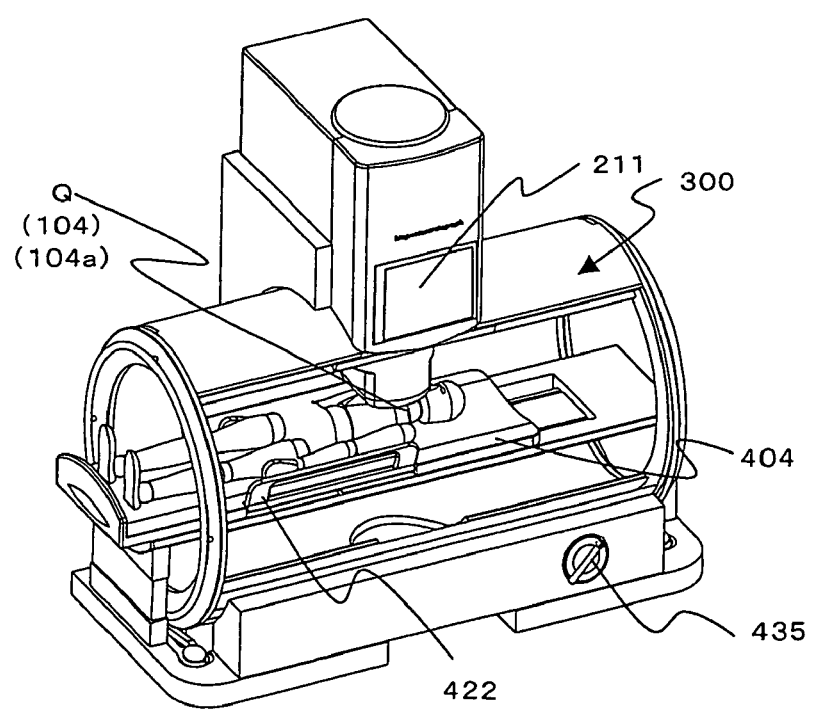
FIG. 52 is a perspective view showing a state in which a Z direction in the first embodiment is aligned.
Figure 53:
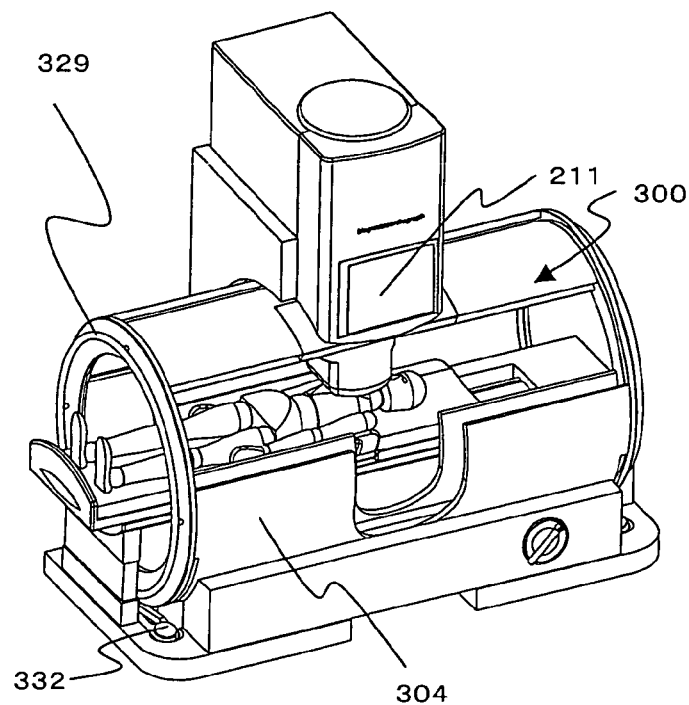
FIG. 53 is a perspective view showing a process for closing an opening/closing body in the first embodiment.
Figure 54:
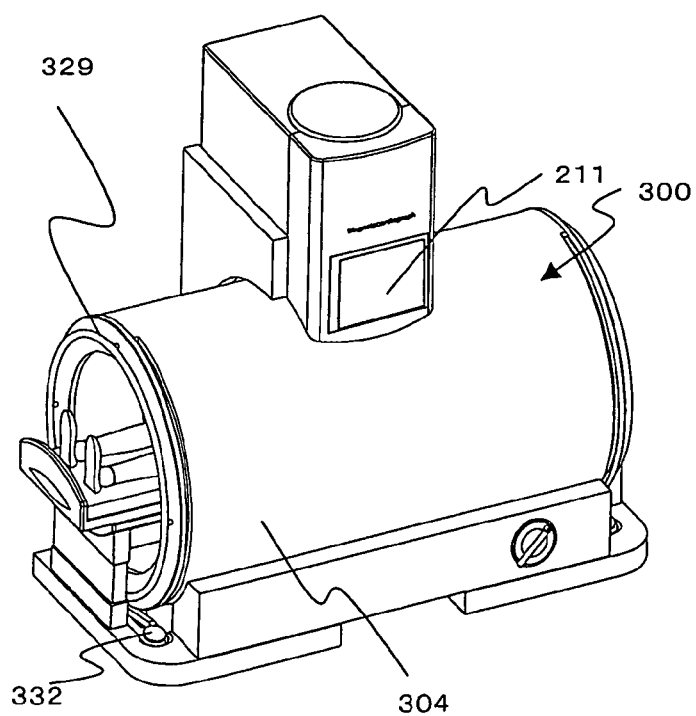
FIG. 54 is a perspective view showing a state in which the opening/closing body in the first embodiment is closed.

Next, referring to FIGS. 49 to 54 and FIG. 41, the operation of the bed moving mechanism 700 and the opening/closing drive mechanism 306 and a method of operating them will be described. FIG. 49 is a perspective view showing a state in which the bed part 404 is pulled out, FIG. 50 is a perspective view showing a state in which the bed part 404 is located in a home position in the magnetically shielded space 307, FIG. 51 is a perspective view showing a state in which the Y direction bed moving mechanism 701 and the X direction bed moving mechanism 702 are operated and alignment in the directions of the x- and y-axes is made, FIG. 52 is a perspective view showing a state in which the Z direction bed moving mechanism 704 is operated and alignment in the direction of the z-axis is made, FIG. 53 is a perspective view showing a process for operating the opening/closing drive mechanism and closing the opening/closing body, and FIG. 54 is a perspective view showing a state in which the opening/closing body is closed.

Figure 50:
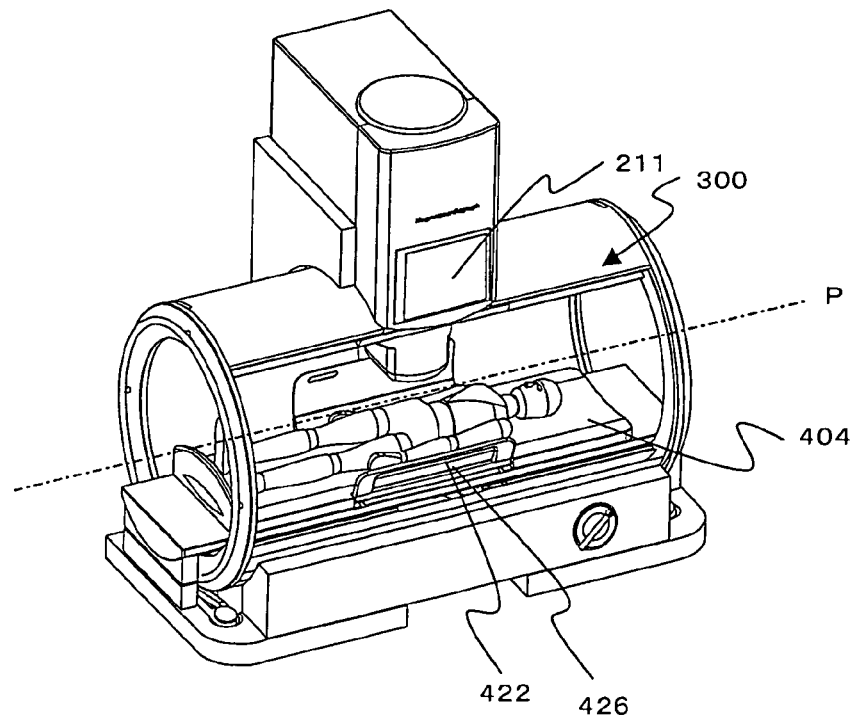
FIG. 50 is a perspective view showing a state in which the bed in the first embodiment is located in a home position.

First, in the cardiac magnetic field measuring device, the longitudinal direction of the bed part 404 is made substantially coincident with the central axis P of the magnetic shield 300 and a home position shown in FIG. 50 in which the bed part 404 can be pulled out forward by the pulling-out mechanism 703 or a state shown in FIG. 49 in which the bed part 404 is pulled out can be made an initialized position when power is off.

When an examination engineer turns on a power switch not shown in FIGS. 21 to 54, the drive controller 436 instructs the thin-type display 211 to display a menu screen not shown in FIGS. 21 to 54. In the description, the description of maintaining the temperature of the measuring sensor 101 is omitted. The examination engineer can select screens for operational guidance and switches respectively not shown in FIGS. 21 to 54 on the menu screen.

In this embodiment, manual operation in which the bed moving mechanism 700 and the opening/closing drive mechanism 306 can be manually operated and automatic operation via the drive mechanism can be selected. These can be selected on the menu screen. Besides, the drive mechanism is detached beforehand in installation and manual operation can be set. Manual operation and automatic operation using the drive mechanism will be described below.

First, manual operation will be described. In manual operation, an examination engineer drives the bed moving mechanism 700 and the opening/closing drive mechanism 306.

In case the home position shown in FIG. 50 is set as an initialized position, an examination engineer can pull out the bed part 404 on this side using the handle 422. As the bed part 404 is temporarily locked by the bed locking mechanism 418 in the home position, the third rail 415 and the fourth rail 417 are coupled. Therefore, a state locked by the bed locking mechanism 418 is easily released by pulling out the bed part 404 on this side, the group of third rollers 416 is moved on the third rail 415 and the fourth rail 417 respectively coupled, and the state shown in FIG. 49 in which the bed part 404 is pulled out is acquired.

An examination engineer releases the fitting of the fitting hole 427 and the locking bar 425 by operating the lever 426 of the handle 422 and can push down the handle 422 on this side. As the bed part can be locked by the pulled-out bed locking mechanism 428 by pushing down the handle 422, the bed part is fixed as shown in FIG. 49.

As in the state shown in FIG. 49, the bed part 404 is fixed and the handle 422 is pushed down, a subject can mount the bed part 404 in comfortable posture and can lie on it.

As for operation for shifting the state shown in FIG. 49 in which the subject lies on the bed part 404 to the home position shown in FIG. 50, operation reverse to the above-mentioned operation is performed. That is, the examination engineer can move the bed part 404 by pulling up the handle 422, locking it in a state in which the handle stands and unlocking the pulled-out bed locking mechanism 428 and can push down the bed part 404 to the original home position via the handle 422. The examination engineer can know that the bed part 404 is moved to the home position because the bed part 404 is temporarily locked by the bed locking mechanism 418.

In the home position shown in FIG. 50, the bed part 404 can be moved in a predetermined examination position by operating the Y direction bed moving mechanism 701, the X direction bed moving mechanism 702 and Z direction bed moving mechanism 704.

For basic operation, positions in the directions of the y- and x-axes are set as shown in FIG. 51. In moving the bed part 404, the handle 422 can be used. An examination engineer can roughly align a diseased part of a subject using the marker 104 provided on the measurement face Q. At this time, the diseased part can be aligned (finely controlled) by providing a mechanism not shown in FIG. 41 for temporarily fixing the position at a predetermined interval with the Y direction bed moving mechanism 701 and the X direction bed moving mechanism 702. The variation of the aligned position can be reduced by the mechanism not shown in FIG. 41.

Next, as shown in FIG. 52, the position in the direction of the z-axis is set. For the position in the direction of the z-axis, the Z direction bed moving mechanism 704 is operated by operating the turning handle 435 and the bed part 404 can be lifted or lowered. In the movement in the direction of the z-axis, distance between the measurement face Q and the subject can be sensed by the sensor 437 provided on the measurement face Q. The drive controller 436 controls so that the distance is informed by a buzzer not shown in FIG. 41 and others at two levels with the assistance of the sensor 437. Hereby, the examination engineer is informed of approximate distance by first detection and can finely control afterward. Safety is maintained by second detection.

In a state shown in FIG. 52, final alignment in the directions of the x-, y- and z-axes can be made using a marker, particularly the projecting marker 104a. As the projecting marker 104a is protruded downward and it is not required to peep on the measurement face Q, alignment is facilitated.

Next, when the final alignment of the diseased part with the measurement face Q is completed, the opening/closing body 304 can be closed using the ring handle 329 as shown in FIGS. 53 and 54. As the opening/closing body 304 is closed so that it is pulled up from the downside to the upside, such an accident that even if a hand of the subject is located at the end of the opening/closing body 304, the hand is caught by opening/closing operation can be reduced.

The opening/closing drive mechanism 306 is fixed by a locking mechanism not shown in FIG. 54 in a state shown in FIG. 54 in which the opening/closing body 304 is closed. The locking mechanism can be released by operating the release lever 332.

An examination engineer can start measurement by operating a switch displayed on the thin-type display 211 in the state shown in FIG. 54. A measurement screen can be also displayed on the thin-type display 211.

When the measurement is finished, the examination engineer can restore the original state shown in FIG. 49 by reverse operation.

Next, automatic operation using the driving mechanism will be described. In automatic operation, the drive controller 436 controls the drive of the bed moving mechanism 700 and the opening/closing drive mechanism 306. The description of points overlapped with the description of the manual operation are omitted. The sensor 437 is provided in various locations, the drive controller 436 detects a signal from these sensors 437 and controls operation.

In case the home position shown in FIG. 50 is set as an initialized position, the drive controller 436 detects whether the bed part 404 is located in the home position or not when an examination engineer pushes down the handle 422 after he/she operates the switch, drives the pulling-out actuator 703a if the bed part is located in the home position, moves the bed part 404 to a position shown in FIG. 49, and locks the bed part using the pulled-out bed locking mechanism 428. It can be detected by providing the sensor 437 to the bed locking mechanism 418 for example whether the bed part 404 is located in the home position or not. In case the bed part 404 is not located in the home position, warning and a switch for returning the bed part to the home position are displayed on the thin-type display 211.

Operation for moving the bed part from the state shown in FIG. 49 in which a subject lies on the bed part 404 to the home position shown in FIG. 50 is reverse to the above-mentioned operation. That is, when an examination engineer pulls up the handle 422, the drive controller 436 operates the pulling-out actuator 703a and moves the bed part 404 to the home position shown in FIG. 50.

As described above, in this embodiment, as the bed moving mechanism 700 is operated by touching the thin-type display 211 of the gantry 200, the operation on the thin-type display 211 becomes difficult when the bed part 404 is pulled out. Then, the bed part 404 can be pulled in or out by operating the handle 422 after the operation of the switch on the thin-type display 211.

When an actuator not shown in FIGS. 49 to 52 is provided to the handle 422 and operation for pulling out the bed part 404 is performed by touching the switch, the drive controller 436 detects whether the bed part 404 is located in the home position or not and may also control so that the actuator not shown in FIGS. 49 to 52 is operated to push down the handle 422 if the bed part is located in the home position and the bed part 404 is pulled out. In this case, safety is enhanced by providing an infrared ray sensor to the front coupling part 405 and ringing a buzzer sound and others when an obstacle is sensed and when the bed part 404 is moved.

Next, when the drive controller 436 detects that the bed part 404 is located in the home position as shown in FIG. 50, it makes a switch for the bed moving mechanism 700 displayed on the thin-type display 211 operable. An examination engineer operates the Y direction bed moving mechanism 701, the X direction bed moving mechanism 702 and/or the Z direction bed moving mechanism 704 by touching the switch and can move the bed part 404 in the predetermined examination position.

For basic operation, first, as shown in FIG. 51, a position in the directions of the y- and x-axes is set. As the thin-type display 211 is arranged in the vicinity of the measurement face Q formed at the end of the measuring part 100 for this operation, an examination engineer can operate on the thin-type display 211, looking at the measurement face Q and a diseased part of a subject. Similarly, as shown in FIG. 52, the movement in the direction of the z-axis is also enabled by operating on the thin-type display 211. Fine control utilizing the projecting marker 104a can be also made in comfortable posture.

Further, as shown in FIGS. 53 and 54, the operation of the opening/closing actuator 311 is also enabled by operating on the thin-type display 211. In this case, an examination engineer can operate in a position close to a subject, talking to him/her and as the examination engineer exists in the neighborhood when the opening/closing body 304 is being closed, the uneasiness of the subject is reduced.

The drive controller 436 drives a locking mechanism not shown in FIGS. 49 to 54 in a state in which the opening/closing body 304 is closed to lock the opening/closing body 304. This locked state can be released by operating the release lever 332.

An examination engineer operates a switch displayed on the thin-type display 211 in the state shown in FIG. 54 and can start measurement.

When the measurement is finished, the examination engineer gradually performs the next operation, the drive controller 436 operates each actuator, and can restore the state shown in FIG. 49. First, the pulling-out mechanism 703 turns the state shown in FIG. 54 into the state shown in FIG. 52 in which the opening/closing body 304 is open via a state shown in FIG. 53. Next, the Z direction bed moving mechanism 704 turns the state shown in FIG. 52 into a state shown in FIG. 51 in which the height in the direction of the z-axis of the bed part 404 is restored to the original height of the home position. Next, the Y direction bed moving mechanism 701 and the X direction bed moving mechanism 702 turn the state shown in FIG. 51 into a state shown in FIG. 50 in which the directions of the x- and y-axes of the bed part 404 are restored to those of the original home position. Next, operation for pushing down the handle 422 turns the state shown in FIG. 50 into the state shown in FIG. 49 in which the bed part 404 is pulled out forward. In these gradual operations, the operations shown in FIGS. 54 to 50 may be also continuously made.

Figure 55:
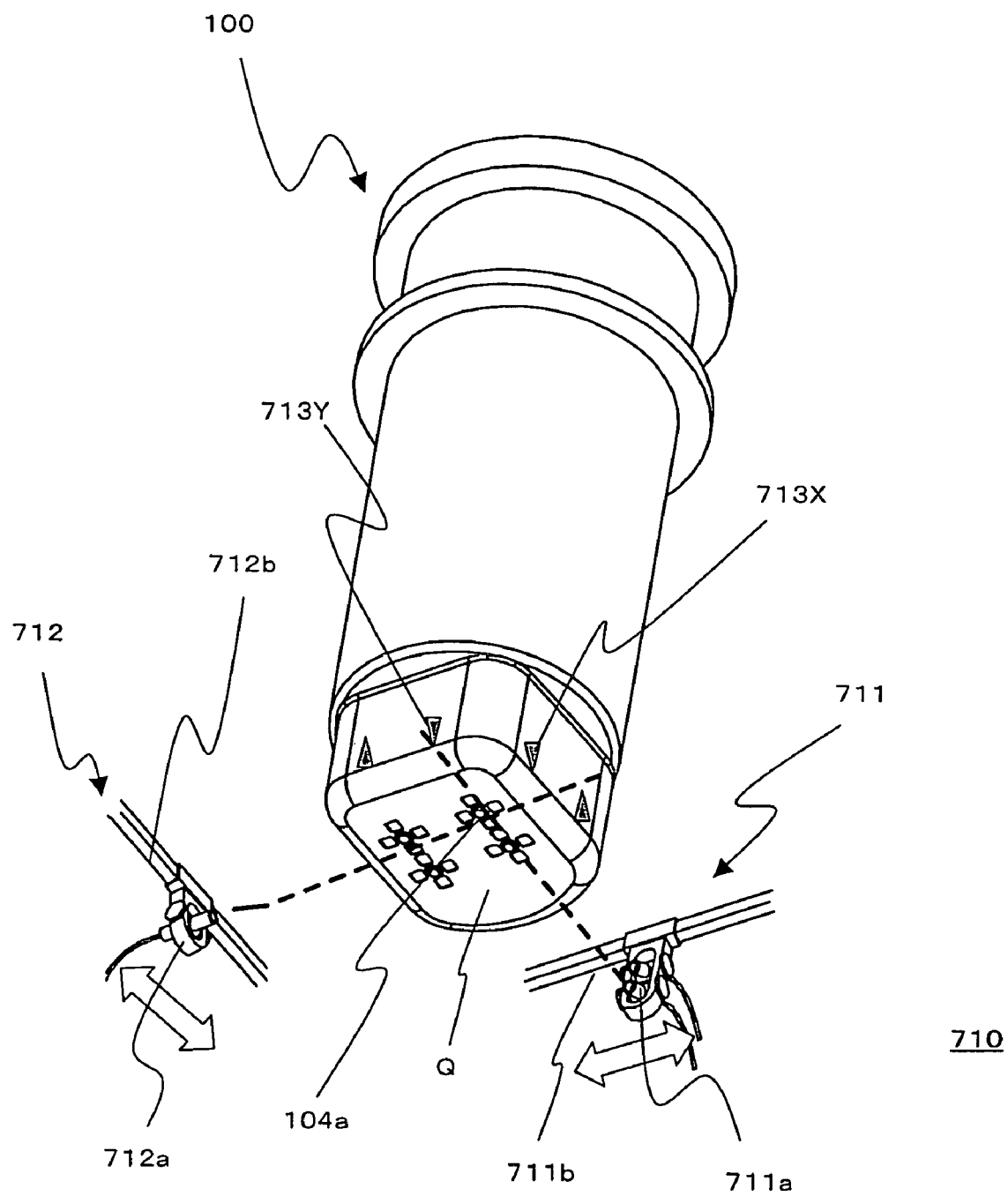
FIG. 55 shows a principle for determining a position of a laser marker mechanism in the first embodiment.
Figure 56:
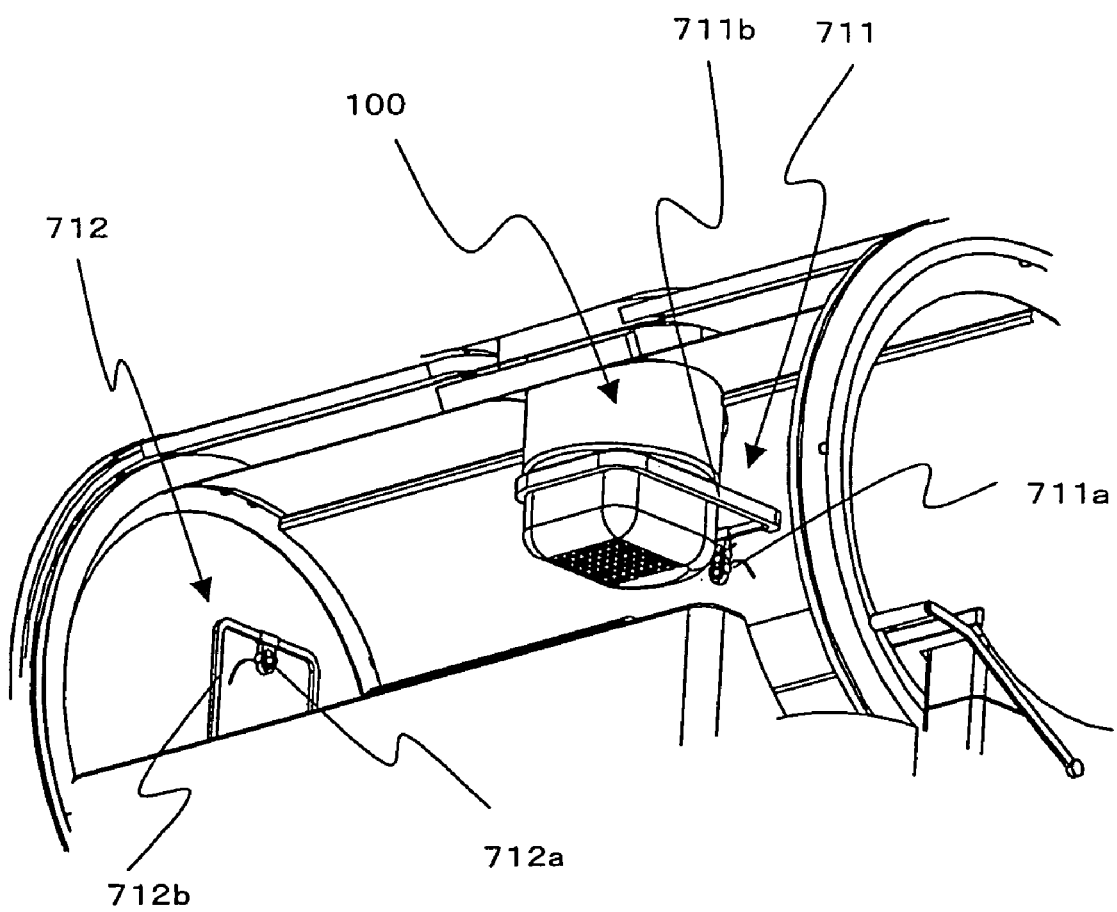
FIG. 56 is a schematic block diagram showing the laser marker mechanism in the first embodiment.
Figure 57:
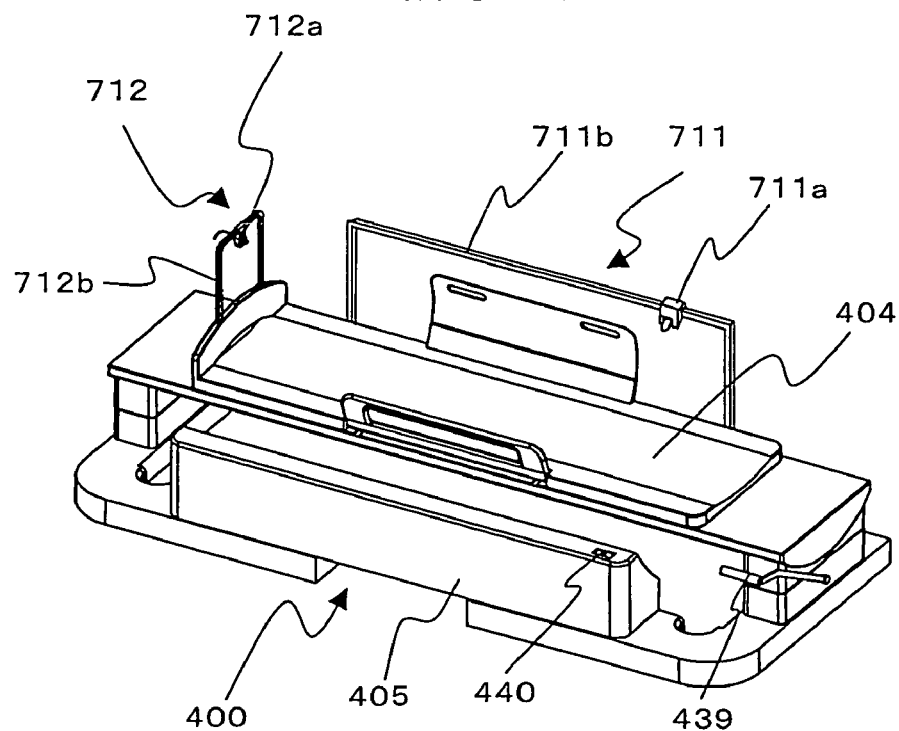
FIGS. 57A to 57C are another schematic block diagrams showing the laser marker mechanism in the first embodiment.
Figure 57:
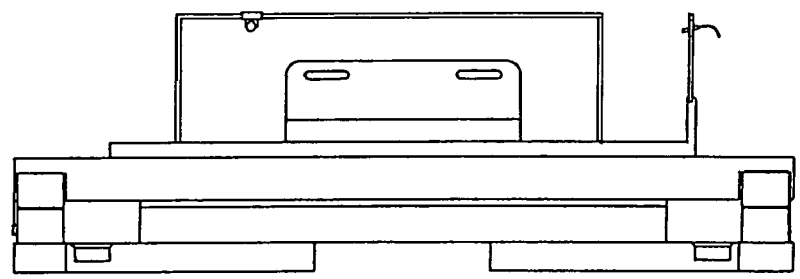
Figure 57:
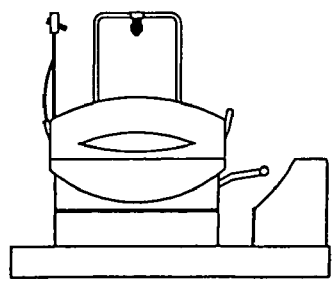
Figure 58:
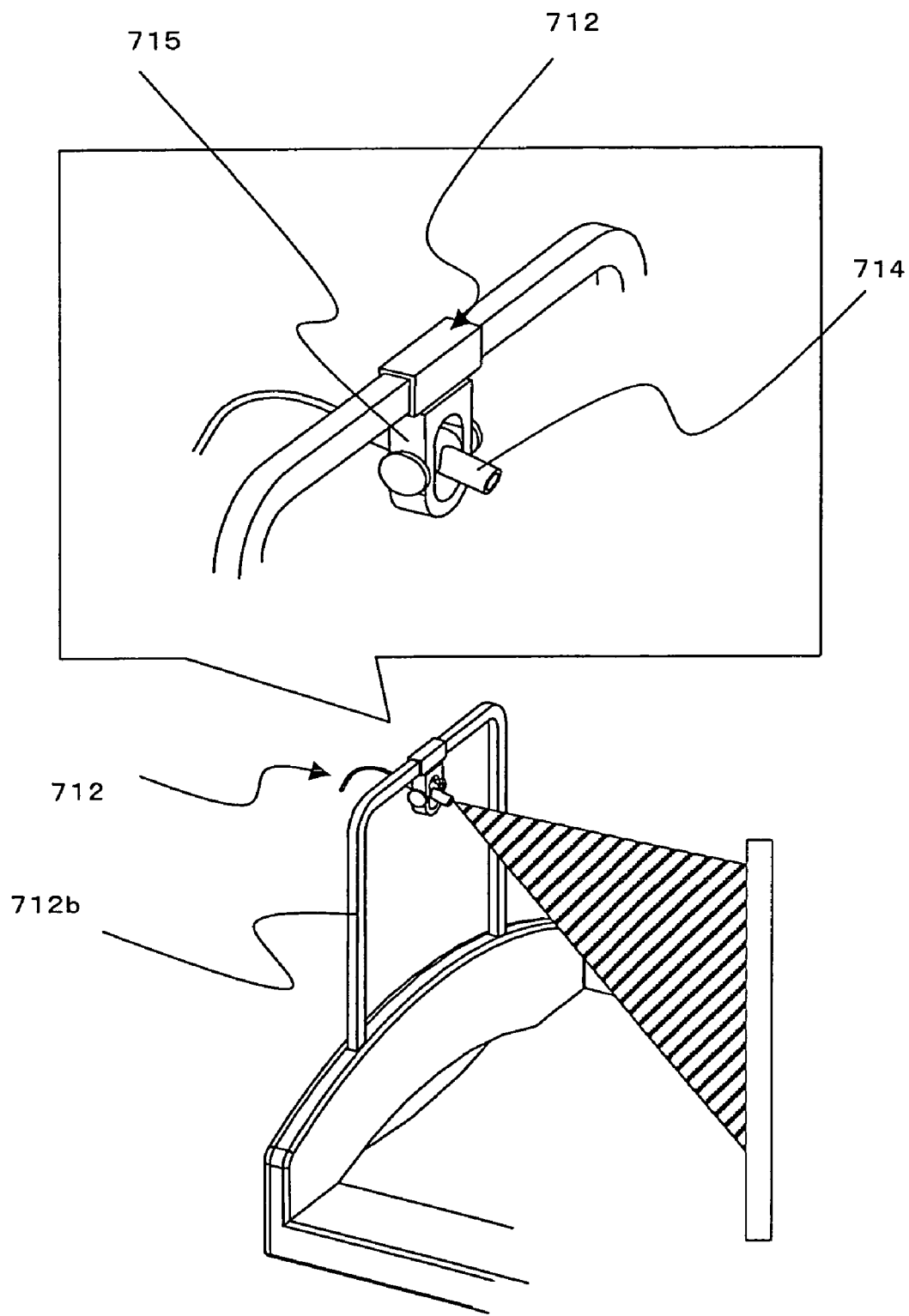
FIG. 58 is a detail drawing showing the laser marker mechanism in the first embodiment.

Next, referring to FIGS. 55 to 58, the marker 104 described in relation to FIGS. 35A to 35E, particularly an optimum laser marker mechanism 710 for alignment using the projecting marker 104a will be described. FIG. 55 shows a principle of determining a position using the laser marker mechanism. FIG. 56 is a schematic block diagram showing the laser marker mechanism attached to the bed and the measuring part. FIGS. 57A to 57C are outside drawings showing another applied example showing a laser marker mechanism attached to the bed, FIG. 57A is a perspective view, FIG. 57B is a back view, and FIG. 57C is a right side view. FIG. 58 is a detail drawing showing the laser marker mechanism.

First, referring to FIG. 55, the principle of the laser marker mechanism 710 will be described. The laser marker mechanism 710 adopts a laser beam to accurately align a predetermined position of a diseased part of a subject with a predetermined position of the measurement face Q. The laser marker mechanism 710 is configured by a Y direction laser 711 for alignment in the direction of the y-axis, an X direction laser 712 for alignment in the direction of the x-axis and a laser-beam feeder not shown in FIG. 55 for supplying a laser beam to the two mechanisms, and if necessary, a marker 713 provided to a circumferential face at the end of the measuring part is included in accordance with a position of the projecting marker 104a provided to the measurement face Q of the measuring part 100.

The Y direction laser 711 is configured by a laser 711a and a Y direction movement support 711b for supporting the laser 711a so that the laser can be moved in the direction of the y-axis which is the longitudinal direction of the bed part 404. The X direction laser 712 is configured by a laser 712a and an X direction movement support 712b for supporting the laser 712a so that the laser can be moved in the direction of the x-axis perpendicular to the direction of the y-axis.

The laser marker mechanism 710 aligns the marker 713 formed on the circumferential face of the measuring part 100 corresponding to a position in the directions of the x- and y-axes of the projection marker 104a with a specific position (for example, an xiphisternum) of a subject using the Y direction laser 711 and the X direction laser 712.

FIG. 55 shows a state in which the Y direction laser 711 is aligned with a marker 713Y in the direction of the y-axis of the projection marker 104a and the X direction laser 712 is aligned with a marker 713X in the direction of the x-axis of the projection marker 104a. In this case, a laser beam used in the laser marker mechanism 710 and vertically radiated at a specific angle as shown in FIG. 58 is adopted. According to the laser beam, as light on a vertical plane is radiated in the direction of the x-axis or in the direction of the y-axis, light on the vertical plane is radiated toward the marker 713 and the specific position of the subject respectively related vertically and therefore, the alignment is simple.

Next, referring to FIG. 56, an embodiment in which a Y direction laser 711 is attached to the end of the measuring part 100 and an X direction laser 712 is attached to the bed part 404 will be described.

In this embodiment, the X direction laser 712 is aligned in the state shown in FIG. 49 in which the bed part 404 is pulled out for example. That is, the laser 712a is moved in the direction of the x-axis via the X direction movement support 712b and the laser 812a is aligned with the xiphisternum of the object who lies on the bed part 404. In a state in which the diseased part shown in FIG. 52 is aligned in a final position, the bed part 404 is moved in the direction of the x-axis by the X direction bed moving mechanism 702 so that a laser beam in the direction of the x-axis irradiates the marker 713X.

In the meantime, the Y direction laser 711 moves the laser 711a via the Y direction movement support 711b so that the laser 711a irradiates the specific projecting marker 104a (the marker 713Y) and fixes a laser beam beforehand. In a state in which the diseased part shown in FIG. 52 is aligned in the final position, the bed part 404 is moved in the direction of the y-axis by the Y direction bed moving mechanism 701 so that a laser beam radiated from the laser 711a irradiates the xiphisternum of the object who lies on the bed part 404. In this case, as the end of the measuring part is cut out in three directions as described in relation to FIGS. 34A to 34E, the Y direction movement support 711b is attached utilizing linear parts cut out in the three directions. Hereby, misregistration can be prevented.

As described above, in this embodiment, as the Y direction laser 711 is constantly fixed to the measuring part 100, the diseased part can be finally aligned by alignment using the Y direction bed moving mechanism 701 and the X direction bed moving mechanism 702 if only the X direction laser 712 is aligned and therefore, the alignment is simple.

Next, referring to FIGS. 57A to 57C, another embodiment in which a Y direction laser 711 and an X direction laser 712 are attached to a bed part 404 will be described. In the embodiment shown in FIG. 56, as the Y direction laser 711 is fixed to the end of the measuring part 100, a subject lies on the bed part 404 in specified posture, and in addition, if the specified posture is posture in which the subject lies on his/her back, the posture is not troublesome and simple. However, depending upon examination, a subject may be measured in posture that he/she lies with his/her face down. In this case, the position of the Y direction laser 711 is required to be adjusted, however, there is a problem that alignment on a ceiling in magnetically shielded space 307 is difficult to adjust.

Then, in the embodiment shown in FIGS. 57A to 57C, lasers 711a, 712a can be aligned in accordance with a lying subject in a state in which the bed part 404 shown in FIG. 49 is pulled out by attaching the Y direction laser 711 and the X direction laser 712 to the bed part 404.

A Y direction movement support 711b is provided with a rail along a longitudinal direction of the bed part 404 and the laser 711a can be moved on the rail. In the meantime, an X direction movement support 712b is provided with a rail along a shorter direction of the bed part 404 and the laser 712a can be moved on the rail. The structure of the X direction laser 712 is the same as that in the embodiment shown in FIG. 56.

As shown in an enlarged view in FIG. 58, as to the lasers 711a, 712a, a laser beam radiator 714 is attached to a base 715 so that the radiator can be vertically moved. An examination engineer can adjust an angle of the laser beam radiator 714 so that a laser beam irradiates a predetermined position of a subject.

According to the embodiment shown in FIGS. 57A to 57C, in a state in which the diseased part shown in FIG. 52 is located in the final position, the diseased part of the subject can be accurately located in a predetermined position by moving the bed part 404 using the Y direction bed moving mechanism 701 and the X direction bed moving mechanism 702 so that a positioned laser beam irradiates a marker 713.

Particularly, this embodiment is effective in case alignment using the Y direction laser 711 is frequent. Besides, in this embodiment, as a position in the directions of the x- and y-axes of the bed part 404 is specified, the alignment of a diseased part can be automated by providing sensors not shown in FIGS. 55 to 58 for sensing positions of the lasers 711a, 712a to the Y direction movement support 711b and the X direction movement support 712b.

That is, as the positions of the two lasers 711a, 712a are specified by the sensors not shown in FIGS. 55 to 58, an intersection at which two laser beams radiated over the bed part 404 intersect can be specified. A drive controller 436 stores the intersection in a memory not shown in FIG. 41 as a home position and can store distance in which a bed moving mechanism 700 is moved from the home position to the determined position in FIG. 52 in the memory. Therefore, when an examination engineer adjusts a laser marker mechanism 710 and changes the intersection in a state in which the bed part 404 is pulled out as shown in FIG. 49, the drive controller 436 calculates difference between the home position of the intersection stored in the memory and an actually aligned intersection and can specify an intersection. Hereby, when the drive controller 436 accepts operation for alignment, it adds difference with a calculated position to the determined position stored in the memory and shown in FIG. 52, operates the bed moving mechanism 700, and can automatically move the diseased part of the subject to a predetermined position of the measurement face Q.

A reference numeral 439 shown in FIGS. 57A to 57C denotes a foot lever for lifting and lowering a Z direction bed moving mechanism 704 and a top plate 401 can be lifted by repeating operation for pushing down the lifting/lowering lever 439 downward. Besides, a reference numeral 440 denotes an emergency stop button and the bed moving mechanism 700 can be released by operating the emergency stop button 440. The emergency stop button 440 is required to be able to be easily operated in emergency and is required to be arranged in a position in which malfunction can be prevented at normal time. In this embodiment, the emergency stop button is provided to the top face of one side of a front coupling part 405, and the action and the effect as an emergency button are achieved.

Figure 59:
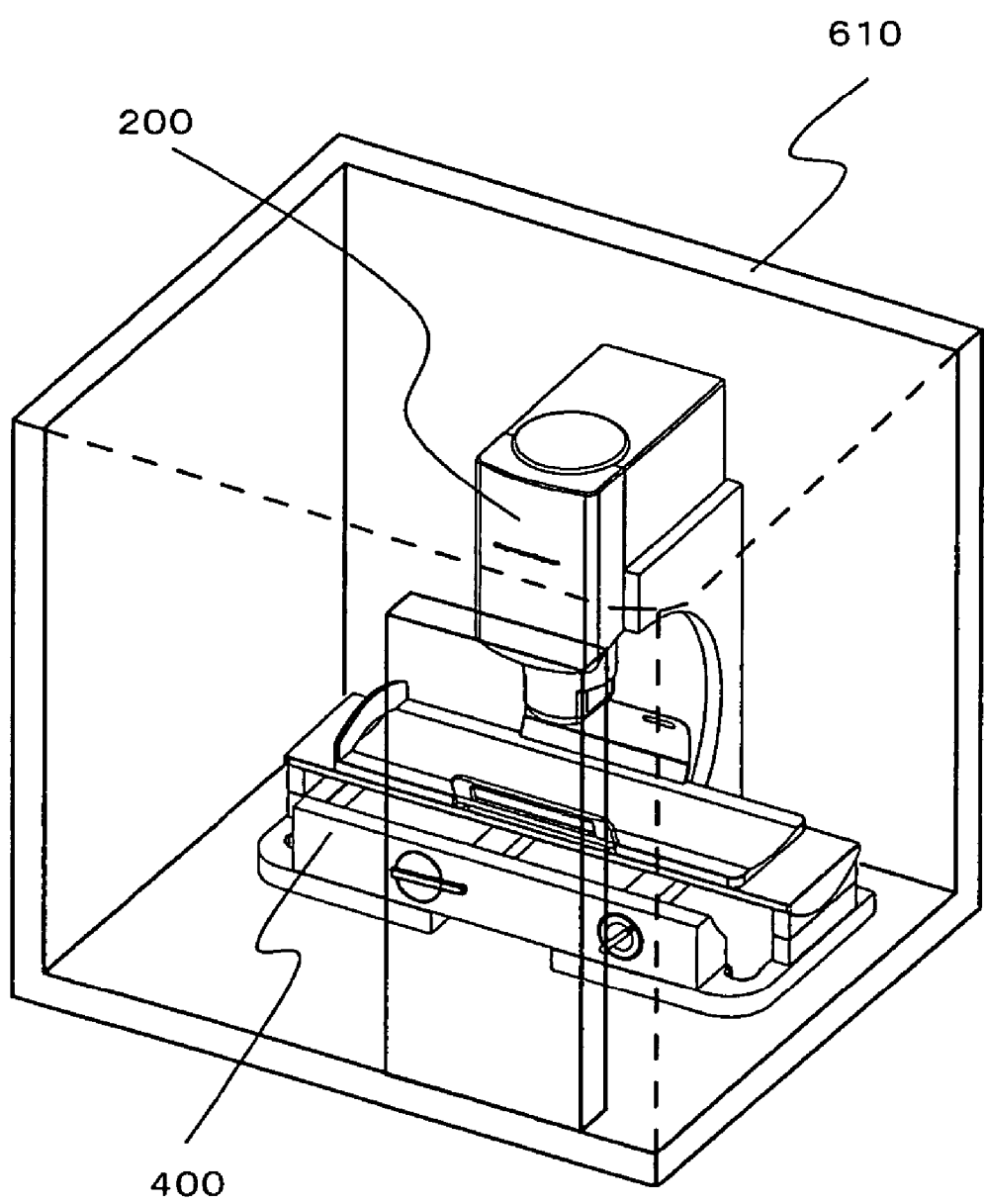
FIG. 59 is a perspective view showing another installation example of the cardiac magnetism measuring device in the first embodiment.

Next, referring to FIG. 59, another installation example of the cardiac magnetic field measuring device will be described. In FIG. 59, the cardiac magnetic field measuring device in which a gantry 200 and a bed 400 are combined is arranged in a large-sized magnetically shielded room 610. FIG. 59 is a perspective view showing another installation state of the device in which the gantry and the bed are combined. As the cardiac magnetic field measuring device measures a feeble magnetic field, it is one choice to adopt the large-sized magnetically shielded room 610 in case there is large space for installation. However, in case the large-sized magnetically shielded room 610 is adopted, the cylindrical magnetic shield 300 is not required. Then, in this embodiment, the large-sized magnetically shielded room 610 is adopted in place of the magnetic shield 300, and the gantry and the bed can be combined in the large-sized magnetically shielded room 610. In this case, it is desirable that a data collection/analysis device 500 and a magnetic measurement drive unit 550 are installed outside the large-sized magnetically shielded room 610 and a drive unit which generates no magnetic field is adopted for each drive unit of the bed moving mechanism 700 or is manually used. It is desirable that the operation of the cardiac magnetic field measuring device is performed via the data collection/analysis device 500.

Second Embodiment

Figure 61:
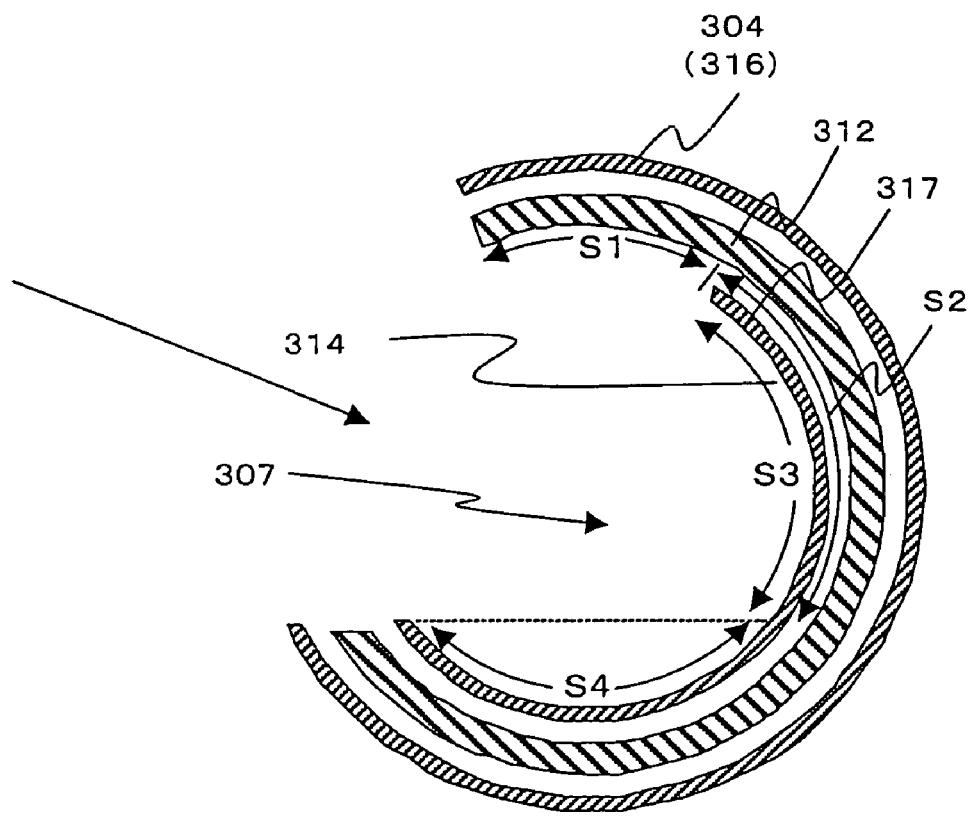
FIGS. 61A and 61B are explanatory drawings for explaining a state in which an opening/closing body in the second embodiment is opened.
Figure 61:
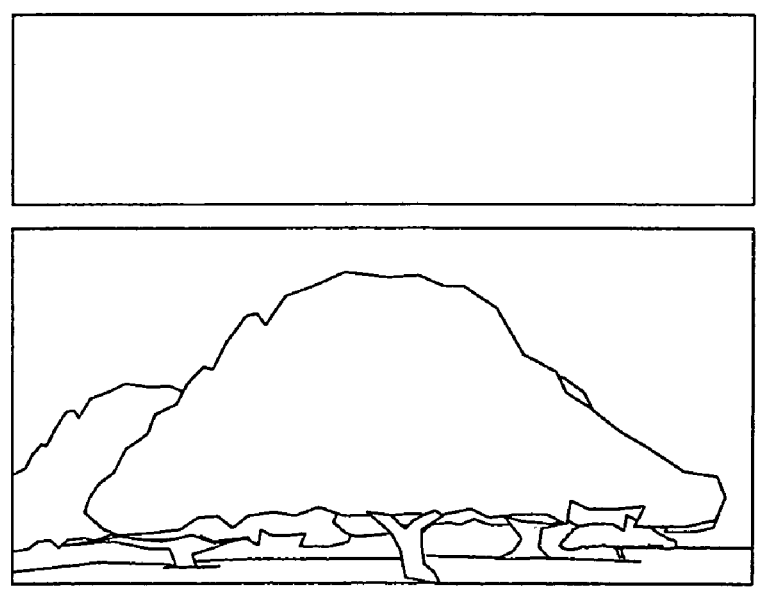
Figure 62:
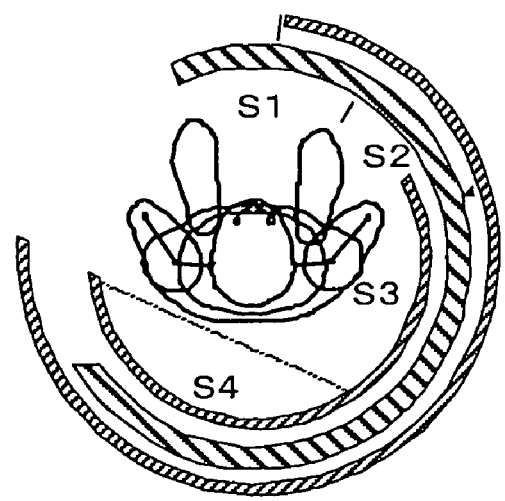
FIGS. 62A to 62C are explanatory drawings for explaining a state in which the opening/closing body in the second embodiment is closed.
Figure 62:
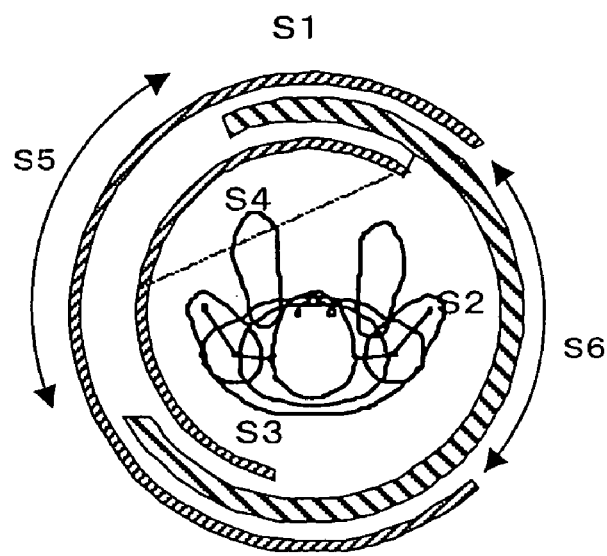
Figure 62:
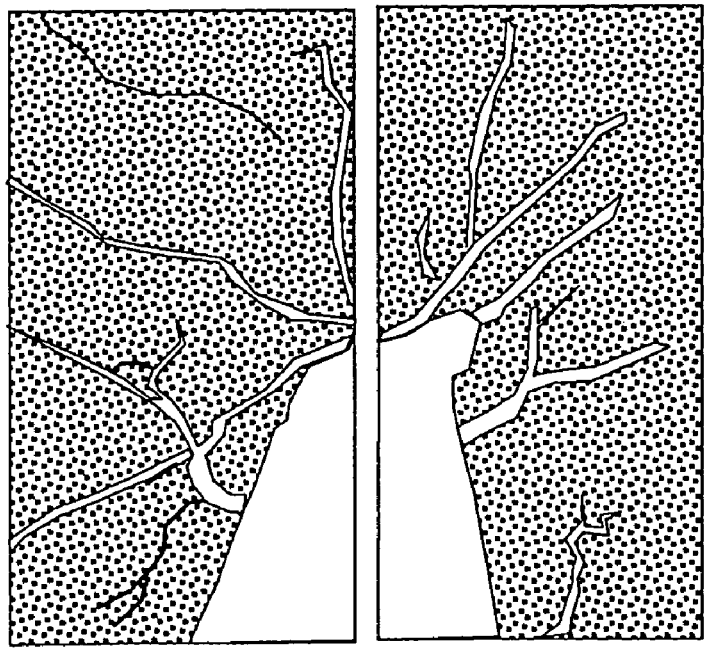

Next, referring to FIGS. 60 to 62, the inside of a magnetic shield 300 will be described. FIGS. 60A to 60E are explanatory drawings showing the inside of the magnetic shield, FIG. 60A is a schematic sectional view, and FIGS. 60B to 60E show patterns on inner walls. FIGS. 61A and 61B are explanatory drawings showing a state in which an opening/closing body 304 is open, FIG. 61A is a schematic sectional view, and FIG. 61B shows a pattern on an inner wall viewed from the outside. FIGS. 62A to 62C are explanatory drawings showing a state in which the opening/closing body 304 is closed, FIGS. 62A and 62B are schematic sectional views, and FIG. 62C shows a pattern on the inner wall viewed inside shielded space.

First, referring to FIGS. 60A to 60E, rough structure in this embodiment will be described. In this embodiment, basic structure shown in FIGS. 60A to 60E is the similar structure to that in the first embodiment. This embodiment is greatly characterized in that a cardiac magnetic field measuring device provided with an interior which gives a subject a sense of security utilizing the structure of the magnetic shield 300 that largely varies in open and closed states is provided.

In the case of the measuring device in the closed space of which a subject gets and has examination, a device for giving the subject a sense of security is also important. Particularly, as in this embodiment, in the measuring device where a state in which the opening/closing body 304 is open and a state in which the opening/closing body 304 is closed are largely different, such a device is particularly important.

This embodiment is based upon that in the magnetic shield 300, in a state in which the opening/closing body 304 is open, an inner wall of the body of the shield 312 and an inner wall of the opening/closing body 304 are housed in an overlapped state and in a state in which the opening/closing body 304 is closed, the overlapped and hidden inner walls are exposed and is characterized in that a subject is given a sense of security by largely changing the inner wall of the magnetic shield 300 viewed from the subject by opening or closing the opening/closing body 304 by drawing patterns on the inner walls.

FIG. 60A is a schematic sectional view showing a state in which the opening/closing body 304 is open. In this embodiment, different patterns are painted on the inner wall S1 of the inside armor 314 of the main armor 312 and the inner wall S2. The inner wall S1 is exposed in the state in which the opening/closing body 304 is open and for example, as shown in FIG. 60B, the pattern of the sky is painted. In the meantime, the inner wall S2 is hidden by the inner wall S3 of the inside cover armor 317 of the cover armor 316 in the state in which the opening/closing body 304 is open and is exposed in the state in which the opening/closing body 304 is closed. On this inner wall S2, for example, an enlarged view (on the right side) viewed from the base of a tree is painted.

In the meantime, the inner wall of the inside cover armor 317 is divided into the inner wall S3 exposed in the state in which the opening/closing body 304 is open and the inner wall S4 hidden by a top plate 401 and patterns are painted on the respective inner walls. For example, a landscape including a large tree is painted on the inner wall S3 and on the inner wall S4, an enlarged view (on the left side) viewed from the base of the tree is painted.

This embodiment is characterized in that related patterns are painted on the inner walls S1 and S3 respectively exposed as a continuous face in the state in which the opening/closing body 304 is open and related patterns are painted on the inner walls S2 and S4 respectively forming a continuous face in the state in which the opening/closing body 304 is closed. According to the magnetic shield 300 provided with such structure, a subject is given large surprise and interest by opening or closing the opening/closing body 304 and uneasiness can be reduced.

FIGS. 61A and 61B are explanatory drawings showing inner walls in a state in which the opening/closing body 304 is open. In the state in which the opening/closing body 304 is open, a subject views magnetically shielded space 307 from the outside. In this state, the subject views a continuous pattern on the inner walls S1 and S3, for example, a picture where a large tree and the sky over it are painted as shown in FIG. 61B. As for a pattern viewed on a ceiling in a state in which the opening/closing body 304 is closed in the magnetic shielded space 307 by the subject who lies on a bed part 404, the landscape till then in the above-mentioned state completely changes to a pattern where the sky is viewed from the inside of the tree as shown in FIG. 62C. Hereby, the subject is interested in the changing patterns and uneasiness can be reduced.

A pattern is not limited to the above-mentioned patterns. In short, respective continuous patterns on the inner walls S1 and S3 and on the inner walls S2 and S4 change by opening or closing the opening/closing body 304.

The change of the patterns viewed from the subject is described above, however, conversely, the change of patterns viewed from an examination engineer and others may be also devised. For example, as shown in FIG. 62B, a decorative pattern may be also painted on an armor S5 hidden in a state in which the opening/closing body 304 is open, largely exposed in a state in which the opening/closing body 304 is closed and closing a doorway for a subject 305. Besides similarly, the similar decorative pattern may be also painted on an armor S6 hidden in the state in which the opening/closing body 304 is open and largely exposed at the back in the state in which the opening/closing body 304 is closed.

Third Embodiment

Figure 63:
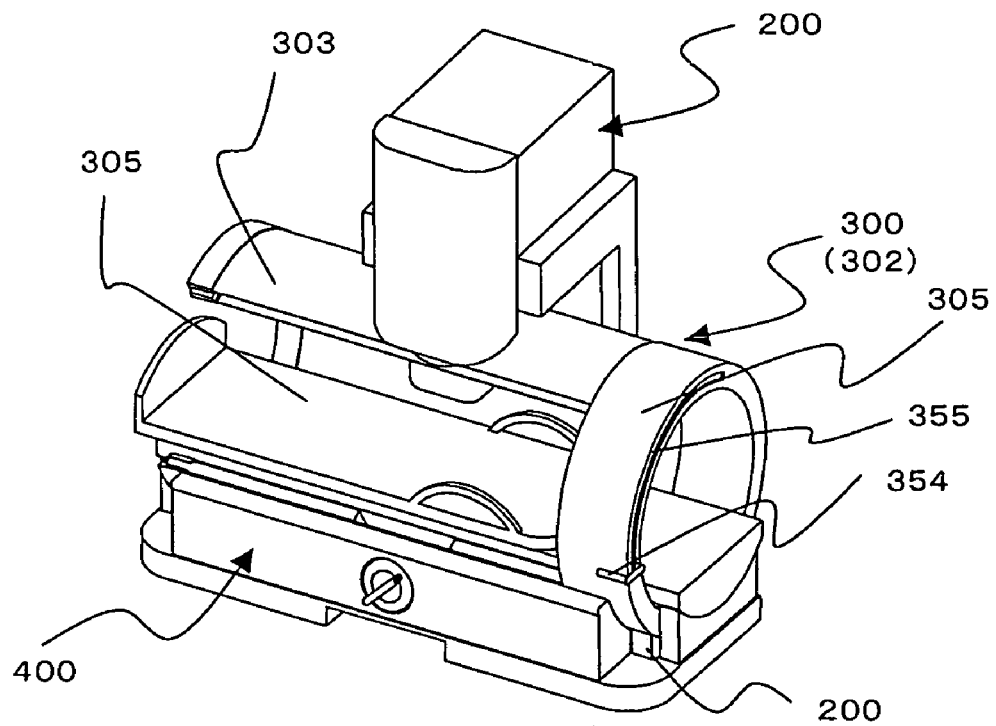
FIGS. 63A and 63B are outside perspective views showing a cardiac magnetism measuring device in a third embodiment.
Figure 63:
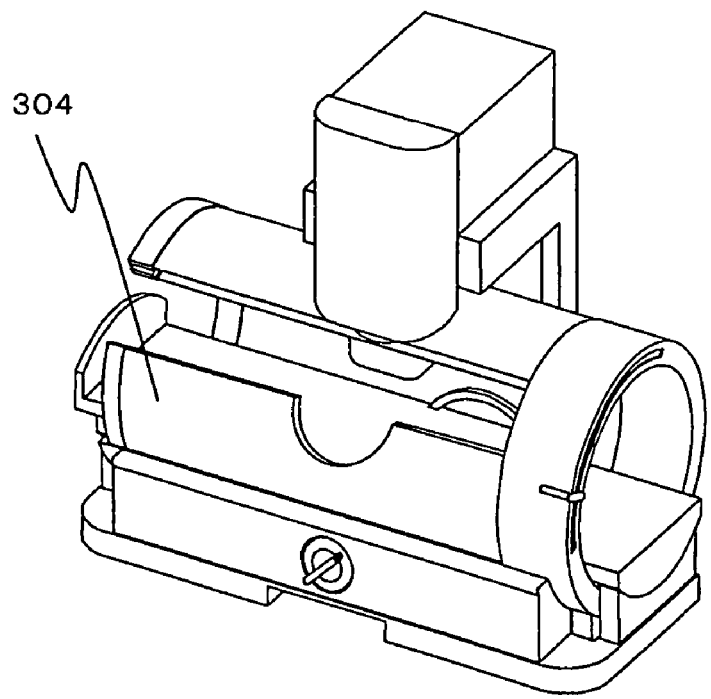
Figure 65:
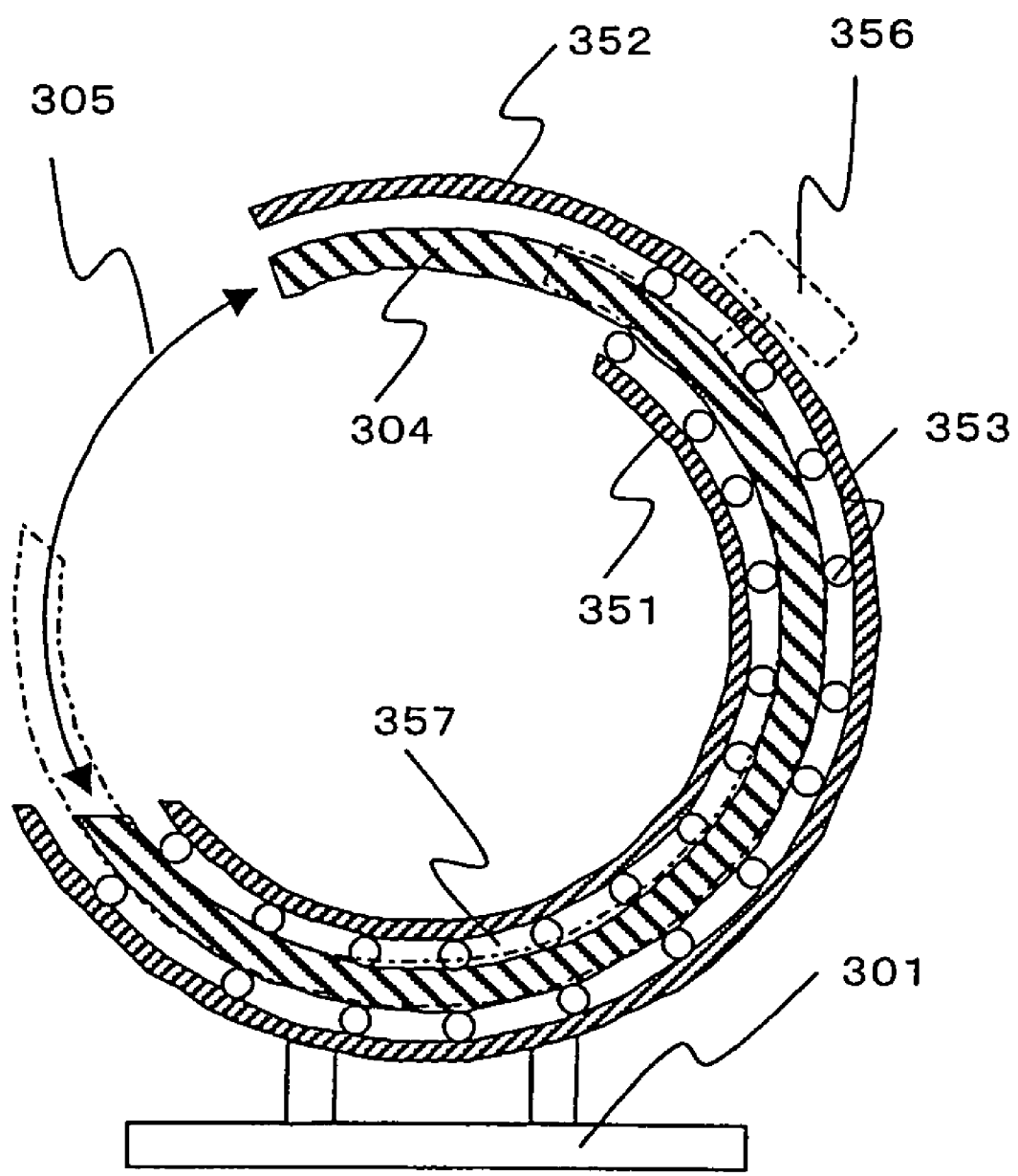
FIG. 65 is a schematic sectional view showing the cardiac magnetism measuring device in the third embodiment.

Next, referring to FIGS. 63 to 65, a cardiac magnetic field measuring device equivalent to a third embodiment will be described. FIGS. 63A and 63B are perspective views showing the appearance of the cardiac magnetic field measuring device equivalent to the embodiment, FIG. 63A is the perspective view showing a state in which the opening/closing body 304 is open and FIG. 62B is the perspective view showing the opening/closing of the opening/closing body 304. FIGS. 64A to 64F are outside drawings showing the cardiac magnetic field measuring device, FIG. 64A is a plan, FIG. 64B is a bottom view, FIG. 64C is a front view, FIG. 64D is a right side view, FIG. 64E is a back view, and FIG. 64F is a left side view. FIG. 65 is a schematic sectional view showing the cardiac magnetic field measuring device.

This embodiment is first characterized in that a cylindrical holding body 350 is provided on one side of a cylindrical magnetic shield 300 to be overhung type structure and opposite other side is open. Besides, this embodiment is second characterized in that the opening/closing body 304 can be housed or exposed inside/from a main body 303. Referring to the drawings, this embodiment will be described further in detail below. In this embodiment, as a gantry 200 and a bed 400 are similar to those in the above-mentioned embodiments, the description is omitted.

As shown in FIGS. 63 to 65, the magnetic shield 300 is configured by a leg 301 and the body of the shield 302. The body of the shield 302 is configured by the main body 303, the opening/closing body 304 and the holding body 350. The main body 303 and the holding body 350 are configured by an inside armor 351 and an outside armor 352 respectively made of material such as Permalloy, the holding body 350 is cylindrical, and the sectional form of the main body 303 is C-type as shown in FIG. 65. The holding body 350 is formed in a state in which the width is narrow on one side of the cylinder in horizontal posture and the main body 303 is formed in a wide state on the other side. The opening/closing body 304 is made of material such as Permalloy and as shown in FIG. 65, the sectional form is C-type. The opening/closing body 304 is housed in space 357 formed between the inside armor 351 and the outside armor 352 as shown in FIG. 65 and is formed so that the opening/closing body can be moved in a circumferential direction via plural rollers 353.

The inside armor 351 and the outside armor 352 are formed so that the main body 303 and the holding body 350 continue and are coupled by a C-type peripheral face acquired by cutting out both ends of the cylinder in the shape of a ring or a part. The leg 301 supports both sides of the outside armor 352.

A doorway for a subject 305 acquired by cutting out a part of the front is formed on the main body 303. The doorway for a subject 305 can be closed by turning the opening/closing body 304 in the circumferential direction from the downside of the doorway 305. A lever 354 is attached on one side of the opening/closing body 304 and is exposed from a groove 355 in the shape of a circular arc formed on a peripheral face of the holding body 350. The opening/closing body 304 can be opened or closed by moving the lever 354 along the circumference.

The opening/closing body 304 is directly coupled to a balance weight 356 attached on the back side as shown in FIG. 65 and can be easily opened or closed by operating the lever 354. The similar structure of such a balance weight 356 can be also adopted in the first embodiment.

In FIG. 64, a base 600 is shown by a dotted line because installation structure is shown, however, it can be also drawn as an opaque plate.

Figure 66:
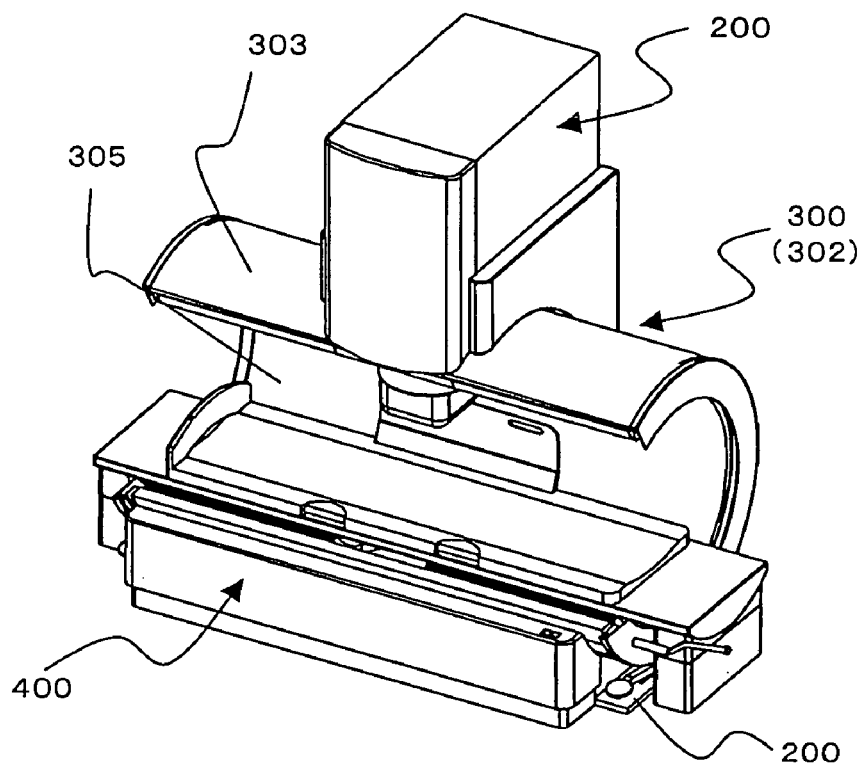
FIGS. 66A and 66B are outside drawings showing a cardiac magnetism measuring device in a fourth embodiment.
Figure 66:
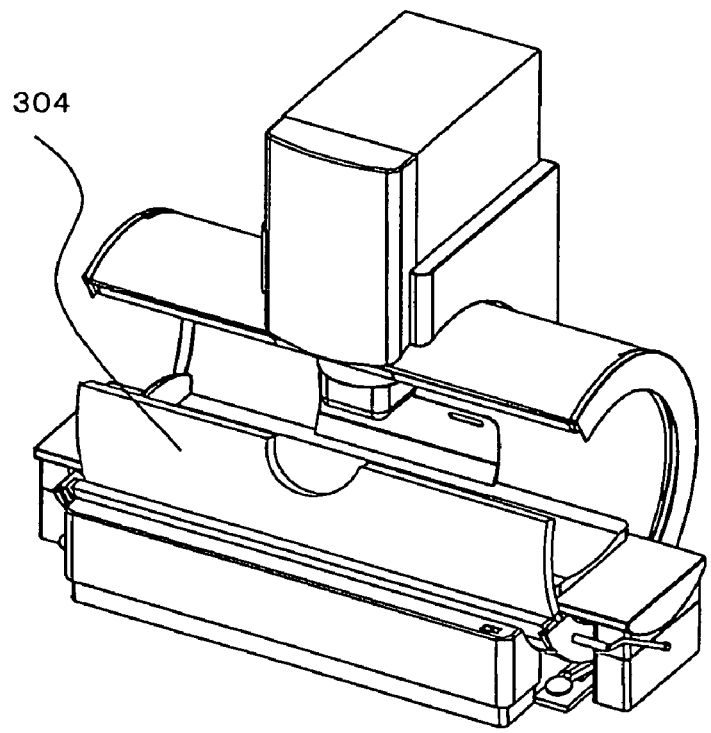
Figure 67:
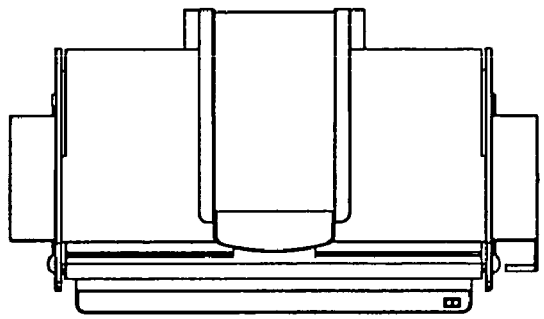
FIGS. 67A to 67E are outside drawings showing the cardiac magnetism measuring device in the fourth embodiment.
Figure 67:
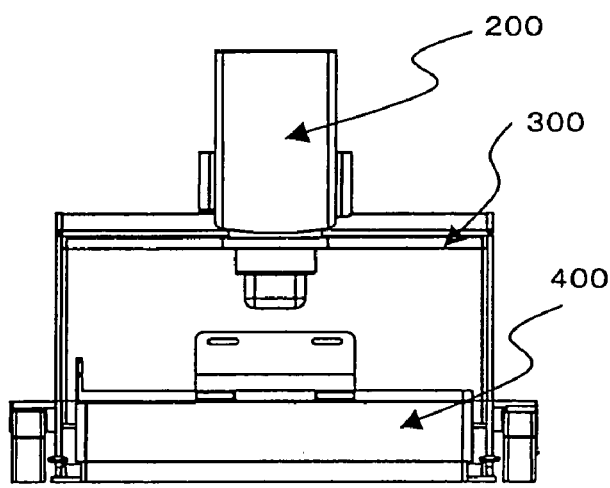
Figure 67:
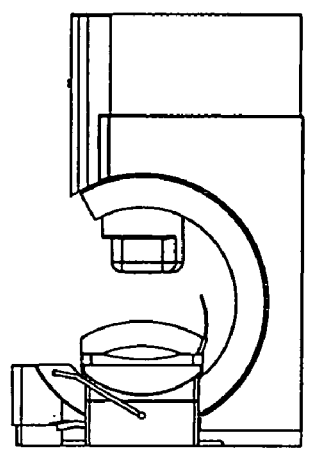
Figure 67:
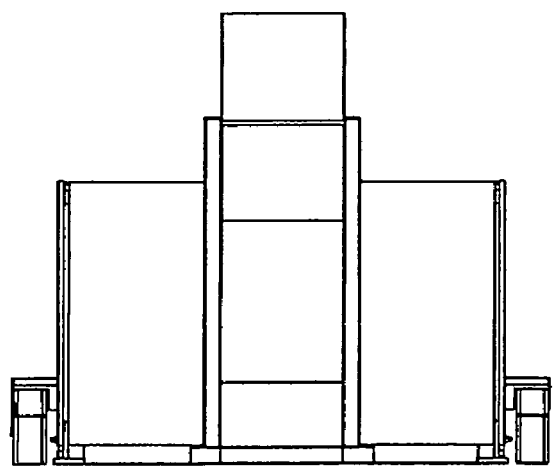
Figure 67:
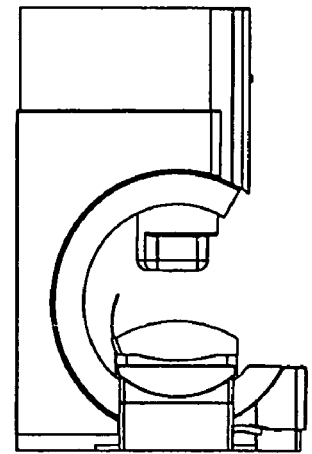
Figure 68:
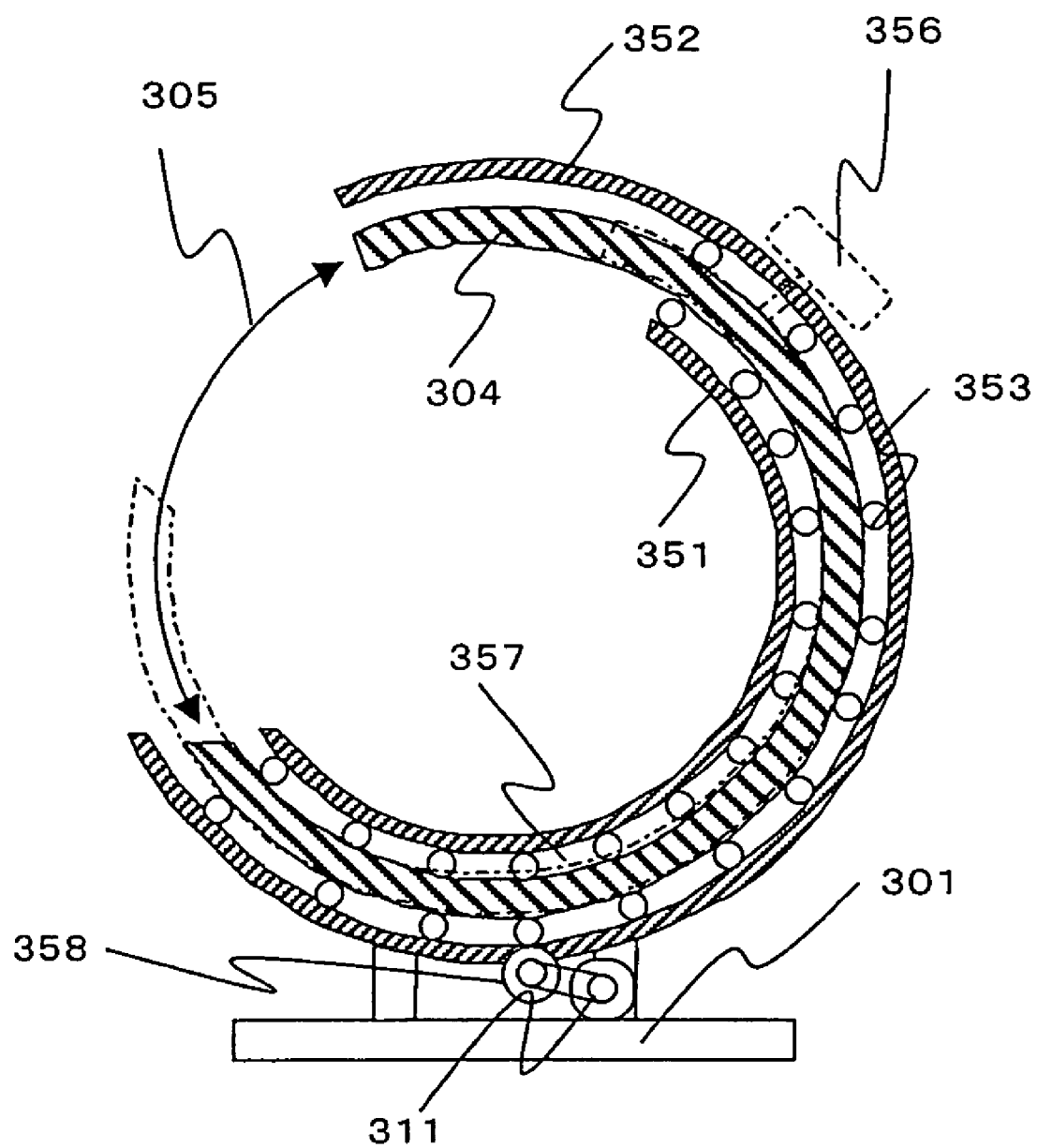
FIG. 68 is a schematic sectional view showing the cardiac magnetism measuring device in the fourth embodiment.

Next, referring to FIGS. 66 to 68, a cardiac magnetic field measuring device equivalent to a fourth embodiment will be described. FIGS. 66A and 66B are perspective views showing the appearance of the cardiac magnetic field measuring device equivalent to the embodiment, FIG. 66A is the perspective view showing a state in which an opening/closing body 304 is open, and FIG. 66B is the perspective view showing the opening/closing of the opening/closing body 304. FIGS. 67A to 67E are outside drawings showing the cardiac magnetic field measuring device, FIG. 67A is a plan, FIG. 67B is a front view, FIG. 67C is a right side view, FIG. 67D is a back view, and FIG. 67E is a left side view. FIG. 68 is a schematic sectional view showing the cardiac magnetic field measuring device.

This embodiment is first characterized in that the sectional form of a cylindrical magnetic shield 300 is C-type and a doorway for a subject 305 is open bilaterally. This embodiment is second characterized in that the opening/closing body 304 can be housed or exposed inside/from a main body 303. Referring to the drawings, this embodiment will be described further in detail below. In this embodiment, as a gantry 200 and a bed 400 are similar to those in the above-mentioned embodiments, the description is omitted.

As shown in FIGS. 66 to 68, the magnetic shield 300 is configured by a leg 301 and the body of the shield 302. The body of the shield 302 is configured by a main body 303 and the opening/closing body 304. The main body 303 is configured by an inside armor 351 and an outside armor 352 respectively made of material such as Permalloy and the sectional form of the main body 303 is C-type as shown in FIG. 68. The opening/closing body 304 is made of material such as Permalloy and the sectional form is C-type as shown in FIG. 68. The opening/closing body 304 is housed in space 357 formed between the inside armor 351 and the outside armor 352 as shown in FIG. 68 and is formed so that it can be moved in a circumferential direction via plural rollers 353.

The inside armor 351 and the outside armor 352 are coupled by a C-type peripheral face a part of which is cut out. The leg 301 supports both sides of the outside armor 352. The doorway for a subject 305 acquired by cutting out a part of the front is formed on the main body 303. The doorway for a subject 305 can be closed by turning the opening/closing body 304 in the circumferential direction from the downside.

As shown in FIG. 68, a driving roller 358 attached to the main body 303 is attached to the opening/closing body 304 and an opening/closing actuator 311 is coupled to the driving roller 358. Owing to the structure, the opening/closing body 304 is moved in the circumferential direction and the doorway for a subject 305 can be opened and closed.

As the back view in FIGS. 67A to 67E is similar to FIG. 64B, the description is omitted. A base 600 is shown by a dotted line to show installation structure, however, it can be drawn as an opaque plate.

OTHER EMBODIMENT

As described above, the biomagnetism measuring device equivalent to this embodiment is provided with a bed 400 having a bed part 404 for mounting a subject on its top face and a cylindrical magnetic shield 300 the central axis P of which is held in horizontal posture, the magnetic shield 300 is provided with a first body (a main body 303) having a doorway for the bed (a doorway for a subject 305) for getting the bed part 404 in or out in a part of a cylindrical circumferential face and a second body (an opening/closing body 304) for opening or closing the doorway for the bed (the doorway for a subject 305), the first body 303 is provided with a measuring part 100 building plural sensors in the center of its upper part, the second body 304 is held by the first body 303 so that the second body can be moved in the cylindrical circumferential direction, and the bed 400 is provided with a top plate 401 for holding the bed part 404, legs 402 for holding the top plate 401 in the cylindrical magnetic shield 300, a pulling-out mechanism 703 for getting the bed part 404 in or out of the magnetic shield 300 through the doorway for the bed 305, a Y direction moving mechanism (a Y direction bed moving mechanism 701) for moving the bed part 404 in a direction of the central axis P of the magnetic shield 300, an X direction moving mechanism (an X direction bed moving mechanism 702) for moving the bed part 404 in a direction perpendicular to the direction of the central axis P of the magnetic shield 300 and a Z direction moving mechanism (a Z direction bed moving mechanism 704) for vertically moving the bed part 404 in the magnetic shield 300.

Besides, another biomagnetism measuring device equivalent to this embodiment is provided with a bed 400 having a bed part 404 for mounting a subject on its top face, a cylindrical magnetic shield 300 the central axis P of which is held in horizontal posture and a gantry 200 in which a measuring part 100 building plural sensors in the center of an upper part of the magnetic shield 300 is located, the magnetic shield 300 is provided with a first body (a main body 303) having a doorway for the bed (a doorway for a subject 305) for getting the bed part 404 in or out in a part of a cylindrical circumferential face and a second body (an opening/closing body 304) for opening or closing the doorway for the bed 305, the second body 304 is held by the first body 303 so that the second body can be moved in the cylindrical circumferential direction, the gantry 200 holds the measuring part 100 so that the end of the measuring part 100 in which plural sensors are arranged is located in the magnetic shield 300, the bed 400 is provided with a top plate 401 for holding the bed part 404, legs 402 for holding the top plate 401 at both ends of the cylindrical magnetic shield 300, a pulling-out mechanism 703 for getting the bed part 404 in or out of the magnetic shield 300 through the doorway for the bed 305, a Y direction moving mechanism (a Y direction bed moving mechanism 701) for moving the bed part 404 in a direction of the central axis P of the magnetic shield 300, an X direction moving mechanism (an X direction bed moving mechanism 702) for moving the bed part 404 in a direction perpendicular to the direction of the central axis P of the magnetic shield 300 and a Z direction moving mechanism (a Z direction bed moving mechanism 704) for vertically moving the bed part 404 in the magnetic shield 300.

In these biomagnetism measuring devices, the first body 303 houses the second body 304 on the circumferential side of a lower part of the first body 303 in a state in which the doorway for the bed 305 is open and the second body 304 has size overlapped with the first body in the circumferential direction in a state in which the doorway for the bed 305 is closed.

Besides, in these biomagnetism measuring devices, the bed 400 is provided with supporting means (a front coupling part 405) for supporting the bed part 404 pulled out in front of the doorway for the bed 305 from the downside.

According to the invention, the cylindrical magnetic shielding apparatus in which the magnetic shielding factor of a leakage magnetic field is enhanced can be realized and the biomagnetism measuring device in which more sensitive and more accurate measurement is enabled can be realized.

What is claimed is:
1. A magnetic shielding apparatus, comprising:
(a) a first cylindrical shield provided with a circumferential part having first thickness and having a first angular range in a circumferential direction of the y-axis perpendicular to the z-axis, a first opening formed on the circumferential part, a portion parallel to the y-axis at both ends of the first angular range, two circular-arc parts parallel to a plane perpendicular to the y-axis and a first auxiliary cylinder where a cylindrical member is connected to the circumferential part in a state in which the central axis of the cylindrical member is coincident with the central axis of the first opening, and made of high-permeability material;

(b) a second cylindrical shield provided with a circumferential part having second thickness and having a second angular range in the circumferential direction of the y-axis and two portions parallel to the y-axis at both ends of the second angular range, made of high-permeability material, and arranged inside the circumferential part of the first cylindrical shield;

(c) a third cylindrical shield provided with a circumferential part having third thickness and having a third angular range in the circumferential direction of the y-axis and two portions parallel to the y-axis at both ends of the third angular range, made of high-permeability material, and arranged outside the circumferential part of the first cylindrical shield;

(d) a base for fixing and supporting the first cylindrical shield in two locations in a direction of the y-axis; and (e) a revolving part for revolving the second and third cylindrical shields in the circumferential direction of the y-axis along the circumferential part of the first cylindrical shield, wherein:

an opening in the circumferential direction of the y-axis is formed by the revolution in one direction; and a leakage magnetic field that invades closed internal space formed in the circumferential direction of the y-axis is screened by the revolution in the other direction.

2. A magnetic shielding apparatus according to claim 1, wherein:

a cryostat arranged on a plane parallel to an XY plane perpendicular to the z-axis for holding a SQUID fluxmeter for detecting a component in a direction of the z-axis of a magnetic field generated from an object of examination put in the internal space at low temperature pierces the inside of the cylindrical member and the first opening; and a flat cutout is provided to a portion on the bottom side of the cryostat and opposite in a direction parallel to the y-axis and a portion on the side that faces an opening in a circumferential direction of the y-axis formed by the revolution in one direction.

3. A magnetic shielding apparatus according to claim 1, comprising:

a flange-type plate having a circumferential face on which an opening having an inside diameter equal to an inside diameter of the first opening is formed, wherein:

a cylindrical member provided with a flange in which the cylindrical member and the flange-type plate are connected so that the central axis of the cylindrical member and the central axis of the opening of the flange-type plate are coincident is formed; and a circumferential face of the flange-type plate connected to the cylindrical member provided with the flange is connected to a circumferential part of the first cylindrical shield.

4. A magnetic shielding apparatus according to claim 1, comprising:

a flange-type plate having a circumferential face on which an opening is formed, wherein:

a cylindrical member provided with a flange in which the cylindrical member and the flange-type plate are connected so that the central axis of the cylindrical member and the central axis of the opening of the flange-type plate are coincident is formed;

when the inside diameter of the first opening is D and D1>D>D2, a first cylindrical member provided with a flange in which the outside diameter of the cylinder is D1 and a second cylindrical member provided with a flange in which the outside diameter of the cylinder is D2 are formed;

a circumferential face of the flange-type plate connected to the first cylindrical member provided with the flange is connected to the outside face of a circumferential part of the first cylindrical shield; and a circumferential face of the flange-type plate connected to the second cylindrical member provided with the flange is connected to the inside face of the circumferential part of the first cylindrical shield.

5. A magnetic shielding apparatus according to claim 1, wherein:

the first and third cylindrical shields are provided with an electromagnetic shielding member in overlapped parts by revolution in the other direction.

6. A magnetic shielding apparatus according to claim 1, wherein:

when internal space closed in a circumferential direction of the y-axis is formed by the revolution in the other direction, length in which the first and second cylindrical shields are overlapped in the circumferential direction of the y-axis and length in which the first and third cylindrical shields are overlapped are equivalent to 10 times or more of a larger interval out of an interval between the inside circumferential face of a circumferential part of the first cylindrical shield and the outside circumferential face of a circumferential part of the second cylindrical shield and an interval between the outside circumferential face of the circumferential part of the first cylindrical shield and the inside circumferential face of a circumferential part of the third cylindrical shield.

7. A magnetic shielding apparatus according to claim 1, wherein:

an angular range in a circumferential direction of the y-axis of an opening in the circumferential direction of the y-axis formed by the revolution in one direction is equivalent to a range including angles of 90 to 110 degrees.

8. A magnetic shielding apparatus, comprising:

(a) a first cylindrical shield provided with a circumferential part having first thickness and having a first angular range in a circumferential direction of the y-axis perpendicular to the z-axis, a first opening formed in the circumferential part, two circular-arc parts parallel to a plane perpendicular to the y-axis and a first auxiliary cylinder in which a cylindrical member is connected to the circumferential part so that the central axis of the cylindrical member is coincident with the central axis of the first opening, which is arranged on a plane parallel to an XY plane perpendicular to the z-axis and in which a cryostat for holding a SQUID fluxmeter for detecting a component in a direction of the z-axis of a magnetic field generated from an object of examination at low temperature pierces the inside of the cylindrical member and the first opening, and made of high-permeability material;

(b) a second cylindrical shield provided with a circumferential part having second thickness and having a second angular range in the circumferential direction of the y-axis, two portions parallel to the y-axis at both ends of the second angular range and a cutout formed at least in one of the two portions, made of high-permeability material, and arranged inside the circumferential part of the first cylindrical shield;

(c) a third cylindrical shield provided with a circumferential part having third thickness and having a third angular range in the circumferential direction of the y-axis, two portions parallel to the y-axis at both ends of the third angular range and a cutout formed at least in one of the two portions, made of high-permeability material, and arranged outside the circumferential part of the first cylindrical shield;

(d) a base for fixing and supporting the first cylindrical shield in two locations in a direction of the y-axis; and (e) a revolving part for revolving the second and third cylindrical shields in the circumferential direction of the y-axis along the circumferential part of the first cylindrical shield, wherein:

an opening for inserting an object of examination is formed in the circumferential direction of the y-axis by the revolution in one direction;

the first auxiliary cylinder is arranged inside the cutout of the second and third cylindrical shields; and a leakage magnetic field that invades closed internal space formed in the circumferential direction of the y-axis is screened by the revolution in the other direction.

9. A magnetic shielding apparatus according to claim 8, wherein:

a cryostat arranged on a plane parallel to an XY plane perpendicular to the z-axis for holding a SQUID fluxmeter for detecting a component in a direction of the z-axis of a magnetic field generated from an object of examination put in the internal space at low temperature pierces the inside of the cylindrical member and the first opening; and a flat cutout is provided to a portion on the bottom side of the cryostat and opposite in a direction parallel to the y-axis and a portion on the side that faces an opening in a circumferential direction of the y-axis formed by the revolution in one direction.

10. A magnetic shielding apparatus according to claim 8, comprising:

a flange-type plate having a circumferential face on which an opening having an inside diameter equal to an inside diameter of the first opening is formed, wherein:

a cylindrical member provided with a flange in which the cylindrical member and the flange-type plate are connected so that the central axis of the cylindrical member and the central axis of the opening of the flange-type plate are coincident is formed; and a circumferential face of the flange-type plate connected to the cylindrical member provided with the flange is connected to a circumferential part of the first cylindrical shield.

11. A magnetic shielding apparatus according to claim 8, comprising:

a flange-type plate having a circumferential face on which an opening is formed, wherein:

a cylindrical member provided with a flange in which the cylindrical member and the flange-type plate are connected so that the central axis of the cylindrical member and the central axis of the opening of the flange-type plate are coincident is formed;

when the inside diameter of the first opening is D and D1>D>D2, a first cylindrical member provided with a flange in which the outside diameter of the cylinder is D1 and a second cylindrical member provided with a flange in which the outside diameter of the cylinder is D2 are formed;

a circumferential face of the flange-type plate connected to the first cylindrical member provided with the flange is connected to the outside face of a circumferential part of the first cylindrical shield; and a circumferential face of the flange-type plate connected to the second cylindrical member provided with the flange is connected to the inside face of the circumferential part of the first cylindrical shield.

12. A magnetic shielding apparatus according to claim 8, wherein:

the first and third cylindrical shields are provided with an electromagnetic shielding member in overlapped parts by revolution in the other direction.

13. A magnetic shielding apparatus according to claim 8, wherein:

when internal space closed in a circumferential direction of the y-axis is formed by the revolution in the other direction, length in which the first and second cylindrical shields are overlapped in the circumferential direction of the y-axis and length in which the first and third cylindrical shields are overlapped are equivalent to 10 times or more of a larger interval out of an interval between the inside circumferential face of a circumferential part of the first cylindrical shield and the outside circumferential face of a circumferential part of the second cylindrical shield and an interval between the outside circumferential face of the circumferential part of the first cylindrical shield and the inside circumferential face of a circumferential part of the third cylindrical shield.

14. A magnetic shielding apparatus according to claim 8, wherein:

an angular range in a circumferential direction of the y-axis of an opening in the circumferential direction of the y-axis formed by the revolution in one direction is equivalent to a range including angles of 90 to 110 degrees.

* * * * *